US012428408B2

(12) United States Patent
Facchini et al.

(10) Patent No.: US 12,428,408 B2
(45) Date of Patent: Sep. 30, 2025

(54) FUSED HETEROCYCLIC MESCALINE DERIVATIVES

(71) Applicant: Enveric Biosciences Canada Inc., Calgary (CA)

(72) Inventors: Peter J. Facchini, Calgary (CA); Jillian M. Hagel, Calgary (CA); Chang-Chun Ling, Calgary (CA); Ye Cai, Edmonton (CA); David James Press, Calgary (CA); Glynnis Elizabeth Jensen, Calgary (CA); Jessica Bik-Jing Lee, Calgary (CA); Kaveh Matinkhoo, Calgary (CA)

(73) Assignee: Enveric Biosciences Canada Inc., Calgary (CA)

( * ) Notice: Subject to any disclaimer, the term of this patent is extended or adjusted under 35 U.S.C. 154(b) by 0 days.

(21) Appl. No.: 18/230,332

(22) Filed: Aug. 4, 2023

(65) Prior Publication Data
US 2024/0116907 A1 Apr. 11, 2024

Related U.S. Application Data

(60) Provisional application No. 63/418,878, filed on Oct. 24, 2022, provisional application No. 63/395,492, filed on Aug. 5, 2022.

(51) Int. Cl.
*C07D 407/12* (2006.01)
*C07D 317/58* (2006.01)
*C07D 405/06* (2006.01)
*C07D 405/12* (2006.01)

(52) U.S. Cl.
CPC ......... *C07D 407/12* (2013.01); *C07D 317/58* (2013.01); *C07D 405/06* (2013.01); *C07D 405/12* (2013.01)

(58) Field of Classification Search
CPC .. C07D 407/12; C07D 317/58; C07D 405/06; C07D 405/12
See application file for complete search history.

(56) References Cited

U.S. PATENT DOCUMENTS 10,435,394 B2 * 10/2019 Nakano ................ C07D 295/03

FOREIGN PATENT DOCUMENTS

WO 2023/044574 A1 3/2023

OTHER PUBLICATIONS

Registry No. 801235-02-9, File Registry on STN, entered Dec. 22, 2004.*
Registry No. 2776951-49-4, File Registry on STN, entered Jun. 23, 2022.*
Registry No. 1011230-37-7, File Registry on STN, entered Apr. 1, 2008.*
Registry No. 1301122-06-4, File Registry on STN, entered May 26, 2011.*
Registy No. 1015671-18-7, File Registry on STN, entered Apr. 18, 2008.*
Hall and Strange. Brit. J. Pharmacol. 121:731-736, 1997.
Mackenzie et al., Eur. J. Pharmacol. 266:79-85, 1994.
Cao, D. et al. Science 2022, 375:403-411.
Maier et al., J. Pharmacol. Exp. Therap. 330:342-351, 2009.
Wurch et al., J. Neurochem. 68: 410-418, 1997.
Bryant et al., [Life Sci. 15: 1259-1268, 1996.
Shen et al., J. Biol. Chem. 268: 18200-18204, 1993.
Pacholczyk et al., Nature 350: 350-354, 1991.
Roloff et al., 2013, BMC Neuroscience 14:141-155.
Saeger and Olson, 2022, Journal of Neurochemistry 162:109-127.
Roloff et al., 2015, PLOS ONE e0118536:1-14.
Olson, 2022, Biochemistry 61:127-136.
Bogenschutz, M.P. and Johnson M. W. (2016), Prog. in Neuro-Psychopharmacol. & Biol. Psychiatry 64; 250-258.
Garcia-Romeu, A.G. et al., (2017), Exp. Clin. Psychopharmacol. Aug. 2016; 24(4): 229-268.
McCorvy and Roth, 2015, Pharmacology and Therapeutics 150: 129-142.
Bock and Bermudez, 2021, FEBS Journal 288: 2513-2528.
Weis and Kobilka, 2018, Annual Review of Biochemistry 87: 897-919.
Inserra et al., 2020, Pharmacol. Rev 73: 202.
Haleem, D.j. Behav. Pharm. 2015, 26:45-58.
Amidfar, Meysam et al. Curr. Pharm. Des. 2018, 24:2541-2548.
McClure-Begley, T.D. et al. Nat. Rev. Drug Discov. 2022, 21:463-473.
Devroye, Celine et al. Pharmacol. Ther. 2018, 181:143-155.
Segelcke, Daniel et al. Cephalalgia 2017, 37:365-371.
Orsolini, Laura et al. Expert Rev. Neurother. 2016, 16:483-95.
Przegaliński, Edmund et al., 2023, Nutrients 15:1449.
Quintero-Villegas and Valdés-Ferrer, 2022, Molecular Medicine 28:70.
Saggu et al., 2023, Molecular Psychiatry 28: 588-600.
Boiko et al., 2022, Neurochemical Research 47: 2909-2924.
Salatino-Olivera, Angelica et al. Am. J. Med. Genet. B Neuropsychiatr. Genet. 2018, 177:211-231.
Outhred, Tim et al. Neurosci. Biobehav. Rev, 2013, 37:1786-800.
Polter and Li, 2010, Cell Signaling 22:1406-1412.
Finnin, B. and Morgan, T.M., 1999 J. Pharm. Sci, 88 (10), 955-958.
Y. Zou et al., Eur. J. Med. Chem., 138, 199-211 (2017).
K. N. Campbell et al., J. Org. Chem., 16, 1736 -1740 (1951).
Langin et al., Eur. J. Pharmacol. 167:95-104, 1989.
M. G. Cabiddu et al., Tetrahedron 59, 4383-4387 (2003).
Kozell et al., 2023, Journal of Pharmacology and Experimental Therapeutics 385:62-75.
Singh et al., 2023, Cell 186:2160-2175.
Islas and Scior, 2022, Molecules 27: 2977-2995.

(Continued)

Primary Examiner — Rebecca L Anderson
(74) Attorney, Agent, or Firm — Smart & Biggar LP; Michael Fenwick

(57) ABSTRACT

Disclosed are novel fused heterocyclic mescaline derivative compounds, notably fused heterocyclic mescaline derivatives and pharmaceutical and recreational drug formulations containing the same. Methods of making and using these compounds are also disclosed.

19 Claims, 49 Drawing Sheets

(56) References Cited

OTHER PUBLICATIONS

Bulling et al., (2009, Journal of Biological Chemistry 287:18524-18534.
Zwartsen et al., 2017, Toxicology in Vitro 45:60-71.
Halberstadt and Geyer 2013, Psychopharmacology 227: 727-739.
Gonzalez-Maeso et al., 2007, Neuron 53:439-452.
Halberstadt et al., 2019, Journal of Psychopharmacology 33:406-414.
Fantegrossi et al., 2004, Psychopharmacology 173: 270-277.
Jaster et al., 2022, Psychopharmacology 239: 1665-1677.
Glennon, 1992, In: Boulton, Baker, Wu [Eds] Animal Models of Drug Addiction. Neuromethods 24, Humana Press.
Rickli et al., 2015, Neuropharmacology 99: 546.
Simmler et al., 2013, British J. Pharmacol. 168: 458.
Rickli et al., 2016, Eur. Neuropharm. 26: 1327.
Halberstadt, 2015, Behav. Brain Res. 277: 99.
Owens et al., 1997, Journal of Pharmacology and Experimental Therapeutics 283:1305-1322.
Rojas and Felder, 2016, Frontiers in Cellular Neuroscience 10:272.
Marcher-Rørsted et al., 2020, ACS Chem. Neurosci. 11: 1238.
Witt-Endersby and Dubocovich. Mol. Pharmacol. 50:166-174, 1996.
Pristupa et al., [Mol. Pharmacol. 45: 125-135, 1994.
Ly et al., 2018, Cell Reports 23:3170-3182.
Pittenger and Duman, 2008, Neuropsychopharmacology 33:88-109.
Braun et al. Centrally Active N-Substituted Analogs of 3,4-Methylenedioxyphenylisopropylamine (3,4-Methylenedioxyamphetamine), J Pharm Sci. 1980, 69(2), pp. 192-195.

* cited by examiner

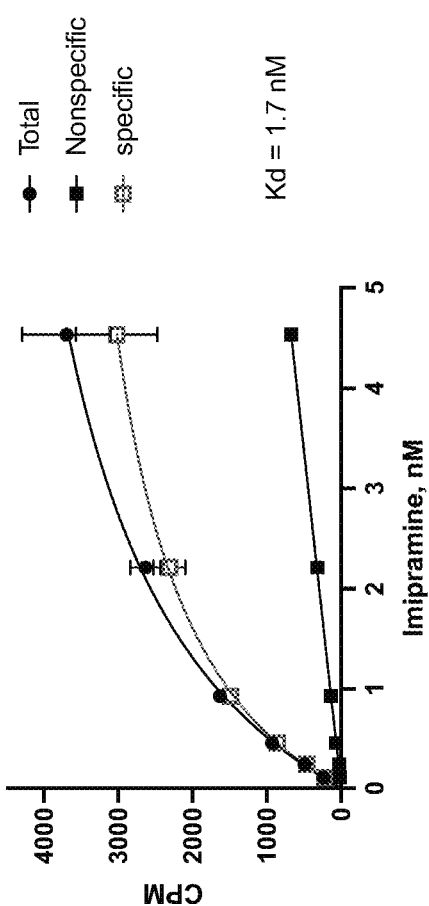
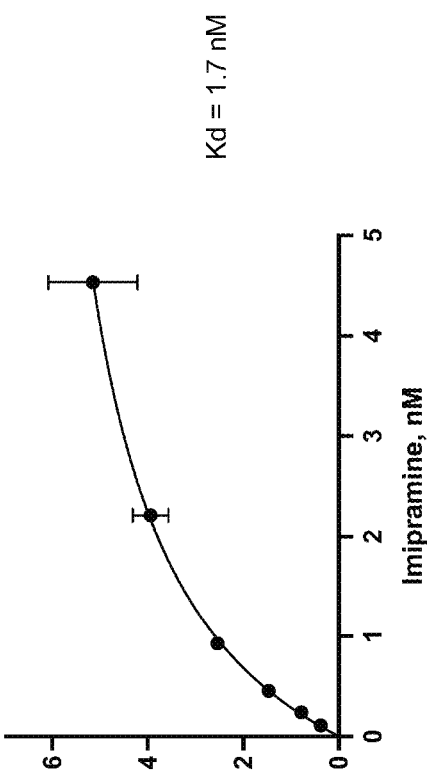
FIG. 38B
FIG. 38A

FUSED HETEROCYCLIC MESCALINE DERIVATIVES

RELATED APPLICATIONS

This application claims the benefit of U.S. Provisional Application No. 63/395,492 filed Aug. 5, 2022 and U.S. Provisional Application No. 63/418,878 filed Oct. 24, 2022; the entire contents of U.S. Patent Application Nos. 63/395,492 and 63/418,878 are hereby incorporated by reference.

FIELD OF THE DISCLOSURE

The compositions and methods disclosed herein relate to a chemical compound known as mescaline. Furthermore, the compositions and methods disclosed herein relate, in particular, to fused heterocyclic derivatives of mescaline.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Mescaline (chemical name 3,4,5 trimethoxyphenethylamine), for example, is a secondary metabolite that is naturally produced by certain cactus species belonging to a variety of genera within the plant family of Cactaceae. Cactus species which can produce mescaline include, for example, cactus species belonging to the genus *Lophophora*, including *Lophophora williamsii* (peyote) and *Lophophora diffusa* and cactus species belonging to the genus *Echinopsis/Trichocereus*, including *Echinopsis pachanoi/Trichocereus pachanoi* (also known as San Pedro), *Echinopsis peruviana/Trichocereus peruvianus* (also known as Peruvian torch), (*Echinopsis lageniformis/Trichocereus bridgesii/* (also known as Bolivian torch), and *Echinopsis scopulicola/Trichocereus scopulicola*.

The interest of the art in mescaline is well established. Thus, for example, mescaline is a psychoactive compound and is therefore used as a recreational drug. Mescaline is also used in Native American religious ceremonies, and for spiritual purposes by Andean indigenous cultures. Furthermore, mescaline has been evaluated for its potential in the treatment of addictions, notably alcohol addiction (Bogenschutz, M. P. and Johnson M. W. (2016), Prog. in Neuro-Psychopharmacol. & Biol. Psychiatry 64; 250-258; Romeu, A. G. et al., (2017), Exp. Clin. Psychopharmacol. 2016 August; 24(4): 229-268).

Although the toxicity of mescaline is low, adverse side effects, including, for example, panic attacks, paranoia, and psychotic states, sometimes together or individually referred to as "a bad trip", are not infrequently experienced by mescaline users. Furthermore, mescaline can induce nausea and vomiting.

There exists therefore a need in the art for improved mescaline compounds.

SUMMARY OF THE DISCLOSURE

The following paragraphs are intended to introduce the reader to the more detailed description, not to define or limit the claimed subject matter of the present disclosure.

In one aspect, the present disclosure relates to mescaline and derivative compounds.

In another aspect, the present disclosure relates to fused heterocyclic mescaline derivatives and methods of making and using these compounds.

Accordingly, in one aspect, the present disclosure provides, in at least one embodiment, in accordance with the teachings herein, a chemical compound selected from a first chemical compound having chemical formula (I), and a second chemical compound having chemical formula (II):

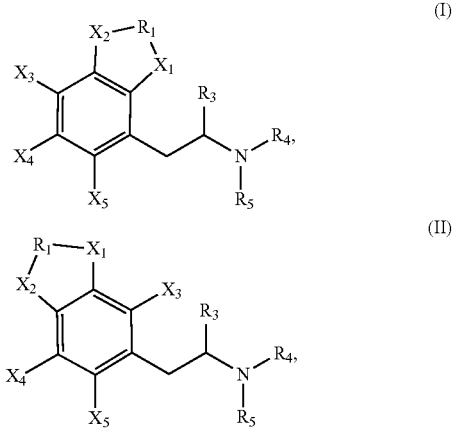

wherein, in each chemical formula (I) and (II)
- $R_1$ is an optionally substituted alkylene group having 1-3 carbon atoms or a carbonyl group (—C(=O));
- $X_1$ and $X_2$ are independently selected from an oxygen atom, a sulfur atom, —NH, or an N-alkyl group;
- $X_3$, $X_4$, or $X_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of $X_3$, $X_4$, or $X_5$ are a hydrogen atom;
- $R_3$ is a methyl group, oxo group, a cyano group, or a hydrogen atom; and
- $R_4$ and $R_5$ are independently selected from an alkyl group, an alkoxy group, a cyclo-alkyl group, a hydroxyalkyl group, an N-substituted amino group, an alkyl-aryl group wherein the aryl is optionally substituted, an alkyl-heteroaryl group wherein the heteroaryl is optionally substituted, or a hydrogen atom, or
- $R_4$ and $R_5$ are joined together, along with a nitrogen atom to which they are attached, to form a 3-10-membered optionally substituted heterocyclic ring.

In at least one embodiment, in an aspect, the amino group (—NR$_4$R$_5$) in the compounds of formula (I) and (II) can be protonated to form (—N$^+$HR$_4$R$_5$), and chemical formula (I) or (II) further includes a negatively charged anion balancing the positively charged nitrogen atom.

In at least one embodiment, in an aspect, $R_1$ can be an alkylene group having one carbon atom and $X_1$ and $X_2$ can each be an oxygen atom.

In at least one embodiment, in an aspect, $R_1$ can be a substituted alkylene group having one carbon atom, wherein the carbon atom is substituted with one or two halogen atoms, and $X_1$ and $X_2$ can each be an oxygen atom.

In at least one embodiment, in an aspect, $R_1$ can be a substituted alkylene group having one carbon atom, wherein the carbon atom is substituted with one or two fluorine atoms, and $X_1$ and $X_2$ can each be an oxygen atom.

In at least one embodiment, in an aspect, $R_1$ can be an alkylene group having two carbons atom and $X_1$ and $X_2$ can each be an oxygen atom.

In at least one embodiment, in an aspect, $X_3$, $X_4$, and $X_5$ can each be a hydrogen atom.

In least one embodiment, in an aspect, one of $X_3$, $X_4$, and $X_5$ can be a halogen or an alkoxy group.

In least one embodiment, in an aspect, $X_5$ can be a halogen or an alkoxy group.

In least one embodiment, in an aspect, $X_5$ can be a halogen or an $(C_1-C_{10})$-alkoxy group.

In least one embodiment, in an aspect, $X_5$ can be a halogen or an $(C_1-C_3)$-alkoxy group.

In least one embodiment, in an aspect, $X_5$ can be a bromine or a methoxy group.

In at least one embodiment, in an aspect, $R_4$ and $R_5$ can be joined together, along with the nitrogen atom to which they are attached, to form a 4-6-membered optionally substituted heterocyclic ring, and wherein the heterocyclic ring optionally includes a second hetero atom.

In at least one embodiment, in an aspect, $R_4$ and $R_5$, can be joined together, along with the nitrogen atom to which they are attached, to form a 6-membered non-substituted heterocyclic ring, and wherein the heterocyclic ring includes a second hetero atom.

In at least one embodiment, in an aspect, the second heteroatom can be an oxygen atom.

In at least one embodiment, in an aspect, the heterocyclic ring formed by $R_4$ and $R_5$ can be substituted with an amino group or a substituted amino group.

In at least one embodiment, in an aspect, the substituted amino group can be substituted with tert-butyloxycarbonyl.

In at least one embodiment, in an aspect, the alkyl-aryl group can be a $(C_1-C_{10})$-alkylene aryl group.

In at least one embodiment, in an aspect, the alkyl-aryl group can be an alkylene phenyl group or an alkylene naphthyl group.

In at least one embodiment, in an aspect, the substituted aryl group can be fused to a 5 or 6 membered heterocyclic ring.

In at least one embodiment, in an aspect, the heterocyclic ring can contain one or two oxygen atoms.

In at least one embodiment, in an aspect, in the substituted alkyl-aryl group, the aryl group can be additionally substituted with a halogen atom.

In at least one embodiment, in an aspect, in the substituted alkyl-aryl group, the aryl group can be additionally substituted with an alkoxy group.

In at least one embodiment, in an aspect, in the substituted alkyl-aryl group, the aryl group can be additionally substituted with a methoxy group.

In at least one embodiment, in an aspect, the alkyl-heteroaryl group can be a $(C_5-C_{10})$-heteroaryl group.

In at least one embodiment, in an aspect, the alkyl-heteroaryl group can be a $(C_1-C_{10})$-alkylene heteroaryl group.

In at least one embodiment, in an aspect, the alkyl-heteroaryl group can be an alkylene indole group.

In at least one embodiment, in an aspect, the alkyl-heteroaryl group can be a $(C_1-C_3)$-alkylene indole group.

In at least one embodiment, in an aspect, at least one of the $R_4$ and $R_5$ groups can be a $(C_1-C_{10})$-alkyl group.

In at least one embodiment, in an aspect, at least one of the $R_4$ and $R_5$ groups can be a $(C_1-C_3)$-alkyl group.

In at least one embodiment, in an aspect, at least one of the $R_4$ and $R_5$ groups can be a $(C_3-C_{10})$-cyclo-alkyl group.

In at least one embodiment, in an aspect, at least one of the $R_4$ and $R_5$ groups can be a $(C_3-C_6)$-cyclo-alkyl group.

In at least one embodiment, in an aspect, at least one of the $R_4$ and $R_5$ groups can be a $C_4$-cyclo-alkyl group.

In at least one embodiment, in an aspect, at least one of the $R_4$ and $R_5$ groups can be a $(C_1-C_{10})$-alkoxy group.

In at least one embodiment, in an aspect, at least one of the $R_4$ and $R_5$ groups can be a $(C_1-C_3)$-alkoxy group.

In at least one embodiment, in an aspect, at least one of the $R_4$ and $R_5$ groups can be a $(C_1-C_{10})$-hydroxyalkyl group.

In at least one embodiment, in an aspect, at least one of the $R_4$ and $R_5$ groups can be a $(C_1-C_3)$-hydroxyalkyl group.

In at least one embodiment, in an aspect, at least one of the $R_4$ and $R_5$ groups can be a substituted amino group.

In at least one embodiment, in an aspect, at least one of the $R_4$ and $R_5$ groups can be a $(C_1-C_{10})$-alkyl substituted amino group.

In at least one embodiment, in an aspect, at least one of the $R_4$ and $R_5$ groups can be a $(C_1-C_3)$-alkyl substituted amino group.

In at least one embodiment, in an aspect, each of the $R_4$ and $R_5$ groups can be a $CH_3$-substituted amino group.

In at least one embodiment, in an aspect, the chemical compound having formula (I) or (II) can be selected from the group of compounds selected from: A(I); A(II); A(III); A(IV); A(V); A(VI); A(VII); A(VIII); A(IX); A(X); A(XI); A(XII); A(XIII); A(XIV); A(XV); A(XVI); A(XVII); A(XVIII); A(XIX); A(XX); A(XXI); A(XXII); A(XXIII); A(XXIV); A(XXV); A(XXVI); A(XXVII); A(XXVIII); A(XXIX); A(XXX); A(XXXI): and A(XXXII):

A(I)
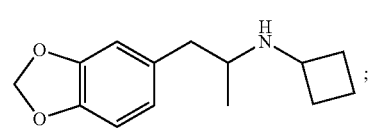

A(II)
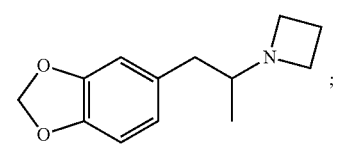

A(III)
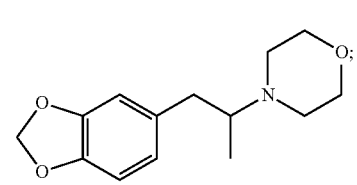

A(IV)
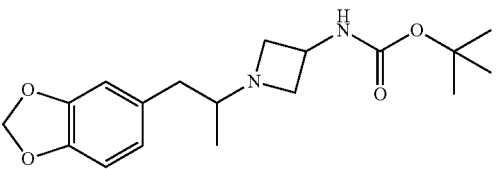

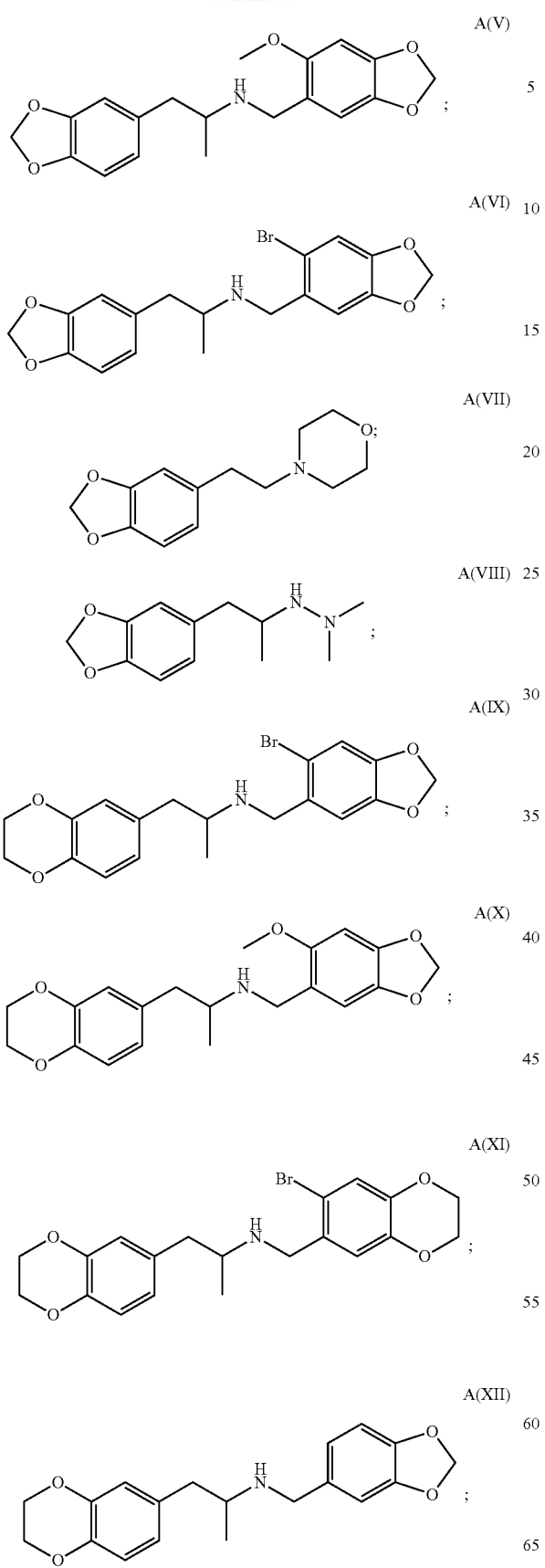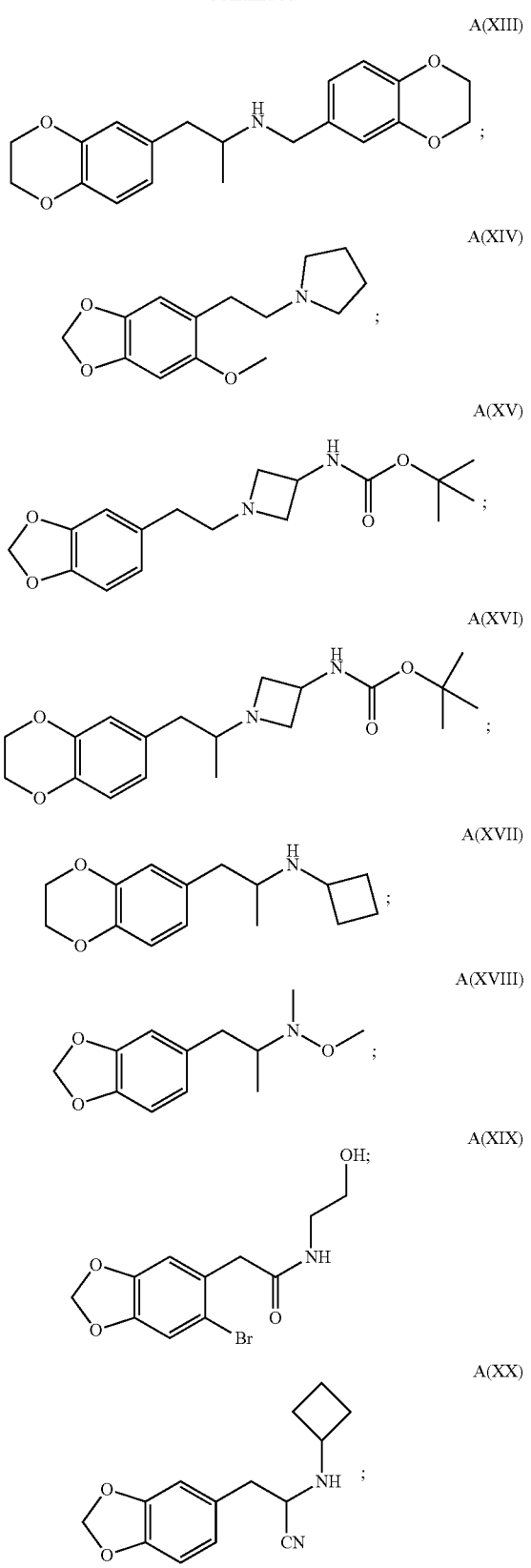

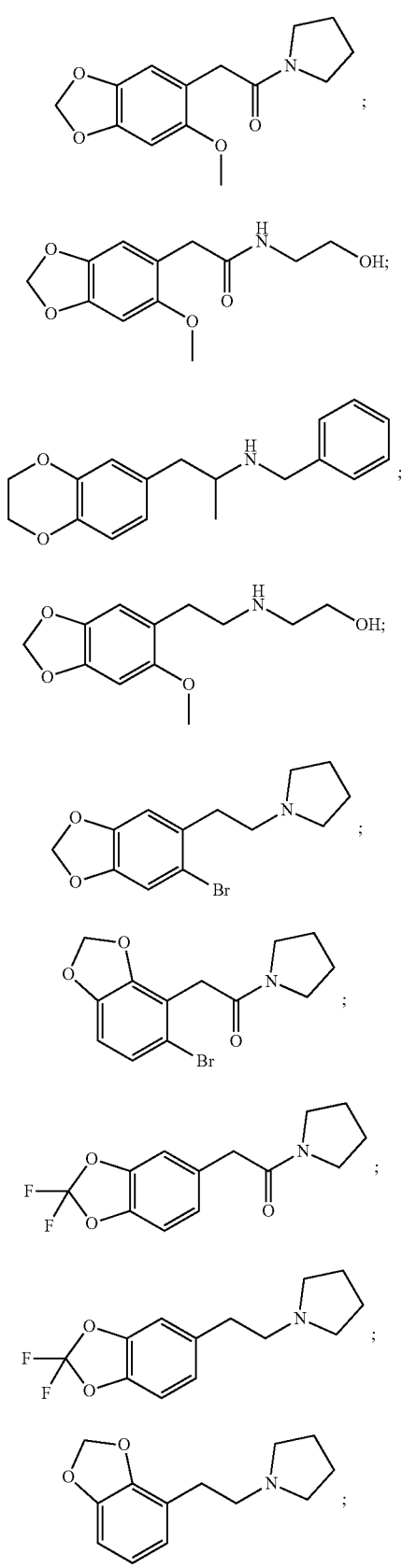

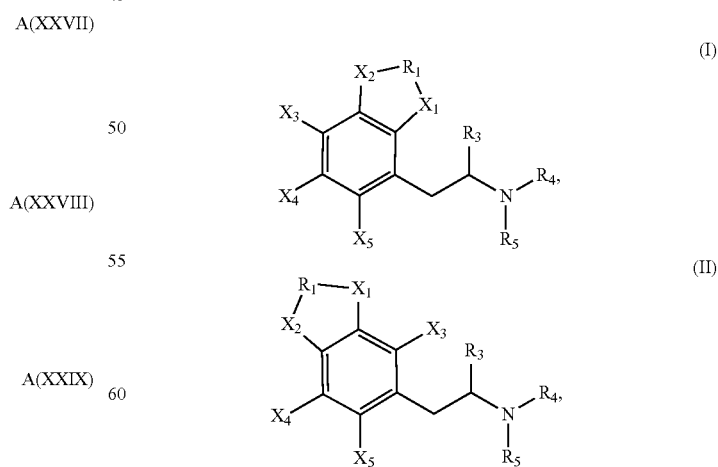

wherein in each of compound A(I) to A(XXXII), optionally, the nitrogen atom of the ethyl amine chain may be protonated and includes a negatively charged anion balancing the positively charged nitrogen atom.

In another aspect, the present disclosure relates to pharmaceutical and recreational drug formulations comprising fused heterocyclic mescaline derivatives. Accordingly, in one aspect, the present disclosure provides, in at least one embodiment, a pharmaceutical or recreational drug formulation comprising an effective amount of a chemical compound selected from a first chemical compound having chemical formula (I), and a second chemical compound having chemical formula (II):

wherein, in each chemical formula (I) and (II)
$R_1$ is an optionally substituted alkylene group having 1-3 carbon atoms or a carbonyl group (—C(═O));

$X_1$ and $X_2$ are independently selected from an oxygen atom, a sulfur atom, —NH, or an N-alkyl group; and $X_3$, $X_4$, or $X_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of $X_3$, $X_4$, or $X_5$ are a hydrogen atom;

$R_3$ is a methyl group, oxo group, a cyano group, or a hydrogen atom; and $R_4$ and $R_5$ are independently selected from an alkyl group, an alkoxy group, a cyclo-alkyl group, a hydroxyalkyl group, an N-substituted amino group, an alkyl-aryl group wherein the aryl is optionally substituted, an alkyl-heteroaryl group wherein the heteroaryl is optionally substituted, or a hydrogen atom, or $R_4$ and $R_5$ are joined together, along with a nitrogen atom to which they are attached, to form a 3-10-membered optionally substituted heterocyclic ring, together with a pharmaceutically acceptable excipient, diluent, or carrier.

In another aspect, the present disclosure relates to methods of treatment of brain neurological disorders. Accordingly, the present disclosure further provides, in one embodiment, a method for treating a brain neurological disorder, the method comprising administering to a subject in need thereof a pharmaceutical formulation comprising a chemical compound selected from a first chemical compound having chemical formula (I), and a second chemical compound having chemical formula (II):

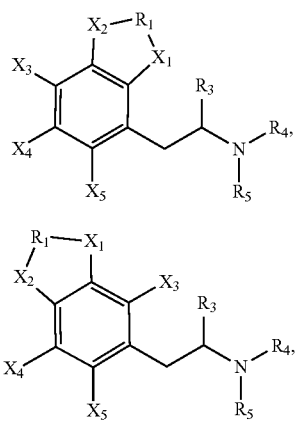

wherein, in each chemical formula (I) and (II)

$R_1$ is an optionally substituted alkylene group having 1-3 carbon atoms or a carbonyl group (—C(=O));

$X_1$ and $X_2$ are independently selected from an oxygen atom, a sulfur atom, —NH, or an N-alkyl group; and $X_3$, $X_4$, or $X_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of $X_3$, $X_4$, or $X_5$ are a hydrogen atom;

$R_3$ is a methyl group, oxo group, a cyano group, or a hydrogen atom; and $R_4$ and $R_5$ are independently selected from an alkyl group, an alkoxy group, a cyclo-alkyl group, a hydroxyalkyl group, an N-substituted amino group, an alkyl-aryl group wherein the aryl is optionally substituted, an alkyl-heteroaryl group wherein the heteroaryl is optionally substituted, or a hydrogen atom, or $R_4$ and $R_5$ are joined together, along with a nitrogen atom to which they are attached, to form a 3-10-membered optionally substituted heterocyclic ring, wherein the pharmaceutical formulation is administered in an effective amount to treat the brain neurological disorder in the subject.

In at least one embodiment, in an aspect, upon administration the compound having chemical formula (I) or (II) can interact with a receptor in the subject to thereby modulate the receptor and exert a pharmacological effect.

In at least one embodiment, in an aspect, upon administration the compound having chemical formula (I) or (II) can exert a neuroplastic effect on brain neuronal cells of the subject.

In at least one embodiment, in an aspect, the receptor can be a G-protein coupled receptor (GPCR).

In at least one embodiment, in an aspect, the receptor can be a 5-HT receptor.

In at least one embodiment, in an aspect, the receptor can be a $5\text{-HT}_{1A}$ receptor, a $5\text{-HT}_{2A}$ receptor, a $5\text{-HT}_{1B}$ receptor, a $5\text{-HT}_{2B}$ receptor, a $5\text{-HT}_{3A}$ receptor, a $5\text{-HT}_{2C}$ receptor, a $5\text{-HT}_{1D}$ receptor, a $5\text{-HT}_7$ receptor, an $\alpha_{2A}$ receptor, a $D_2$ receptor, a $D_3$ receptor, or an $MT_1$ receptor.

In at least one embodiment, in an aspect, upon administration the compound having chemical formula (I) or (II) can interact with a transmembrane transport protein in the subject to thereby modulate the transmembrane transport protein and exert a pharmacological effect.

In at least one embodiment, in an aspect, the transmembrane transport protein can be a dopamine active transporter (DAT), a norephedrine transporter (NET), or a serotonin transporter (SERT) transmembrane transport protein.

In at least one embodiment, in an aspect, the disorder can be a G-protein coupled receptor (GPCR)-mediated disorder.

In at least one embodiment, in an aspect, the disorder can be a 5-HT receptor-mediated disorder.

In at least one embodiment, in an aspect, the disorder can be a $5\text{-HT}_{1A}$ receptor-mediated disorder, a $5\text{-HT}_{2A}$ receptor-mediated disorder, a $5\text{-HT}_{1B}$ receptor-mediated disorder, a $5\text{-HT}_{2B}$ receptor-mediated disorder, a $5\text{-HT}_{3A}$ receptor-mediated disorder, a $5\text{-HT}_{2C}$ receptor-mediated disorder, a $5\text{-HT}_{1D}$ receptor-mediated disorder, a $5\text{-HT}_7$ receptor-mediated disorder, a $\alpha_{2A}$ receptor-mediated disorder, a CNR1 receptor-mediated disorder, a DRD1 receptor-mediated disorder, a $D_2$ receptor-mediated disorder, a $D_3$ receptor-mediated disorder, or an $MT_1$ receptor-mediated disorder.

In at least one embodiment, in an aspect, a dose can be administered of about 0.001 mg to about 5,000 mg.

In another aspect, the present disclosure provides, in at least one embodiment, a method for modulating (i) a receptor selected from $5\text{-HT}_{1A}$ receptor, a $5\text{-HT}_{2A}$ receptor, a $5\text{-HT}_{1B}$ receptor, a $5\text{-HT}_{2B}$ receptor, a $5\text{-HT}_{3A}$ receptor, a $5\text{-HT}_{2C}$ receptor, a $5\text{-HT}_{1D}$ receptor, a $5\text{-HT}_7$ receptor, an $\alpha_{2A}$ receptor, a $D_2$ receptor, a $D_3$ receptor, or an $MT_1$ receptor; or (ii) a transmembrane transport protein selected from a dopamine active transporter (DAT), a norephedrine transporter (NET) or a serotonin transporter (SERT) transmembrane transport protein, the method comprising contacting (i) the $5\text{-HT}_{1A}$ receptor, the $5\text{-HT}_{2A}$ receptor, the $5\text{-HT}_{1B}$ receptor, the $5\text{-HT}_{2B}$ receptor, the $5\text{-HT}_{3A}$ receptor, the $5\text{-HT}_{2C}$ receptor, the $5\text{-HT}_{1D}$ receptor, the $5\text{-HT}_7$ receptor, the α$_{2A}$ receptor, the D$_2$ receptor, the D$_3$ receptor, or the MT$_1$ receptor; or (ii) the dopamine active transporter (DAT), the norephedrine transporter (NET), or the serotonin transporter (SERT) transmembrane transport protein with a selected from a first chemical compound having chemical formula (I), and a second chemical compound having chemical formula (II):

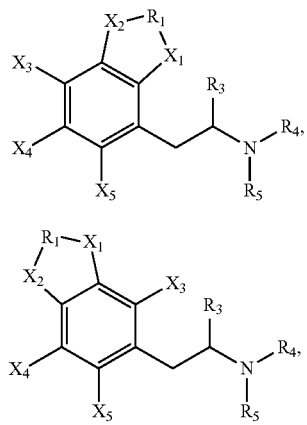

wherein, in each chemical formula (I) and (II)
R$_1$ is an optionally substituted alkylene group having 1-3 carbon atoms or a carbonyl group (—C(=O));
X$_1$ and X$_2$ are independently selected from an oxygen atom, a sulfur atom, —NH, or an N-alkyl group;
X$_3$, X$_4$, or X$_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of X$_3$, X$_4$, or X$_5$ are a hydrogen atom;
R$_3$ is a methyl group, oxo group, a cyano group, or a hydrogen atom; and
R$_4$ and R$_5$ are independently selected from an alkyl group, an alkoxy group, a cyclo-alkyl group, a hydroxyalkyl group, an N-substituted amino group, an alkyl-aryl group wherein the aryl is optionally substituted, an alkyl-heteroaryl group wherein the heteroaryl is optionally substituted, or a hydrogen atom, or
R$_4$ and R$_5$ are joined together, along with a nitrogen atom to which they are attached, to form a 3-10-membered optionally substituted heterocyclic ring,
under reaction conditions sufficient to modulate (i) the 5-HT$_{1A}$ receptor, the 5-HT$_{2A}$ receptor, the 5-HT$_{1B}$ receptor, the 5-HT$_{2B}$ receptor, the 5-HT$_{3A}$ receptor, the 5-HT$_{2C}$ receptor, the 5-HT$_{1D}$ receptor, the 5-HT$_7$ receptor, the α$_{2A}$ receptor, the D$_2$ receptor, the D$_3$ receptor, or the MT$_1$ receptor; (ii) the dopamine active transporter (DAT), the norephedrine transporter (NET), or the serotonin transporter (SERT) transmembrane transport protein.

In at least one embodiment, in an aspect, the reaction conditions can be in vitro reaction conditions.

In at least one embodiment, in an aspect, the reaction conditions can be in vivo reaction conditions.

In another aspect, the present disclosure includes methods of making fused mescaline derivatives. Accordingly, included herein are methods of making a first chemical compound having chemical formula (I), or a second chemical compound having chemical formula (II):

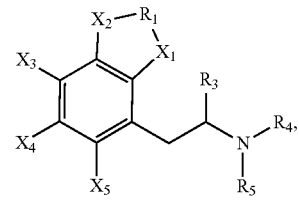

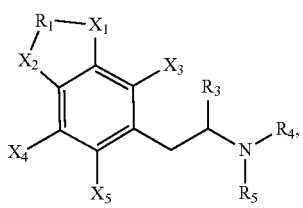

wherein, in each chemical formula (I) and (II)
R$_1$ is an optionally substituted alkylene group having 1-3 carbon atoms or a carbonyl group (—C(=O));
X$_1$ and X$_2$ are independently selected from an oxygen atom, a sulfur atom, —NH, or an N-alkyl group; and
X$_3$, X$_4$, or X$_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of X$_3$, X$_4$, or X$_5$ are a hydrogen atom;
R$_3$ is a methyl group, oxo group, a cyano group, or a hydrogen atom; and
R$_4$ and R$_5$ are independently selected from an alkyl group, an alkoxy group, a cyclo-alkyl group, a hydroxyalkyl group, an N-substituted amino group, an alkyl-aryl group wherein the aryl is optionally substituted, or a hydrogen atom, or
R$_4$ and R$_5$ are joined together, along with a nitrogen atom to which they are attached, to form a 3-10-membered optionally substituted heterocyclic ring,
wherein the method involves the performance of at least one chemical synthesis reaction selected from the reactions depicted in FIG. 3A-3C, 4, 5A-5B, 6, 7, 8A 8C, 9, 10, 11A-11C, 12, 13, 14, 15, 16A-16B, 17, 18, 19A-19B, 20, 21, 22, 23, 24, 25, 26, 27A-27C, 28A-28B, 29A-29B, 30, 31, 32A-32C, 33, or 34.

In at least one embodiment, in an aspect, the compound having chemical formula (II) can be a compound having formula A(I):

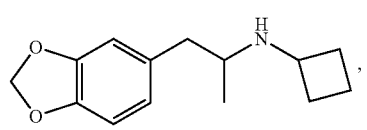

and the at least one chemical synthesis reaction is the chemical synthesis reaction depicted in FIG. 5A, and optionally, FIG. 5B.

In at least one embodiment, in an aspect, the compound having chemical formula (II) can be a compound having formula A(II):

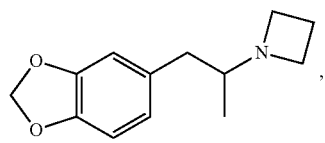

A(II)

And the at least one chemical synthesis reaction is the chemical synthesis reaction depicted in FIG. 6, and optionally, FIG. 5B.

In at least one embodiment, in an aspect, the compound having chemical formula (II) can be a compound having formula A(III):

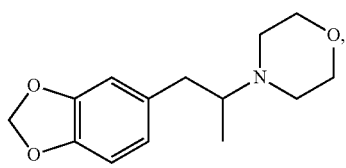

A(III)

and the at least one chemical synthesis reaction is the chemical synthesis reaction depicted in FIG. 7, and optionally, FIG. 5B.

In at least one embodiment, in an aspect, the compound having chemical formula (II) can be a compound having a formula A(IV):

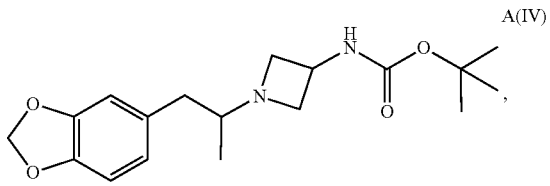 [SMILES: CC(Cc1ccc2c(c1)OCO2)N1CC(NC(=O)OC(C)(C)C)C1]

A(IV)

and the at least one chemical synthesis reaction is the chemical synthesis reaction depicted in FIG. 9, and optionally, FIG. 5B.

In at least one embodiment, in an aspect, the compound having chemical formula (II) can be a compound having a formula A(V):

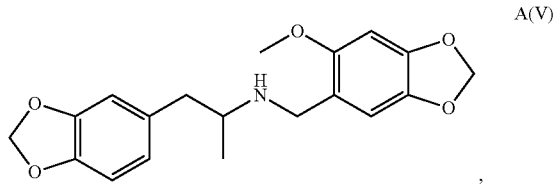 [SMILES: COc1cc2c(cc1CNC(C)Cc1ccc3c(c1)OCO3)OCO2]

A(V)

and the at least one chemical synthesis reaction is the chemical synthesis reaction depicted in FIG. 3A, and optionally, FIG. 3C, and further optionally, FIG. 3B.

In at least one embodiment, in an aspect, the compound having chemical formula (II) can be a compound having a formula A(VI):

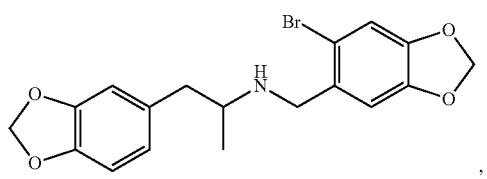

A(VI)

and the at least one chemical synthesis reaction is the chemical synthesis reaction depicted in FIG. 4, and optionally, FIG. 3C, and further optionally, FIG. 3B.

In at least one embodiment, in an aspect, the compound having chemical formula (II) can be a compound having a formula A(VII):

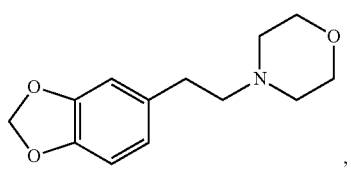

A(VII)

and the at least one chemical synthesis reaction is the chemical synthesis reaction depicted in FIG. 8A, and optionally, FIG. 8C, and further optionally, FIG. 8B.

In at least one embodiment, in an aspect, the compound having chemical formula (II) can be a compound having a formula A(VIII):

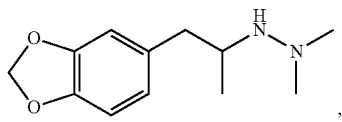

A(VIII)

and the at least one chemical synthesis reaction is the chemical synthesis reaction depicted in FIG. 10, and optionally, FIG. 5B.

In at least one embodiment, in an aspect, the compound having chemical formula (II) can be a compound having a formula A(IX):

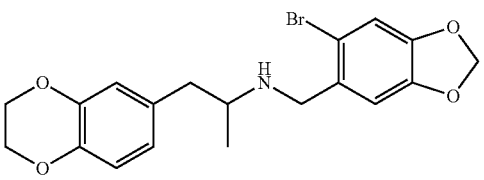

A(IX)

and the at least one chemical synthesis reaction is the chemical synthesis reaction depicted in FIG. 11A, and optionally, FIG. 11C, and further optionally, FIG. 11B.

In at least one embodiment, in an aspect, the compound having chemical formula (II) can be a compound having a formula A(X):

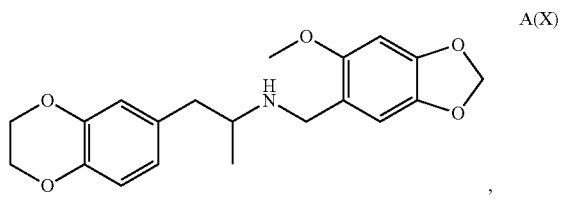 [SMILES: COc1cc2c(cc1CNC(C)Cc1ccc3c(c1)OCCO3)OCO2]

A(X)

, and the at least one chemical synthesis reaction is the chemical synthesis reaction depicted in FIG. 12, and optionally FIG. 11C, and further optionally, FIG. 11B.

In at least one embodiment, in an aspect, the compound having chemical formula (II) can be a compound having a formula A(XI):

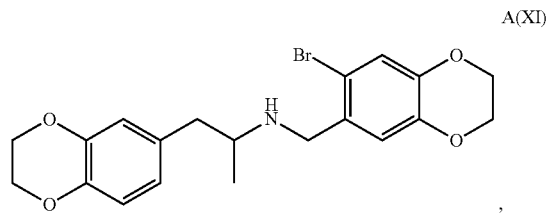 [SMILES: CC(Cc1ccc2c(c1)OCCO2)NCc1cc2c(cc1Br)OCCO2]

A(XI)

, and the at least one chemical synthesis reaction is the chemical synthesis reaction depicted in FIG. 13, and optionally, FIG. 11C, and further optionally, FIG. 11B.

In at least one embodiment, in an aspect, the compound having chemical formula (II) can be a compound having a formula A(XII):

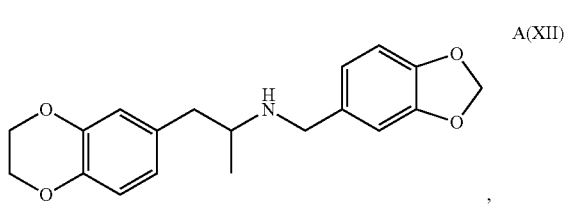 [SMILES: CC(Cc1ccc2c(c1)OCCO2)NCc1ccc2c(c1)OCO2]

A(XII)

, and the at least one chemical synthesis reaction is the chemical synthesis reaction depicted in FIG. 14, and optionally, FIG. 11C, and further optionally, FIG. 11B.

In at least one embodiment, in an aspect, the compound having chemical formula (II) can be a compound having a formula A(XIII):

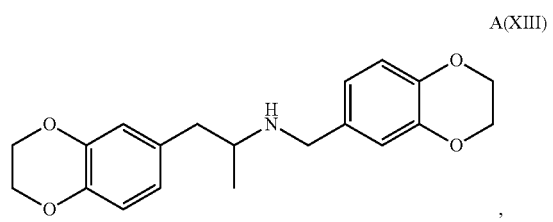 [SMILES: CC(Cc1ccc2c(c1)OCCO2)NCc1ccc2c(c1)OCCO2]

A(XIII)

, and the at least one chemical synthesis reaction is the chemical synthesis reaction depicted in FIG. 15, and optionally, FIG. 11C, and further optionally, FIG. 11B.

In at least one embodiment, in an aspect, the compound having chemical formula (II) can be a compound having a formula A(XIV):

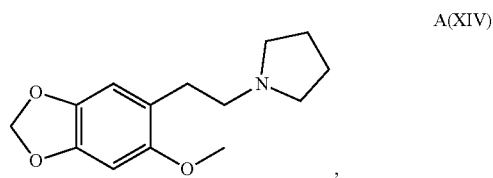 [SMILES: COc1cc2c(cc1CCN1CCCC1)OCO2]

A(XIV)

, and the at least one chemical synthesis reaction is the chemical synthesis reaction depicted in FIG. 17, and optionally, FIG. 16B.

In at least one embodiment, in an aspect, the compound having chemical formula (II) can be a compound having a formula A(XV):

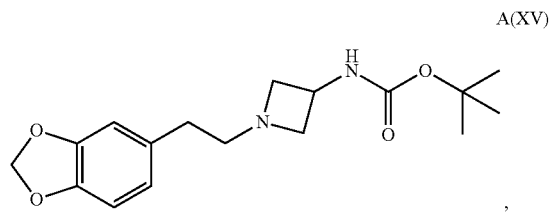 [SMILES: CC(C)(C)OC(=O)NC1CN(CCc2ccc3c(c2)OCO3)C1]

A(XV)

, and the at least one chemical synthesis reaction is the chemical synthesis reactions depicted in FIG. 18, and optionally, FIG. 8C, and further optionally, FIG. 8B.

In at least one embodiment, in an aspect, the compound having chemical formula (II) can be a compound having a formula A(XVI):

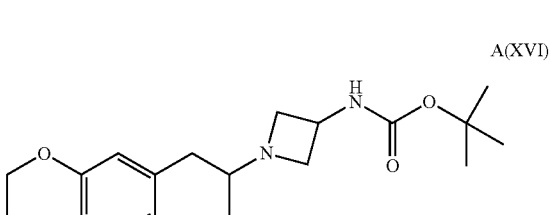

A(XVI)

, and the at least one chemical synthesis reaction is the chemical synthesis reaction depicted in FIG. 19A, and optionally, FIG. 19B.

In at least one embodiment, in an aspect, the compound having chemical formula (II) can be a compound having a formula A(XVII):

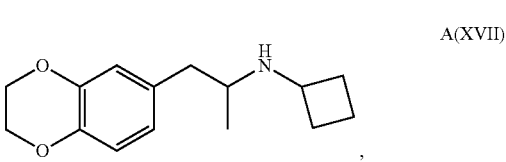 [SMILES: CC(Cc1ccc2c(c1)OCCO2)NC1CCC1]

A(XVII)

, and the at least one chemical synthesis reaction is the chemical synthesis reaction depicted in FIG. 20, and optionally, FIG. 19B.

In at least one embodiment, in an aspect, the compound having chemical formula (II) can be a compound having a formula A(XVIII):

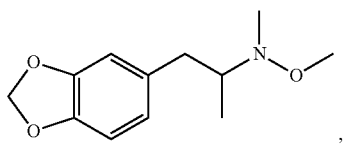

A(XVIII)

And the at least one chemical synthesis reaction is the chemical synthesis reaction depicted in FIG. 21, and optionally, FIG. 5B.

In at least one embodiment, in an aspect, the compound having chemical formula (II) can be a compound having a formula A(XIX):

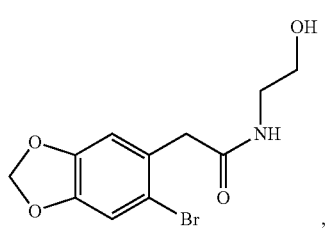

A(XIX)

and the at least one chemical synthesis reaction is the chemical synthesis reaction depicted in FIG. 22.

In at least one embodiment, in an aspect, the compound having chemical formula (II) can be a compound having a formula A(XX):

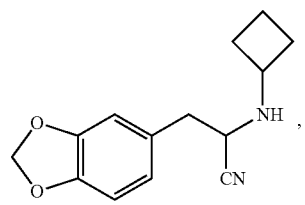

A(XX)

and the at least one chemical synthesis reaction is the chemical synthesis reaction depicted in FIG. 23, and optionally, FIG. 8C, and further optionally, FIG. 8B.

In at least one embodiment, in an aspect, the compound having chemical formula (II) can be a compound having a formula A(XXI):

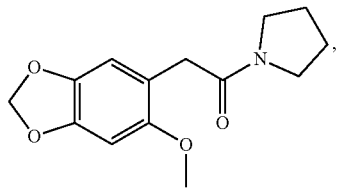

A(XXI)

and the at least one chemical synthesis reaction is the chemical synthesis reaction depicted in FIG. 16A, and optionally, FIG. 16B.

In at least one embodiment, in an aspect, the compound having chemical formula (II) can be a compound having a formula A(XXII):

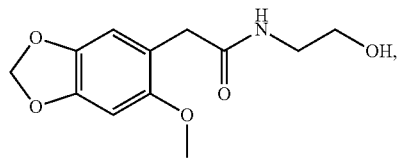

A(XXII)

and the at least one chemical synthesis reaction is the chemical synthesis reaction depicted in FIG. 24, and optionally, FIG. 16B.

In at least one embodiment, in an aspect, the compound having chemical formula (II) can be a compound having a formula A(XXIII):

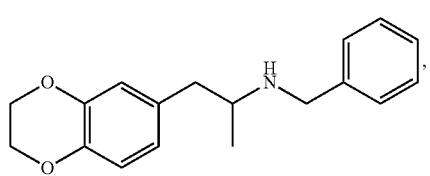

A(XXIII)

and the at least one chemical synthesis reaction is the chemical synthesis reaction depicted in FIG. 25, and optionally, FIG. 3C, and further optionally, FIG. 3B.

In at least one embodiment, in an aspect, the compound having chemical formula (II) can be a compound having a formula A(XXIV):

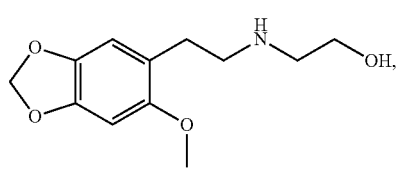

A(XXIV)

and the at least one chemical synthesis reaction is the chemical synthesis reaction depicted in FIG. 26, and optionally, FIG. 24, and further optionally, FIG. 16B.

In at least one embodiment, in an aspect, the compound having chemical formula (II) can be a compound having a formula A(XXV):

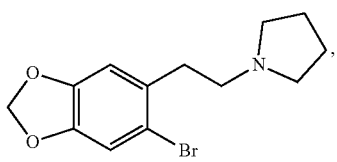

A(XXV)

and the at least one chemical synthesis reaction is the chemical synthesis reaction depicted in FIG. 27C, and optionally, FIG. 27B, and further optionally, FIG. 27A.

In at least one embodiment, in an aspect, the compound having chemical formula (I) can be a compound having a formula A(XXVI):

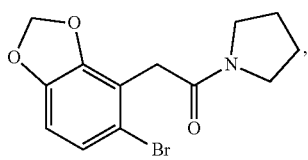

A(XXVI)

and the at least one chemical synthesis reaction is the chemical synthesis reaction depicted in FIG. 28B, and optionally, FIG. 28A.

In at least one embodiment, in an aspect, the compound having chemical formula (II) can be a compound having a formula A(XXVII):

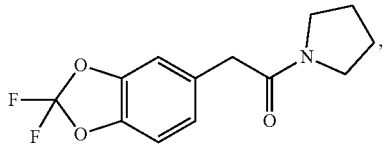

A(XXVII)

and the at least one chemical synthesis reaction is the chemical synthesis reaction depicted in FIG. 29B, and optionally, FIG. 29A.

In at least one embodiment, in an aspect, the compound having chemical formula (II) can be a compound having a formula A(XXVIII):

A(XXVIII)

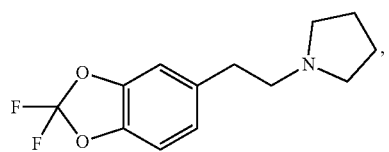

and the at least one chemical synthesis reaction is the chemical synthesis reaction depicted in FIG. 30, and optionally, FIG. 29B, and further optionally, FIG. 29A.

In at least one embodiment, in an aspect, the compound having chemical formula (I) can be a compound having a formula A(XXIX):

A(XXIX)

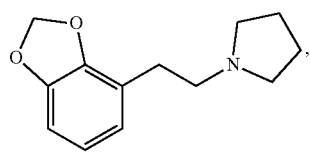

and the at least one chemical synthesis reaction is the chemical synthesis reaction depicted in FIG. 31, and optionally, FIG. 28B, and further optionally, FIG. 28A.

In at least one embodiment, in an aspect, the compound having chemical formula (II) can be a compound having a formula A(XXX):

A(XXX)

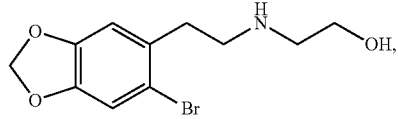

and the at least one chemical synthesis reaction is the chemical synthesis reaction depicted in FIG. 32C, and optionally, FIG. 32B, and further optionally, FIG. 32A.

In at least one embodiment, in an aspect, the compound having chemical formula (II) can be a compound having a formula A(XXXI):

A(XXXI)

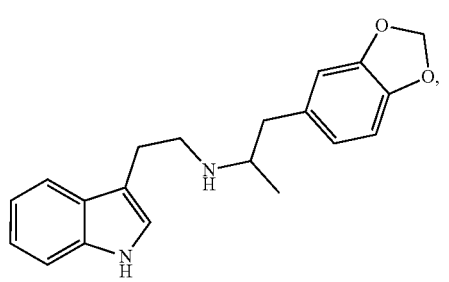

and the at least one chemical synthesis reaction is the chemical synthesis reaction depicted in FIG. 33.

In at least one embodiment, in an aspect, the compound having chemical formula (II) can be a compound having a formula A(XXXII):

A(XXXII)

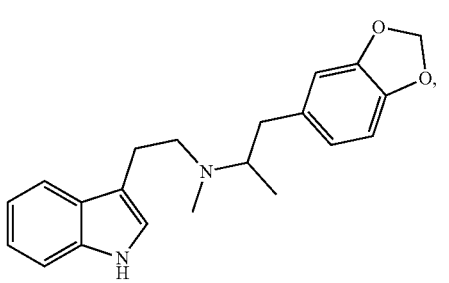

and the at least one chemical synthesis reaction is the chemical synthesis reaction depicted in FIG. 34.

In another aspect the present disclosure provides, in at least one embodiment, a use of a chemical compound selected from a first chemical compound having chemical formula (I), or a second chemical compound having chemical formula (II):

(I)

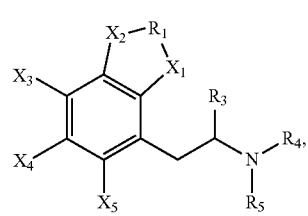

-continued

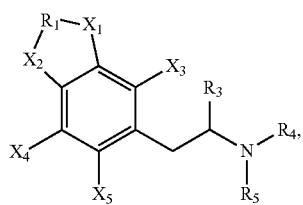

(II)

wherein, in each chemical formula (I) and (II)
  $R_1$ is an optionally substituted alkylene group having 1-3 carbon atoms or a carbonyl group (—C(=O));
  $X_1$ and $X_2$ are independently selected from an oxygen atom, a sulfur atom, —NH, or an N-alkyl group; and $X_3$, $X_4$, or $X_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of $X_3$, $X_4$, or $X_5$ are a hydrogen atom;
  $R_3$ is a methyl group, oxo group, a cyano group, or a hydrogen atom; and
  $R_4$ and $R_5$ are independently selected from an alkyl group, an alkoxy group, a cyclo-alkyl group, a hydroxyalkyl group, an N-substituted amino group, an alkyl-aryl group wherein the aryl is optionally substituted, an alkyl-heteroaryl group wherein the heteroaryl is optionally substituted, or a hydrogen atom, or
  $R_4$ and $R_5$ are joined together, along with a nitrogen atom to which they are attached, to form a 3-10-membered optionally substituted heterocyclic ring,
in the manufacture of a pharmaceutical or recreational drug formulation.

In at least one embodiment, the manufacture can comprise formulating the chemical compound with an excipient, diluent, or carrier.

In another aspect, the present disclosure provides, in at least one embodiment, a use of a chemical compound selected from a first chemical compound having chemical formula (I), and a second chemical compound having chemical formula (II):

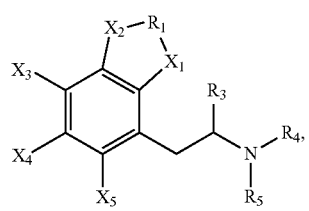

(I)

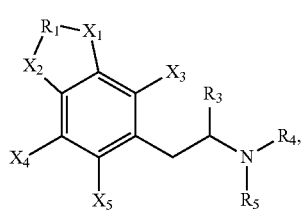

(II)

wherein, in each chemical formula (I) and (II)
  $R_1$ is an optionally substituted alkylene group having 1-3 carbon atoms or a carbonyl group (—C(=O));
  $X_1$ and $X_2$ are independently selected from an oxygen atom, a sulfur atom, —NH, or an N-alkyl group; and $X_3$, $X_4$, or $X_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of $X_3$, $X_4$, or $X_5$ are a hydrogen atom;
  $R_3$ is a methyl group, oxo group, a cyano group, or a hydrogen atom; and
  $R_4$ and $R_5$ are independently selected from an alkyl group, an alkoxy group, a cyclo-alkyl group, a hydroxyalkyl group, an N-substituted amino group, an alkyl-aryl group wherein the aryl is optionally substituted, an alkyl-heteroaryl group wherein the heteroaryl is optionally substituted, or a hydrogen atom, or
  $R_4$ and $R_5$ are joined together, along with a nitrogen atom to which they are attached, to form a 3-10-membered optionally substituted heterocyclic ring, together with a diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

FIGS. 38A, 38B, 38C, 38D, 38E, 38F, 38G, 38H, 38I, 38J, 38K, 38L, and 38M depict various graphs representing certain experimental results, notably graphs obtained in the performance of experimental assays to evaluate the pharmaceutical efficacy of an example compound having chemical formula A(VI), notably a radioligand serotonin transporter (SERT) saturation binding assay using imipramine (binding curve) (FIGS. 38A, 38B); a SERT receptor competition assay using serotonin (positive control) (FIG. 38C); a SERT receptor competition assay using DMSO (negative control) (FIG. 38D); a SERT receptor competition assay using tryptophan (negative control) (FIG. 38E); a SERT receptor competition assay using mescaline (positive control) (FIG. 38F); a SERT receptor competition assay using 2C-B (positive control) (FIG. 38G); a SERT receptor competition assay using MDMA (positive control) (FIG. 38H); a SERT receptor competition assay using escaline (FIG. 38I); a SERT receptor competition assay using proscaline (FIG. 38J); a SERT receptor competition assay using fluoxetine (positive control) (FIG. 38K); a SERT receptor competition assay using vortioxetine (positive control) (FIG. 38L); a SERT receptor competition assay using the compound with formula A(VI) (FIG. 38M).

Figure 1:
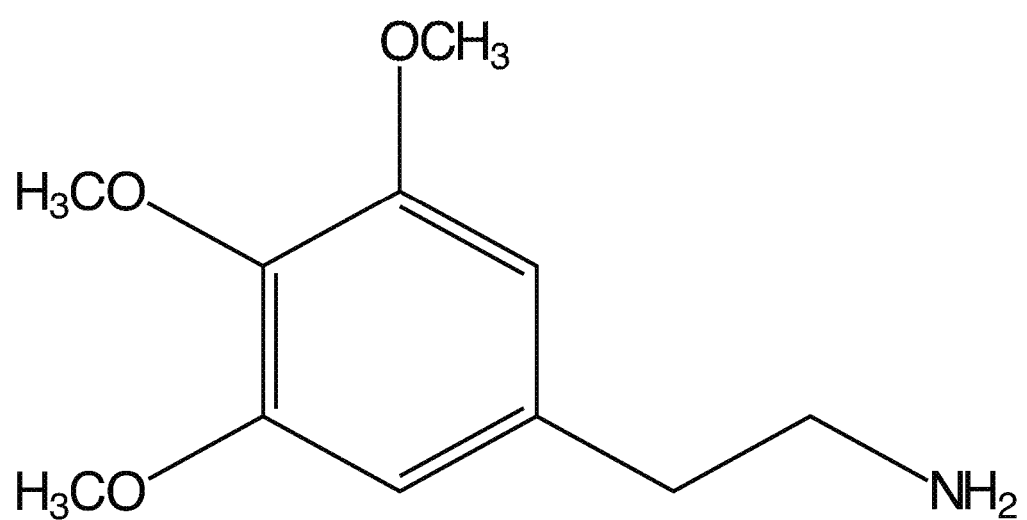
FIG. 1 depicts the chemical structure of mescaline.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner (s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner (s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore, any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and Definitions

The term "mescaline" refers to a chemical compound having the structure set forth in FIG. 1. It is noted that mescaline is also known in the art as 3,4,5 trimethoxyphenethylamine.

Figure 2:
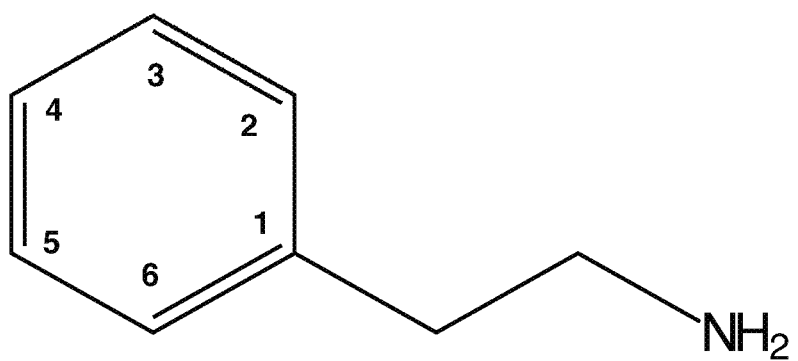
FIG. 2 depicts a certain prototype structure of mescaline and mescaline derivative compounds. Certain carbon atoms may be referred to herein by reference to their position within the prototype structure, i.e., $C_1$, $C_2$, $C_3$ etc. The pertinent atom numbering is shown. Furthermore, certain compounds may be named in accordance with the same. Thus, for example, in 3,4,5 trimethoxyphenethylamine (mescaline) $C_3$, $C_4$, $C_5$ are each bonded to a methoxy group.

The term "mescaline prototype structure" refers to the chemical structures shown in FIG. 2. It is noted that specific carbon atoms in the mescaline prototype structures are numbered. Reference may be made herein to these carbon and numbers herein, for example $C_1$, $C_2$, $C_3$, and so forth. It is noted that the ethylamine chain extends from the $C_1$ carbon atom, and that mescaline includes methoxy groups extending from the $C_3$, $C_4$, and $C_5$ carbon atoms.

The terms "hydroxy group", and "hydroxy", as used herein refers to a molecule containing one atom of oxygen bonded to one atom of hydrogen and having the chemical formula —OH. A hydroxy group through its oxygen atom may be chemically bonded to another entity.

The terms "halogen", "halogen group", "halo-" and "halogenated", as used herein, refer to the class of chemical elements consisting of fluorine (F), chlorine (Cl), bromine (Br), and iodine (I). Accordingly, halogenated compounds can refer to "fluorinated", "chlorinated", "brominated", or "iodinated" compounds.

The terms "amino" and "amino group", as used herein, refers to a molecule containing one atom of nitrogen bonded to hydrogen atoms and having the formula —$NH_2$. An amino group also may be protonated and having the formula —$NH_3^+$. In its protonated form the amino group may form an ammonium salt, for example, a chloride or sulfate ammonium salt, or an organic ammonium salt, all of which may be represented herein as —$NH_3^+Z^-$. An amino group through its nitrogen atom may be chemically bonded to another entity. Furthermore, it is noted that an entity attached to an amino group may be referred to herein as an "aminated" entity, e.g., an aminated mescaline derivative is a mescaline derivative possessing an amino group.

The term "N-substituted amino group", as used herein, refers to an amino group wherein at least one of the hydrogens has been substituted by another atom or group, such as, for example, an alkyl group, an acyl group, an aryl group, a sulfonyl group. An N-substituted amino group may also be protonated, and the amino group through its nitrogen atom may be bonded to another entity.

The term "amide group", as used herein, refers to a molecule having the chemical formula —$CONH_2$. An amide group through its carbon atom may be chemically bonded to another entity.

The term "substituted amide group", as used herein, refers to an amide group wherein at least one of the hydrogens has been substituted by another atom or group, such as, for example, an alkyl group, an acyl group, an aryl group, a sulfonyl group. An N-substituted amide group may also be protonated, and the amide group through its carbon atom may be bonded to another entity.

The term "substituted amido group", as used herein, refers to a molecule having the formula —NHCOR, wherein R is a substituent group, for example an alkyl group, acyl group, or aryl group. A substituted amido group through its nitrogen atom may be chemically bonded to another entity.

The terms "Boc" or "Boc group", as used herein, refer to a tert-butyloxy carbonyl group

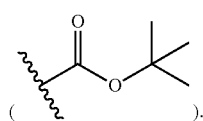

The terms "cyano" and "cyano group", as used herein, refer to a molecule containing one atom of carbon bonded to a nitrogen atom and having the formula

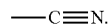

It is to be understood that a cyano group through its carbon atom may be chemically bonded to another entity. Furthermore, it is noted that an entity attached to a nitrile group may be referred to herein as a "cyanated" entity, e.g., a cyanated mescaline derivative is a mescaline derivative possessing a cyano group.

The term "oxo group", as used herein, as used herein refers to the group =O, and can be formed by replacing two hydrogens bonded to the same carbon atom with =O.

The terms "carbonyl" and "carbonyl group", as used herein, refer to a molecule containing one atom of carbon and one atom of oxygen and having the formula

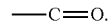

A carbonyl group through its carbon atom may be chemically bonded to another entity.

The terms "carboxy", "carboxyl" and "carboxy group", as used herein, refer to a molecule containing one atom of carbon bonded to an oxygen atom and a hydroxy group and having the formula —COOH. A carboxyl group includes a deprotonated carboxyl group, i.e., a carboxyl ion, having the formula —COO—. In its deprotonated form a carboxyl group may form a carboxyl salt, for example, a sodium or potassium carboxyl salt, or an organic carboxyl salt, all of which may be represented herein as COO⁻M⁺. It is further to be understood that a carboxyl group through its carbon atom may be chemically bonded to another entity. Furthermore, it is noted that an entity attached to a carboxyl group may be referred to herein as a "carboxylated" entity, e.g., a carboxylated mescaline derivative is a mescaline derivative possessing a carboxyl group.

The terms "thiol" and "thiol group", as used herein, refer to a molecule containing one atom of sulfur bonded to a hydrogen atom, and having the chemical formula —SH. Other entities bonded to the thiol group may be referred to as thiolated entities, e.g., a thiolated mescaline derivative. A thiol group through its sulfur atom may be chemically bonded to another entity.

The terms "thioether" and "thioether group", as used herein, refer to a molecule containing one atom of sulfur and bonded to other entities which are not hydrogen atoms, and having the chemical formula $R_1$—S—$R_2$. $R_1$ and $R_2$ can, for example, be the same or different alkane groups (e.g., a ($C_1$-$C_5$)-alkyl group), or the same of different aryl groups, e.g., a phenyl group.

The term "alkyl group" refers to a hydrocarbon group arranged in a chain having the chemical formula —$C_nH_{2n+1}$, or a branched alkyl group, i.e., wherein the hydrocarbon chain includes a fork. Alkyl groups include, without limitation, methyl groups (—$CH_3$), ethyl groups (—$C_2H_5$), propyl groups (—$C_3H_7$) and butyl groups (—$C_4H_9$), and branched alkyl groups, such as, isopropyl, iso-butyl, sec-butyl, tert-butyl. The alkyl groups (including the alkyl groups present in O-alkyl, and the alkyl groups present in acyl and O-acyl) in any of the embodiments of the disclosure can be ($C_1$-$C_{20}$)-alkyl. In other embodiments, the alkyl groups can be ($C_1$-$C_{10}$)-alkyl. In other embodiments, the alkyl group can be ($C_1$-$C_6$)-alkyl or ($C_1$-$C_3$)-alkyl. In other embodiments, the alkyl group can be methyl (—$CH_3$), ethyl (—$C_2H_5$), propyl (—$C_3H_7$), butyl (—$C_4H_9$) or pentyl (—$C_5H_{11}$).

The terms "O-alkyl group", and "alkoxy group", which may be used interchangeably herein, refer to a hydrocarbon group arranged in a chain having the chemical formula —O—$C_nH_{2n+1}$. Alkyl groups include, without limitation, O-methyl groups or methoxy groups (—O—$CH_3$), O-ethyl groups or ethoxy groups (—O—$C_2H_5$), O-propyl groups or propoxy groups (—O—$C_3H_7$) and O-butyl groups or butoxy groups (—O—$C_4H_9$).

The term "cyclo-alkyl", as used herein, refers to cyclo-alkyl groups, including ($C_3$-$C_{20}$)—, ($C_3$-$C_{10}$)—, and ($C_3$-$C_6$)-cyclo-alkyl groups, and includes saturated and partially saturated cyclo-alkyl groups, further including cyclo-propane, cyclo-butane, cyclo-pentane, cyclo-hexane, cyclo-heptane, cyclopentene and cyclohexene.

The term "alkyl-alcohol" or "hydroxyalcohol", as used herein refer to an alkyl group substituted with a hydroxy group. The alkyl-alcohol or hydroxyalkyl groups in any of the embodiments of the disclosure include ($C_1$-$C_{20}$)-alkyl-alcohol. In another embodiment, the alkyl-alcohol or hydroxyalkyl group is ($C_1$-$C_{10}$)-alkyl-alcohol. In another embodiment, the alkyl group is ($C_1$-$C_6$)-alkyl alkyl-alcohol. In another embodiment, the alkyl-alcohol or hydroxyalkyl group is methanol (—$CH_2OH$), ethanol (—$CH_2$—$CH_2OH$), propanol (—$C_2H_4$—$CH_2OH$), butanol (—$C_3H_6$—$CH_2OH$), or pentanol (—$C_4H_8$—$CH_2OH$).

The term "heterocyclic ring", as used herein, means a cyclic group, in which one or two ring atoms are a heteroatom selected from N, O, or S, the remaining ring atoms being C. Included are, for example, ($C_3$-$C_{20}$)—, ($C_3$-$C_{10}$)—, and ($C_3$-$C_6$)-cyclic groups comprising one or two hetero atoms selected from O, S, or N.

The term "alkylene", as used herein, refers to a divalent group derived from an alkane by removal of two hydrogen atoms from the same carbon atom. Examples of alkylenes include, without limitation, ethylene (—$C_2H_4$)—), propylene (—$C_3H_6$)—), and butylene (—$C_4H_8$)—). For the purposes of the present application further understood to be an alkylene is methylene (—$CH_2$—).

The term "acyl group", as used herein, refers to a carbon atom double bonded to an oxygen and single bonded to an alkyl group. The carbon atom further can be bonded to another entity. An acyl group can be described by the chemical formula: —C(=O)—$C_nH_{2n+1}$.

The term "aryl group", as used herein, refers to an aromatic ring compound in which at least one hydrogen compound has been removed from the aromatic ring to permit the bonding of a carbon atom in the aromatic ring to another entity. The aryl groups can optionally be a substituted ($C_6$-$C_{14}$)-aryl. The aryl group can further optionally be substituted ($C_6$-$C_{10}$)-aryl, or phenyl. Further aryl groups include phenyl, naphthyl, tetrahydronaphthyl, phenanthrenyl, biphenylenyl, indanyl, or indenyl and the like.

The term "alkyl-aryl", as used herein, refers to an alkylene substituted with aryl, wherein the aryl is further optionally substituted.

The term "heteroaryl group", as used herein, refers to an aromatic ring compound containing at least one heteroatom, such as O, S or N, in which at least one hydrogen compound has been removed from the aromatic ring to permit the bonding of a carbon atom in the aromatic ring to another entity. The heteroaryl groups can optionally be a substituted ($C_5$-$C_{14}$)-heteroaryl. The heteroaryl group can further optionally be substituted ($C_5$-$C_{10}$)-heteroaryl, or phenyl. Further heteroaryl groups include indole, isoindole, indazole, furan, pyrrole, thiophenem, benzofuran, quinoline, isoquinoline, imidazole, oxazole, pyrazole, pyridazine, pyrimidine, purine, and the like.

The term "alkyl-heteroaryl", as used herein, refers to an alkylene substituted with heteroaryl, wherein the heteroaryl is further optionally substituted.

The term "receptor", as used herein, refers to a protein present on the surface of a cell, or in a cell not associated with a cellular surface (e.g., a soluble receptor) capable of mediating signaling to and/or from the cell, or within the cell and thereby affect cellular physiology. Receptors may be classified in classes, such as the G-protein coupled receptors ("GPCRs"), families, such as 5-HT receptors, and sub-families such as $5-HT_{1A}$ receptors, $5-HT_{1B}$ receptors, $5-HT_{2A}$ receptors, and $5-HT_{2B}$ receptors, and so on. In this respect, "signaling" refers to a response in the form of a series of chemical reactions which can occur when a molecule, including, for example, the fused heterocyclic mescaline derivatives disclosed herein, interacts with a receptor. Signaling generally proceeds across a cellular membrane and/or within a cell, to reach a target molecule or chemical reaction, and results in a modulation in cellular physiology. Thus, signaling can be thought of as a transduction process by which a molecule interacting with a receptor can modulate cellular physiology, and, furthermore, signaling can be a process by which molecules inside a cell can be modulated by molecules outside a cell. Signaling and interactions between molecules and receptors, including, for example, affinity, binding efficiency, and kinetics, can be evaluated through a variety of assays, including, for example, assays known as receptor binding assays (for example, radioligand binding assays, such as e.g., [$^3$H]ketanserin assays may be used to evaluate receptor $5-HT_{2A}$ receptor activity), competition assays, and saturation binding assays, and the like.

The term "G-protein coupled receptor" or "GPCR", as used herein, refers to a class of evolutionarily related transmembrane receptors capable of interacting with a class of proteins known as G-proteins (guanine nucleotide binding proteins). GPCRs can mediate cellular responses to external stimuli (Weis and Kobilka, 2018, Annual Review of Biochemistry 87: 897-919) and can be activated by interacting with a ligand, including neurotransmitters, such as serotonin or dopamine, for example, which, can then initiate an interaction of the receptor with a G-protein and can elicit dissociation of the G-protein into α and βγ subunits. In turn, these α and βγ subunits can mediate further downstream signaling. GPCRs can also activate other signaling pathways, for example, through arrestin proteins and kinases. Certain ligands can preferentially activate a subset of all GPCR signaling pathways. Signaling pathways downstream of a GPCR can mediate therapeutic efficacy, or can cause drug adverse effects (Bock and Bermudez, 2021, FEBS Journal 288: 2513-2528).

The term 5-HT receptor", as used herein, refers to a family of GPCRs receptors found in the central and peripheral nervous system and include sub-families, such as, $5-HT_{1A}$ receptors, $5-HT_{1B}$ receptors, $5-HT_{2A}$ receptors, and $5-HT_{2B}$ receptors. 5-HT receptors can mediate signaling through specific G-proteins, including notably $G\alpha_i$, $G\alpha_{q/11}$, and $G\alpha_s$ and can be involved in the control of multiple physiological processes including cognition, mood, and modulation of sleep-wake cycles, for example (McCorvy and Roth, 2015, Pharmacology and Therapeutics 150: 129-142). 5-HT receptors can further mediate signaling through arrestin as well as G-protein independent signaling pathways. 5-HT-receptors are implicated in multiple brain neurological disorders including migraine headaches, and neuropsychiatric disorders, such as schizophrenia and depression, for example.

The term "$5-HT_{1A}$ receptor", as used herein, refers to a sub-family of a family of receptors for the neurotransmitter and peripheral signal mediator serotonin. $5-HT_{1A}$ receptors can mediate a plurality of central and peripheral physiologic functions of serotonin. Ligand activity at $5-HT_{1A}$ is generally not associated with hallucination, although many hallucinogenic compounds are known to modulate $5-HT_1A$ receptors to impart physiological responses (Inserra et al., 2020, Pharmacol. Rev 73: 202). $5-HT_{1A}$ receptors are implicated in various brain neurological disorders, including depression and anxiety, schizophrenia, and Parkinson's disease (Behav. Pharm. 2015, 26:45-58).

The term "$5-HT_{1B}$ receptor" (also referred to herein as "$HT_1B$" and "HTR1B"), as used herein, refers to a sub-family of a family of receptors for the neurotransmitter and peripheral signal mediator serotonin. $5-HT_{1B}$ receptors can mediate a plurality of central and peripheral physiologic functions of serotonin. Ligand activity at $5-HT_{1B}$ is generally not associated with hallucination, although many hallucinogenic compounds are known to modulate $5-HT_{1B}$ receptors to impart physiological responses (Inserra et al., 2020, Pharmacol. Rev. 73: 202). $5-HT_{1B}$ receptors are implicated in various brain neurological disorders, including depression (Curr. Pharm. Des. 2018, 24:2541-2548).

The term "$5-HT_{2A}$ receptor", as used herein, refers to a sub-family of a family of receptors for the neurotransmitter and peripheral signal mediator serotonin. $5-HT_{2A}$ receptors can mediate a plurality of central and peripheral physiologic functions of serotonin. Central nervous system effects can include mediation of hallucinogenic effects of hallucinogenic compounds. $5-HT_{2A}$ receptors are implicated in various brain neurological disorders (Nat. Rev. Drug Discov. 2022, 21:463-473, Science 2022, 375:403-411).

The term "$5-HT_{2B}$ receptor" (also referred to herein as "$HT_{2B}$" and "HTR2B"), as used herein, refers to a sub-family of a family of receptors for the neurotransmitter and peripheral signal mediator serotonin. $5-HT_{2B}$ receptors can mediate a plurality of central and peripheral physiologic functions of serotonin. Central nervous system effects can include mediation of hallucinogenic effects of hallucinogenic compounds. $5-HT_{2B}$ receptors are implicated in various brain neurological disorders, including schizophrenia (Pharmacol. Ther. 2018, 181:143-155) and migraine (Cephalalgia 2017, 37:365-371).

The term "$5-HT_{3A}$ receptor", as used herein, refers to a sub-family of a family of receptors for the neurotransmitter and peripheral signal mediator serotonin. $5-HT_{3A}$ receptors can mediate a plurality of central and peripheral physiologic functions of serotonin. $5-HT_{3A}$ receptors are implicated in various brain neurological disorders, including depression (Expert Rev. Neurother. 2016, 16:483-95).

The term "$5-HT_{2C}$ receptor" (also referred to herein as "$HT_2C$" and "HTR2C"), as used herein, refers to a sub-family of a family of receptors for the neurotransmitter and peripheral signal mediator serotonin. Antagonism of $5-HT_{2C}$ receptors by drugs such as agomelatine can increase availability of norepinephrine and dopamine in the prefrontal cortex, and can lead to antidepressant and nootropic effects (Savino et al., 2023, Brain Science 13: 734). Further, 5-HT$_{2C}$ receptors can play a role in food intake and body weight control (Przegaliński et al., 2023, Nutrients 15:1449).

The term "5-HT$_{1D}$ receptor" (also referred to herein as "HT$_1$D" and "HTR1D"), as used herein, refers to a subfamily of a family of receptors for the neurotransmitter and peripheral signal mediator serotonin. 5-HT$_{1D}$ receptors are implicated in various brain neurological disorders, including depression (Orsolini et al., 2016, Expert Review of Neurotheraeutics 16: 483-495).

The term "5-HT$_7$ receptor" (also referred to herein as "HT$_7$" and "HTR7"), as used herein, refers to a sub-family of a family of receptors for the neurotransmitter and peripheral signal mediator serotonin. 5-HT$_{1D}$ receptors are implicated in various brain neurological disorders, including Alzheimer's, dementia, and associated depressive disorders (Quintero-Villegas and Valdés-Ferrer, 2022, Molecular Medicine 28: 70).

The term "$\alpha_{2A}$ receptor" (also referred to herein as "$\alpha$-2A", and "alpha2A") as used herein, refers to a subfamily of a family of receptors for catecholamine neurotransmitters and signal mediators such as norepinephrine (noradrenaline) and epinephrine (adrenaline). $\alpha$-2A receptors are implicated in various brain neurological disorders, including schizophrenia, bipolar disorders, and post-traumatic stress disorder (PTSD) (Saggu et al., 2023, Molecular Psychiatry 28: 588-600).

The term "D$_2$ receptor" (also referred to herein as "D$_2$"), used herein, refers to a sub-family of a family of receptors for the neural transmitter and signal mediator dopamine. D$_2$ receptors are implicated in various brain neurological disorders, including schizophrenia, Parkinson's disease, depression, and anxiety (Żuk et al., 2022, Pharmacological Reports 74: 406-424).

The term "D$_3$ receptor" (also referred to herein as "D$_3$"), used herein, refers to a sub-family of a family of receptors for the neural transmitter and signal mediator dopamine. D$_3$ receptors are implicated in various brain neurological disorders, including schizophrenia, drug addiction, and Parkinson's disease (Kim, 2023, International Journal of Molecular Sciences 24: 6742).

The term "MT$_1$ receptor" (also referred to herein as "MT$_1$"), used herein, refers to a sub-family of a family of receptors for the neural transmitter and signal mediator melatonin. MT$_1$ receptors are implicated in various brain neurological disorders, including sleep disorders and depression (Boiko et al., 2022, Neurochemical Research 47: 2909-2924).

The term "DAT", as used herein, refers to a transmembrane transport protein also known as "dopamine active transporter", which is involved of transporting dopamine into the cytosol. DAT is implicated in various brain neurological disorders, notably dopamine related disorders such as attention deficit hyperactivity disorder (ADHD), bipolar disorder, and clinical depression, anxiety (Am. J. Med. Genet. B Neuropsychiatr. Genet. 2018, 177:211-231).

The term "NET", as used herein, refers to a transmembrane transport protein also known as "norepinephrine transporter" or "noradrenaline transporter" or "NAT" which is involved in Na$^+$/Cl$^-$ dependent re-uptake of extracellular norepinephrine or noradrenaline. NET is implicated in various brain neurological disorders, including attention deficit hyperactivity disorder (ADHD) and clinical depression (Neurosci. Biobehav. Rev, 2013, 37:1786-800).

The term "SERT", as used herein, refers to a transmembrane transport protein also known as "serotonin transporter" which is involved in neuronal serotonin transport, notably from the synaptic cleft back to the presynaptic neuron, thereby terminating the action of serotonin. SERT is implicated in various brain neurological disorders, including anxiety and depression (Pharmacol. Rep. 2018, 70:37-46).

The term "modulating receptors", as used herein, refers to the ability of a compound disclosed herein to alter the function of receptors. A receptor modulator may activate the activity of a receptor or inhibit the activity of a receptor depending on the concentration of the compound exposed to the receptor. Such activation or inhibition may be contingent on the occurrence of a specific event, such as activation of a signal transduction pathway, and/or maybe manifest only in particular cell types. The term "modulating receptors," also refers to altering the function of a receptor by increasing or decreasing the probability that a complex forms between a receptor and a natural binding partner to form a multimer. A receptor modulator may increase the probability that such a complex forms between the receptor and the natural binding partner, may increase or decrease the probability that a complex forms between the receptor and the natural binding partner depending on the concentration of the compound exposed to the receptor, and or may decrease the probability that a complex forms between the receptor and the natural binding partner. It is further noted that the fused heterocyclic mescaline derivatives of the present disclosure may alter the function of a receptor by acting as an agonist or antagonist of the receptor, and that fused heterocyclic mescaline derivatives according to the present disclosure may alter the function of a receptor by directly interacting therewith or binding thereto, or by indirectly interacting therewith through one or more other molecular entities. In general, the receptor may be any receptor, including any receptor set forth herein, such as, any of a 5-HT$_{1A}$, 5-HT$_{1B}$, 5-HT$_{2A}$, a 5-HT$_{2B}$, 5-HT$_{3A}$, 5-HT$_{2C}$, 5-HT$_{1D}$, 5-HT$_7$, $\alpha_{2A}$, D$_2$, D$_3$, MT$_1$ receptor, for example. Accordingly, it will be clear, that in order to refer modulating specific receptors, terms such as "modulating 5-HT$_{1A}$ receptors", "modulating 5-HT$_{1B}$ receptors", "modulating 5-HT$_{2A}$ receptors", "modulating 5-HT$_{2B}$ receptors", and so forth, may be used herein.

The term "receptor-mediated disorder", as used herein, refers to a disorder that is characterized by abnormal receptor activity. A receptor-mediated disorder may be completely or partially mediated by modulating a receptor. In particular, a receptor-mediated disorder is one in which modulation of the receptor results in some effect on an underlying disorder e.g., administration of a receptor modulator results in some improvement in at least some of the subjects being treated. In general, the receptor may be any receptor, including any receptor set forth herein, such as any of a 5-HT$_{1A}$, 5-HT$_{1B}$, 5-HT$_{2A}$, a 5-HT$_{2B}$, 5-HT$_{3A}$, 5-HT$_{2C}$, 5-HT$_{1D}$, 5-HT$_7$, $\alpha_{2A}$, D$_2$, D$_3$, MT$_1$ receptor, for example. Accordingly, it will be clear, that in order to refer specific receptor-mediated disorders, terms such as "5-HT$_{1A}$ receptor-mediated disorder", "5-HT$_{1B}$ receptor-mediated disorder", "5-HT$_{2A}$ receptor-mediated disorder", "5-HT$_{2B}$ receptor-mediated disorder", and so forth, may be used.

The term "neuroplastic effect", as used herein, refers to the ability of neuronal cells in response to certain stimuli, including stimuli provided by pharmaceutical compounds, to change, grow and/or reorganize. Neuroplastic effects can include, for example, the formation of protrusions from the neuronal cellular body known as neurites (a process referred to in the art as neurite outgrowth), or the formation of neuronal dendrites.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental, brain neurological, and psychiatric diseases and disorders. Clinical evidence of the prevention or treatment may vary with the disorder, or disease, the subject, and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The terms "substantially pure" and "isolated", as may be used interchangeably herein describe a compound, e.g., a mescaline derivative, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

General Implementation

As hereinbefore mentioned, the present disclosure relates to mescaline derivatives. In particular, the present disclosure provides novel fused heterocyclic mescaline derivatives. In general, the herein provided compositions exhibit functional properties which deviate from the functional properties of mescaline. Thus, for example, the fused heterocyclic mescaline derivatives, can exhibit pharmacological properties which deviate from mescaline. Furthermore, the fused heterocyclic mescaline derivatives may exhibit physico-chemical properties which differ from mescaline. Thus, for example, the fused heterocyclic mescaline derivatives may exhibit superior solubility in a solvent, for example, an aqueous solvent. The mescaline derivatives in this respect are useful in the formulation of pharmaceutical and recreational drug formulations. In one embodiment, the fused heterocyclic mescaline derivatives of the present disclosure can conveniently be chemically synthesized. The practice of this method avoids the extraction of mescaline from cactus plants and the performance of subsequent chemical reactions to achieve the fused heterocyclic mescaline derivatives. Furthermore, the growth of cactus plants can be avoided thus limiting the dependence on climate and weather, and potential legal and social challenges associated with the cultivation of cactus plants containing psychoactive compounds. The method can efficiently yield substantial quantities of the fused heterocyclic mescaline derivatives.

In what follows selected embodiments are described with reference to the drawings.

Initially example fused heterocyclic mescaline derivatives will be described. Thereafter example methods of using and making the fused heterocyclic mescaline derivatives will be described.

Accordingly, in one aspect the present disclosure provides derivatives of a compound known as mescaline of which the chemical structure is shown in FIG. 1. The derivatives herein provided are, in particular, fused heterocyclic derivatives of mescaline and further generally comprise and can be understood to be derivatives of a mescaline prototype structure (FIG. 2). It is noted that in this respect, that the term "fused heterocyclic", refers to a derivative wherein a heterocyclic molecule is bonded to two adjacent carbon atoms present in the phenyl ring of the mescaline prototype structure.

Thus, in one aspect, the present disclosure provides, in accordance with the teachings herein, in at least one embodiment, a chemical compound selected from a first chemical compound having chemical formula (I), and a second chemical compound having chemical formula (II):

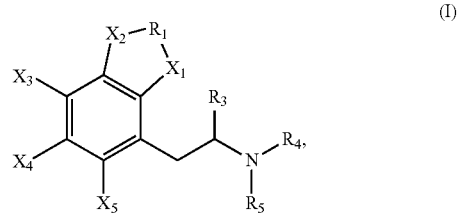

-continued

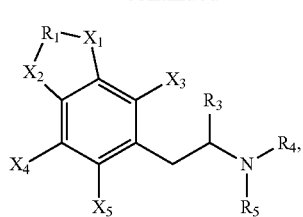

(II)

wherein, in each chemical formula (I) and (II)

$R_1$ is an optionally substituted alkylene group having 1-3 carbon atoms or a carbonyl group (—C(=O));

$X_1$ and $X_2$ are independently selected from an oxygen atom, a sulfur atom, —NH, or an N-alkyl group; and $X_3$, $X_4$, or $X_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of $X_3$, $X_4$, or $X_5$ are a hydrogen atom;

$R_3$ is a methyl group, oxo group, a cyano group, or a hydrogen atom; and $R_4$ and $R_5$ are independently selected from an alkyl group, an alkoxy group, a cyclo-alkyl group, a hydroxyalkyl group, an N-substituted amino group, an alkyl-aryl group wherein the aryl is optionally substituted, an alkyl-heteroaryl group wherein the heteroaryl is optionally substituted, or a hydrogen atom, or $R_4$ and $R_5$ are joined together, along with a nitrogen atom to which they are attached, to form a 3-10-membered optionally substituted heterocyclic ring.

Thus, referring to the first and second chemical compounds having the chemical formulae (I) and (II), respectively, it is initially noted that $R_1$ can be an optionally substituted alkylene group selected to have one carbon atom (a methylene group (—CH$_2$—)), or two carbon atoms (an ethylene group (—CH$_2$CH$_2$—)), or three carbon atoms (a propylene group (—CH$_2$CH$_2$CH$_2$—)), or $R_1$ can be a carbonyl group (—C=O) or a substituted alkylene group. Thus, for example, $R_1$ can have one, two or three carbons, wherein one or more of the carbons are substituted with one or more substituent groups, for example a halogen (F, Cl, Br, I). Thus, for example, $R_1$ can be a substituted methylene group, possessing one or two halogens. Furthermore, regardless of whether the optionally substituted alkylene group is selected to have one carbon atom, or two carbon atoms, or three carbon atoms, or $R_1$ is a carbonyl group or $R_1$ is a substituted alkylene group, $X_1$ and $X_2$ can be independently selected from an oxygen atom, a sulfur atom, —NH, or an N-alkyl group. Thus, it will be clear that $X_1$ and $X_2$ can be identical (i.e., two oxygen atoms, two sulfur atoms, two —NH groups, or two N-alkyl groups), or non-identical, e.g., an oxygen atom and a sulfur atom; an oxygen atom and —NH; or an oxygen and an N-alkyl, and so forth. It is noted that when $X_1$ or $X_2$ are selected to be an N-alkyl, the N-alkyl in example embodiments can be selected to be a ($C_1$-$C_{10}$)-alkyl, a ($C_1$-$C_6$)-alkyl, or a ($C_1$-$C_3$)-alkyl (—CH$_3$ (methyl), —C$_2$H$_5$ (ethyl), or —C$_3$H$_7$ (propyl). It is further noted that $X_1$—$R_1$—$X_2$ together with the $C_2$-$C_3$ or $C_3$-$C_4$ portion of the benzene ring can be said to form a heterocycle.

In one example embodiment, $R_1$ can be an alkylene group having one carbon atom (—CH$_2$— (methylene)) and $X_1$ and $X_2$ can each be an oxygen atom.

In one example embodiment, $R_1$ can be a substituted alkylene group having one carbon atom (—CHR$_{1a}$-(substituted methylene)), wherein $R_{1a}$ is a substituent, for example a halogen, and $X_1$ and $X_2$ can each be an oxygen atom.

In one example embodiment, $R_1$ can be a substituted alkylene group having one carbon atom (—CR$_{1a}$R$_{1b}$-(substituted methylene)), wherein $R_{1a}$ and $R_{1b}$ each are a substituent, for example an independently selected halogen and $X_1$ and $X_2$ can each be an oxygen atom.

In a further example embodiment, $R_1$ can be an alkylene group having two carbons atom (—CH$_2$—CH$_2$— (ethylene)) and $X_1$ and $X_2$ can each be an oxygen atom.

In a further example embodiment, $R_1$ can be a substituted alkylene group having two carbons atom (—CR$_{1a}$R$_{1b}$—CR$_{1c}$R$_{1d}$— (ethylene)), wherein one, two, three or four of $R_{1a}$, $R_{1b}$, $R_{1c}$, and $R_{1d}$ are a substituent, for example an independently selected halogen, and $X_1$ and $X_2$ can each be an oxygen atom.

Continuing, referring to the first and second chemical compounds having the chemical formulae (I) and (II), respectively, $X_3$, $X_4$, or $X_5$ can be independently selected from a hydrogen atom, a halogen, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, provided however that, either two or three of $X_3$, $X_4$, or $X_5$ are a hydrogen atom.

In some embodiments, in chemical formula (I) or (II), each of $X_3$, $X_4$, or $X_5$ can be a hydrogen atom.

In some embodiments, in chemical formula (I) or (II), one of $X_3$, $X_4$, or $X_5$ can be a halogen ($C_1$, Br, Cl, F). It is noted that in such embodiments, $X_3$, $X_4$, or $X_5$ which are not a halogen, are a hydrogen atom.

In some embodiments, in chemical formula (I) or (II), one of $X_3$, $X_4$, or $X_5$, can be an alkyl group, including, for example, a ($C_1$-$C_{10}$)-alkyl, a ($C_1$-$C_6$)-alkyl, or a ($C_1$-$C_3$)-alkyl, including a —CH$_3$ (methyl), —C$_2$H$_5$ (ethyl), —C$_3$H$_7$ (propyl), —C$_4$H$_9$ (butanyl), —C$_5$H$_{11}$ (pentanyl), —C$_6$H$_{13}$ (hexanyl), —C$_7$H$_{15}$ (heptanyl), —C$_8$H$_{17}$ (octanyl), or a —C$_9$H$_{19}$ (nonanyl) group. It is noted that in such embodiments, $X_3$, $X_4$, or $X_5$ which are not an alkyl group, are a hydrogen atom.

In some embodiments, in chemical formula (I) or (II), one of $X_3$, $X_4$, or $X_5$ can be an alkoxy group, including, for example, —OCH$_3$ (methoxy), —OC$_2$H$_5$ (ethoxy), —OC$_3$H$_7$ (propoxy), —OC$_4$H$_9$ (butoxy), —OC$_5$H$_{11}$ (pentoxy), —OC$_6$H$_{13}$ (hexoxy), —OC$_7$H$_{15}$ (heptoxy), —OC$_8$H$_{17}$ (octoxy) or a —OC$_9$H$_{19}$ (nonoxy) group. It is noted that in such embodiments, $X_3$, $X_4$, or $X_5$ which are not an alkoxy group, are a hydrogen atom.

In some embodiments, in chemical formula (I) or (II), one of $X_3$, $X_4$, or $X_5$, can be a cyclo-alkyl group, including, for example, a ($C_3$-$C_{10}$)-cyclo-alkyl, a ($C_3$-$C_6$)-cyclo-alkyl (cyclo-hexyl, cyclo-pentyl, cyclo-butyl, or cyclo-propyl). It is noted that in such embodiments, $X_3$, $X_4$, or $X_5$ which are not a cyclo-alkyl, are a hydrogen atom.

In some embodiments, in chemical formula (I) or (II), one of $X_3$, $X_4$, or $X_5$, can be an acyl group, including a ($C_1$-$C_{10}$)-acyl group, a ($C_1$-$C_6$)-acyl group, or a ($C_1$-$C_3$)-acyl group (—C(=O)—C$_3$H$_7$, —C(=O)—C$_2$H$_5$, or —C(=O)—CH$_3$). It is noted that in such embodiments, $X_3$, $X_4$, or $X_5$ which are not an acyl group, are a hydrogen atom.

In some embodiments, in chemical formula (I) or (II), one of $X_3$, $X_4$, or $X_5$ can be an amino group. It is noted that the amino group may be protonated and form a positively charged ammonium group. The positive charge may be counterbalanced with a negatively charged ion, such as a chlorine (Cl⁻) or a sulfate ($SO_4^{2-}$) ion. Thus, included herein are also salts of the first and second chemical compound, wherein one of $X_3$, $X_4$, or $X_5$ can be is an amino group. It is noted that in such embodiments, $X_3$, $X_4$, or $X_5$ which are not an amino group, are a hydrogen atom.

In some embodiments, in chemical formula (I) or (II), one of $X_3$, $X_4$, or $X_5$ can be an N-substituted amino group. It is noted that the N-substituted amino group may be protonated and be positively charged. The positive charge may be counterbalanced with a negatively charged ion, such as a chlorine or a sulfate ion. Thus, included herein are also salts of the first and second chemical compound, wherein one of $X_3$, $X_4$, or $X_5$ can be an N-substituted amino group. It is noted that in such embodiments, $X_3$, $X_4$, or $X_5$ which are not an n-substituted amino group, are a hydrogen atom.

In some embodiments, in chemical formula (I) or (II), one of $X_3$, $X_4$, or $X_5$ can be an amide group, or substituted amide group, for example, an alkyl substituted amide group, e.g., a ($C_1$-$C_{10}$)-alkyl, a ($C_1$-$C_6$)-alkyl, or a ($C_1$-$C_3$)-alkyl, including a —$CH_3$ (methyl), —$C_2H_5$ (ethyl), —$C_3H_7$ (propyl), —$C_4H_9$ (butanyl), —$C_5H_{11}$ (pentanyl), —$C_6H_{13}$ (hexanyl), —$C_7H_{15}$ (heptanyl), —$C_8H_{17}$ (octanyl), or a —$C_9H_{19}$ (nonanyl) group. It is noted that in such embodiments, $X_3$, $X_4$, or $X_5$ which are not an amide group or substituted amide group, are a hydrogen atom.

In some embodiments, in chemical formula (I) or (II), one of $X_3$, $X_4$, or $X_5$ can be a substituted amido group, for example, an alkyl substituted amido group, e.g., a ($C_1$-$C_{10}$)-alkyl, a ($C_1$-$C_6$)-alkyl, or a ($C_1$-$C_3$)-alkyl, including a —$CH_3$ (methyl), —$C_2H_5$ (ethyl), —$C_3H_7$ (propyl), —$C_4H_9$ (butanyl), —$C_5H_{11}$ (pentanyl), —$C_6H_{13}$ (hexanyl), —$C_7H_{15}$ (heptanyl), —$C_8H_{17}$ (octanyl), or a —$C_9H_{19}$ (nonanyl) group. It is noted that in such embodiments, $X_3$, $X_4$, or $X_5$ which are not a substituted amido group, are a hydrogen atom.

In some embodiments, in chemical formula (I) or (II), one of $X_3$, $X_4$, or $X_5$ can be a hydroxy group. It is noted that in such embodiments, $X_3$, $X_4$, or $X_5$ which are not a hydroxy group, are a hydrogen atom.

In some embodiments, in chemical formula (I) or (II), one of $X_3$, $X_4$, or $X_5$ can be a cyano group. It is noted that in such embodiments, $X_3$, $X_4$, or $X_5$ which are not a cyano group, are a hydrogen atom.

In some embodiments, in chemical formula (I) or (II), one of $X_3$, $X_4$, or $X_5$ can be a carboxy group. It is noted that the carboxy group may be deprotonated and form a negatively charged group. The negative charge may be counterbalanced with a positively charged ion, such as a sodium ion ($Na^+$), an ammonium ion ($NH_4+$), a potassium ion ($K^+$) etc. Thus, included herein are also salts of the first and second chemical compound. It is noted that in such embodiments, $X_3$, $X_4$, or $X_5$ which are not a carboxy group, are a hydrogen atom.

In some embodiments, in chemical formula (I) or (II), one of $X_3$, $X_4$, or $X_5$ can be a thiol group. It is noted that in such embodiments, $X_3$, $X_4$, or $X_5$ which are not a thiol group are a hydrogen atom.

In some embodiments, in chemical formula (I) or (II), one of $X_3$, $X_4$, or $X_5$ can be a thioether group. It is noted that in such embodiments, $X_3$, $X_4$, or $X_5$ which are not a thioether group, are a hydrogen atom.

In example embodiments, one of $X_3$, $X_4$, and $X_5$ can be a halogen (Br, Cl, F, I), or an alkoxy group, for example, —$OCH_3$ (methoxy), —$OC_2H_5$ (ethoxy), —$OC_3H_7$ (propoxy), —$OC_4H_9$ (butoxy), —$OC_5H_{11}$ (pentoxy), —$OC_6H_{13}$ (hexoxy), —$OC_7H_{15}$ (heptoxy), —$OC_8H_{17}$ (octoxy) or a —$OC_9H_{19}$ (nonoxy) group. It is noted that in such embodiments, $X_3$, $X_4$, or $X_5$ which are not a halogen or an alkoxy group, are a hydrogen atom.

In example embodiments, $X_5$ can be a halogen (Br, Cl, F, I), or an alkoxy group, for example, —$OCH_3$ (methoxy), —$OC_2H_5$ (ethoxy), —$OC_3H_7$ (propoxy), —$OC_4H_9$ (butoxy), —$OC_5H_{11}$ (pentoxy), —$OC_6H_{13}$ (hexoxy), —$OC_7H_{15}$ (heptoxy), —$OC_8H_{17}$ (octoxy) or a —$OC_9H_{19}$ (nonoxy) group. It is noted that in such embodiments, $X_3$, and $X_4$ are a hydrogen atom.

In example embodiments, $X_5$ can be a halogen (Br, Cl, F, I), or a ($C_1$-$C_{10}$)-alkyl group. It is noted that in such embodiments, $X_3$, and $X_4$ are a hydrogen. It is noted that in such embodiments, $X_3$, and $X_4$ are a hydrogen atom.

In example embodiments, $X_5$ can be a halogen (Br, Cl, F, I) or a ($C_1$-$C_3$)-alkyl group (methyl, ethyl, propyl). It is noted that in such embodiments, $X_3$, and $X_4$ are a hydrogen atom.

In example embodiments, $X_5$ can be a bromine or a methoxy group. It is noted that in such embodiments, $X_3$, and $X_4$ are a hydrogen atom.

Continuing, referring to the first and second chemical compounds having the chemical formulae (I) and (II), respectively, $R_3$ can be a methyl group, oxo group, a cyano group, or a hydrogen atom.

Continuing, referring to the first and second chemical compounds having the chemical formulae (I) and (II), respectively, $R_4$ and $R_5$ are independently selected from an alkyl group, an alkoxy group, a cyclo-alkyl group, a hydroxyalkyl group, an N-substituted amino group, an alkyl-aryl group wherein the aryl is optionally substituted, or a hydrogen atom, or $R_4$ and $R_5$ are joined together, along with a nitrogen atom to which they are attached, to form a 3-10-membered optionally substituted heterocyclic ring.

In one embodiment, in an aspect, the amino group (—$NR_4R_5$) in the compounds of formula (I) and (II) can be protonated to form (—$N^+HR_4R_5$), and chemical formula (I) or (II) further includes a negatively charged anion, for example a chloride ion (Cl⁻) or a sulfate ion ($SO_4^{2-}$), balancing the positively charged nitrogen atom.

In some embodiments, the $R_4$, and $R_5$, groups can be independently selected from an alkyl group, an alkoxy group, a cyclo-alkyl group, an alkyl-alcohol group, an N-substituted amino group, an alkyl-aryl group wherein the aryl is optionally substituted, a hydrogen atom, or the $R_4$, and $R_5$, groups can be joined together, along with a nitrogen atom to which they are attached, to form a 3-10-membered optionally substituted heterocyclic ring. As noted, in some embodiments, the amino group (—$NR_4R_5$) in the compounds of formula (I) and (II) can be protonated to form (—$N^+HR_4R_5$), and chemical formula (I) or (II) can further include a negatively charged anion, for example a chloride ion (Cl⁻) or a sulfate ion ($SO_4^{2-}$), balancing the positively charged nitrogen atom.

In some embodiments, in chemical formula (I) or (II), the $R_4$ and/or $R_5$, can be an alkyl group, including, for example, a ($C_1$-$C_{10}$)-alkyl, a ($C_1$-$C_6$)-alkyl, or a ($C_1$-$C_3$)-alkyl, including a —$CH_3$ (methyl), —$C_2H_5$ (ethyl), —$C_3H_7$ (propyl), —$C_4H_9$ (butanyl), —$C_5H_{11}$ (pentanyl), —$C_6H_{13}$ (hexanyl), —$C_7H_{15}$ (heptanyl), —$C_8H_{17}$ (octanyl), or a —$C_9H_{19}$ (nonanyl) group. As noted, in some embodiments, the amino group (—$NR_4R_5$) in the compounds of formula (I) and (II) can be protonated to form (—$N^+HR_4R_5$), and chemical formula (I) or (II) can further include a negatively charged anion, for example a chloride ion or a sulfate ion, balancing the positively charged nitrogen atom.

In some embodiments, in chemical formula (I) or (II), the $R_4$, and/or $R_5$, groups can be an alkoxy group, including for example, —OCH$_3$ (methoxy), —OC$_2$H$_5$ (ethoxy), —OC$_3$H$_7$ (propoxy), —OC$_4$H$_9$ (butoxy), —OC$_5$H$_{11}$ (pentoxy), —OC$_6$H$_{13}$ (hexoxy), —OC$_7$H$_{15}$ (heptoxy), —OC$_8$H$_{17}$ (octoxy) or a —OC$_9$H$_{19}$ (nonoxy) group. As noted, in some embodiments, the amino group (—NR$_4$R$_5$) in the compounds of formula (I) and (II) can be protonated to form (—N$^+$HR$_4$R$_5$), and chemical formula (I) or (II) can further include a negatively charged anion, for example, a chloride ion (Cl$^-$) or a sulfate ion (SO$_4^{2-}$), balancing the positively charged nitrogen atom.

In some embodiments, in chemical formula (I) or (II), the R$_4$, and/or R$_5$, groups, can be a cyclo-alkyl group, including for example, a (C$_3$-C$_{10}$)-cyclo-alkyl, a (C$_3$-C$_6$) cyclo-alkyl (cyclo-hexyl, cyclo-pentyl, cyclo-butyl, or cyclo-propyl). As noted, in some embodiments, the amino group (—NR$_4$R$_5$) in the compounds of formula (I) and (II) can be protonated to form (—N$^+$HR$_4$R$_5$), and chemical formula (I) or (II) can further include a negatively charged anion, for example a chloride ion (Cl$^-$) or a sulfate ion (SO$_4^{2-}$), balancing the positively charged nitrogen atom.

In some embodiments, in chemical formula (I) or (II), the R$_4$, and/or R$_5$, groups can be an alkyl-alcohol group, including, for example, a (C$_1$-C$_{10}$)-alkyl-alcohol, a (C$_1$-C$_6$)-alkyl-alcohol, or a (C$_1$-C$_3$)-alkyl-alcohol, including a —CH$_2$OH (methanol), —C$_2$H$_4$OH (ethanol), —C$_3$H$_6$OH (propanol), C$_4$H$_8$OH (butanol), C$_5$H$_{10}$OH (pentanol), and a C$_6$H$_{12}$OH (hexanol) group. As noted, in some embodiments, the amino group (—NR$_4$R$_5$) in the compounds of formula (I) and (II) can be protonated to form (—N$^+$HR$_4$R$_5$), and chemical formula (I) or (II) can further include a negatively charged anion, for example a chloride ion (Cl$^-$) or a sulfate ion (SO$_4^{2-}$), balancing the positively charged nitrogen atom.

In some embodiments, at least one of the R$_4$ and R$_5$ groups can be a substituted amino group, for example, a (C$_1$-C$_{10}$)-alkyl substituted amino group, a (C$_1$-C$_6$)-alkyl substituted amino group, or a (C$_1$-C$_3$)-alkyl substituted amino group, including a —CH$_3$ (methyl) substituted amino group, —C$_2$H$_5$ (ethyl) substituted amino group, —C$_3$H$_7$ (propyl) substituted amino group, —C$_4$H$_9$ (butanyl) substituted amino group, —C$_5$H$_{11}$ (pentanyl) substituted amino group, —C$_6$H$_{13}$ (hexanyl) substituted amino group, —C$_7$H$_{15}$ (heptanyl) substituted amino group, —C$_8$H$_{17}$ (octanyl) substituted amino group, or a —C$_9$H$_{19}$ (nonanyl) substituted amino group. In one embodiment, each of the R$_4$ and R$_5$ groups can be a CH$_3$-substituted amino group.

In some embodiments, in chemical formula (I) or (II), the R$_4$, and/or R$_5$, groups can be a substituted amino group, wherein the substituent is tert-butyloxycarbonyl. As noted, in some embodiments, the amino group (—NR$_4$R$_5$) in the compounds of formula (I) and (II) can be protonated to form (—N$^+$HR$_4$R$_5$), and chemical formula (I) or (II) can further include a negatively charged anion, for example a chloride ion (Cl$^-$) or a sulfate ion (SO$_4^{2-}$), balancing the positively charged nitrogen atom.

In some embodiments, in chemical formula (I) or (II), the R$_4$, and/or R$_5$ groups can be an alkyl-aryl group, including, for example, a (C$_1$-C$_{10}$)-alkylene-aryl, a (C$_1$-C$_6$)-alkylene-aryl, or a (C$_1$-C$_3$)-alkyene-aryl group. The alkyl-aryl group can, for example, be an alkylene phenyl or alkylene naphthyl. Furthermore, the aryl group in the alkyl-aryl group can be optionally substituted, including, for example, with a halogen atom (Br, F, Cl, I), or the aryl group can be substituted, and be fused to a 5 or 6 membered a heterocyclic group. In this respect in example embodiments, the heterocyclic group may contain one or two oxygen atoms. As noted, in some embodiments, the amino group (—NR$_4$R$_5$) in the compounds of formula (I) and (II) can be protonated to form (—N$^+$HR$_4$R$_5$), and chemical formula (I) or (II) can further include a negatively charged anion, for example a chloride ion (Cl$^-$) or a sulfate ion (SO$_4^{2-}$), balancing the positively charged nitrogen atom.

In some embodiments, in chemical formula (I) or (II), the R$_4$, and/or R$_5$ groups can be an alkyl-heteroaryl group, including, for example, a (C$_1$-C$_{10}$)-alkylene-heteroaryl, a (C$_1$-C$_6$)-alkylene-heteroaryl, or a (C$_1$-C$_3$)-alkylene-heteroaryl group. The alkyl-heteroaryl group can, for example, be an alkylene indole. Furthermore, the heteroaryl group in the alkyl-heteroaryl group can be optionally substituted, including, for example, with a halogen atom (Br, F, Cl, I), or the heteroaryl group can be substituted, and be fused to a 5 or 6 membered a heterocyclic group. In this respect in example embodiments, the heterocyclic group may contain one or two oxygen atoms, or a nitrogen atom.

In some embodiments, in chemical formula (I) or (II), the R$_4$ and R$_5$ groups can be joined together, along with a nitrogen atom to which they are attached, to form a 3-10-membered optionally substituted heterocyclic ring. In some embodiments, the optionally substituted heterocyclic ring can be a 3-10 membered optionally substituted heterocyclo-alkyl ring, or a 3-6 membered optionally substituted heterocyclo-alkyl ring, or a 4, 5 or 6 membered optionally substituted heterocyclo-alkyl ring, wherein in each case the heterocyclo-alkyl ring includes at least the nitrogen atom. In some embodiments, a 3-10 membered optionally substituted heterocyclo-alkyl ring, a 3-6 membered optionally substituted ring, or a 4, 5 or 6 membered optionally substituted heterocyclo-alkyl ring includes a single hetero atom, namely, the nitrogen atom. In some embodiments, a 3-10 membered optionally substituted heterocyclo-alkyl ring, a 3-6 membered optionally substituted ring, or a 4, 5 or 6 membered optionally substituted heterocyclo-alkyl ring includes two or more hetero atoms, namely, the nitrogen atom, and one or more additional hetero atoms, for example, an oxygen atom, a sulfur atom, or a second nitrogen atom. In further embodiments, the heterocyclic-alkyl ring may be substituted, for example, with an amino group or a substituted amino group, including, for example, a tert-butyloxy-carbonyl group. As noted, in some embodiments, the amino group (—NR$_4$R$_5$) in the compounds of formula (I) and (II) can be protonated to form (—N$^+$HR$_4$R$_5$), and chemical formula (I) or (II) can further include a negatively charged anion, for example a chloride ion (Cl$^-$) or a sulfate ion (SO$_4^{2-}$), balancing the positively charged nitrogen atom.

Next, in order to further exemplify the mescaline derivative compounds that are provided in accordance with the present disclosure, examples compounds in accordance with formula (I) or (II) are provided. These include compounds having the chemical formula: A(I); A(II); A(III); A(IV); A(V); A(VI); A(VII); A(VIII); A(IX); A(X); A(XI); A(XII); A(XIII); A(XIV); A(XV); A(XVI); A(XVII); A(XVIII); A(XIX); A(XX); A(XXI); A(XXII); A(XXIV); A(XXV); A(XXVI); A(XXVII); A(XXVIII); A(XXIX); A(XXX); A(XXXI); and A(XXXII), as hereinafter depicted.

Thus, in an example embodiment, in an aspect, the present disclosure provides a compound having chemical formula A(I):

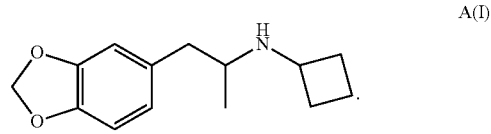 [SMILES: CC(Cc1ccc2c(c1)OCO2)NC1CCC1]

A(I)

In a further example embodiment, in an aspect, the present disclosure provides a compound having chemical formula A(II):

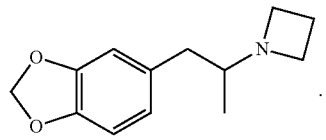
A(II)

In a further example embodiment, in an aspect, the present disclosure provides a compound having chemical formula A(III):

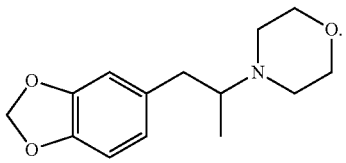
A(III)

In a further example embodiment, in an aspect, the present disclosure provides a compound having chemical formula A(IV):

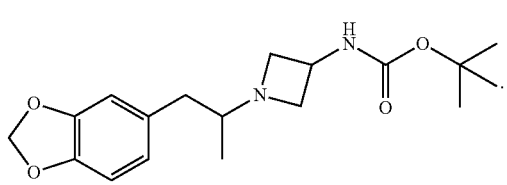
A(IV)

In a further example embodiment, in an aspect, the present disclosure provides a compound having chemical formula A(V):

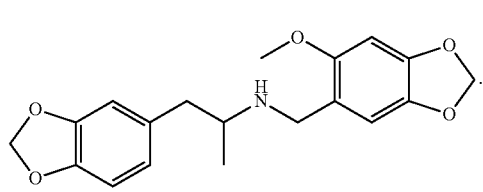
A(V)

In a further example embodiment, in an aspect, the present disclosure provides a compound having chemical formula A(VI):

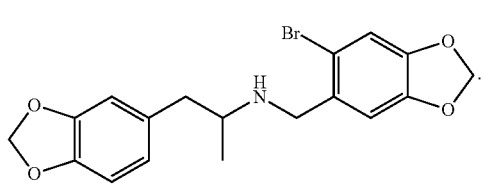
A(VI)

In a further example embodiment, in an aspect, the present disclosure provides a compound having chemical formula A(VII):

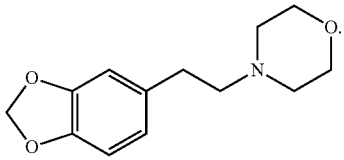
A(VII)

In a further example embodiment, in an aspect, the present disclosure provides a compound having chemical formula A(VIII):

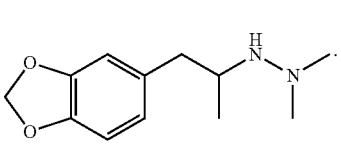
A(VIII)

In a further example embodiment, in an aspect, the present disclosure provides a compound having chemical formula A(IX):

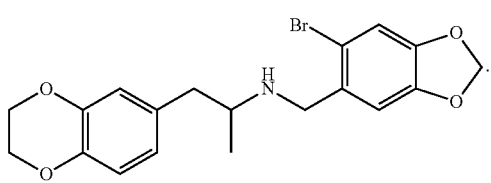
A(IX)

In a further example embodiment, in an aspect, the present disclosure provides a compound having chemical formula A(X):

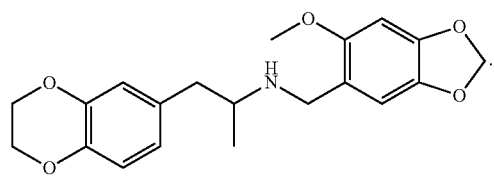
A(X)

In a further example embodiment, in an aspect, the present disclosure provides a compound having chemical formula A(XI):

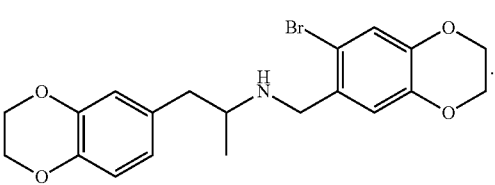
A(XI)

In a further example embodiment, in an aspect, the present disclosure provides a compound having chemical formula A(XII):

A(XII)

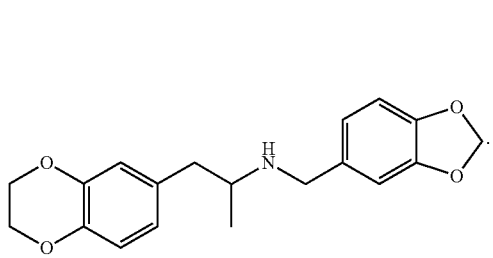

In a further example embodiment, in an aspect, the present disclosure provides a compound having chemical formula A(XIII):

A(XIII)

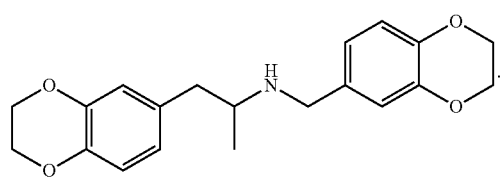

In a further example embodiment, in an aspect, the present disclosure provides a compound having chemical formula A(XIV):

A(XIV)

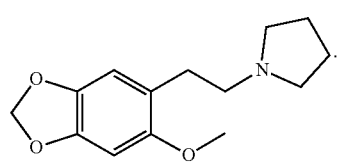

In a further example embodiment, in an aspect, the present disclosure provides a compound having chemical formula A(XV):

A(XV)

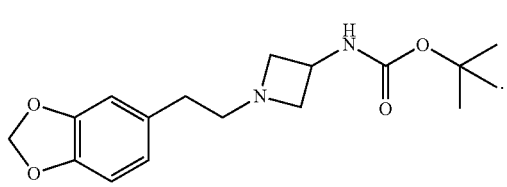

In a further example embodiment, in an aspect, the present disclosure provides a compound having chemical formula A(XVI):

A(XVI)

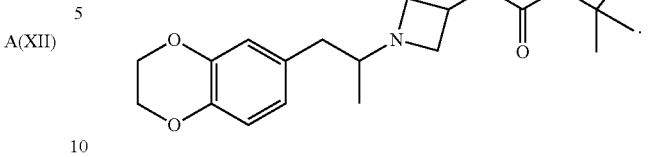

In a further example embodiment, in an aspect, the present disclosure provides a compound having chemical formula A(XVII):

A(XVII)

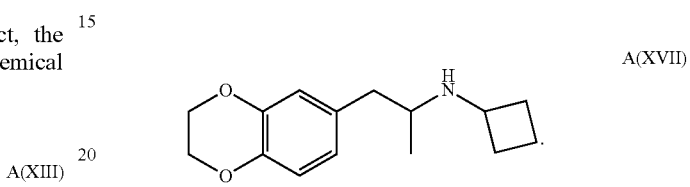

In a further example embodiment, in an aspect, the present disclosure provides a compound having chemical formula A(XVIII):

A(XVIII)

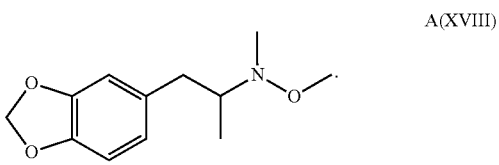 [SMILES: CON(C)C(C)Cc1ccc2c(c1)OCO2]

In a further example embodiment, in an aspect, the present disclosure provides a compound having chemical formula A(XIX):

A(XIX)

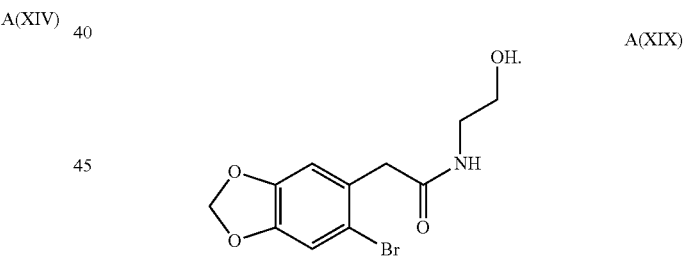

In a further example embodiment, in an aspect, the present disclosure provides a compound having chemical formula A(XX):

A(XX)

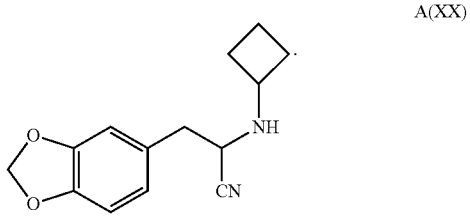 [SMILES: N#CC(Cc1ccc2c(c1)OCO2)NC1CCC1]

In a further example embodiment, in an aspect, the present disclosure provides a compound having chemical formula A(XXI):

A(XXI)

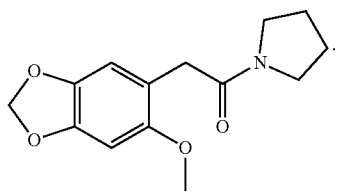

In a yet further example embodiment, in an aspect, the present disclosure provides a compound having chemical formula A(XXII):

A(XXII)

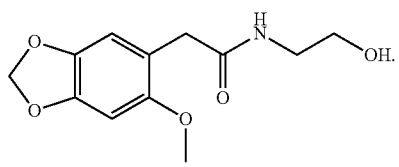

In a yet further example embodiment, in an aspect, the present disclosure provides a compound having chemical formula A(XXIII):

A(XXIII)

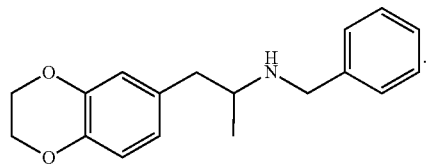

In a yet further example embodiment, in an aspect, the present disclosure provides a compound having chemical formula A(XXIV):

A(XXIV)

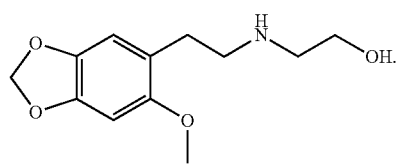

In a yet further example embodiment, in an aspect, the present disclosure provides a compound having chemical formula A(XXV):

A(XXV)

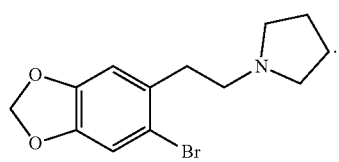

In a yet further example embodiment, in an aspect, the present disclosure provides a compound having chemical formula A(XXVI):

A(XXVI)

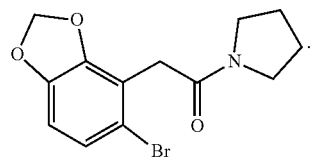

In a yet further example embodiment, in an aspect, the present disclosure provides a compound having chemical formula A(XXVII):

A(XXVII)

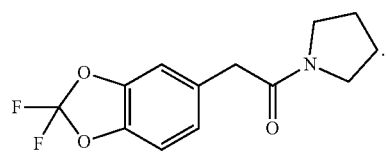

In a yet further example embodiment, in an aspect, the present disclosure provides a compound having chemical formula A(XXVIII):

A(XXVIII)

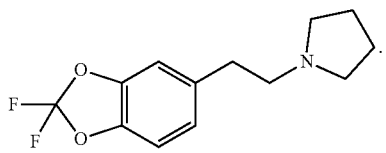

In a yet further example embodiment, in an aspect, the present disclosure provides a compound having chemical formula A(XXIX):

A(XXIX)

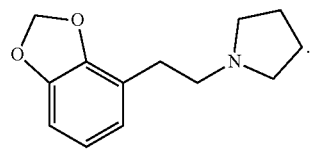

In a yet further example embodiment, in an aspect, the present disclosure provides a compound having chemical formula A(XXX):

A(XXX)

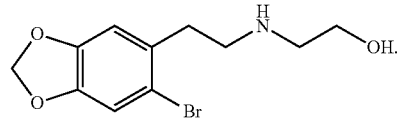

In yet a further example embodiment, in an aspect, the present disclosure provides a compound having chemical formula A(XXXI):

A(XXXI)

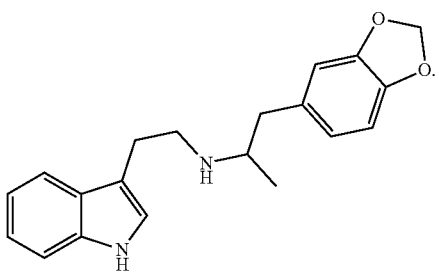

In yet a further example embodiment, in an aspect, the present disclosure provides a compound having chemical formula A(XXXII):

A(XXXII)

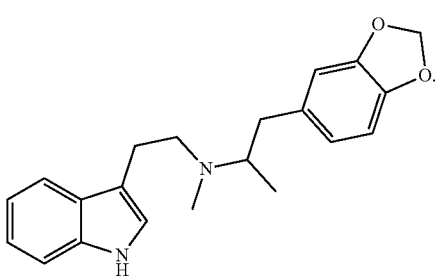

It is noted that in some embodiments, the amine group in each of the foregoing compounds A(I)-A(XXXII) (i.e., the amine group of the ethylamine extending from the $C_1$ carbon atom of the heterocyclized benzene ring, and attached to $R_4$ or $R_5$ in formula (I) or (II)) may be protonated, and the formulas may be counter balanced with a negatively charged anion, such as a chlorine or sulfate ion, for example.

Thus, to briefly summarize, in an aspect, the present disclosure provides novel chemical compounds which are derivatives of mescaline. The novel chemical compounds have chemical formula (I), or chemical formula (II):

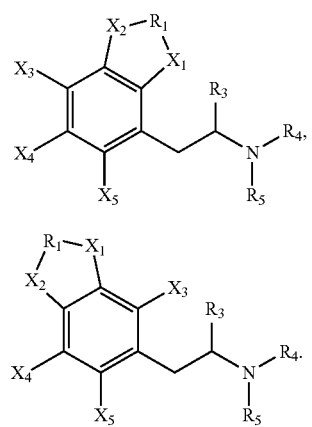

In each chemical formula (I) and (II), $R_1$ is either an optionally substituted alkylene group having 1-3 carbon atoms ($—CH_2—$, $—CH_2CH_2—$, $—CH_2CH_2CH_2—$, or substituted derivatives thereof), or a carbonyl group ($—C(=O)—$). Furthermore, in each chemical formula (I) and (II), $X_1$ and $X_2$ are independently selected from an oxygen atom, a sulfur atom, $—NH$, or an N-alkyl group (e.g., $—(N)(C_1-C_{20})$, $—(N)(C_1-C_{10})$, $—(N)(C_1-C_6)$, $—(N)(C_1-C_3)$), N-methyl ($—N—CH_3$), N-ethyl ($—N—C_2H_5$), N-propyl ($—N—C_3H_7$)). Furthermore, in each chemical formula (I) and (II), $X_3$, $X_4$, or $X_5$ are independently selected from a hydrogen atom, a halogen ($C_1$, Br, F, I), an alkyl group (e.g., $—(C_1-C_3)$-alkyl, $—(C_1-C_6)$-alkyl, $—(C_1-C_{10})$-alkyl, $—(C_1-C_{20})$-alkyl, methyl ($—CH_3$), ethyl ($—C_2H_5$), propyl ($—C_3H_7$), butyl ($—C_4H_9$)), an alkoxy group (e.g., $—(C_1-C_3)—O$-alkyl, $—(C_1-C_6)—O$-alkyl, $—(C_1-C_{10})—O$-alkyl, $—(C_1-C_{20})—O$-alkyl, methoxy ($—O—CH_3$), ethoxy ($—O—C_2H_5$), propoxy ($—O—C_3H_7$), butoxy ($—O—C_4H_9$)), an acyl group (e.g., $—C(=O)(C_1-C_{20})$-alkyl, $—C(=O)(C_1-C_{10})$-alkyl, $—C(=O)(C_1-C_6)$-alkyl, $—C(=O)(C_1-C_3)$-alkyl), $—C(=O)—CH_2CH_2CH_3$, $—C(=O)—CH_2CH_3$, $—C(=O)—CH_3$), an amino group, an N-substituted amino group, an amide group, a substituted amide group, a substituted amido group, a hydroxy group, a cyano group, a carboxy group, a thiol group, or a thioether group, and either two or all three of $X_3$, $X_4$, or $X_5$ are a hydrogen atom. Furthermore, in each chemical formula (I) and (II), $R_3$ is a methyl group, oxo group, a cyano group, or a hydrogen atom. Furthermore, in each chemical formula (I) and (II), $R_4$ and $R_5$, are independently selected from an alkyl group (e.g., $—(C_1-C_3)$-alkyl, $—(C_1-C_6)$-alkyl), $—(C_1-C_{10})$-alkyl, $—(C_1-C_{20})$-alkyl, methyl ($—CH_3$), ethyl ($—C_2H_5$), propyl ($—C_3H_7$), butyl ($—C_4H_9$), iso-propyl, iso-butyl, sec-butyl, tert-butyl), an alkoxy group (e.g., $—(C_1-C_3)—O$-alkyl, $—(C_1-C_6)—O$-alkyl, $—(C_1-C_{10})—O$-alkyl, $—(C_1-C_{20})—O$-alkyl, methoxy ($—O—CH_3$), ethoxy ($—O—C_2H_5$), propoxy ($—O—C_3H_7$), butoxy ($—O—C_4H_9$)), a cyclo-alkyl group (e.g., $(C_3-C_{14})$-cyclo-alkyl, $(C_3-C_{10})$-cyclo-alkyl, $(C_3-C_6)$-cyclo-alkyl, cyclo-propyl, cyclo-butyl, cyclo-pentyl, cyclo-hexyl), a hydroxyalkyl group (e.g., $(C_1-C_{10})$-alkyl-alcohol, $(C_1-C_6)$-alkyl-alcohol, $(C_1-C_3)$-alkyl-alcohol, methanol ($—CH_2OH$), ethanol ($—C_2H_4OH$), propanol ($—C_3H_6OH$), butanol ($—C_4H_8OH$), pentanol ($C_5H_{10}OH$), hexanol ($C_6H_{12}OH$)), an N-substituted amino group, an alkyl-aryl group (e.g., $—(C_1-C_3)$-alkyl-aryl, $—(C_1-C_6)$-alkyl-aryl), $—(C_1-C_{10})$-alkyl-aryl, $—(C_1-C_{20})$-alkyl-aryl, $—(C_1-C_3)$-alkyl-phenyl, $—(C_1-C_6)$-alkyl-phenyl), $—(C_1-C_{10})$-alkyl-phenyl, $—(C_1-C_{20})$-alkyl-phenyl, $—CH_2$-phenyl, $—C_2H_4$-phenyl, $—C_3H_6$-phenyl) wherein the aryl is optionally substituted, an alkyl-heteroaryl group wherein the heteroaryl is optionally substituted e.g., a $(C_5-C_{10})$-heteroaryl, a $(C_5)$-heteroaryl, a $(C_6)$-heteroaryl, a $(C_7)$-heteroaryl, a $(C_9)$-heteroaryl, a $(C_{10})$-heteroaryl, a $—(C_1-C_3)$-alkyl-heteroaryl, $—(C_1-C_6)$-alkyl-heteroaryl), $—(C_1-C_{10})$-alkyl-heteroaryl, $—(C_1-C_{20})$-alkyl-heteroaryl, $—(C_1-C_3)$-alkyl-indole, $—(C_1-C_6)$-alkyl-indole, $—(C_1-C_{10})$-alkyl-indole, $—(C_1-C_{20})$-alkyl-indole, $—CH_2$-indole, $—C_2H_4$-indole, $—C_3H_6$-indole), wherein the heteroaryl is optionally substituted; or a hydrogen atom, or, alternatively, $R_4$, and $R_5$, are joined together, along with a nitrogen atom to which they are attached, to form a 3-10-membered optionally substituted heterocyclic ring. The amino group ($—NR_4R_5$) in the compounds of formula (I) and (II) can be protonated to form ($—N^+HR_4R_5$), and chemical formula (I) or (II) further includes a negatively charged anion balancing the positively charged nitrogen atom.

The fused heterocyclic mescaline derivatives of the present disclosure may be used to prepare a pharmaceutical or recreational drug formulation. Thus, in one embodiment, the present disclosure further provides in another aspect, pharmaceutical and recreational drug formulations comprising fused heterocyclic mescaline derivatives. Accordingly, in one aspect, the present disclosure provides in a further embodiment a pharmaceutical or recreational drug formulation comprising a chemical compound a chemical compound selected from a first chemical compound having chemical formula (I), and a second chemical compound having chemical formula (II):

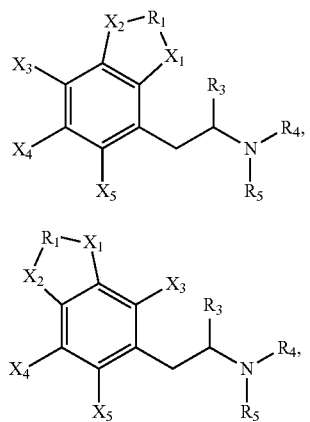

wherein, in each chemical formula (I) and (II)
  $R_1$ is an optionally substituted alkylene group having 1-3 carbon atoms or a carbonyl group (—C(=O));
  $X_1$ and $X_2$ are independently selected from an oxygen atom, a sulfur atom, —NH, or an N-alkyl group; and $X_3$, $X_4$, or $X_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of $X_3$, $X_4$, or $X_5$ are a hydrogen atom;
  $R_3$ is a methyl group, oxo group, a cyano group, or a hydrogen atom; and
  $R_4$ and $R_5$ are independently selected from an alkyl group, an alkoxy group, a cyclo-alkyl group, a hydroxyalkyl group, an N-substituted amino group, an alkyl-aryl group wherein the aryl is optionally substituted, an alkyl-heteroaryl group wherein the heteroaryl is optionally substituted, or a hydrogen atom, or
  $R_4$ and $R_5$ are joined together, along with a nitrogen atom to which they are attached, to form a 3-10-membered optionally substituted heterocyclic ring, together with a diluent, carrier, or excipient.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the fused heterocyclic mescaline derivative compound together with an excipient. The term "excipient" as used herein means any ingredient other than the chemical compound of the disclosure. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22nd Edition (Pharmaceutical Press and Philadelphia College of Pharmacy at the University of the Sciences, 2012).

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated, or prophylaxis is conducted, on the mode of delivery of the compound, or on whether further active compounds are administered in addition to the compounds of the present disclosure. Representative doses of the present invention include, but are not limited to, about 0.001 mg to about 5,000 mg, about 0.001 mg to about 2,500 mg, about 0.001 mg to about 1,000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg, or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical and drug formulations comprising the fused heterocyclic mescaline derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories, and sprays.

Liquid formulations include suspensions, solutions, syrups, and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80.

When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the fused heterocyclic mescaline derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include antioxidants, colourants, flavouring agents, preservatives, and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the fused heterocyclic mescaline derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates, and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the fused heterocyclic mescaline derivatives of the present disclosure for parenteral administration may be formulated to be immediate and/or modified release. Modified release formulations include delayed-, sustained-, pulsed-, controlled-, targeted and programmed release. Thus, the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e., dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous, or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device, or the nebulizing device can be attached to a face mask tent, or intermittent positive pressure breathing machine. Solution, suspension, or powder pharmaceutical compositions can be administered, e.g., orally, or nasally, from devices that deliver the formulation in an appropriate manner.

In further embodiments, in which the fused heterocycle mescaline compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

The pharmaceutical formulations comprising the chemical compounds of the present disclosure may be used to treat a subject, and in particular to treat a brain neurological disorder in a subject. Accordingly, the present disclosure includes in a further embodiment, a method for treating a brain neurological disorder, the method comprising administering to a subject in need thereof a pharmaceutical formulation comprising a chemical compound selected from a first chemical compound having chemical formula (I), and a second chemical compound having chemical formula (II):

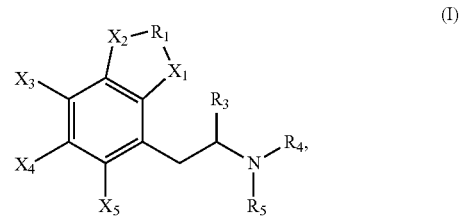

(I)

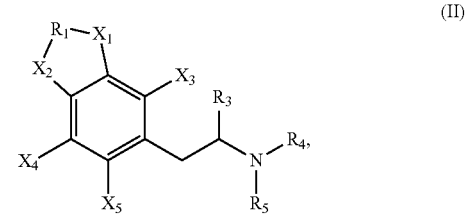

(II)

wherein, in each chemical formula (I) and (II)
- $R_1$ is an optionally substituted alkylene group having 1-3 carbon atoms or a carbonyl group (—C(=O));
- $X_1$ and $X_2$ are independently selected from an oxygen atom, a sulfur atom, —NH, or an N-alkyl group; and $X_3$, $X_4$, or $X_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of $X_3$, $X_4$, or $X_5$ are a hydrogen atom;
- $R_3$ is a methyl group, oxo group, a cyano group, or a hydrogen atom; and
- $R_4$ and $R_5$ are independently selected from an alkyl group, an alkoxy group, a cyclo-alkyl group, a hydroxyalkyl group, an N-substituted amino group, an alkyl-aryl group wherein the aryl is optionally substituted, an alkyl-heteroaryl group wherein the heteroaryl is optionally substituted, or a hydrogen atom, or
- $R_4$ and $R_5$ are joined together, along with a nitrogen atom to which they are attached, to form a 3-10-membered optionally substituted heterocyclic ring, together with a diluent, carrier, or excipient.

Brain neurological disorders, including psychiatric disorders, that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder (MDD), persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J. Psychiatr. Res. 137: 273-282); substance-related disorders, such as alcohol-related disorders, *cannabis* related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder. Brain neurological disorders that may be treated further include headache disorders, including migraines, including, for example, aural migraine, non-aural migraine, menstrual migraine, chronic migraine, vestibular migraine, abdominal migraine, hemiplegic migraine, and other headache disorders.

In an aspect, the compounds of the present disclosure may be used to be contacted with a receptor to thereby modulate the receptor. Such contacting includes bringing a compound of the present disclosure and receptor together under in vitro conditions, for example, by introducing the compounds in a sample containing a receptor, for example, a sample containing purified receptors, or a sample containing cells comprising receptors. In vitro conditions further include the conditions described in Example 15 hereof. Contacting further includes bringing a compound of the present disclosure and receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. In vivo conditions further include the conditions described in Example 3 hereof. Upon having contacted the receptor, the compound may activate the receptor or inhibit the receptor.

In an aspect, receptors with which the compounds of the present disclosure may be contacted include, for example, the 5-$HT_{1A}$ receptor, the 5-$HT_{2A}$ receptor, the 5-$HT_{1B}$ receptor, the 5-$HT_{2B}$ receptor, the 5-$HT_{3A}$ receptor, the 5-$HT_{2C}$ receptor, the 5-$HT_{1D}$ receptor, the 5-$HT_7$ receptor, the $\alpha_{2A}$ receptor, the $D_2$ receptor, the $D_3$ receptor, or the $MT_1$ receptor.

Thus, in a further aspect, the condition that may be treated in accordance herewith can be any receptor mediated disorder, including, for example, a 5-$HT_{1A}$ receptor-mediated disorder, a 5-$HT_{2A}$ receptor-mediated disorder, a 5-$HT_{1B}$ receptor-mediated disorder, a 5-$HT_{2B}$ receptor-mediated disorder, a 5-$HT_{3A}$ receptor-mediated disorder, a 5-$HT_{2C}$ receptor-mediated disorder, a 5-$HT_{1D}$ receptor-mediated disorder, a 5-$HT_7$ receptor-mediated disorder, a $\alpha_{2A}$ receptor-mediated disorder, a $D_2$ receptor-mediated disorder, a $D_3$ receptor-mediated disorder, or a $MT_1$ receptor-mediated disorder. Such disorders include, but are not limited to schizophrenia, psychotic disorder, attention deficit hyperactivity disorder, autism, and bipolar disorder.

In some embodiments, upon having contacted a receptor and a receptor, the compound may modulate the receptor. However, at the same time other receptors may not be modulated. E.g., a compound may activate or inhibit a first receptor, e.g., a 5-$HT_{1A}$ receptor, however the compound may at the same time not modulate a second receptor, e.g., a 5-$HT_{2A}$ receptor, or upon having contacted a first 5-$HT_{2A}$ receptor and a second 5-$HT_{1A}$ receptor, the compound may modulate the first 5-$HT_{2A}$ receptor, e.g., activate or inhibit the 5-$HT_{2A}$ receptor, however the compound may at the same time not modulate the second 5-$HT_{1A}$ receptor.

In one embodiment, upon administration the compound having chemical formula (I) or (II) can exert a neuroplastic effect on brain neuronal cells of the subject. The neuroplastic effect can include the formation of neurites, a process also referred to in the art as neurite outgrowth, and/or the formation of dendrites.

In one embodiment, in an aspect, upon administration the compounds of the present disclosure can interact with transmembrane transport protein in the subject to thereby modulate transmembrane transport protein and exert a pharmacological effect. Such contacting includes bringing a compound of the present disclosure transmembrane transport protein together under in vitro conditions, for example, by introducing the compounds in a sample containing a transmembrane transport protein, for example, a sample containing a purified transmembrane transport protein, or a sample containing cells comprising a transmembrane transport protein. Contacting further includes bringing a compound of the present disclosure and a transmembrane transport protein together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject.

In one embodiment, in an aspect, the transmembrane transport protein can be a dopamine active transporter (DAT), a norephedrine transporter (NET), or a serotonin transporter (SERT) transmembrane transport protein.

Turning now to methods of making the fused heterocyclic mescaline derivatives of the present disclosure, it is initially noted, by way of general comment that the fused heterocyclic mescaline derivatives of the present disclosure may be prepared in any suitable manner, including by any organic chemical synthesis methods, biosynthetic methods, or a combination thereof.

Examples of suitable chemical reactions that may be performed in accordance herewith are depicted in FIGS. 3A-3C, 4, 5A-5B, 6, 7, 8A-8C, 9, 10, 11A-11C, 12, 13, 14, 15, 16A-16B, 17, 18, 19A-19B, 20, 21, 22, 23, 24, 25, 26, 27A-27C, 28A-28B, 29A-29B, 30, 31, 32A-32C, 33, and 34 and are further additionally detailed hereinafter in the Example section.

In general, as is known to those of skill in the art, in order to perform chemical synthetic reactions selected reactants are reacted under reaction conditions which permit the reactants to chemically react with each other and form a product, i.e., the heterocyclic mescaline derivatives of the present disclosure. Such reactions conditions may be selected, adjusted, and optimized as known by those of skill in the art. The reactions may be conducted in any suitable reaction vessel (e.g., a tube, bottle). Suitable solvents that may be used are polar solvents such as, for example, dichloromethane, dichloroethane, toluene, and so called participating solvents such as acetonitrile and diethyl ether. Suitable temperatures may range from, for example, e.g., from about −78° C. to about 60° C. Furthermore, catalysts, also known as promoters, may be included in the reaction such as iodonium dicollidine perchlorate (IDCP), any silver or mercury salts, trimethylsilyl trifluoromethanesulfonate (TMS-triflate, TMSOTf), or trifluoronmethanesulfonic acid (triflic acid, TfOH), N-iodosuccinimide, methyl triflate. Furthermore, reaction times may be varied. As will readily be appreciated by those of skill in the art, the reaction conditions may be optimized, for example, by preparing several reactant preparations and reacting these in separate reaction vessels under different reaction conditions, for example, different temperatures, using different solvents etc., evaluating the obtained fused heterocyclic mescaline derivative reaction product, adjusting reaction conditions, and selecting a desired reaction condition. Further general guidance regarding appropriate reaction conditions for performing the reactions may be found in for example: Y. Zou et al., Eur. J. Med. Chem., 138, 199-211 (2017). K. N. Campbell et al., J. Org. Chem., 16, 1736-1740 (1951). D. Ghosh, et al., Tetrahedr. Lett., 58, 2014-2018 (2017). M. G. Cabiddu et al., Tetrahedron 59, 4383-4387 (2003).

In accordance with the foregoing, in an aspect, included herein, in accordance with at least one embodiment, is a method of making a first chemical compound having chemical formula (I), and a second chemical compound having chemical formula (II):

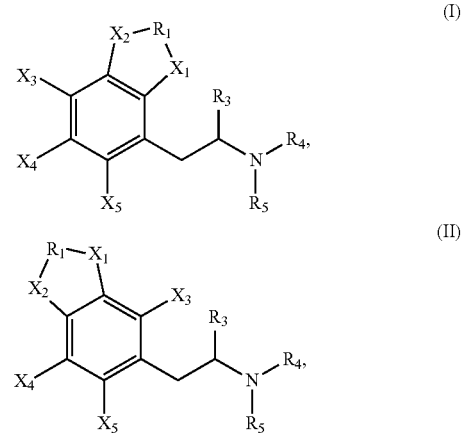

wherein, in each chemical formula (I) and (II)

$R_1$ is an optionally substituted alkylene group having 1-3 carbon atoms or a carbonyl group (—C(═O));

$X_1$ and $X_2$ are independently selected from an oxygen atom, a sulfur atom, —NH, or an N-alkyl group; and $X_3$, $X_4$, or $X_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of $X_3$, $X_4$, or $X_5$ are a hydrogen atom;

$R_3$ is a methyl group, oxo group, a cyano group, or a hydrogen atom; and $R_4$ and $R_5$ are independently selected from an alkyl group, an alkoxy group, a cyclo-alkyl group, a hydroxyalkyl group, an N-substituted amino group, an alkyl-aryl group wherein the aryl is optionally substituted, an alkyl-heteroaryl group wherein the heteroaryl is optionally substituted, or a hydrogen atom, or $R_4$ and $R_5$ are joined together, along with a nitrogen atom to which they are attached, to form a 3-10-membered optionally substituted heterocyclic ring, wherein the method involves the performance of at least one chemical synthesis reaction selected from the reactions depicted in FIGS. 3A-3C, 4, 5A-5B, 6, 7, 8A 8C, 9, 10, 11A-11C, 12, 13, 14, 15, 16A-16B, 17, 18, 19A-19B, 20, 21, 22, 23, 24, 25, 26, 27A-27C, 28A-28B, 29A-29B, 30, 31, 32A-32C, 33, or 34.

Figure 5A:
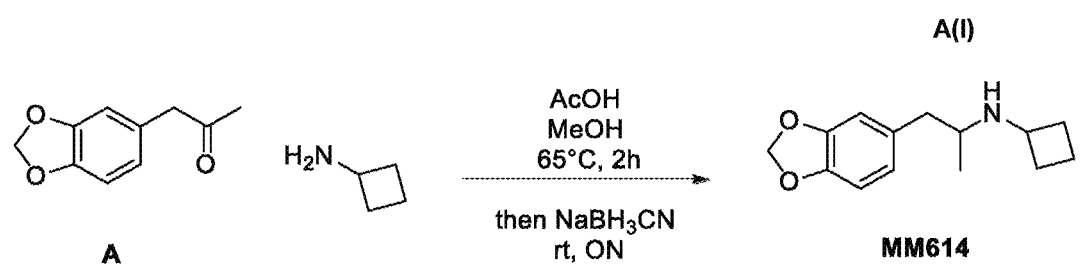
FIGS. 5A and 5B depict other example chemical synthesis pathways, notably another example chemical synthesis pathway for synthesizing another example mescaline derivative compound according to the present disclosure (FIG. 5A), and an example chemical synthesis pathway for synthesizing an example precursor compound of the starting point chemical compound A for the example chemical synthesis pathway shown in FIG. 5A (FIG. 5B).
Figure 5B:
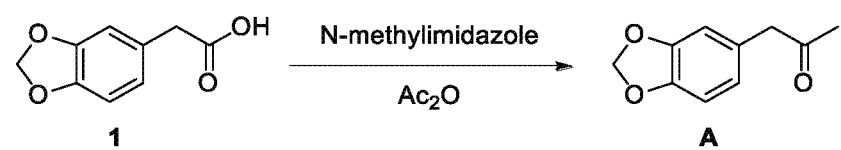

Referring to FIGS. 5A and 5B, in one embodiment, the compound having chemical formula (II) can be a compound having formula A(I):

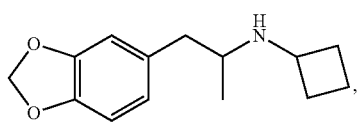

A(I)

and the at least one chemical synthesis reaction is the chemical synthesis reaction depicted in FIG. 5A. The performance of the chemical synthesis reaction depicted in FIG. 5A can optionally be preceded by the performance of the chemical synthesis reaction depicted in FIG. 5B.

Figure 6:
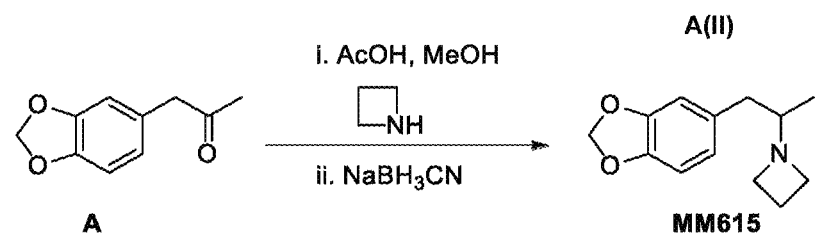
FIG. 6 depicts another example chemical synthesis pathway for synthesizing another example mescaline derivative compound according to the present disclosure.

Referring next to FIGS. 5B and 6, in one embodiment, the compound having chemical formula (II) can be a compound having formula A(II):

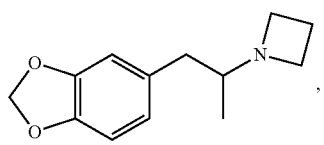

A(II)

and the at least one chemical synthesis reaction is the chemical synthesis reaction depicted in FIG. 6. The performance of the chemical synthesis reaction depicted in FIG. 6 can optionally be preceded by the performance of the chemical synthesis reaction depicted in FIG. 5B.

Figure 7:
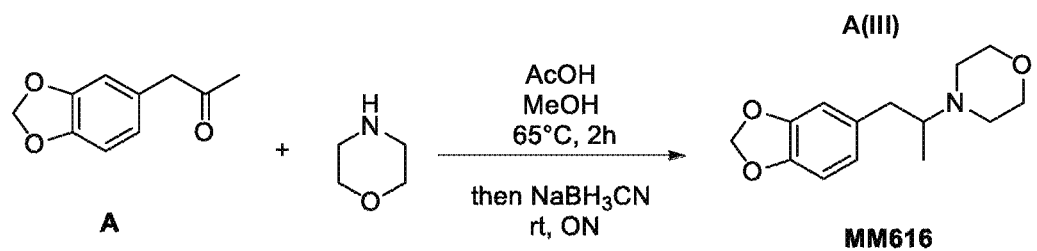
FIG. 7 depicts another example chemical synthesis pathway for synthesizing another example mescaline derivative compound according to the present disclosure.

Referring next to FIGS. 5B and 7, in one embodiment, in an aspect, the compound having chemical formula (II) can be a compound having formula A(III):

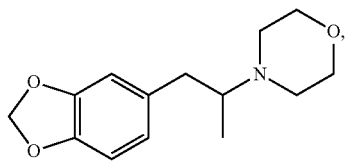

A(III)

and the at least one chemical synthesis reaction is the chemical synthesis reaction depicted in FIG. 7. The performance of the chemical synthesis reaction depicted in FIG. 7 can optionally be preceded by the performance of the chemical synthesis reaction depicted in FIG. 5B.

Figure 9:
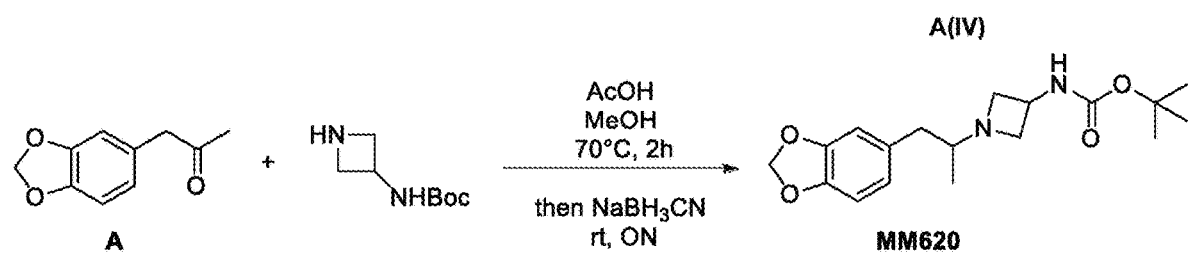
FIG. 9 depicts another example chemical synthesis pathway for synthesizing another example mescaline derivative compound according to the present disclosure.

Referring next to FIGS. 5B and 9, in one embodiment, the compound having chemical formula (II) can be a compound having a formula A(IV):

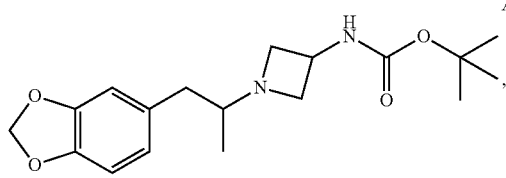

A(IV)

and the at least one chemical synthesis reaction is the chemical synthesis reaction depicted in FIG. 9. The performance of the chemical synthesis reaction depicted in FIG. 9 can optionally be preceded by the performance of the chemical synthesis reaction depicted in FIG. 5B.

Figure 3A:
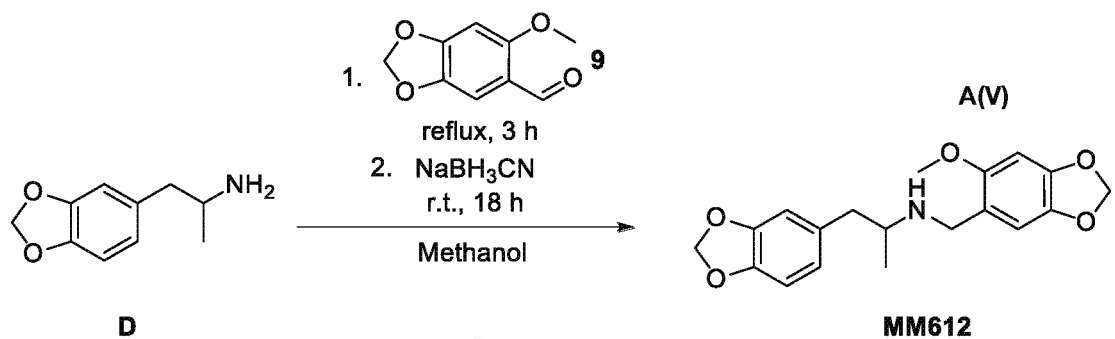
FIGS. 3A, 3B, and 3C depict example chemical synthesis pathways, notably an example chemical synthesis pathway for synthesizing an example mescaline derivative compound according to the present disclosure (FIG. 3A), and an example chemical synthesis pathway for synthesizing an example precursor compound of the starting point chemical compound D for the example chemical synthesis pathway shown in FIG. 3A (FIGS. 3B and 3C).
Figure 3B:
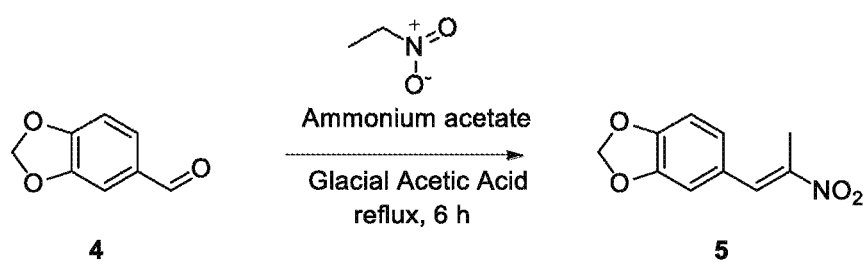
Figure 3C:
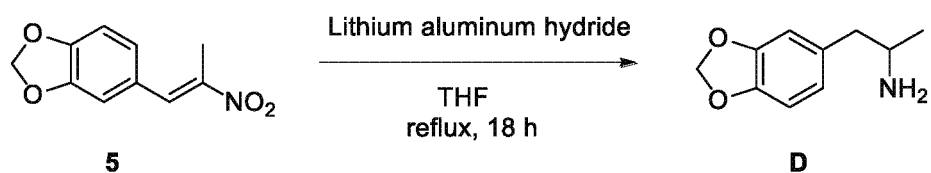

Referring next to FIGS. 3A, 3B, and 3C, in one embodiment, the compound having chemical formula (II) can be a compound having a formula A(V):

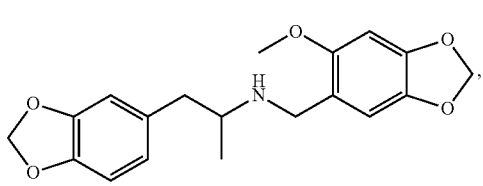

A(V)

and the at least one chemical synthesis reaction is the chemical synthesis reaction depicted in FIG. 3A. The performance of the chemical synthesis reaction depicted in FIG. 3A can optionally be preceded by the performance of the chemical synthesis reaction depicted in FIG. 3C. In turn, the performance of the chemical synthesis reaction depicted in FIG. 3C can optionally be preceded by the performance of the chemical synthesis reaction depicted in FIG. 3B.

Figure 4:
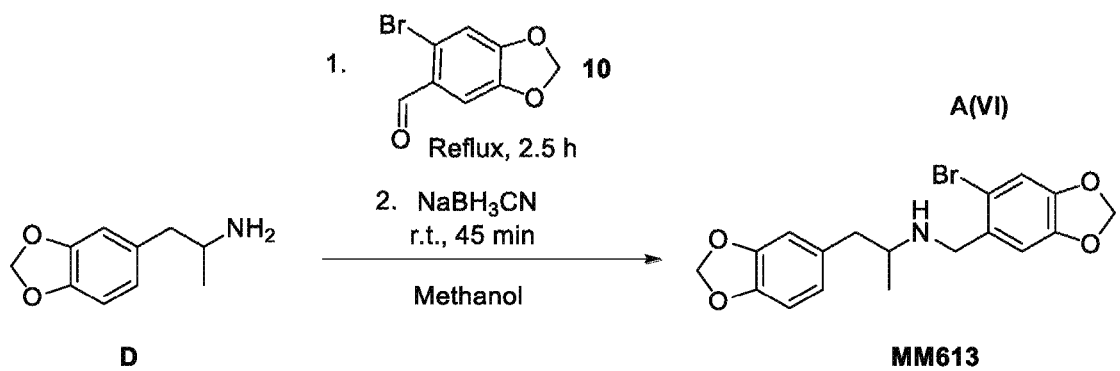
FIG. 4 depicts another example chemical synthesis pathway for synthesizing another example mescaline derivative compound according to the present disclosure.

Referring next to FIGS. 3B, 3C, and 4, in one embodiment, the compound having chemical formula (II) can be a compound having a formula A(VI):

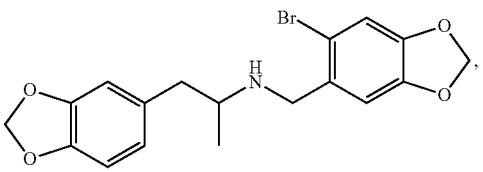

A(VI)

and the at least one chemical synthesis reaction is the chemical synthesis reaction depicted in FIG. 4. The performance of the chemical synthesis reaction depicted in FIG. 4 can optionally be preceded by the performance of the chemical synthesis reaction depicted in FIG. 3C. In turn, the performance of the chemical synthesis reaction depicted in FIG. 3C can optionally be preceded by the performance of the chemical synthesis reaction depicted in FIG. 3B.

Figure 8A:
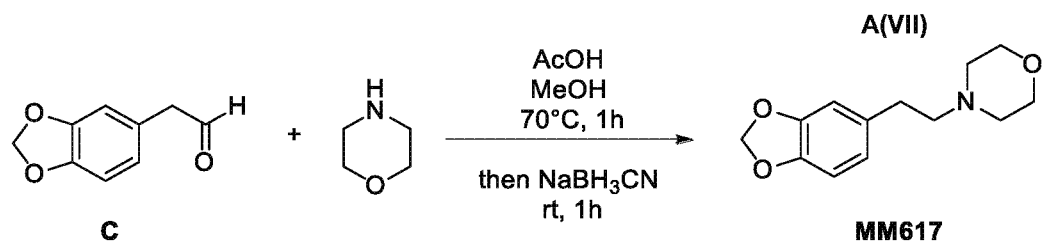
FIGS. 8A, 8B, and 8C depict other example chemical synthesis pathways, notably another example chemical synthesis pathway for synthesizing another example mescaline derivative compound according to the present disclosure (FIG. 8A), and an example chemical synthesis pathway for synthesizing an example precursor compound of the starting point chemical compound C for the example chemical synthesis pathway shown in FIG. 8A (FIGS. 8B and 8C).
Figure 8B:
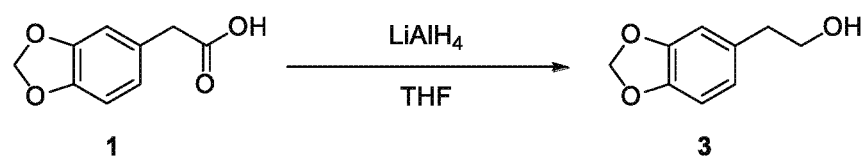
Figure 8C:
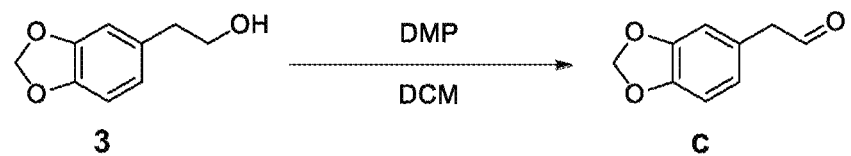

Referring next to FIGS. 8A, 8B, and 8C, In one embodiment, the compound having chemical formula (II) can be a compound having a formula A(VII):

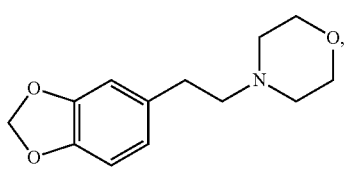

A(VII)

and the at least one chemical synthesis reaction is the chemical synthesis reaction depicted in FIG. 8A. The performance of the chemical synthesis reaction depicted in FIG. 8A can optionally be preceded by the performance of the chemical synthesis reaction depicted in FIG. 8C. In turn, the performance of the chemical synthesis reaction depicted in FIG. 8C can optionally be preceded by the performance of the chemical synthesis reaction depicted in FIG. 8B.

Figure 10:
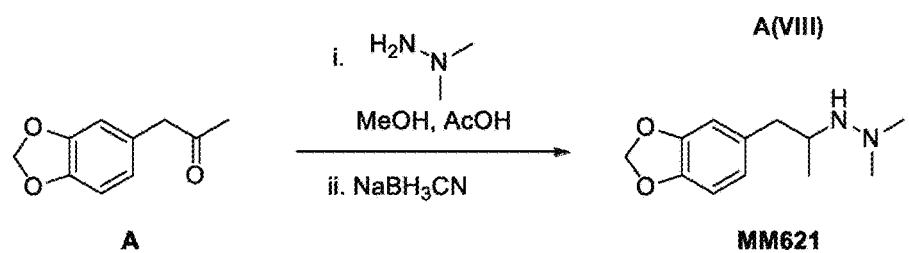
FIG. 10 depicts another example chemical synthesis pathway for synthesizing another example mescaline derivative compound according to the present disclosure.

Referring next to FIGS. 5B and 10, in one embodiment, the compound having chemical formula (II) can be a compound having a formula A(VIII):

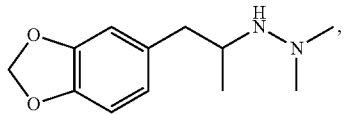

A(VIII)

and the at least one chemical synthesis reaction is the chemical synthesis reaction depicted in FIG. 10. The performance of the chemical synthesis reaction depicted in FIG. 10 can optionally be preceded by the performance of the chemical synthesis reaction depicted in FIG. 5B.

Figure 11A:
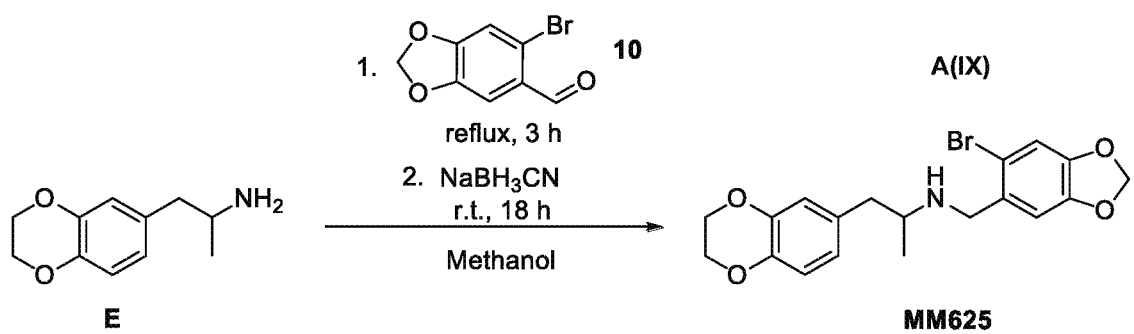
FIGS. 11A, 11B, and 11C depict other example chemical synthesis pathways, notably another example chemical synthesis pathway for synthesizing another example mescaline derivative compound according to the present disclosure (FIG. 11A), and an example chemical synthesis pathway for synthesizing an example precursor compound of the starting point chemical compound E for the example chemical synthesis pathway shown in FIG. 11A (FIGS. 11B and 11C).
Figure 11B:
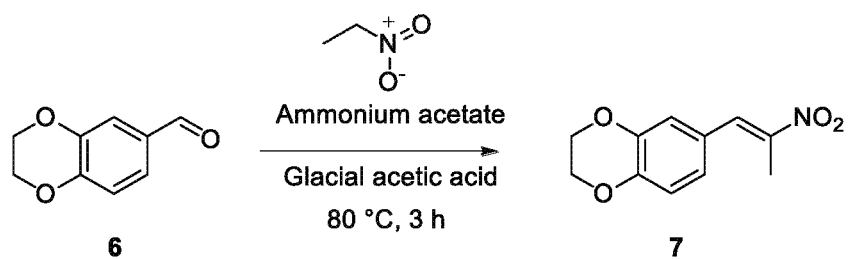
Figure 11C:
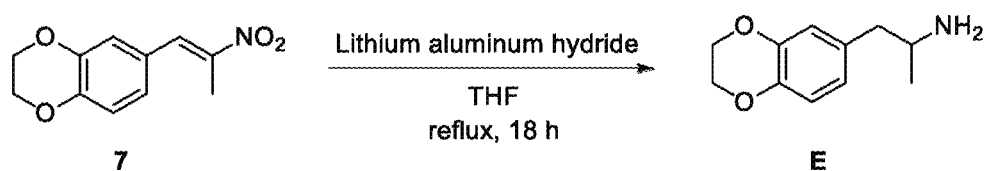

Referring next to FIGS. 11A, 11B, and 11C, in one embodiment, the compound having chemical formula (II) can be a compound having a formula A(IX):

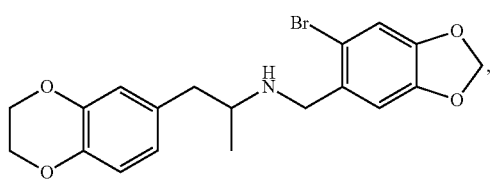

A(IX)

and the at least one chemical synthesis reaction is the chemical synthesis reaction depicted in FIG. 11A. The performance of the chemical synthesis reaction depicted in FIG. 11A can optionally be preceded by the performance of the chemical synthesis reaction depicted in FIG. 11C. In turn, the performance of the chemical synthesis reaction depicted in FIG. 11C can optionally be preceded by the performance of the chemical synthesis reaction depicted in FIG. 11B.

Figure 12:
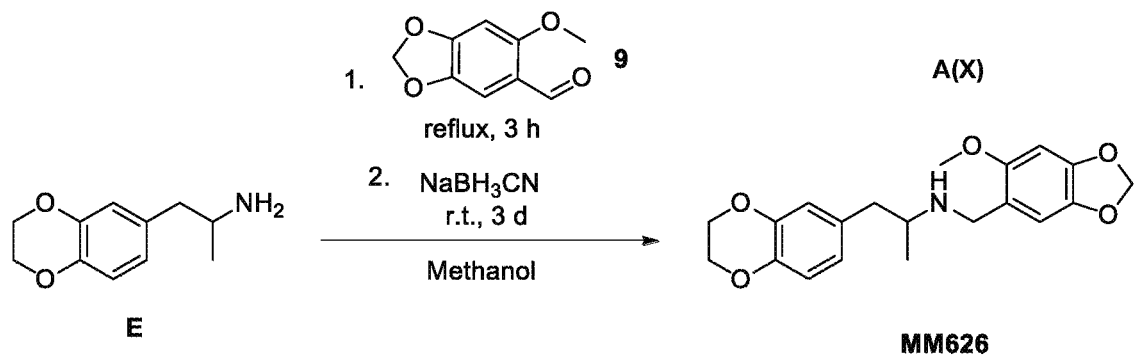
FIG. 12 depicts another example chemical synthesis pathway for synthesizing another example mescaline derivative compound according to the present disclosure.

Referring next to FIGS. 11B, 11C, and 12, in one embodiment, the compound having chemical formula (II) can be a compound having a formula A(X):

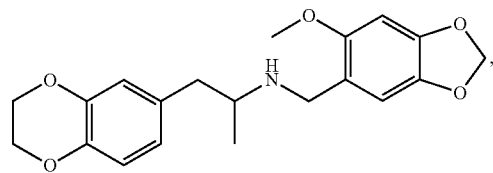

A(X)

and the at least one chemical synthesis reaction is the chemical synthesis reaction depicted in FIG. 12. The performance of the chemical synthesis reaction depicted in FIG. 12 can optionally be preceded by the performance of the chemical synthesis reaction depicted in FIG. 11C. In turn, the performance of the chemical synthesis reaction depicted in FIG. 11C can optionally be preceded by the performance of the chemical synthesis reaction depicted in FIG. 11B.

Figure 13:
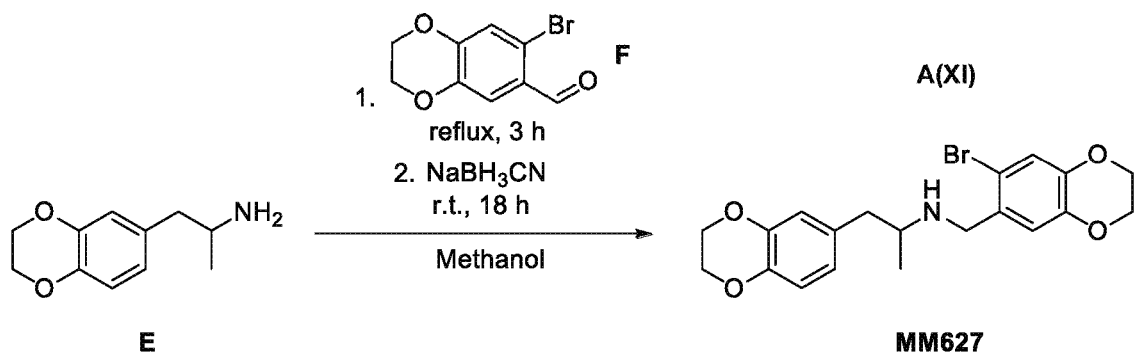
FIG. 13 depicts another example chemical synthesis pathway for synthesizing another example mescaline derivative compound according to the present disclosure.

Referring next to FIGS. 11B, 11C, and 13, in one embodiment, the compound having chemical formula (II) can be a compound having a formula A(XI):

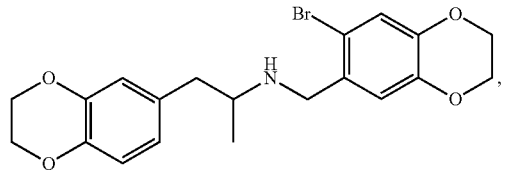

A(XI)

and the at least one chemical synthesis reaction is the chemical synthesis reaction depicted in FIG. 13. The performance of the chemical synthesis reaction depicted in FIG. 13 can optionally be preceded by the performance of the chemical synthesis reaction depicted in FIG. 11C. In turn, the performance of the chemical synthesis reaction depicted in FIG. 11C can optionally be preceded by the performance of the chemical synthesis reaction depicted in FIG. 11B.

Figure 14:
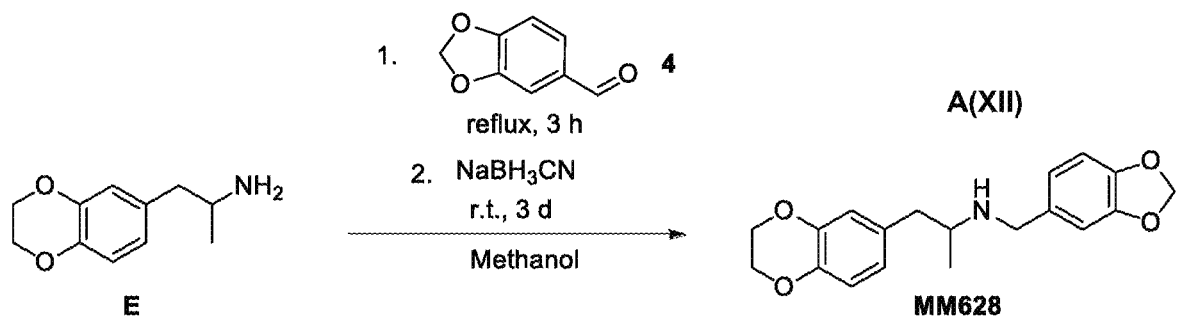
FIG. 14 depicts another example chemical synthesis pathway for synthesizing another example mescaline derivative compound according to the present disclosure.

Referring next to FIGS. 11B, 11C, and 14, in one embodiment, the compound having chemical formula (II) can be a compound having a formula A(XII):

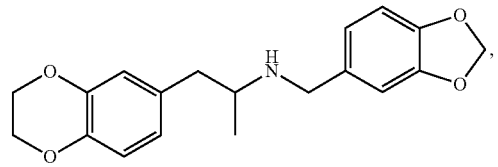

A(XII)

and the at least one chemical synthesis reaction is the chemical synthesis reaction depicted in FIG. 14. The performance of the chemical synthesis reaction depicted in FIG. 14 can optionally be preceded by the performance of the chemical synthesis reaction depicted in FIG. 11C. In turn, the performance of the chemical synthesis reaction depicted in FIG. 11C can optionally be preceded by the performance of the chemical synthesis reaction depicted in FIG. 11B.

Figure 15:
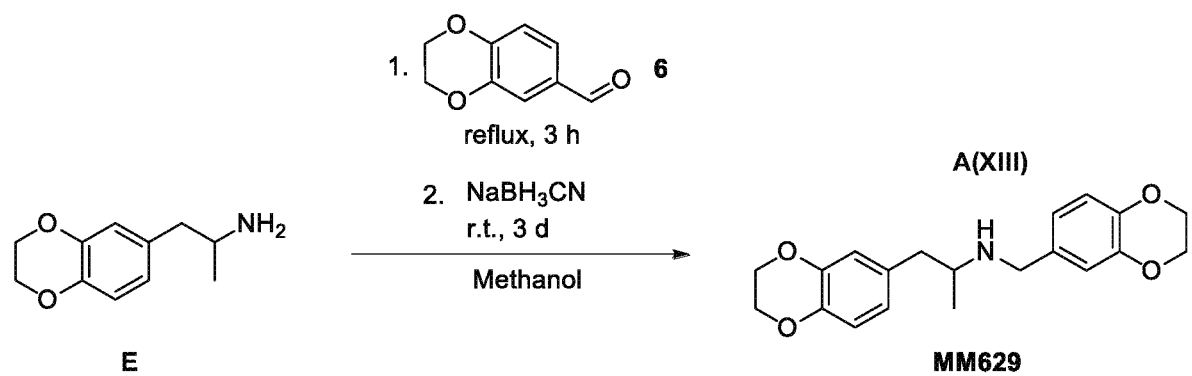
FIG. 15 depicts another example chemical synthesis pathway for synthesizing another example mescaline derivative compound according to the present disclosure.

Referring next to FIGS. 11B, 11C, and 15, in one embodiment, the compound having chemical formula (II) can be a compound having a formula A(XIII):

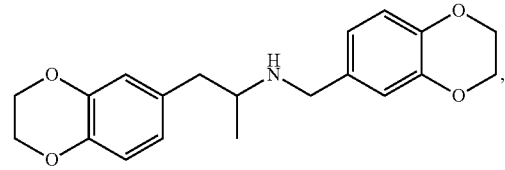

A(XIII)

and the at least one chemical synthesis reaction is the chemical synthesis reaction depicted in FIG. 15. The performance of the chemical synthesis reaction depicted in FIG. 15 can optionally be preceded by the performance of the chemical synthesis reaction depicted in FIG. 11C. In turn, the performance of the chemical synthesis reaction depicted in FIG. 11C can optionally be preceded by the performance of the chemical synthesis reaction depicted in FIG. 11B.

Figure 16A:
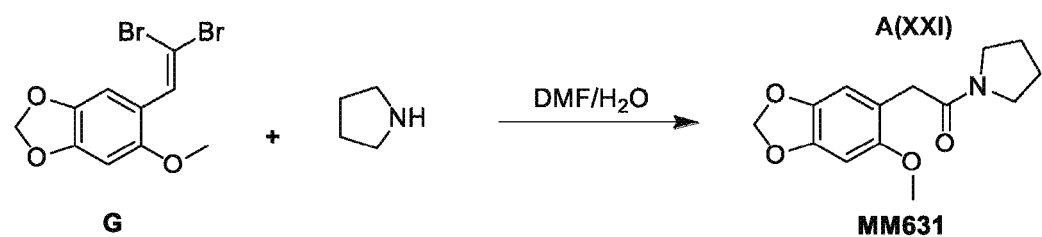
FIGS. 16A and 16B depict other example chemical synthesis pathways, notably another example chemical synthesis pathway for synthesizing another example mescaline derivative compound according to the present disclosure (FIG. 16A), and an example chemical synthesis pathway for synthesizing an example precursor compound of the starting point chemical compound G for the example chemical synthesis pathway shown in FIG. 16A (FIG. 16B).
Figure 16B:
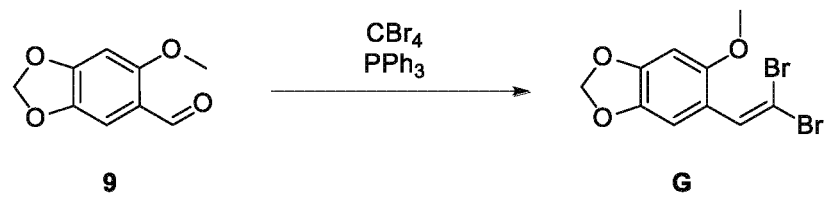
Figure 17:
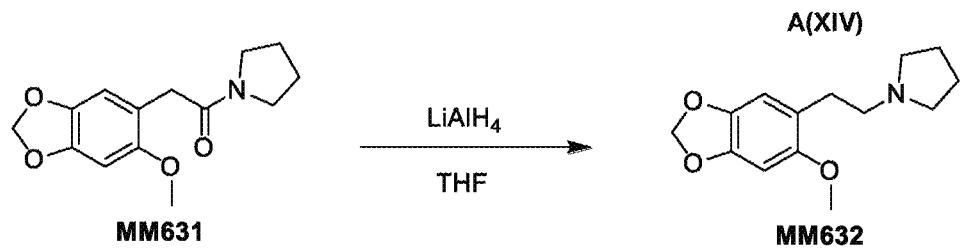
FIG. 17 depicts another example chemical synthesis pathway for synthesizing another example mescaline derivative compound according to the present disclosure.

Referring next to FIGS. 16B and 17, in one embodiment, the compound having chemical formula (II) can be a compound having a formula A(XIV):

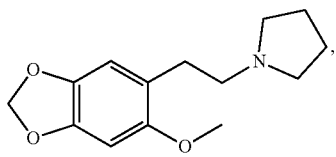

A(XIV)

and the at least one chemical synthesis reaction is the chemical synthesis reaction depicted in FIG. 17. The performance of the chemical synthesis reaction depicted in FIG. 17 can optionally be preceded by the performance of the chemical synthesis reaction depicted in FIG. 16B.

Figure 18:
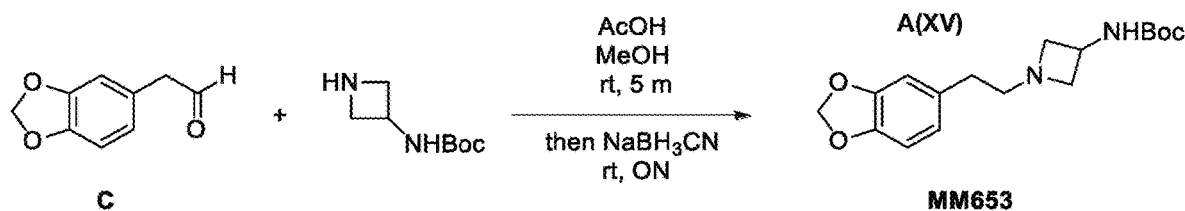
FIG. 18 depicts another example chemical synthesis pathway for synthesizing another example mescaline derivative compound according to the present disclosure.

Referring next to FIGS. 8B, 8C, and 18, in one embodiment, the compound having chemical formula (II) can be a compound having a formula A(XV):

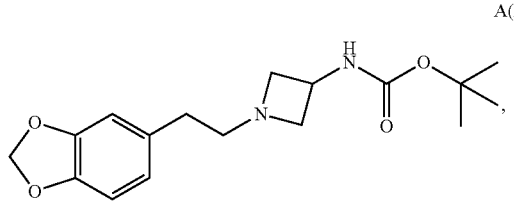

A(XV)

and the at least one chemical synthesis reaction is the chemical synthesis reactions depicted in FIG. 18. The performance of the chemical synthesis reaction depicted in FIG. 18 can optionally be preceded by the performance of the chemical synthesis reaction depicted in FIG. 8C. In turn, the performance of the chemical synthesis reaction depicted in FIG. 8C can optionally be preceded by the performance of the chemical synthesis reaction depicted in FIG. 8B.

Figure 19A:
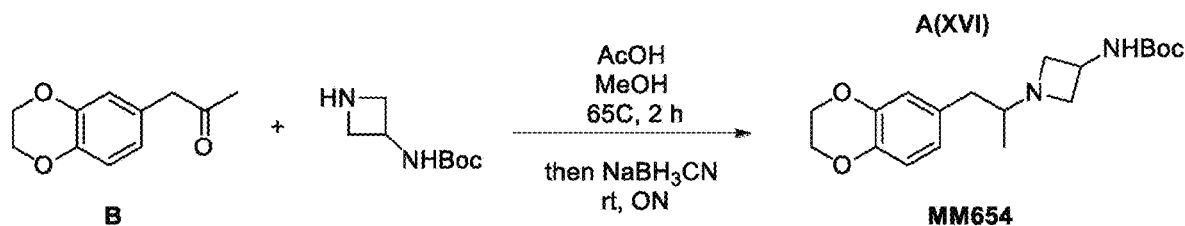
FIGS. 19A and 19B depict other example chemical synthesis pathways, notably another example chemical synthesis pathway for synthesizing another example mescaline derivative compound according to the present disclosure (FIG. 19A), and an example chemical synthesis pathway for synthesizing an example precursor compound of the starting point chemical compound B for the example chemical synthesis pathway shown in FIG. 19A (FIG. 19B).
Figure 19B:
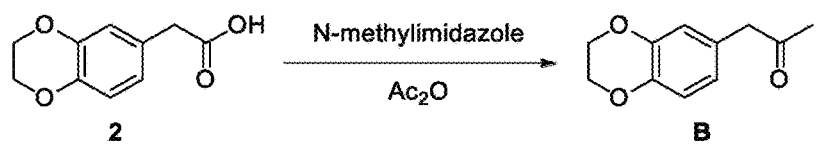

Referring next to FIGS. 19A and 19B, in one embodiment, in an aspect, the compound having chemical formula (II) can be a compound having a formula A(XVI):

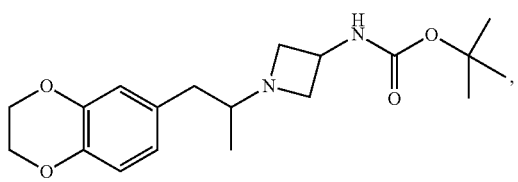

A(XVI)

and the at least one chemical synthesis reaction is the chemical synthesis reaction depicted in FIG. 19A. The performance of the chemical synthesis reaction depicted in FIG. 19A can optionally be preceded by the performance of the chemical synthesis reaction depicted in FIG. 19B.

Figure 20:
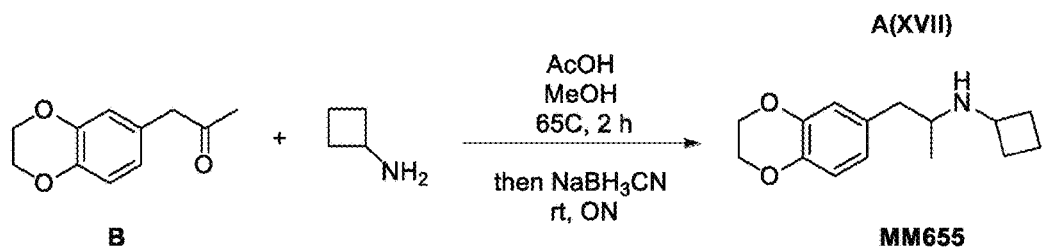
FIG. 20 depicts another example chemical synthesis pathway for synthesizing another example mescaline derivative compound according to the present disclosure.

Referring next to FIGS. 19B and 20, in one embodiment, the compound having chemical formula (II) can be a compound having a formula A(XVII):

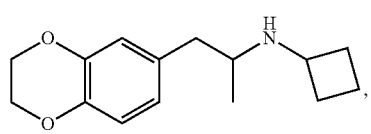

A(XVII)

and the at least one chemical synthesis reaction is the chemical synthesis reaction depicted in FIG. 20. The performance of the chemical synthesis reaction depicted in FIG. 20 can optionally be preceded by the performance of the chemical synthesis reaction depicted in FIG. 19B.

Figure 21:
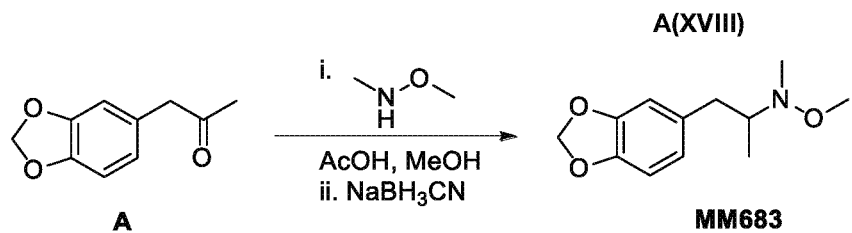
FIG. 21 depicts another example chemical synthesis pathway for synthesizing another example mescaline derivative compound according to the present disclosure.

Referring next to FIGS. 5B and 21, in one embodiment, the compound having chemical formula (II) can be a compound having a formula A(XVIII):

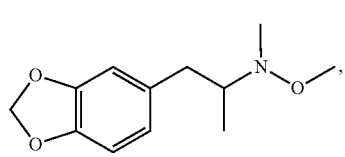

A(XVIII)

and the at least one chemical synthesis reaction is the chemical synthesis reaction depicted in FIG. 21. The performance of the chemical synthesis reaction depicted in FIG. 21 can optionally be preceded by the performance of the chemical synthesis reaction depicted in FIG. 5B.

Figure 22:
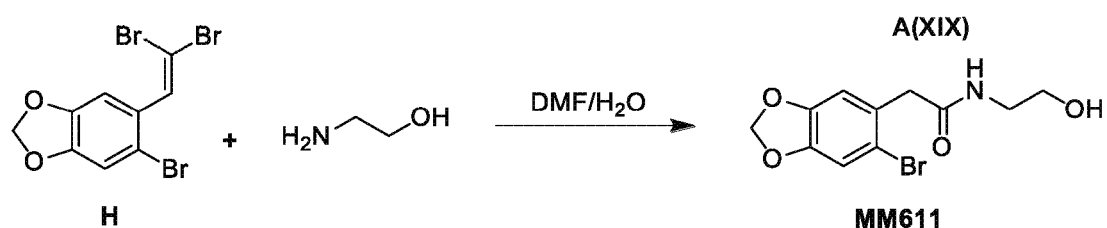
FIG. 22 depicts another example chemical synthesis pathway for synthesizing another example mescaline derivative compound according to the present disclosure.

Referring next to FIG. 22, in one embodiment, the compound having chemical formula (II) can be a compound having a formula A(XIX):

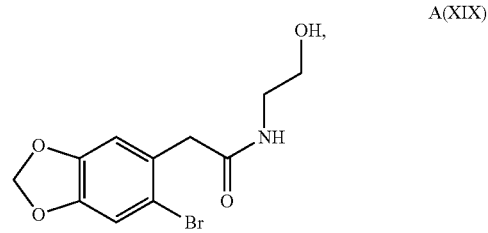 [SMILES: O=C(Cc1cc2c(cc1Br)OCO2)NCCO]

A(XIX)

and the at least one chemical synthesis reaction is the chemical synthesis reaction depicted in FIG. 22.

Figure 23:
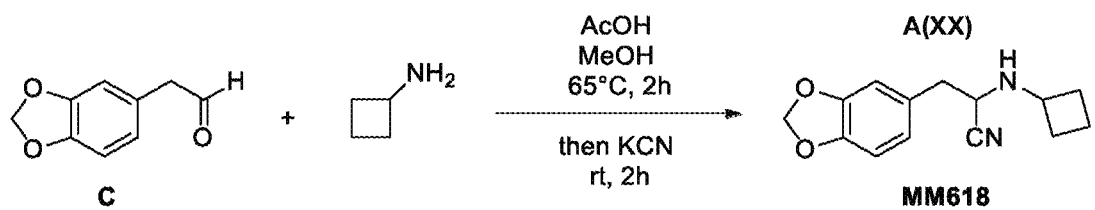
FIG. 23 depicts another example chemical synthesis pathway for synthesizing another example mescaline derivative compound according to the present disclosure.

Referring next to FIGS. 8B, 8C, and 23, in one embodiment, the compound having chemical formula (II) can be a compound having a formula A(XX):

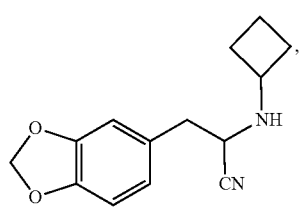

A(XX)

and the at least one chemical synthesis reaction is the chemical synthesis reaction depicted in FIG. 23. The performance of the chemical synthesis reaction depicted in FIG. 23 can optionally be preceded by the performance of the chemical synthesis reaction depicted in FIG. 8C. In turn, the performance of the chemical synthesis reaction depicted in FIG. 8C can optionally be preceded by the performance of the chemical synthesis reaction depicted in FIG. 8B.

Referring next to FIGS. 16A and 16B, in one embodiment, the compound having chemical formula (II) can be a compound having a formula A(XXI):

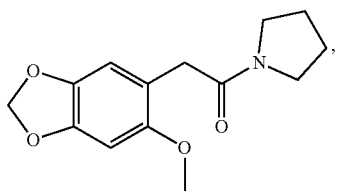

A(XXI)

and the at least one chemical synthesis reaction is the chemical synthesis reaction depicted in FIG. 16A. The performance of the chemical synthesis reaction depicted in FIG. 16A can optionally be preceded by the performance of the chemical synthesis reaction depicted in FIG. 16B.

Figure 24:
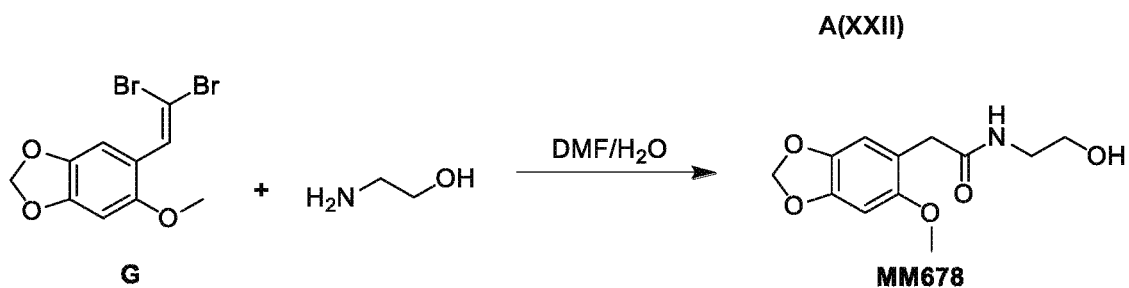
FIG. 24 depicts another example chemical synthesis pathway for synthesizing another example mescaline derivative compound according to the present disclosure.

Referring next to FIGS. 16B and 24, in one embodiment, the compound having chemical formula (II) can be a compound having a formula A(XXII):

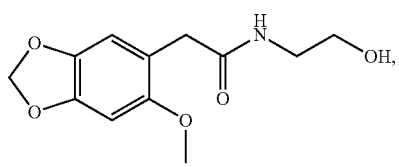

A(XXII)

and the at least one chemical synthesis reaction is the chemical synthesis reaction depicted in FIG. 24. The performance of the chemical synthesis reaction depicted in FIG. 24 can optionally be preceded by the performance of the chemical synthesis reaction depicted in FIG. 16B.

Figure 25:
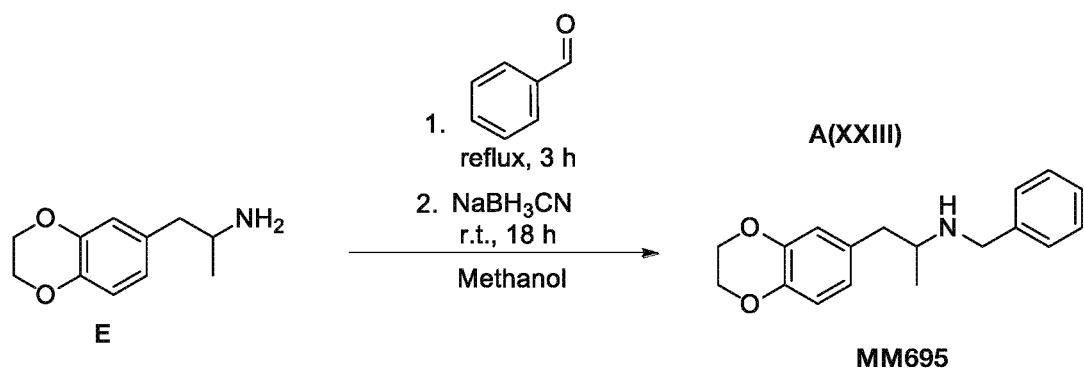
FIG. 25 depicts another example chemical synthesis pathway for synthesizing another example mescaline derivative compound according to the present disclosure.

Referring next to FIGS. 25, 3B, and 3C, in one embodiment, the compound having chemical formula (II) can be a compound having a formula A(XXIII):

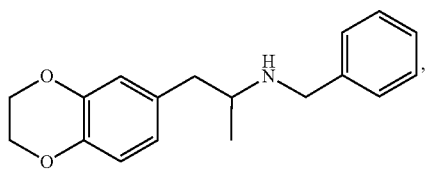

A(XXIII)

and the at least one chemical synthesis reaction is the chemical synthesis reaction depicted in FIG. 25. The performance of the chemical synthesis reaction depicted in FIG. 25 can optionally be preceded by the performance of the chemical synthesis reaction depicted in FIG. 3C. In turn, the performance of the chemical synthesis reaction depicted in FIG. 3C can optionally be preceded by the performance of the chemical synthesis reaction depicted in FIG. 3B.

Figure 26:
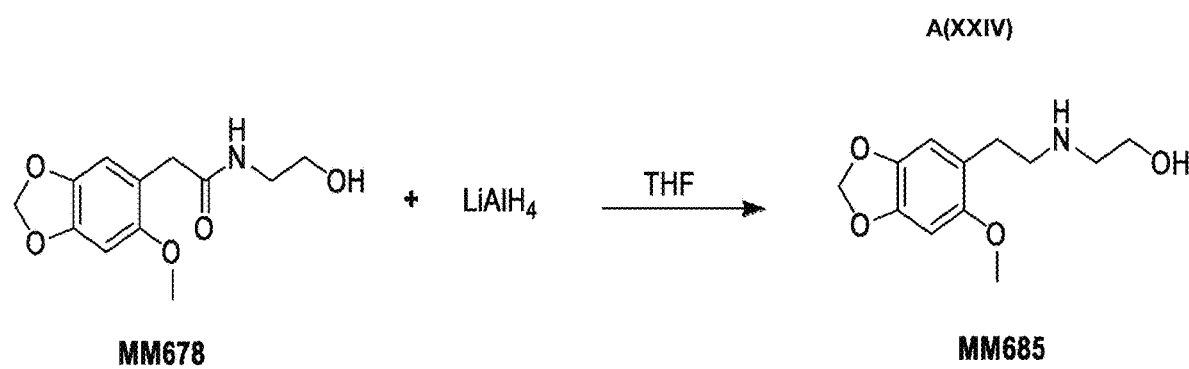
FIG. 26 depicts another example chemical synthesis pathway for synthesizing another example mescaline derivative compound according to the present disclosure.

Referring next to FIGS. 26, 24, and 16B, in one embodiment, the compound having chemical formula (II) can be a compound having a formula A(XXIV):

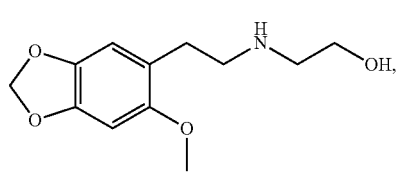

A(XXIV)

and the at least one chemical synthesis reaction is the chemical synthesis reaction depicted in FIG. 26. The performance of the chemical synthesis reaction depicted in FIG. 26 can optionally be preceded by the performance of the chemical synthesis reaction depicted in FIG. 24. In turn, the performance of the chemical synthesis reaction depicted in FIG. 24 can optionally be preceded by the performance of the chemical synthesis reaction depicted in FIG. 16B.

Figure 27A:
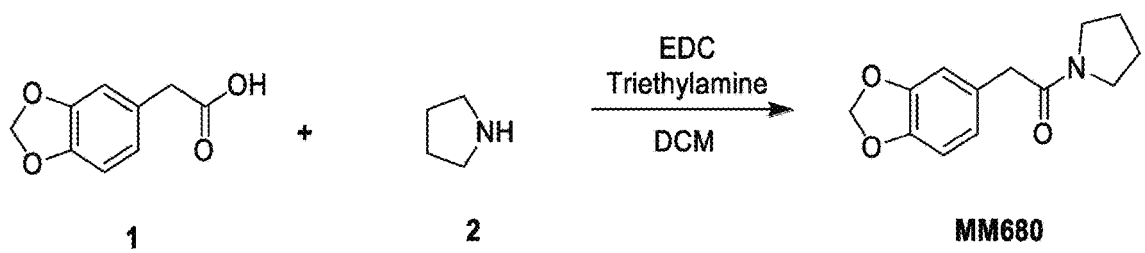
FIGS. 27A, 27B, and 27C depict other example chemical synthesis pathways for synthesizing another example mescaline derivative compound according to the present disclosure.
Figure 27B:
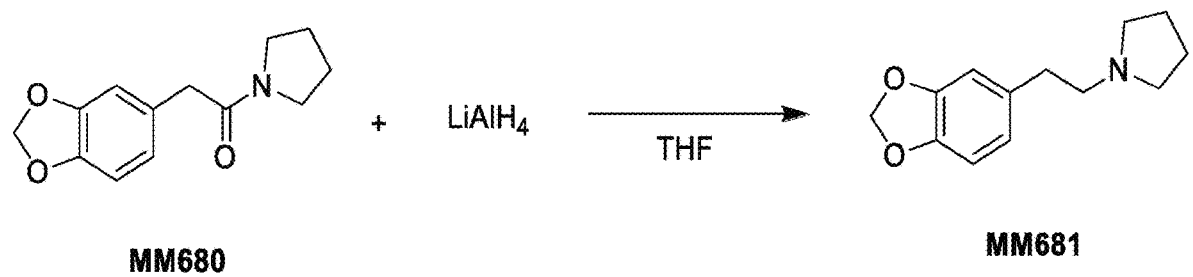
Figure 27C:
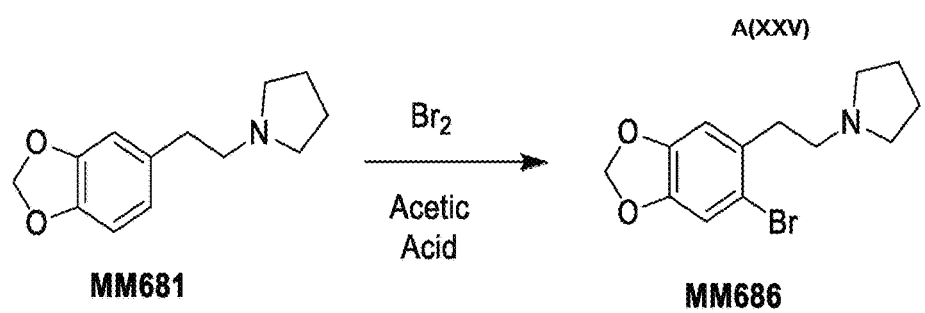

Referring next to FIGS. 27A-27C, in one embodiment, the compound having chemical formula (II) can be a compound having a formula A(XXV):

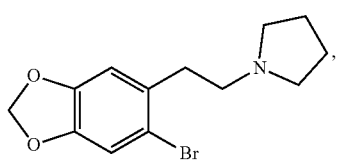

A(XXV)

and the at least one chemical synthesis reaction is the chemical synthesis reaction depicted in FIG. 27C. The performance of the chemical synthesis reaction depicted in FIG. 27C can optionally be preceded by the performance of the chemical synthesis reaction depicted in FIG. 27B. In turn, the performance of the chemical synthesis reaction depicted in FIG. 27B can optionally be preceded by the performance of the chemical synthesis reaction depicted in FIG. 27A.

Figure 28A:
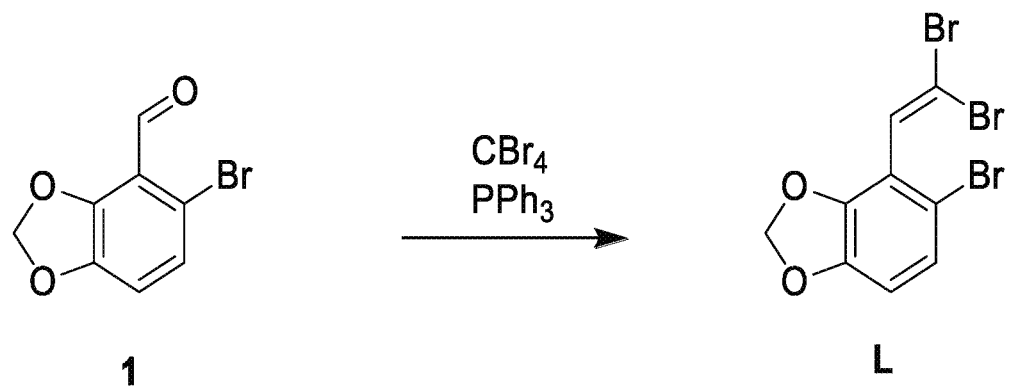
FIGS. 28A and 28B depict other example chemical synthesis pathways for synthesizing another example mescaline derivative compound according to the present disclosure.
Figure 28B:
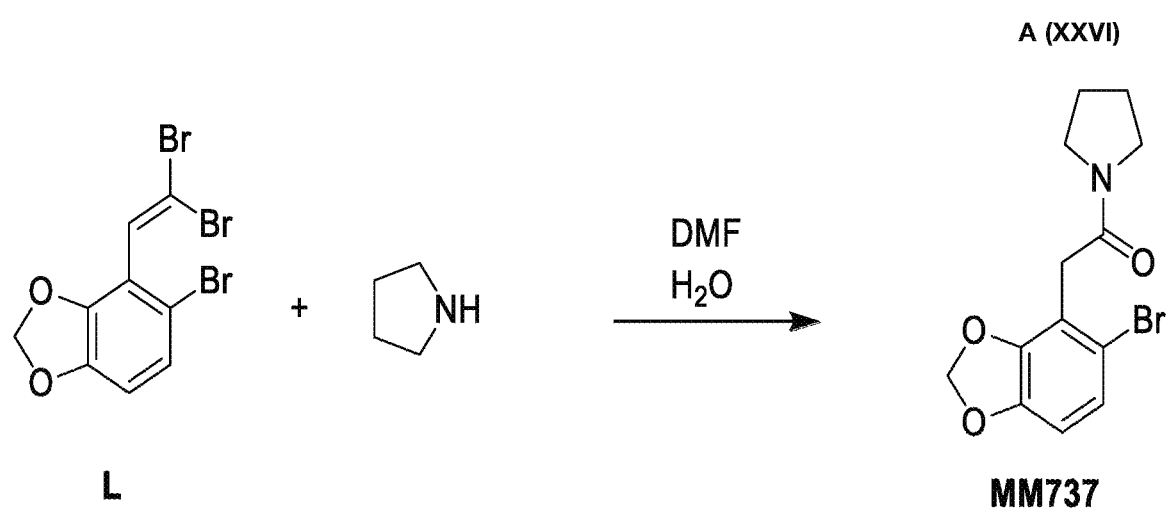

Referring next to FIGS. 28A-28B, in one embodiment, the compound having chemical formula (I) can be a compound having a formula A(XXVI):

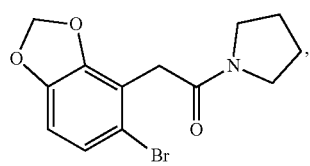

(XXVI)

And the at least one chemical synthesis reaction is the chemical synthesis reaction depicted in FIG. 28B. The performance of the chemical synthesis reaction depicted in FIG. 28B can optionally be preceded by the performance of the chemical synthesis reaction depicted in FIG. 28A.

Figure 29A:
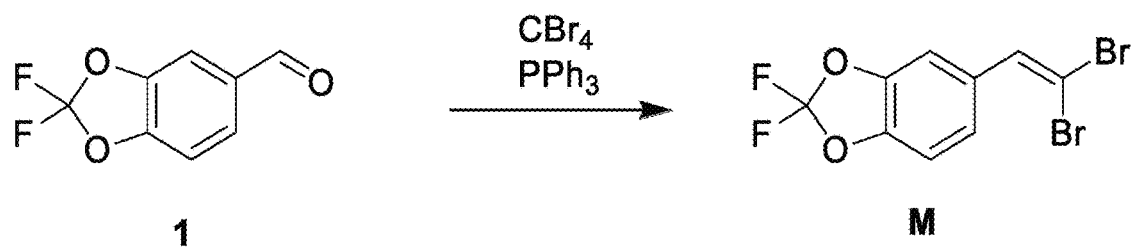
FIGS. 29A and 29B depict other example chemical synthesis pathways for synthesizing another example mescaline derivative compound according to the present disclosure.
Figure 29B:
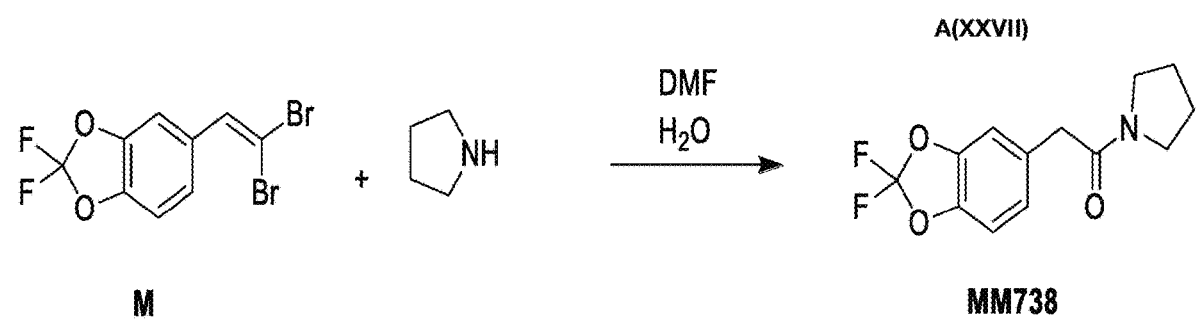

Referring next to FIGS. 29A-29B, in one embodiment, the compound having chemical formula (II) can be a compound having a formula A(XXVII):

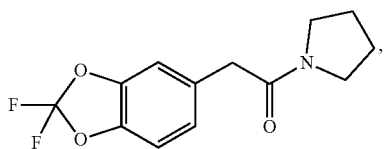

A(XXVII)

and the at least one chemical synthesis reaction is the chemical synthesis reaction depicted in FIG. 29B. The performance of the chemical synthesis reaction depicted in FIG. 29B can optionally be preceded by the performance of the chemical synthesis reaction depicted in FIG. 29A.

Figure 30:
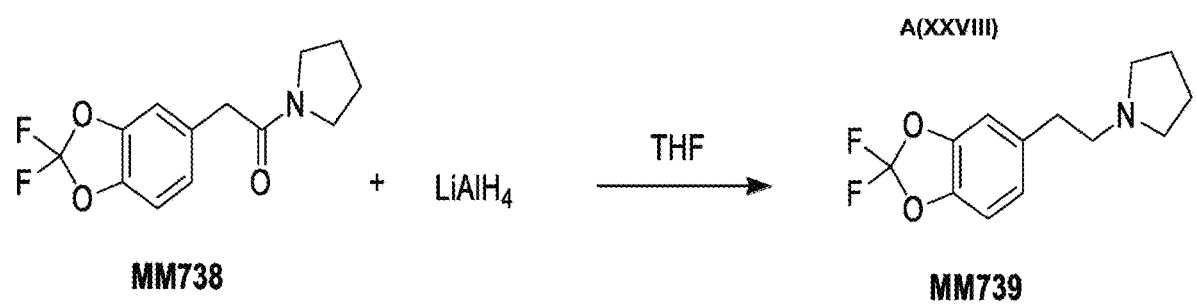
FIG. 30 depicts another example chemical synthesis pathway for synthesizing another example mescaline derivative compound according to the present disclosure.

Referring next to FIGS. 30, 29A, and 29B, in one embodiment, the compound having chemical formula (II) can be a compound having a formula A(XXVIII):

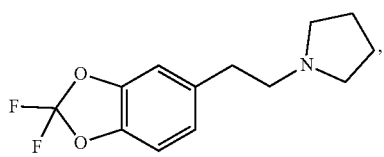

A(XXVII)

and the at least one chemical synthesis reaction is the chemical synthesis reaction depicted in FIG. 30. The performance of the chemical synthesis reaction depicted in FIG. 30 can optionally be preceded by the performance of the chemical synthesis reaction depicted in FIG. 29B. In turn, the performance of the chemical synthesis reaction depicted in FIG. 29B can optionally be preceded by the performance of the chemical synthesis reaction depicted in FIG. 29A.

Figure 31:
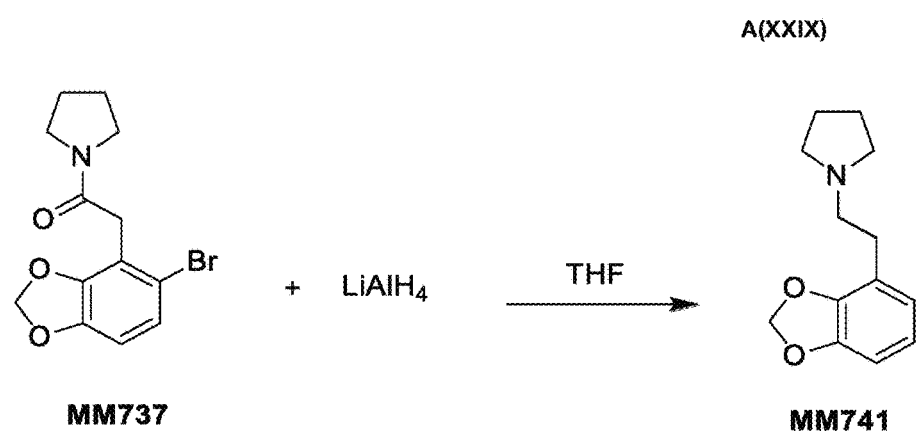
FIG. 31 depicts another example chemical synthesis pathway for synthesizing another example mescaline derivative compound according to the present disclosure.

Referring next to FIGS. 31, 28A, and 28B, in one embodiment, the compound having chemical formula (I) can be a compound having a formula A(XXIX):

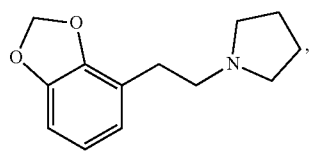

A(XXIX)

and the at least one chemical synthesis reaction is the chemical synthesis reaction depicted in FIG. 31. The performance of the chemical synthesis reaction depicted in FIG. 31 can optionally be preceded by the performance of the chemical synthesis reaction depicted in FIG. 28B. In turn, the performance of the chemical synthesis reaction depicted in FIG. 28B can optionally be preceded by the performance of the chemical synthesis reaction depicted in FIG. 28A.

Figure 32A:
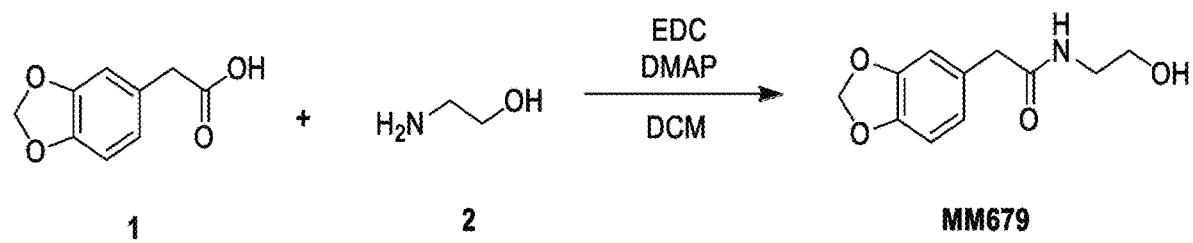
FIGS. 32A, 32B, and 32C depict other example chemical synthesis pathways for synthesizing another example mescaline derivative compound according to the present disclosure.
Figure 32B:
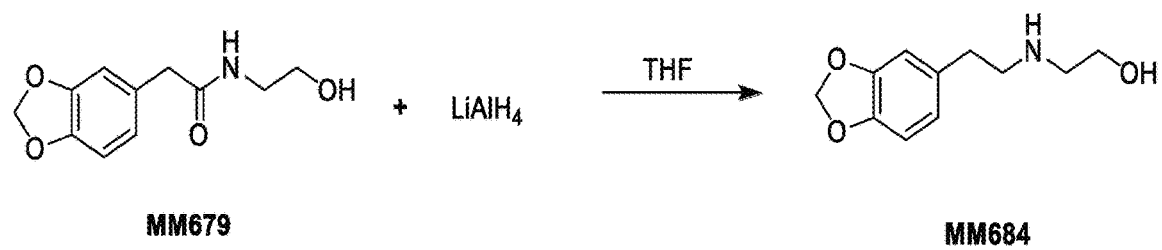
Figure 32C:
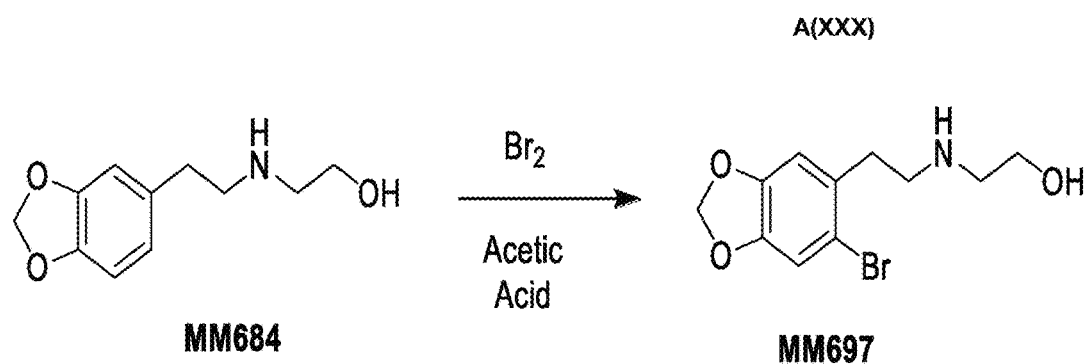

Referring next to FIGS. 32A-32C, in one embodiment, the compound having chemical formula (II) can be a compound having a formula A(XXX):

A(XXX)

and the at least one chemical synthesis reaction is the chemical synthesis reaction depicted in FIG. 32C. The performance of the chemical synthesis reaction depicted in FIG. 32C can optionally be preceded by the performance of the chemical synthesis reaction depicted in FIG. 32B. In turn, the performance of the chemical synthesis reaction depicted in FIG. 32B can optionally be preceded by the performance of the chemical synthesis reaction depicted in FIG. 32A.

Figure 33:
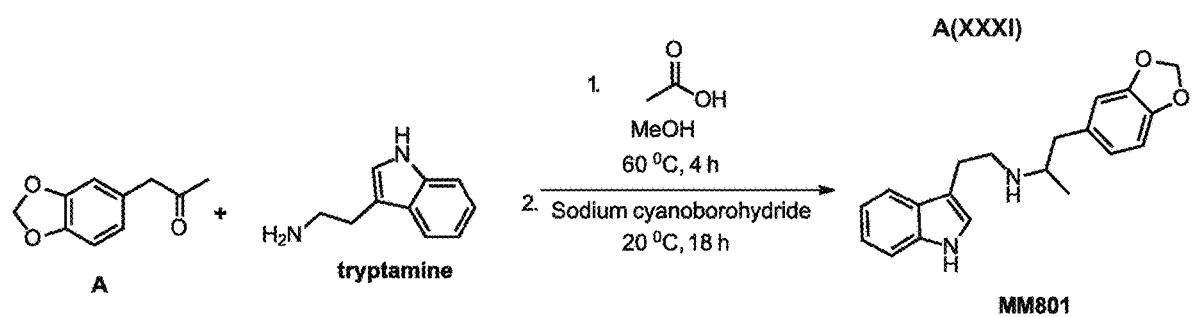
FIG. 33 depicts another example chemical synthesis pathway for synthesizing another example mescaline derivative compound according to the present disclosure.

Referring next to FIG. 33, in one embodiment, the compound having chemical formula (II) can be a compound having a formula A(XXXI):

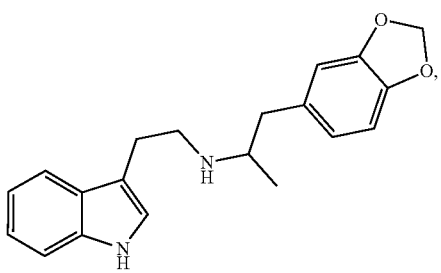

A(XXXI)

and the at least one chemical synthesis reaction is the chemical synthesis reaction depicted in FIG. 33.

Figure 34:
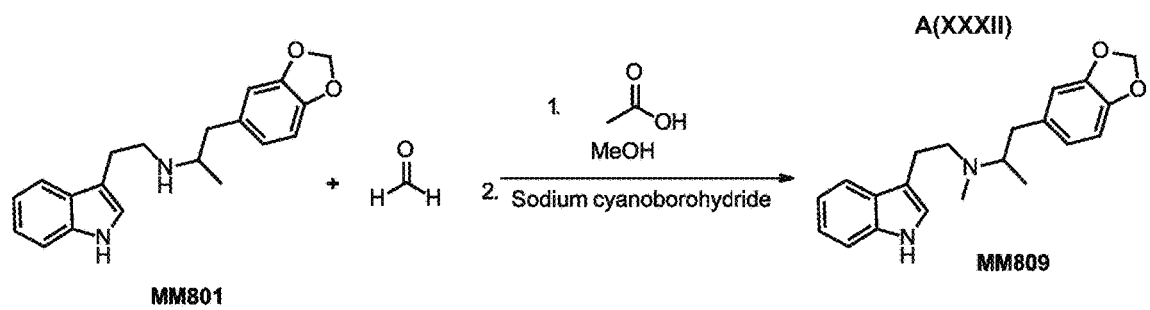
FIG. 34 depicts another example chemical synthesis pathway for synthesizing another example mescaline derivative compound according to the present disclosure.

Referring next to FIG. 34, in one embodiment, the compound having chemical formula (II) can be a compound having a formula A(XXXII):

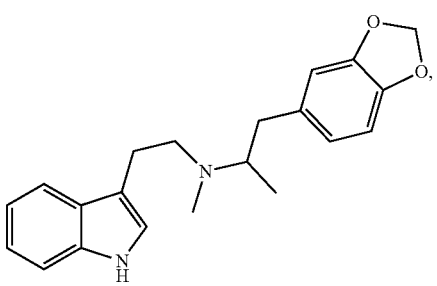

A(XXXII)

and the at least one chemical synthesis reaction is the chemical synthesis reaction depicted in FIG. 34.

It will now be clear from the foregoing that novel heterocyclic mescaline derivatives are disclosed herein. The heterocyclic mescaline derivatives may be formulated for use as a pharmaceutical drug or recreational drug. Example embodiments and implementations of the present disclosure are further illustrated by the following examples.

EXAMPLES

Example 1—Preparation and Pharmacological Analysis of a First Fused Heterocyclic Mescaline Derivative Referring to FIG. 3A, to a solution of D (94.6 mg, 528 µmol) in methanol (2.11 mL) under argon was added 6-methoxy-1,3-benzodioxole-5-carbaldehyde 9 (97.0 mg, 528 µmol). The reaction mixture was refluxed under inert atmosphere for 2.5 h. Following cooling to room temperature, sodium cyanoborohydride (51.0 mg, 771 μmol) was added in small portions and the resulting mixture was allowed to stir at room temperature for 18 h. Solvent was removed under reduced pressure, and the residue was taken up in ethyl acetate (10 mL) and washed with brine (3×10 mL). The organic layer was dried with anhydrous magnesium sulphate and the solvent was removed under reduced pressure. Purification by flash column chromatography on 4 g normal-phase silica using a 15% to 50% ethyl acetate-hexanes eluent system yielded MM612 as a colourless oil (84 mg, 46%). MS-ESI: calculated: 344.1493, observed: 344.1490 m/z [M+H]$^+$. $^1$H NMR (600 MHz, CDCl$_3$) δ 6.71 (d, J=7.8 Hz, 1H), 6.66 (s, 1H), 6.61 (d, J=1.7 Hz, 1H), 6.59 (dd, J=7.9, 1.7 Hz, 1H), 6.44 (s, 1H), 5.92-5.89 (m, 2H), 5.89-5.87 (m, 2H), 3.72 (d, J=13.2 Hz, 1H), 3.61 (s, 3H), 3.58 (d, J=13.3 Hz, 1H), 2.80-2.74 (m, 1H), 2.58-2.56 (m, 2H), 1.82 (s, 1H), 1.07 (d, J=6.2 Hz, 3H). It is noted that compound MM612 corresponds with the compound having chemical formula A(V):

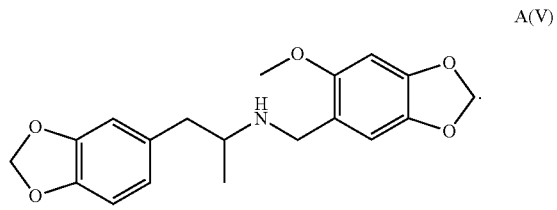 [SMILES: COc1cc2c(cc1CNC(C)Cc1ccc3c(c1)OCO3)OCO2]

A(V)

Referring to FIGS. 3B-3C, it is noted that compound D was synthesized as follows. Referring initially to FIG. 3B, to a solution of 4 (10.0 g, 65.9 mmol) in glacial acetic acid (50.0 mL) under argon was added nitroethane (5.21 mL, 72.5 mmol) followed by ammonium acetate (2.38 mL, 33.0 mmol). The reaction mixture was stirred at reflux for 6 h. Following cooling to room temperature, DI water (30 mL) was added to the reaction mixture and the flask was placed in the fridge overnight. The resulting precipitate was filtered and rinsed with DI water (100 mL). The solid was dried under reduced pressure to yield a bright yellow solid (5) (2.45 g, 18%). $^1$H NMR (600 MHz, CDCl$_3$) δ 8.02 (s, 1H), 6.98 (dd, J=8.1, 1.8 Hz, 1H), 6.95 (d, J=1.7 Hz, 1H), 6.89 (d, J=8.1 Hz, 1H), 6.05 (s, 2H), 2.46 (d, J=1.1 Hz, 3H).

Referring next to FIG. 3C, a flask cooled to 0° C. under inert atmosphere was charged with lithium aluminum hydride (1.50 mL, 3.00 mmol). To the reaction flask at 0° C. was slowly added a solution of 5 (254 mg, 1.23 mmol) in THF (4.50 mL). The resulting mixture was heated to reflux overnight. After cooling to 0° C., excess LAH was quenched with a THF (10 mL)-water (1 mL) solution. Aluminum salts were removed through filtration, and the resulting filtrate was dried over sodium sulfate and concentrated under vacuum to yield D as a tan oil (193 mg, 88%). $^1$H NMR (400 MHz, CDCl$_3$) δ 6.77 (d, J=7.8 Hz, 1H), 6.71 (d, J=1.7 Hz, 1H), 6.66 (dd, J=7.8, 1.7 Hz, 1H), 5.95 (s, 2H), 3.17-3.08 (m, 1H), 2.65 (dd, J=13.4, 5.3 Hz, 1H), 2.45 (dd, J=13.4, 8.1 Hz, 1H), 1.40 (s, 2H), 1.13 (d, J=6.3 Hz, 3H).

5-HT receptor radioligand competition assays. Activity at 5-HT$_{1A}$ and 5-HT$_{2A}$ receptors were assessed as described for Example 15, except the compound with formula A(V) was evaluated in place of the compound with formula A(XIV). Table 1 shows radioligand competition assay results for positive controls, negative controls, and compound with formula A(V), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(V) at the 5-HT$_{1A}$ receptor (1.88 μM, Table 1) indicates ligand-receptor binding. Similarly, the K$_i$ value obtained for the compound with formula A(V) at the 5-HT$_{2A}$ receptor (19 μM, Table 1) indicates ligand-receptor binding.

5-HT transporter (SERT) radioligand competition assay. Activity at the serotonin transporter (SERT) was assessed as described for Example 2, except the compound with formula A(V) was evaluated in place of the compound with formula A(VI). Table 3 shows radioligand competition assay results for positive controls, negative controls, and compound with formula A(V), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(V) at SERT (1.28 μM, Table 3) indicates ligand binding to SERT.

In Vitro Survey of Pharmacological Interaction Profiles at Receptors and Transporters Linked to Targeted Health Conditions.

The compound with formula A(V) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A (α d), D2 (D$_2$), D3 (D$_3$), MT1 (MT$_1$)) and 2 transporters (DAT, NET). Assays were conducted using the same materials and procedures outlined in Example 15, except the compound with formula A(V) was used in place of the compound with formula A(XIV). Overall assay conditions are summarized in Tables 4 and 5 for GPCR and transporters, respectively. Results for all calibrator compounds, control compounds, and test compounds including the compound with formula A(V) are summarized in Table 6.

Example 2—Preparation and Pharmacological Analysis of a Second Fused Heterocyclic Mescaline Derivative Referring to FIG. 4, to a solution of D (43.0 mg, 240 μmol) in methanol (960 μL) under argon was added 6-bromo-1,3-benzodioxole-5-carboxaldehyde 10 (55.5 mg, 240 μmol). The reaction mixture was refluxed under inert atmosphere for 2.5 h. Following cooling to room temperature, sodium cyanoborohydride (20.0 mg, 302 μmol) was added in small portions and the resulting mixture was allowed to stir at room temperature for 45 minutes. Solvent was removed under reduced pressure, and the residue was taken up in ethyl acetate (10 mL) and washed with brine (3×10 mL). The organic layer was dried with anhydrous magnesium sulphate and the solvent removed under reduced pressure. Purification by flash column chromatography on 4 g normal-phase silica using a 10% to 30% ethyl acetate-hexanes eluent system yielded MM613 as a colourless oil (15 mg, 16%). MS-ESI: calculated: 392.0492, observed: 392.0491 m/z [M+H]$^+$. $^1$H NMR (400 MHz, CDCl$_3$) δ 6.97 (s, 1H), 6.81 (s, 1H), 6.75 (d, J=7.7 Hz, 1H), 6.66-6.61 (m, 2H), 5.97 (q, J=1.4 Hz, 2H), 5.95 (s, 2H), 3.80 (d, J=13.7 Hz, 1H), 3.71 (d, J=13.7 Hz, 1H), 2.85 (dt, J=7.2, 6.1 Hz, 1H), 2.68-2.56 (m, 2H), 1.82 (s, 1H), 1.12 (d, J=6.2 Hz, 3H). It is noted that compound MM613 corresponds with the compound having chemical formula A(VI):

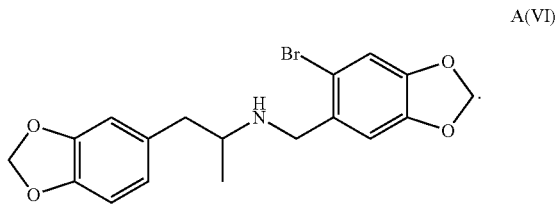 [SMILES: CC(Cc1ccc2c(c1)OCO2)NCc1cc2c(cc1Br)OCO2]

A(VI)

It is noted that compound D was synthesized as described in Example 1.

5-HT receptor radioligand competition assays. Activity at 5-HT$_{1A}$ and 5-HT$_{2A}$ receptors were assessed as described for Example 15, except the compound with formula A(VI) was evaluated in place of the compound with formula A(XIV). Table 1 shows radioligand competition assay results for positive controls, negative controls, and compound with formula A(VI), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(VI) at the 5-HT$_{1A}$ receptor (1.52 µM, Table 1) indicates ligand-receptor binding. Similarly, the K$_i$ value obtained for the compound with formula A(VI) at the 5-HT$_{2A}$ receptor (5.3 µM, Table 1) indicates ligand-receptor binding.

Figure 38D:
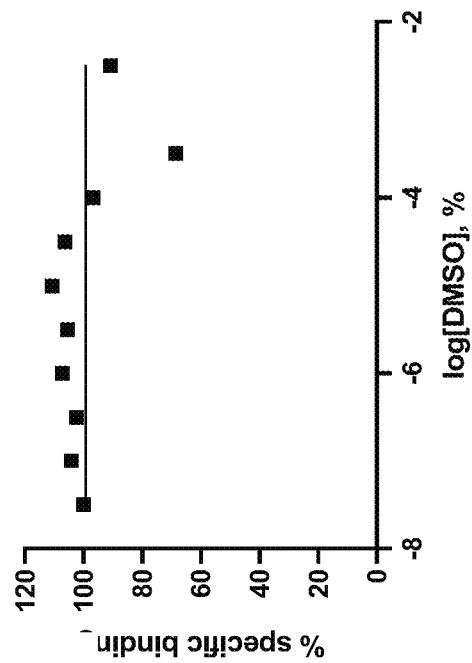
Figure 38C:
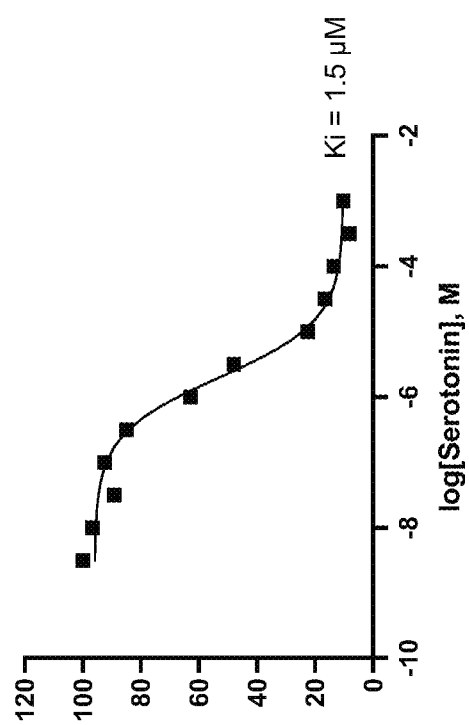
Figure 38F:
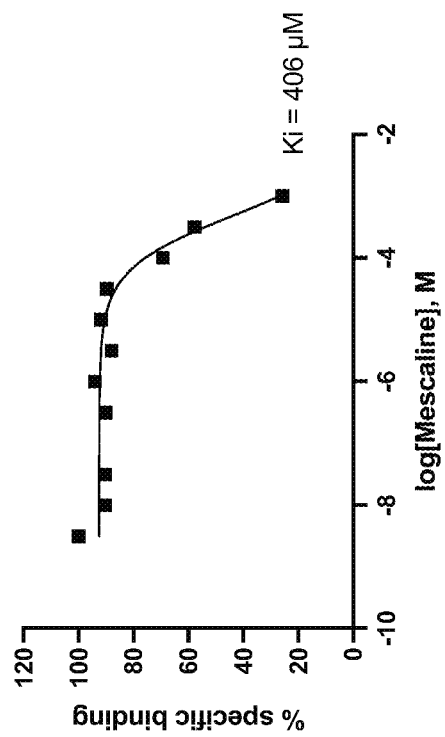
Figure 38E:
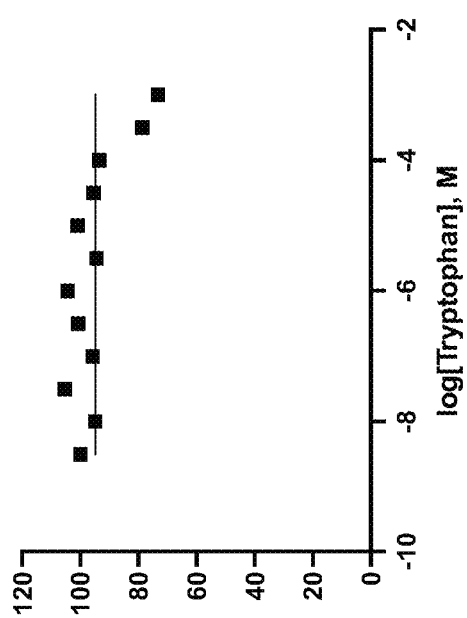
Figure 38H:
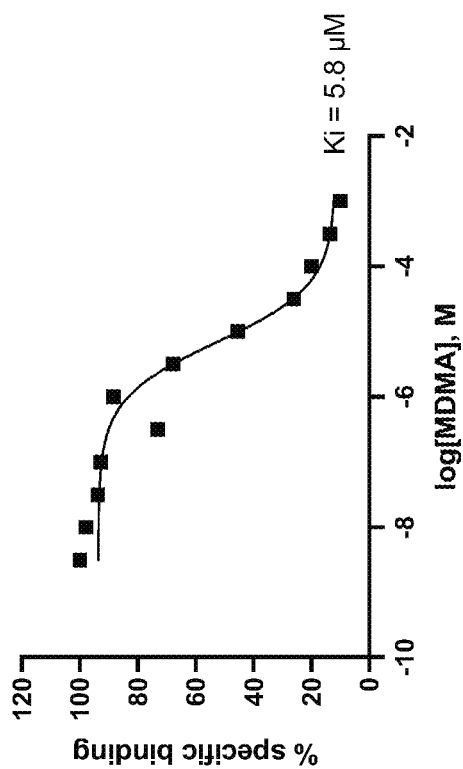
Figure 38G:
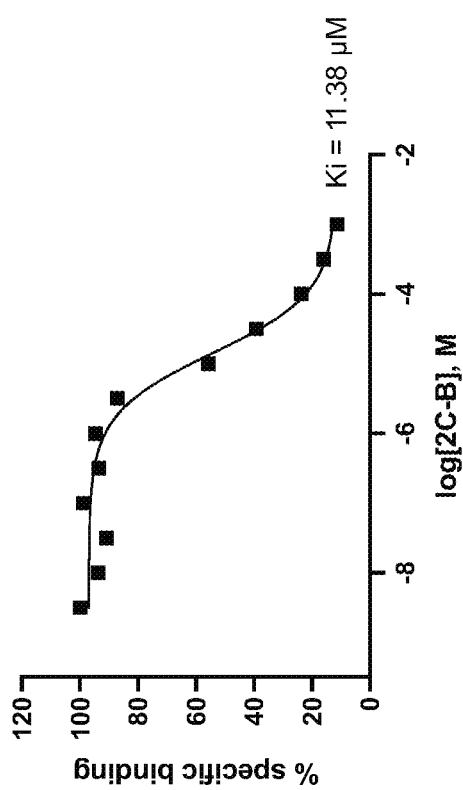
Figure 38J:
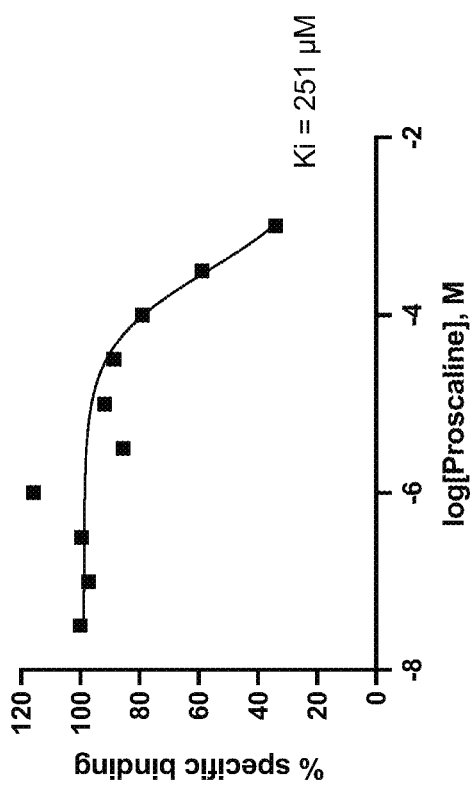
Figure 38I:
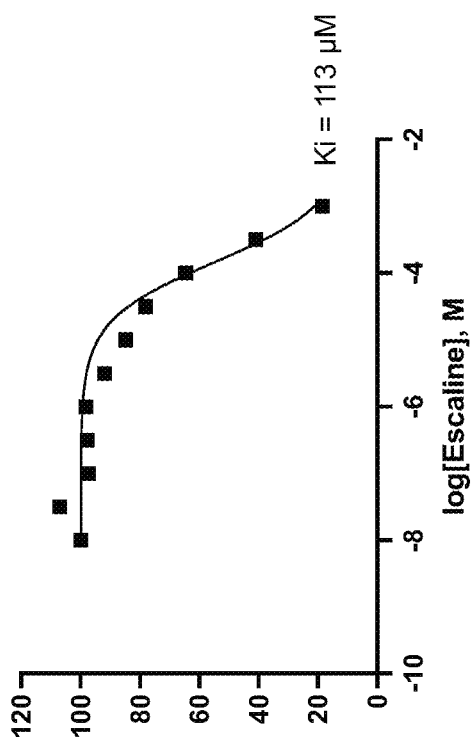
Figure 38L:
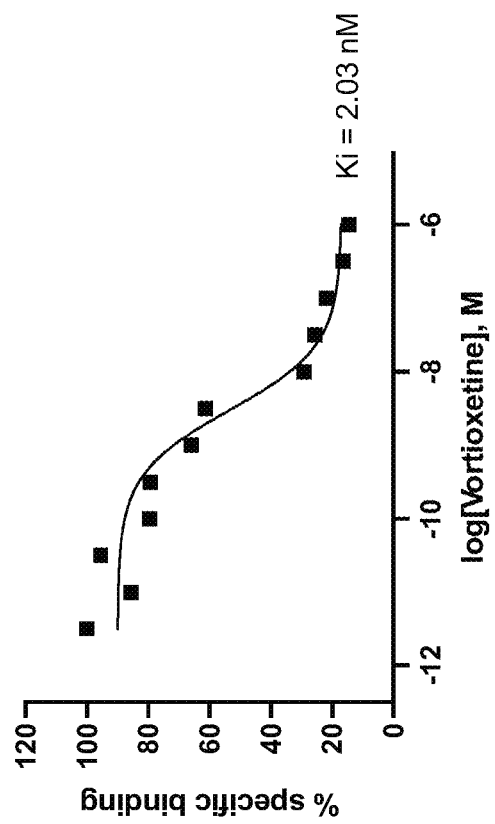
Figure 38K:
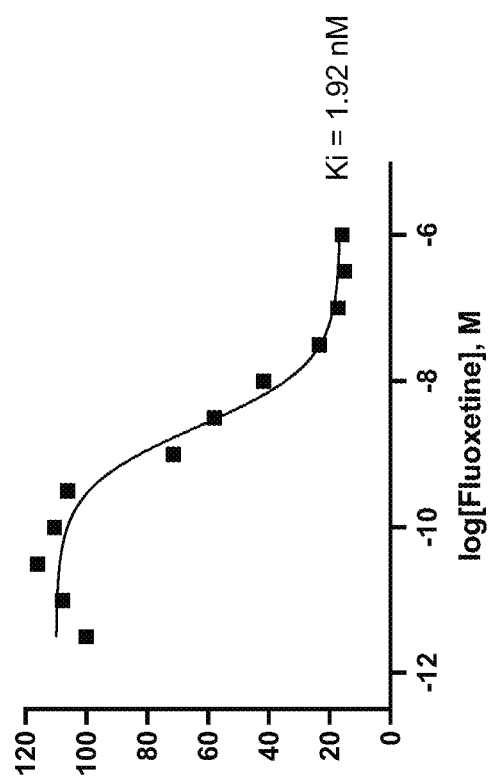
Figure 38M:
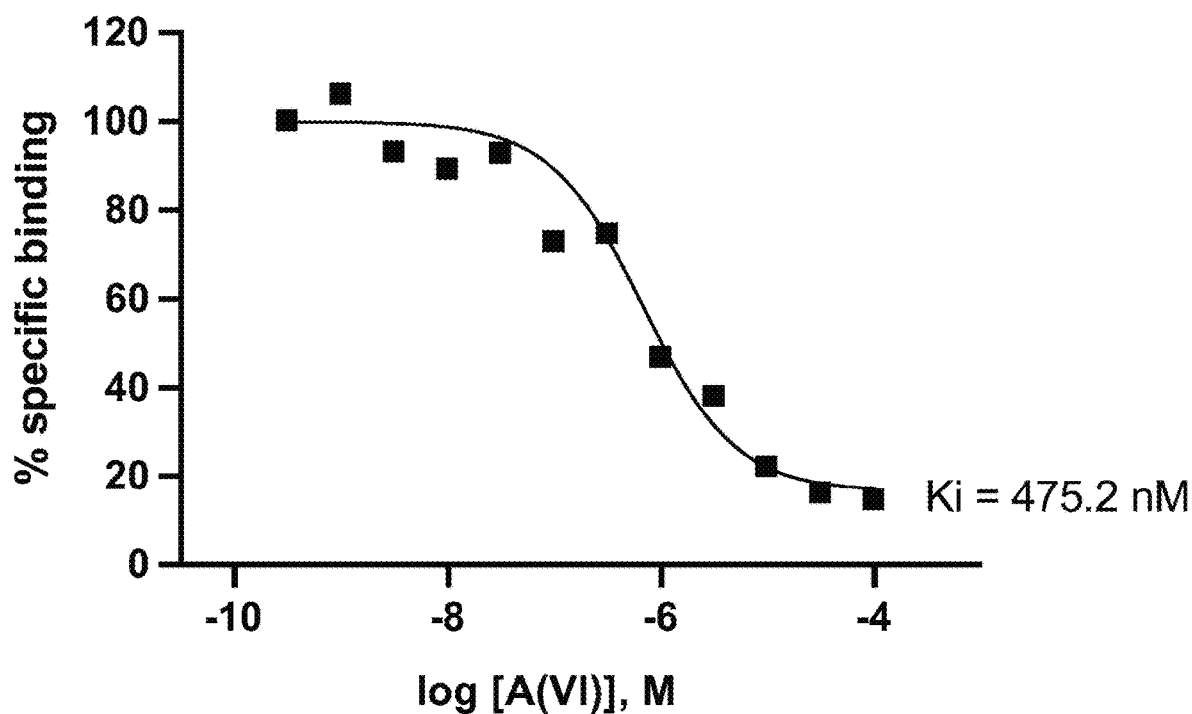

5-HT transporter (SERT) radioligand competition assay. The serotonin transporter (SERT) regulates neurotransmission through the reuptake of serotonin from extra-neuronal regions such as synapses, and its function is closely linked to mental health and neurological homeostasis. SERT is a membrane-localized protein with several binding sites, including one for the cognate substrate serotonin (primary substrate binding site) and an additional allosteric binding site generally targeted by ligands acting as antidepressants, anxiolytics, or other drugs used in the treatment of neuropathologies (Cheng and Bahar, 2019, Nature Structural and Molecular Biology 26:545-556). Ligands acting as allosteric modulators of SERT include SSRIs (selective serotonin reuptake inhibitors) which diminish the ability of SERT to transport serotonin, in effect increasing serotonin presence in synapses. However, other non-SSRI pharmaceuticals such as vortioxetine, which bind tightly to SERT, also act as reuptake inhibitors (Gonda et al., 2019, Expert Opinion on Drug Discovery 14: 81-89). In essence, an ability to bind SERT is viewed as a marker of drug candidate potential, and thus SERT binding assays have become routine screening procedures in the field of drug discovery. Psychedelics such as substituted tryptamines (Kozell et al., 2023, Journal of Pharmacology and Experimental Therapeutics 385:62-75), ibogaine (Singh et al., 2023, Cell 186:2160-2175), and MDMA (Islas and Scior, 2022, Molecules 27: 2977-2995) are known to bind SERT and modulate serotonin reuptake. A commonly applied SERT binding assay involves competition binding assays employing radiolabelled ligands. To assay binding potential of test compounds, the following procedure was adapted from Bulling et al., (2009, Journal of Biological Chemistry 287:18524-18534). SPA beads (RPNQ0011), imipramine hydrochloride [benzene ring—$^3$H(N)] (NET576250UC), membranes containing human serotonin transporter (RBHSTM400UA), and isoplate-96 microplate (6005040) were all purchased from PerkinElmer. Radioactive binding assays were carried out using the Scintillation Proximity Assay (SPA). For saturation binding assay, mixtures of 9 µg of membrane containing human SERT was pre-coupled to 1 mg of SPA beads at room temperature in a tube rotator for 1 hour in binding buffer (50 mM Tris-HCl pH7.4, 120 mM NaCl, 5 mM KCl, 1 mM ascorbic acid, 10 µM pargyline HCl). After pre-coupling, the beads and membrane were aliquoted in an isoplate-96 microplate with increasing amounts of imipramine hydrochloride [benzene ring—$^3$H(N)] (0.1525 nM to 5 nM) and incubated for two hours at room temperature in the dark with shaking. After incubation, the samples are read on a MicroBeta 2 Microplate Counter. Non-specific binding was carried out in the presence of 200 µM of clomipramine hydrochloride (C7291-1 G, Sigma). Equilibrium binding constant for imipramine (K$_D$) was determined from saturation binding curve using one-site saturation binding analysis from GraphPad PRISM software (Version 9.2.0). All test compounds were dissolved to 100 mM in DMSO and dilutions were carried out in assay buffer. Competition binding assays were performed using 1 nM imipramine and different concentrations of DMSO (up to 1% which is the highest used in competition experiments), tryptophan (3 nM to 1 mM), or unlabelled test compounds (3 nM to 1 mM) similar to the saturation binding assay. K$_i$ values were calculated from the competition displacement data using the competitive binding analysis from GraphPad PRISM software. Serotonin is the cognate ligand for SERT and was thus used as a positive control. Tryptophan has no known ability to bind SERT and was thus included as a negative control. Vehicle (DMSO) without drug was used as a negative control. MDMA and 2C-B are known to bind SERT (Zwartsen et al., 2017, Toxicology in Vitro 45:60-71) and were used as positive controls. The binding mode of mescaline, escaline, and proscaline to SERT are poorly studied, but these compounds were nonetheless included as calibrators owing to their potential use in psychedelic-inspired medicine and structural similarities to the test compounds. Fluoxetine and vortioxetine are commonly prescribed mental health drugs known to tightly bind SERT and were used as positive controls. FIGS. 38A and 38B illustrate overall K$_D$ determination and specific binding results for imipramine. FIGS. 38C and 38D illustrate binding curves for serotonin and vehicle (DMSO), which reveal binding and no binding, respectively. The binding curve for the negative control tryptophan (FIG. 38E) reveals no binding to SERT, and no K$_i$ determination was possible (i.e., K$_i$>1000 µM). FIG. 38F illustrates the binding curve for mescaline, which suggests SERT binding at higher ligand concentrations. The binding curves of FIGS. 38G, 38H, 38I and 38J demonstrate that the respective ligands 2C-B, MDMA, escaline and proscaline all bind SERT to varying degrees. The binding curves of FIGS. 38K and 38L demonstrate very tight interaction of drugs fluoxetine and vortioxetine to SERT, respectively. The binding curve of FIG. 38M demonstrates that compound with formula A(VI) binds SERT. The K$_i$ values of all controls, calibrators, and test compounds are summarized in Table 3.

TABLE 3

Data summary for SERT radioligand binding competition assays

| Molecule | SERT, K$_i$ (µM) |
| --- | --- |
| DMSO | >1000 |
| tryptophan | >1000 |
| serotonin | 1.5 |
| mescaline | 406 |
| 2C-B | 11.38 |
| MDMA | 5.8 |
| escaline | 113 |
| proscaline | 251 |

TABLE 3-continued

Data summary for SERT radioligand binding competition assays

| Molecule | SERT, $K_i$ (μM) |
|---|---|
| fluoxetine | 0.00192 |
| vortioxetine | 0.00203 |
| A(I) | 1.1 |
| A(II) | 1.87 |
| A(III) | 26.3 |
| A(IV) | 49.8 |
| A(V) | 1.28 |
| A(VI) | 0.4752 |
| A(VII) | 29.9 |
| A(VIII) | 22.6 |
| A(IX) | 0.223 |
| A(X) | 2.36 |
| A(XI) | 0.191 |
| A(XII) | 2.39 |
| A(XIII) | 2.91 |
| A(XIV) | 23.2 |
| A(XV) | 64.3 |
| A(XVI) | 58.1 |
| A(XVII) | 1.71 |
| A(XVIII) | 98 |
| A(XIX) | >1000 |
| A(XX) | 286 |
| A(XXI) | 846.7 |
| A(XXII) | 52.3 |
| A(XXIII) | 2.75 |
| A(XXIV) | 52.18 |
| A(XXV) | 10.89 |
| A(XXVI) | N.D. |
| A(XXVII) | 633.9 |
| A(XXVIII) | 23.72 |
| A(XXIX) | 10.08 |
| A(XXX) | 84.26 |

N.D. = not determined

In Vitro Survey of Pharmacological Interaction Profiles at Receptors and Transporters Linked to Targeted Health Conditions.

The compound with formula A(VI) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(VI) was used in place of the compound with formula A(XIV). Overall assay conditions are summarized in Tables 4 and 5 for GPCR and transporters, respectively. Results for all calibrator compounds, control compounds, and test compounds including the compound with formula A(VI) are summarized in Table 6.

Example 3—Preparation and Pharmacological Analysis of a Third Fused Heterocyclic Mescaline Derivative Referring to FIG. 5A, to compound A (100 mg, 561 μmol) was dissolved in MeOH (6 mL) followed by the addition of acetic acid (38.6 μL, 673 μmol). The reaction mixture was stirred for a few minutes before the addition of Cyclobutylamine (33.1 mg, 1.14 mmol); the reaction mixture was then heated at 65° C. and stirred for 2 hours. pH of the mixture was checked (around 6). After 2 hours, Sodium cyanoborohydride (111 mg, 1.68 mmol) was added to the mixture and reaction was stirred overnight at room temperature. Half-saturated NaHCO$_3$ (aq.) and EtOAc was added to the mixture, aqueous phase was extracted with EtOAc, combined organic layers were dried over Na$_2$SO$_4$, filtered, and concentrated in vacuo. Crude material was purified on silica gel column (0 to 20% MeOH in DCM), fractions contained product were pooled, dried in vacuo to afford MM614 (60.0 mg, 46%) as a light brown oil. MS-ESI: calculated: 233.1416 observed: M+H=234.1483 m/z [M+H]$^+$ $^1$H NMR (400 MHz, CDCl$_3$) δ 6.74 (d, J=7.9 Hz, 1H), 6.66 (d, J=1.7 Hz, 1H), 6.62 (dd, J=7.9, 1.7 Hz, 1H), 5.93 (s, 2H), 3.38 (p, J=7.7 Hz, 1H), 2.87 (h, J=6.5 Hz, 1H), 2.65 (dd, J=13.4, 6.9 Hz, 1H), 2.51 (dd, J=13.4, 6.9 Hz, 1H), 2.30-2.14 (m, 2H), 1.80-1.52 (m, 4H), 1.03 (d, J=6.2 Hz, 3H). It is noted that compound MM614 corresponds with the compound having chemical formula A(I):

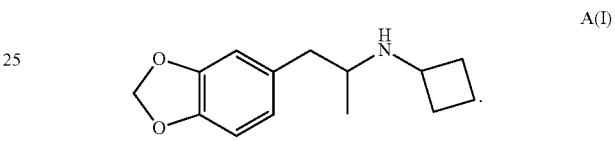

A(I)

Referring to FIG. 5B, it is noted that compound A was synthesized as follows. 3,4-(methylenedioxy)phenylacetic acid 1 (10.0 g, 55.5 mmol) was dissolved in acetic anhydride (26.8 mL, 278 mmol) at room temperature, and the solution was stirred and purged with nitrogen for several minutes. The reaction was initiated by the dropwise addition of 1-methylimidazole (NMI) (2.23 mL, 27.8 mmol), and was continuously purged with a slow flow of nitrogen at room temperature until the starting material completely disappeared (TLC). After completion (16 h), water (5 mL) was added to the reaction flask. The reaction mixture was extracted with ethyl acetate (3×75 mL). The organic layers were combined and washed with saturated aq. NaHCO$_3$ (50 mL) followed by water, then dried over Na$_2$SO$_4$, filtered and concentrated. The crude product was purified using silica gel (120 g, EA/hex 0:100 to 50:50, 8 CV, product eluting at 20% EA) to afford the pure product A as a clear colorless oil (7.35 g, 74%). $^1$H NMR (400 MHz, CDCl$_3$) δ 6.77 (d, J=7.8 Hz, 1H), 6.71-6.66 (m, 1H), 6.64 (ddd, J=7.8, 1.8, 0.5 Hz, 1H), 5.95 (s, 2H), 3.60 (s, 2H), 2.15 (s, 3H).

5-HT receptor radioligand competition assays. Activity at 5-HT$_{1A}$ and 5-HT$_{2A}$ receptors were assessed as described for Example 15, except the compound with formula A(I) was evaluated in place of the compound with formula A(XIV). Table 1 shows radioligand competition assay results for positive controls, negative controls, and compound with formula A(I), in the form of $K_i$ values. In view of results for both positive and negative controls, wherein negative controls yield data insufficient for reliable $K_i$ calculations (i.e., $K_i$>1000 μM) the $K_i$ value obtained for the compound with formula A(I) at the 5-HT$_{1A}$ receptor (20.8 μM, Table 1) indicates ligand-receptor binding. Similarly, the $K_i$ value obtained for the compound with formula A(I) at the 5-HT$_{2A}$ receptor (516.9 μM, Table 1) indicates ligand-receptor binding. [00374] 5-HT transporter (SERT) radioligand competition assay. Activity at the serotonin transporter (SERT) was assessed as described for Example 2, except the compound with formula A(I) was evaluated in place of the compound with formula A(VI). Table 3 shows radioligand competition assay results for positive controls, negative controls, and compound with formula A(I), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(I) at SERT (1.1 µM, Table 3) indicates ligand binding to SERT.

In Vitro Survey of Pharmacological Interaction Profiles at Receptors and Transporters Linked to Targeted Health Conditions.

The compound with formula A(I) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(I) was used in place of the compound with formula A(XIV). Overall assay conditions are summarized in Tables 4 and 5 for GPCR and transporters, respectively. Results for all calibrator compounds, control compounds, and test compounds including the compound with formula A(I) are summarized in Table 6.

Head Twitch Response (HTR) Assay.

Figure 39A:
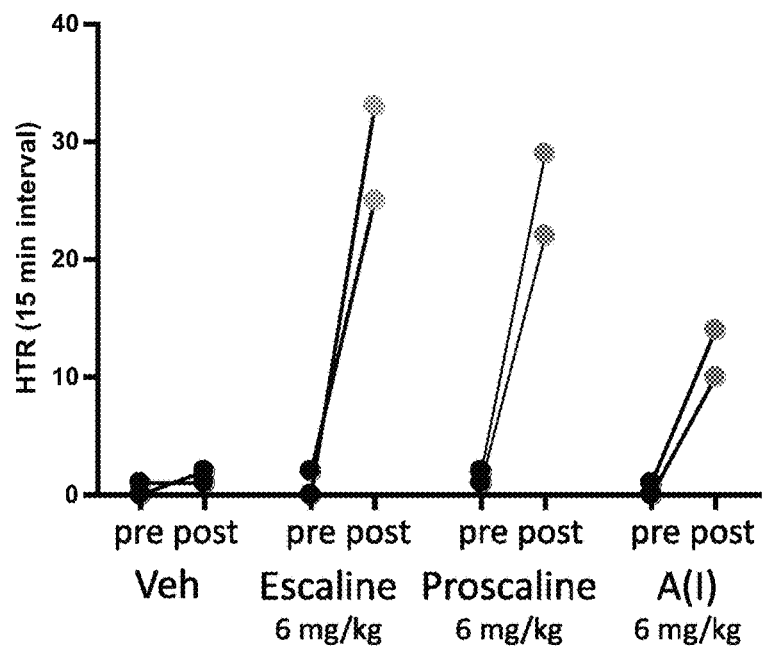
FIGS. 39A and 39B depict various graphs representing certain experimental results, notably graphs obtained in the performance of experimental assays to evaluate the pharmaceutical efficacy of an example compound having chemical formula A(I), notably a mouse head twitch response (HTR) assay (FIG. 39A), and a mouse ear scratch response (ESR) assay (FIG. 39B).

Drug-induced Head Twitch Response (HTR), a rapid, involuntary movement of the mouse's head with little or no involvement of the trunk, is an established in vivo model behavior used to measure neuronal 5-HT$_{2A}$ receptor (5-HT2AR) engagement by established and novel hallucinogenic compounds (Canal and Morgan 2012, Drug Testing Analysis, 4:556-576). Indeed, HTR is widely utilized as a behavioral proxy in mice and rats to predict human hallucinogenic potential and can reliably differentiate between hallucinogenic and non-hallucinogenic 5-HT2AR agonists (Halberstadt and Geyer 2013, Psychopharmacology 227: 727-739; Gonzalez-Maeso et al., 2007, Neuron 53:439-452). Despite arguably lower binding affinity for phenylalkylamine (PAA)-type compounds (such as MDMA and mescaline) at 5-HT2AR compared to tryptamine-type molecules (such as DMT and psilocin), HT2AR engagement of PAA-type compounds is demonstrably sufficient to elicit HTR. For example, mescaline, escaline, proscaline and MDMA are all known to elicit HTR behaviour (Halberstadt et al., 2019, Journal of Psychopharmacology 33:406-414; Fantegrossi et al., 2004, Psychopharmacology 173: 270-277). Furthermore, evidence has shown that hallucination induced by PAA-type compounds is 5-HT2AR-mediated (Jaster et al., 2022, Psychopharmacology 239: 1665-1677). To evaluate 5-HT2AR agonisms in vivo, HTR was measured in mice treated with controls and test compounds over a fixed window of time post-administration. All experiments were approved by the University of Calgary Animal Care and Use Committee in accordance with Canadian Council on Animal Care guidelines. Briefly, 8-week old C57BL/6-Elite male and female mice were obtained from Charles River. Prior to compound administration, all mice were group-housed, then single-housed on a 12:12 h light/dark schedule (lights on at 07:00 hours) with ad libitum access to food and water. Before any behavioral screening, mice were handled and exposed to the testing chamber for at least 5 min each day for three successive days and habituated to the experimental room 1 h before testing. The testing chamber was cleaned with a 70% ethanol solution between experiments. Control and test compounds, which were prepared at stock concentrations of 100 mM in DMSO, were diluted in sterile saline solution (0.9% NaCl). Prior to drug administration, mice were video monitored for 30 minutes in a plexiglass testing chamber (25.5×12.5×12.5 cm [L×W×H]) to allow for acclimation to the testing environment and to examine pre-drug spontaneous HTRs. After 30 minutes, compounds were administered via intraperitoneal (i.p.) injection at 6 mg/kg and mice were video monitored for 30 minutes then returned to their home cage. HTR analysis was conducted by an individual blinded to the subject treatment group using Behavioral Observation Research Interactive Software (BORIS, version 7, DOI: 10.1111/2041-210X.12584). Pre-drug behavior was examined during the 15-to-30-minute window prior to drug administration. Post-drug behavior was analyzed during the 15-to-30-minute window following drug administration. HTR associated with i.p. administration of escaline and proscaline were included as positive control measures. HTR associated with i.p. administration of vehicle (0.9% NaCl) was included as a negative control measure. Elevated incidences of HTR within the defined period of monitoring was observed in (1) escaline-treated mice, (2) proscaline-treated mice, and (2) those treated with the compound with formula A(I), relative to control mice treated with i.p. injected vehicle (0.9% NaCl). These results are illustrated in FIG. 39A, wherein vehicle is designated "Veh" and compound with formula A(I) is designated "A(I)," pre-drug data is designated "pre-", and post-drug data is designated "post." Each replicate mouse is shown as a dot, with connecting lines revealing pre- and post-data for each mouse.

Ear-Scratch Response (ESR) Assay.

Figure 39B:
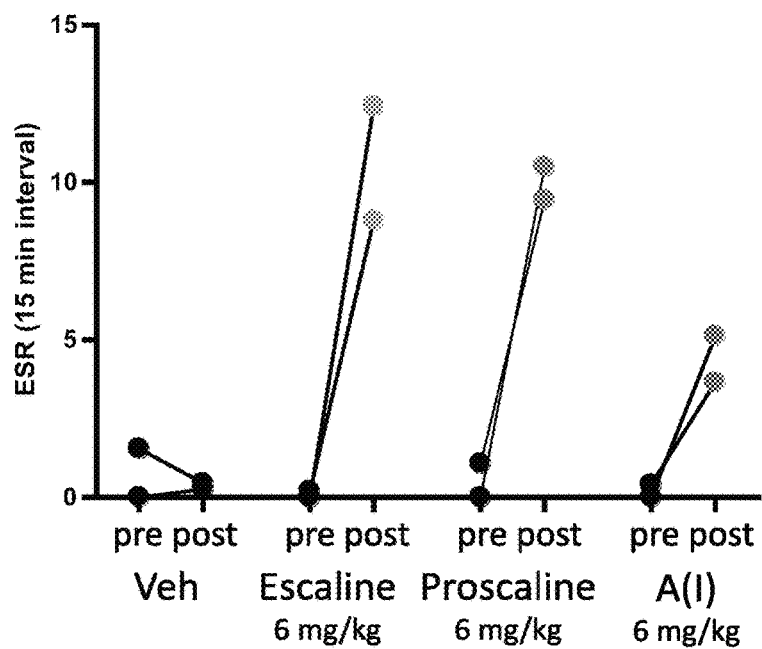

Beyond the head twitch response (HTR) assay, an additional behavioural model with established correlation to hallucinogenic potential is the ear scratch response (ESR) assay. A rapid scratching movement of the head and/or neck area by a hindlimb is a behavioural response notably elevated in mice treated with phenylalkylamines, including DOI and mescaline (Glennon, 1992, In: Boulton, Baker, Wu [Eds] Animal Models of Drug Addiction. Neuromethods 24, Humana Press). The ESR, also referred to as scratch-reflex stereotypy, is believed to be mediated by 5-HT$_2$-type receptors and can be attenuated by pre-treatment with selective antagonists ketanserin or spiperone. However, ESR does not occur universally (González-Maeso et al., Neuron 53: 439-452) and it has been suggested that ESR is a behaviour specific to the PAA structural class of hallucinogens (Darmani et al., Pharmacology Biochemistry and Behavior 37: 95-99). Herein, the ESR assay was conducted using the same mice described in the HTR assay, using the same videos acquired pre- and post-drug administration. Thus, the same individuals undergoing the same treatment as described under the section "Head Twitch Response (HTR) assay" were used to monitor for two distinct behaviours. The only difference between the HTR and ESR experiments was that these same videos were monitored for ESR, rather than HTR, by a trained observer. Elevated incidences of ESR within the defined period of monitoring was observed in (1) escaline-treated mice, (2) proscaline-treated mice, and (2) those treated with the compound with formula A(I), relative to control mice treated with i.p. injected vehicle (0.9% NaCl). These results are illustrated in FIG. 39B, wherein vehicle is designated "Veh" and compound with formula A(I) is designated "A(I)," pre-drug data is designated "pre-", and post-drug data is designated "post." Each replicate mouse is shown as a dot, with connecting lines revealing pre- and post-data for each mouse.

Example 4—Preparation and Pharmacological Analysis of a Fourth Fused Heterocyclic Mescaline Derivative Referring to FIG. 6, to compound A (100 mg, 561 µmol) was dissolved in MeOH (5.61 mL) followed by the addition of acetic acid (38.6 µL, 673 µmol). The reaction was stirred for a few minutes before the addition of azetidine (75.7 µL, 1.12 mmol). The reaction mixture was then heated up to 60° C. and stirred for 2 h. After 2 h, reaction was cooled to RT and sodium cyanoborohydride (111 mg, 1.68 mmol) was added to the mixture and stirring was continued at room temperature for 2 h. Triethylamine (100 µL) was added to the reaction and the volatiles were removed in vacuo. The crude residue was directly purified by FC on silica gel (12 g, MeOH/DCM 0:100 to 15:85, product eluting at 9% MeOH) to afford the pure product (MM615) as a yellow oil (60 mg, 49%).

MS-ESI: $C_{13}H_{18}NO_2$ $[M+H]^+$; calculated: 220.1332; observed: 220.1318 m/z. $^1$H NMR (400 MHz, CDCl$_3$) δ 6.82-6.75 (m, 1H), 6.71 (d, J=7.4 Hz, 2H), 5.97 (s, 2H), 3.99 (d, J=7.9 Hz, 4H), 3.39 (dp, J=8.3, 6.5 Hz, 1H), 2.94 (dd, J=13.9, 6.2 Hz, 1H), 2.67 (dd, J=13.9, 8.4 Hz, 1H), 1.22 (d, J=6.5 Hz, 3H). It is noted that compound MM615 corresponds with the compound having chemical formula A(II):

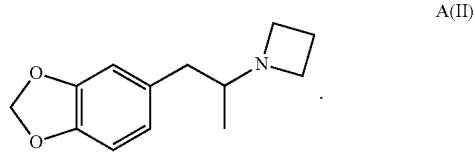 [SMILES: CC(Cc1ccc2c(c1)OCO2)N1CCC1]

A(II)

It is noted that compound A was synthesized as described in Example 3.

5-HT receptor radioligand competition assays. Activity at 5-HT$_{1A}$ and 5-HT$_{2A}$ receptors were assessed as described for Example 15, except the compound with formula A(II) was evaluated in place of the compound with formula A(XIV). Table 1 shows radioligand competition assay results for positive controls, negative controls, and compound with formula A(II), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(II) at the 5-HT$_{1A}$ receptor (0.926 µM, Table 1) indicates ligand-receptor binding. Similarly, the K$_i$ value obtained for the compound with formula A(II) at the 5-HT$_{2A}$ receptor (13 µM, Table 1) indicates ligand-receptor binding.

5-HT transporter (SERT) radioligand competition assay. Activity at the serotonin transporter (SERT) was assessed as described for Example 2, except the compound with formula A(II) was evaluated in place of the compound with formula A(VI). Table 3 shows radioligand competition assay results for positive controls, negative controls, and compound with formula A(II), in the form of K$_i$ values. In view of results for both positive and negative controls, wherein negative controls yield data insufficient for reliable K$_i$ calculations, (i.e., K$_i$>1000 µM) the K$_i$ value obtained for the compound with formula A(II) at SERT (1.87 µM, Table 3) indicates ligand binding to SERT.

In Vitro Survey of Pharmacological Interaction Profiles at Receptors and Transporters Linked to Targeted Health Conditions.

The compound with formula A(II) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(II) was used in place of the compound with formula A(XIV). Overall assay conditions are summarized in Tables 4 and 5 for GPCR and transporters, respectively. Results for all calibrator compounds, control compounds, and test compounds including the compound with formula A(II) are summarized in Table 6.

Example 5—Preparation and Pharmacological Analysis of a Fifth Fused Heterocyclic Mescaline Derivative Referring to FIG. 7, compound A (100 mg, 561 µmol was dissolved in MeOH (6 mL) followed by the addition of Acetic acid (38.6 µL, 673 µmol). The reaction mixture was stirred for a few minutes before the addition of morpholine (100 µL, 1.13 mmol); the reaction mixture was then heated at 65° C. and stirred for 2 hours. pH of the mixture was checked (around 6). After 2 hours, Sodium cyanoborohydride (111 mg, 1.68 mmol) was added to the mixture and reaction was stirred overnight at room temperature. Half-saturated NaHCO$_3$ (aq.) and EtOAc were added to the mixture, aqueous phase was extracted with EtOAc, combined organic layers were dried over Na$_2$SO$_4$, filtered, and concentrated in vacuo. Crude material was purified on silica gel column (0 to 20% MeOH in DCM), fractions contained product were pooled, dried in vacuo to afford MM616 (52.0 mg, 37%) as a colorless oil. MS-ESI: calculated: 249.13649 observed: M+H=250.14160 m/z [M+H]$^+$ $^1$H NMR (400 MHz, CDCl$_3$) δ 6.72 (d, J=7.9 Hz, 1H), 6.67 (d, J=1.7 Hz, 1H), 6.60 (dd, J=7, 9, 1.7 Hz, 1H), 5.92 (s, 2H), 3.78-3.69 (m, 4H), 2.91 (dd, J=13.2, 4.4 Hz, 1H), 2.70 (dqd, J=9.6, 6.6, 4.5 Hz, 1H), 2.63-2.57 (m, 4H), 2.33 (dd. J=13.2, 9.5 Hz, 1H), 0.95 (d, J=6.5 Hz, 3H). slight trace of IPA. It is noted that compound MM616 corresponds with the compound having chemical formula A(III):

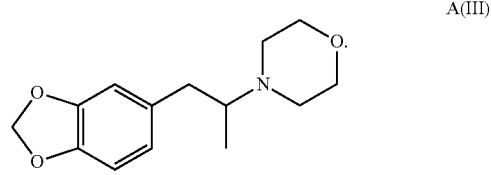 [SMILES: CC(Cc1ccc2c(c1)OCO2)N1CCOCC1]

A(III)

It is noted that compound A was synthesized as described in Example 3.

5-HT receptor radioligand competition assays. Activity at 5-HT$_{1A}$ and 5-HT$_{2A}$ receptors were assessed as described for Example 15, except the compound with formula A(III) was evaluated in place of the compound with formula A(XIV). Table 1 shows radioligand competition assay results for positive controls, negative controls, and compound with formula A(III), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(III) at the 5-HT$_{1A}$ receptor (38.6 µM, Table 1) indicates ligand-receptor binding. Similarly, the $K_i$ value obtained for the compound with formula A(III) at the 5-HT$_{2A}$ receptor (42 µM, Table 1) indicates ligand-receptor binding.

5-HT transporter (SERT) radioligand competition assay. Activity at the serotonin transporter (SERT) was assessed as described for Example 2, except the compound with formula A(III) was evaluated in place of the compound with formula A(VI). Table 3 shows radioligand competition assay results for positive controls, negative controls, and compound with formula A(III), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(III) at SERT (26.3 µM, Table 3) indicates ligand binding to SERT.

In Vitro Survey of Pharmacological Interaction Profiles at Receptors and Transporters Linked to Targeted Health Conditions.

The compound with formula A(III) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(III) was used in place of the compound with formula A(XIV). Overall assay conditions are summarized in Tables 4 and 5 for GPCR and transporters, respectively. Results for all calibrator compounds, control compounds, and test compounds including the compound with formula A(III) are summarized in Table 6.

Example 6—Preparation and Pharmacological Analysis of a Sixth Fused Heterocyclic Mescaline Derivative Referring to FIG. 8A, compound C (100 mg, 609 µmol) was dissolved in MeOH (6 mL) followed by the addition of Acetic acid (41.8 µL, 731 µmol). The reaction mixture was stirred for a few minutes before the addition of morpholine (109 µL, 1.23 mmol); the reaction mixture was then heated at 70° C. and stirred for 1 hour. After 1 hour, Sodium cyanoborohydride (121 mg, 1.83 mmol) was added to the mixture and reaction was stirred at room temperature for 1 hour. Half-saturated NaHCO$_3$ (aq.) and EtOAc was added to the mixture, aqueous phase was extracted with EtOAc, combined organics was dried over Na$_2$SO$_4$, filtered, and concentrated in vacuo. The crude material was purified on silica gel column (0 to 20% MeOH in DCM), fractions containing desired product were pooled, dried in vacuo to afford MM617 (90.5 mg, 63%) as a colourless oil. MS-ESI: calculated: 235.2830 observed: M+H=236.1266 m/z [M+H]$^+$ $^1$H NMR (400 MHz, CDCl$_3$) δ 6.73 (d, J=7.8 Hz, 1H), 6.70 (d, J=1.7 Hz, 1H), 6.64 (dd, J=7.9, 1.7 Hz, 1H), 5.92 (s, 2H), 3.77-3.70 (m, 4H), 2.76-2.68 (m, 2H), 2.59-2.47 (m, 6H). It is noted that compound MM617 corresponds with the compound having chemical formula A(VII):

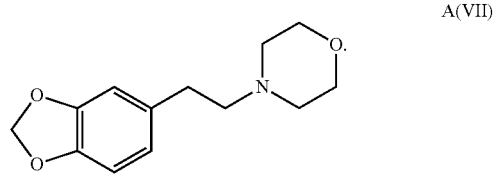 [SMILES: c1cc2c(cc1CCN1CCOCC1)OCO2]

A(VII)

Referring to FIGS. 8B-8C, it is noted that compound C was synthesized as follows. Referring initially to FIG. 8B, a 2 M solution of lithium aluminum hydride (16.7 mL, 33.3 mmol) in THF (25 mL) was cooled down in an ice bath. To it was added dropwise a solution of 3,4-(methylenedioxy)phenylacetic acid 1 (5.00 g, 27.8 mmol) in THF (30 mL), and the resulting mixture was warmed up to RT and stirred at RT for 1 h (or until completion). The reaction was quenched with sat'd aq. NaHCO$_3$ and filtered (monitor gas evolution during the quench). The filter cake was washed with EtOAc. The filtrate was concentrated under reduced pressure and taken up in EtOAc/H$_2$O. The layers were separated, and the aq. layer was extracted with EtOAc (3×50 mL). The combined organic layers were washed with brine, dried over anhydrous Na$_2$SO$_4$, filtered, and concentrated to afford the crude product (3). The crude material (light-yellow/colorless oil) was used in the next step without further purification. $^1$H NMR (400 MHz, CDCl$_3$) δ 6.77 (d, J=7.9 Hz, 1H), 6.74-6.73 (m, 1H), 6.69 (ddd, J=7.9, 1.5, 0.9 Hz, 1H), 5.94 (s, 2H), 3.80 (t, J=6.5 Hz, 2H), 2.79 (t, J=6.6 Hz, 2H).

Referring next to FIG. 8C, compound 3 (1.50 g, 9.03 mmol) was dissolved in DCM (40 mL) and Dess-Martin periodinane (5.74 g, 13.5 mmol) was added. After 1 h (or until completion), the reaction mixture was diluted with DCM and subsequently extracted with 1 M aq. NaOH, water and brine. The organic layer was dried over Na$_2$SO$_4$ and concentrated in vacuo. The crude material was purified by FC on silica gel (24 g, EA/hex 0:100 to 70:30, product eluting at 25% EA) to afford the pure product (C) as a light-yellow oil (1.10 g, 74% over two steps). $^1$H NMR (400 MHz, CDCl$_3$) δ 9.72 (t, J=2.3 Hz, 1H), 6.82 (d, J=7.9 Hz, 1H), 6.71 (d, J=1.7 Hz, 1H), 6.69-6.66 (m, 1H), 5.98 (s, 2H), 3.62 (d, J=2.4 Hz, 2H).

5-HT receptor radioligand competition assays. Activity at 5-HT$_{1A}$ and 5-HT$_{2A}$ receptors were assessed as described for Example 15, except the compound with formula A(VII) was evaluated in place of the compound with formula A(XIV). Table 1 shows radioligand competition assay results for positive controls, negative controls, and compound with formula A(VII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(VII) at the 5-HT$_{1A}$ receptor (24.1 µM, Table 1) indicates ligand-receptor binding. Similarly, the $K_i$ value obtained for the compound with formula A(VII) at the 5-HT$_{2A}$ receptor (6 µM, Table 1) indicates ligand-receptor binding.

5-HT transporter (SERT) radioligand competition assay. Activity at the serotonin transporter (SERT) was assessed as described for Example 2, except the compound with formula A(VII) was evaluated in place of the compound with formula A(VI). Table 3 shows radioligand competition assay results for positive controls, negative controls, and compound with formula A(VII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(VII) at SERT (29.9 µM, Table 3) indicates ligand binding to SERT.

In Vitro Survey of Pharmacological Interaction Profiles at Receptors and Transporters Linked to Targeted Health Conditions.

The compound with formula A(VII) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-$HT_{1B}$), HTR1D (5-$HT_{1D}$), HTR2B (5-$HT_{2B}$), HTR2C (5-$HT_{2C}$), HTR7 (5-$HT_7$), alpha2A ($\alpha_{2A}$), D2 ($D_2$), D3 ($D_3$), MT1 ($MT_1$)) and 2 transporters (DAT, NET). Assays were conducted using the same materials and procedures outlined in Example 15, except the compound with formula A(VII) was used in place of the compound with formula A(XIV). Overall assay conditions are summarized in Tables 4 and 5 for GPCR and transporters, respectively. Results for all calibrator compounds, control compounds, and test compounds including the compound with formula A(VII) are summarized in Table 6.

Head Twitch Response (HTR) Assay.

Figure 40A:
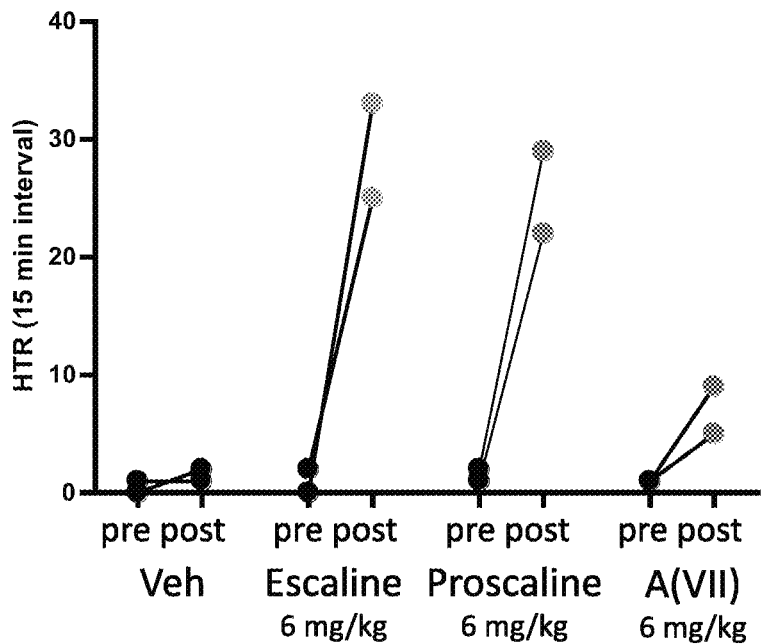
FIGS. 40A and 40B depict various graphs representing certain experimental results, notably graphs obtained in the performance of experimental assays to evaluate the pharmaceutical efficacy of an example compound having chemical formula A(VII), notably a mouse head twitch response (HTR) assay (FIG. 40A), and a mouse ear scratch response (ESR) assay (FIG. 40B).

The Head Twitch Response (HTR) in vivo mouse assay was conducted in the same manner as described for Example 3, except that compound with formula A(VII) was used in place of the compound with formula A(I). Elevated incidences of HTR within the defined period of monitoring was observed in (1) escaline-treated mice, (2) proscaline-treated mice, and (2) those treated with the compound with formula A(VII), relative to control mice treated with i.p. injected vehicle (0.9% NaCl). These results are illustrated in FIG. 40A, wherein vehicle is designated "Veh" and compound with formula A(VII) is designated "A(VII)," pre-drug data is designated "pre-", and post-drug data is designated "post." Each replicate mouse is shown as a dot, with connecting lines revealing pre- and post-data for each mouse.

Ear-Scratch Response (ESR) Assay.

Figure 40B:
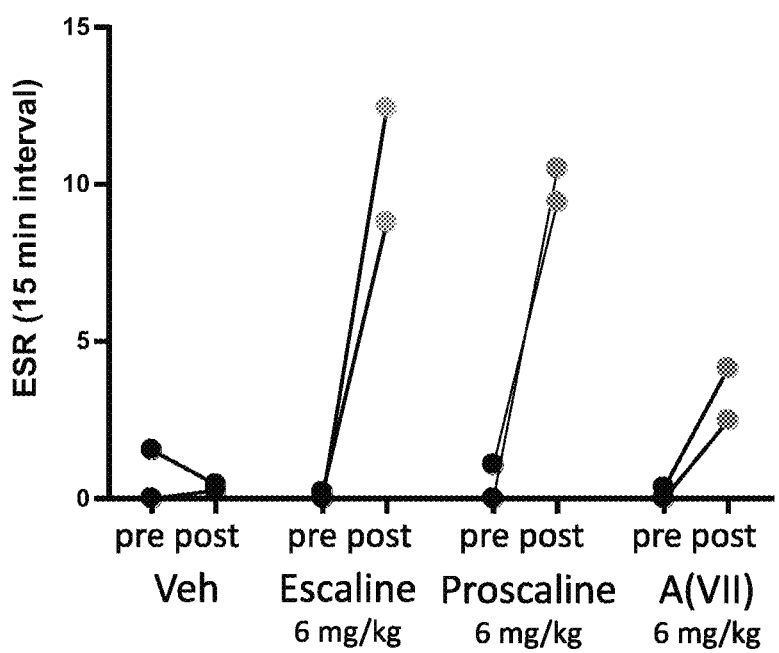

The Ear Scratch Response (ESR) in vivo mouse assay was conducted in the same manner as described for Example 3, except that compound with formula A(VII) was used in place of the compound with formula A(I). Elevated incidences of ESR within the defined period of monitoring was observed in (1) escaline-treated mice, (2) proscaline-treated mice, and (2) those treated with the compound with formula A(VII), relative to control mice treated with i.p. injected vehicle (0.9% NaCl). These results are illustrated in FIG. 40B, wherein vehicle is designated "Veh" and compound with formula A(VII) is designated "A(VII)," pre-drug data is designated "pre", and post-drug data is designated "post." Each replicate mouse is shown as a dot, with connecting lines revealing pre- and post-data for each mouse.

Example 7—Preparation and Pharmacological Analysis of a Seventh Fused Heterocyclic Mescaline Derivative Referring to FIG. 9, compound A (150 mg, 842 µmol) was dissolved in MeOH (9.00 mL) followed by the addition of Acetic acid (57.8 µL, 1.01 mmol), reaction mixture was let stirred for a few minutes before the addition of t-Butyl azetidin-3-ylcarbamate (302 mg, 1.70 mmol), pH of the mixture was checked, (around 6), reaction mixture was then heated up to 70° C. and stirred for 2 hours. After 2 hours, Sodium cyanoborohydride (170 mg, 2.57 mmol) was added to the mixture and reaction was stirred overnight at room temperature, Half sat, $NaHCO_3$ and EtOAc was added to the mixture, aqueous phase was extracted with EtOAc, combined organics was dried over $Na_2SO_4$, filtered, and concentrated in vacuo. Crude material was purified on silica gel column (0 to 20% MeOH in DCM), fractions contained product were pooled, dried in vacuo to afford MM620 (149 mg, 53%) as dark-yellow solid. MS-ESI: calculated: 334.18926 observed: M+H=335.1963 m/z [M+H]$^+$ $^1$H NMR (400 MHz, $CDCl_3$) δ 6.72 (d, J=7.8 Hz, 1H) 6.63 (d, J=1.7 Hz, 1H), 6.59 (dd, J=7.9, 1.7 Hz, 1H), 5.92 (s, 2H), 4.86 (s, 1H), 4.36-4.16 (m, 1H), 3.65 (t, J=7.3 Hz, 2H), 2.88 (s, 2H), 2.69 (dd, J=13.2, 4.4 Hz, 1H), 2.36 (d, J=8.7 Hz, 1H), 2.24 (dd, J=13.2, 8.7 Hz, 1H), 1.43 (s, 9H), 0.85 (d, J=6.2 Hz, 3H). It is noted that compound MM620 corresponds with the compound having chemical formula A(IV):

A(IV)

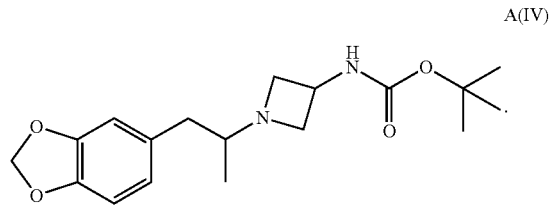 [SMILES: CC(Cc1ccc2c(c1)OCO2)N1CC(NC(=O)OC(C)(C)C)C1]

It is noted that compound A was synthesized as described in Example 3.

5-HT receptor radioligand competition assays. Activity at 5-$HT_{1A}$ and 5-$HT_{2A}$ receptors were assessed as described for Example 15, except the compound with formula A(IV) was evaluated in place of the compound with formula A(XIV). Table 1 shows radioligand competition assay results for positive controls, negative controls, and compound with formula A(IV), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(IV) at the 5-$HT_{1A}$ receptor (1.6 µM, Table 1) indicates ligand-receptor binding. Similarly, the $K_i$ value obtained for the compound with formula A(IV) at the 5-$HT_{2A}$ receptor (15 µM, Table 1) indicates ligand-receptor binding.

5-HT transporter (SERT) radioligand competition assay. Activity at the serotonin transporter (SERT) was assessed as described for Example 2, except the compound with formula A(IV) was evaluated in place of the compound with formula A(VI). Table 3 shows radioligand competition assay results for positive controls, negative controls, and compound with formula A(IV), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(IV) at SERT (49.8 µM, Table 3) indicates ligand binding to SERT.

In Vitro Survey of Pharmacological Interaction Profiles at Receptors and Transporters Linked to Targeted Health Conditions.

The compound with formula A(IV) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(IV) was used in place of the compound with formula A(XIV). Overall assay conditions are summarized in Tables 4 and 5 for GPCR and transporters, respectively. Results for all calibrator compounds, control compounds, and test compounds including the compound with formula A(IV) are summarized in Table 6.

Example 8—Preparation and Pharmacological Analysis of an Eighth Fused Heterocyclic Mescaline Derivative Referring to FIG. 10, compound A (100 mg, 561 µmol) was dissolved in MeOH (6 mL) followed by the addition of Acetic acid (38.6 µL, 673 µmol), reaction mixture was stirred for a few minutes before the addition of 1,1-dimethylhydrazine hydrochloride (108.5, 1.17 mmol). The mixture was then stirred at 65° C. for 2 h and monitored by TLC (H:E 5:1). Reaction was cooled down to RT and Sodium cyanoborohydride (106 mg, 1.75 mmol) was added to the mixture, and reaction was stirred at room temperature overnight and monitored by TLC (H:E 5:1). The reaction was quenched by Sat. NaHCO$_3$ and then extracted with DCM three times. The combined organic layers were dried over anhydrous Na$_2$SO$_4$ and concentrated under reduced pressure. The resulting residue was purified on a silica gel column (4 g) on a CombiFlash system (10% to 20% EtOAc in hexane) to provide the desired compound MM621 as colorless oil (33 mg, 26.5%). MS-ESI: Calculated for C$_{12}$H$_{19}$N$_2$O$_2$ [M+H]$^+$: 223.1447, found: 223.1439. $^1$H-NMR (400 MHz, CDCl$_3$) δ 6.84-6.51 (m, 3H), 5.94 (s, 2H), 3.01 (h, J=6.4 Hz, 1H), 2.68 (dd, J=13.6, 6.9 Hz, 1H), 2.51 (dd, J=13.6, 6.7 Hz, 1H), 2.38 (s, 6H), 2.22 (s, 1H), 1.04 (d, J=6.1 Hz, 3H). It is noted that compound MM621 corresponds with the compound having chemical formula A(VIII):

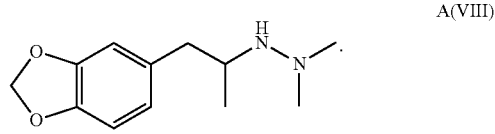 [SMILES: CC(Cc1ccc2c(c1)OCO2)NN(C)C]

A(VIII)

It is noted that compound A was synthesized as described in Example 3.

5-HT receptor radioligand competition assays. Activity at 5-HT$_{1A}$ and 5-HT$_{2A}$ receptors were assessed as described for Example 15, except the compound with formula A(VIII) was evaluated in place of the compound with formula A(XIV). Table 1 shows radioligand competition assay results for positive controls, negative controls, and compound with formula A(VIII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(VIII) at the 5-HT$_{1A}$ receptor (19.6 µM, Table 1) indicates ligand-receptor binding. Similarly, the $K_i$ value obtained for the compound with formula A(VIII) at the 5-HT$_{2A}$ receptor (3.38 µM, Table 1) indicates ligand-receptor binding.

5-HT transporter (SERT) radioligand competition assay. Activity at the serotonin transporter (SERT) was assessed as described for Example 2, except the compound with formula A(VIII) was evaluated in place of the compound with formula A(VI). Table 3 shows radioligand competition assay results for positive controls, negative controls, and compound with formula A(VIII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(VIII) at SERT (22.6 µM, Table 3) indicates ligand binding to SERT.

In Vitro Survey of Pharmacological Interaction Profiles at Receptors and Transporters Linked to Targeted Health Conditions.

The compound with formula A(VIII) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(VIII) was used in place of the compound with formula A(XIV). Overall assay conditions are summarized in Tables 4 and 5 for GPCR and transporters, respectively. Results for all calibrator compounds, control compounds, and test compounds including the compound with formula A(VIII) are summarized in Table 6.

Example 9—Preparation and Pharmacological Analysis of a Nineth Fused Heterocyclic Mescaline Derivative Referring to FIG. 11A, to a solution of E (100 mg, 517 µmol) in methanol (3.07 mL) under argon was added 6-bromo-1,3-benzodioxole-5-carboxaldehyde 10 (121 mg, 528 µmol). The reaction mixture was refluxed under inert atmosphere for 3 h. Following cooling to room temperature, sodium cyanoborohydride (90.0 mg, 1.36 mmol) was added in small portions and the resulting mixture allowed to stir at room temperature for 18 h. Solvent was removed under reduced pressure, and the residue taken up in ethyl acetate (10 mL) and washed with brine (3×10 mL). The organic layer was dried with anhydrous magnesium sulphate and solvent removed under reduced pressure. Purification by flash column chromatography on 4 g normal-phase silica using a 10% to 25% ethyl acetate-hexanes eluent system yielded MM625 as a colourless oil (114 mg, 54%). MS-ESI: calculated: 406.0649; observed: 406.0640 m/z [M+H]$^+$. $^1$H NMR (400 MHz, CDCl$_3$) δ 6.96 (s, 1H), 6.82-6.75 (m, 2H), 6.67 (d, J=2.1 Hz, 1H), 6.63 (dd, J=8.1, 2.1 Hz, 1H), 5.96 (s, 2H), 4.25 (s, 4H), 3.78 (d, J=13.7 Hz, 1H), 3.70 (d, J=13.7 Hz, 1H), 2.89-2.80 (m, 1H), 2.59 (qd, J=13.5, 6.8 Hz, 2H), 1.80 (s, 1H), 1.11 (d, J=6.2 Hz, 3H). It is noted that compound MM625 corresponds with the compound having chemical formula A(IX):

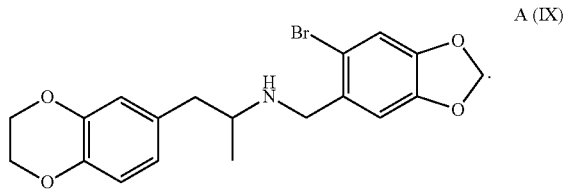 [SMILES: CC(Cc1ccc2c(c1)OCCO2)NCc1cc2c(cc1Br)OCO2]

A (IX)

Referring to FIGS. 11B-11C, it is noted that compound E was synthesized as follows. Referring initially to FIG. 11B, to a solution of 1,4-Benzodioxan-6-carboxaldehyde, 6 (5.04 g, 30.1 mmol) in glacial acetic acid (30.1 mL) under argon was added nitroethane (10.8 mL, 150 mmol) followed by ammonium acetate (7.10 g, 90.3 mmol). The reaction mixture was stirred at 80° C. for 3 h. Following cooling to room temperature, the reaction mixture was diluted with DI water (100 mL) and extracted with DCM (3×80 mL). The combined organic extracts were then washed with aqueous 0.1 M NaOH (80 mL). The organic phase was dried with magnesium sulphate and concentrated under reduced pressure to yield a crude solid. Purification by column chromatography on 80 g normal-phase silica using a 11 to 16% ethyl acetate-hexanes eluent system yielded compound 7 as a yellow solid (1.3 g, 20%). $^1$H NMR (400 MHz, CDCl$_3$) δ 8.02 (s, 1H), 7.05-6.92 (m, 3H), 4.38-4.29 (m, 4H), 2.48 (s, 3H).

Referring next to FIG. 11C, a flask cooled to 0° C. under inert atmosphere was charged with lithium aluminum hydride (7.35 mL, 14.7 mmol), to which a solution of 7 (1.30 g, 5.88 mmol) in THF (23.5 mL) was slowly added over 30 minutes. The reaction was heated to reflux overnight. Following cooling to 0° C., excess lithium aluminum hydride was quenched via the Fieser workup: the reaction mixture was diluted with THF (50 mL) and DI water (0.6 mL) was slowly added dropwise; after the reaction stopped bubbling, 15% aqueous NaOH (0.6 mL) was added dropwise, followed by DI water (1.8 mL). The reaction mixture was warmed to room temperature, magnesium sulphate was added, and the slurry allowed to stir for 15 minutes. Following filtration, the filtrate was concentrated under reduced pressure to yield a colourless oil (E) (1.11 g, 97%). The crude material was used in subsequent reactions without any purification. $^1$H NMR (400 MHz, CDCl$_3$) δ 6.81 (d, J=8.2 Hz, 1H), 6.71 (d, J=2.1 Hz, 1H), 6.67 (dd, J=8.2, 2.1 Hz, 1H), 4.26 (s, 4H), 3.17-3.08 (m, 1H), 2.63 (dd, J=13.4, 5.3 Hz, 1H), 2.41 (dd, J=13.4, 8.1 Hz, 1H), 1.36 (s, 2H), 1.12 (d, J=6.3 Hz, 3H).

5-HT receptor radioligand competition assays. Activity at 5-HT$_{1A}$ and 5-HT$_{2A}$ receptors were assessed as described for Example 15, except the compound with formula A(IX) was evaluated in place of the compound with formula A(XIV). Table 1 shows radioligand competition assay results for positive controls, negative controls, and compound with formula A(IX), in the form of $K_i$ values. In view of results for both positive and negative controls, wherein negative controls yield data insufficient for reliable $K_i$ calculations (i.e., $K_i$>1000 μM) the $K_i$ value obtained for the compound with formula A(IX) at the 5-HT$_{1A}$ receptor (0.986 μM, Table 1) indicates ligand-receptor binding. Similarly, the $K_i$ value obtained for the compound with formula A(IX) at the 5-HT$_{2A}$ receptor (19 μM, Table 1) indicates ligand-receptor binding.

5-HT transporter (SERT) radioligand competition assay. Activity at the serotonin transporter (SERT) was assessed as described for Example 2, except the compound with formula A(IX) was evaluated in place of the compound with formula A(VI). Table 3 shows radioligand competition assay results for positive controls, negative controls, and compound with formula A(IX), in the form of $K_i$ values. In view of results for both positive and negative controls, wherein negative controls yield data insufficient for reliable $K_i$ calculations (i.e., $K_i$>1000 μM) the $K_i$ value obtained for the compound with formula A(IX) at SERT (0.223 μM, Table 3) indicates ligand binding to SERT.

In Vitro Survey of Pharmacological Interaction Profiles at Receptors and Transporters Linked to Targeted Health Conditions.

The compound with formula A(IX) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(IX) was used in place of the compound with formula A(XIV). Overall assay conditions are summarized in Tables 4 and 5 for GPCR and transporters, respectively. Results for all calibrator compounds, control compounds, and test compounds including the compound with formula A(IX) are summarized in Table 6.

Example 10—Preparation and Pharmacological Analysis of a Tenth Fused Heterocyclic Mescaline Derivative Referring to FIG. 12, to a solution of E (102 mg, 528 μmol) in methanol (2.11 mL) under argon was added 6-methoxy-1,3-benzodioxole-5-carbaldehyde 9 (97.0 mg, 528 μmol). The reaction mixture was refluxed under inert atmosphere for 3 h. Following cooling to room temperature, sodium cyanoborohydride (74.0 mg, 1.18 mmol) was added in small portions and the resulting mixture allowed to stir at room temperature for 3 d. Solvent was removed under reduced pressure, and the residue taken up in ethyl acetate (10 mL) and washed with brine (3×10 mL). The organic layer was dried with anhydrous magnesium sulphate and solvent removed under reduced pressure. Purification by flash column chromatography on 4 g normal-phase silica using a 15% to 35% ethyl acetate-hexanes eluent system yielded MM626 as a colourless oil (103 mg, 55%). MS-ESI: calculated: 358.1649; observed: 358.1641 m/z [M+H]$^+$. $^1$H NMR (600 MHz, CDCl$_3$) δ 6.74 (d, J=8.2 Hz, 1H), 6.66 (s, 1H), 6.64 (d, J=2.0 Hz, 1H), 6.59 (dd, J=8.2, 2.1 Hz, 1H), 6.44 (s, 1H), 5.87 (d, J=1.6 Hz, 1H), 5.86 (d, J=1.5 Hz, 1H), 4.21 (d, J=1.2 Hz, 4H), 3.72 (d, J=13.2 Hz, 1H), 3.61-3.57 (m, 4H), 2.78 (dp, J=7.5, 6.2 Hz, 1H), 2.55 (h, J=7.5 Hz, 2H), 1.93 (s, 1H), 1.06 (d, J=6.2 Hz, 3H). It is noted that compound MM626 corresponds with the compound having chemical formula A(X):

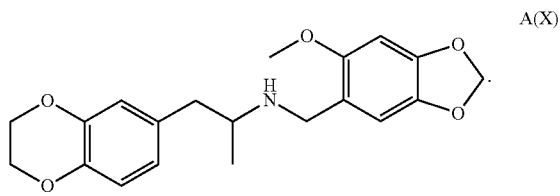 [SMILES: COc1cc2c(cc1CNC(C)Cc1ccc3c(c1)OCCO3)OCO2]

A(X)

It is noted that compound E was synthesized as described in Example 9.

5-HT receptor radioligand competition assays. Activity at 5-HT$_{1A}$ and 5-HT$_{2A}$ receptors were assessed as described for Example 15, except the compound with formula A(X) was evaluated in place of the compound with formula A(XIV). Table 1 shows radioligand competition assay results for positive controls, negative controls, and compound with formula A(X), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(X) at the 5-HT$_{1A}$ receptor (1.1 µM, Table 1) indicates ligand-receptor binding. Similarly, the K$_i$ value obtained for the compound with formula A(X) at the 5-HT$_{2A}$ receptor (12 µM, Table 1) indicates ligand-receptor binding.

5-HT transporter (SERT) radioligand competition assay. Activity at the serotonin transporter (SERT) was assessed as described for Example 2, except the compound with formula A(X) was evaluated in place of the compound with formula A(VI). Table 3 shows radioligand competition assay results for positive controls, negative controls, and compound with formula A(X), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(X) at SERT (2.36 µM, Table 3) indicates ligand binding to SERT.

In Vitro Survey of Pharmacological Interaction Profiles at Receptors and Transporters Linked to Targeted Health Conditions.

The compound with formula A(X) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($α_{2A}$), D2 (D$_2$), D3 (D$_3$), MT1 (MT$_1$)) and 2 transporters (DAT, NET). Assays were conducted using the same materials and procedures outlined in Example 15, except the compound with formula A(X) was used in place of the compound with formula A(XIV). Overall assay conditions are summarized in Tables 4 and 5 for GPCR and transporters, respectively. Results for all calibrator compounds, control compounds, and test compounds including the compound with formula A(X) are summarized in Table 6.

Example 11—Preparation and Pharmacological Analysis of an Eleventh Fused Heterocyclic Mescaline Derivative Referring to FIG. 13, to a solution of E (100 mg, 517 µmol) in methanol (3.07 mL) under argon was added 7-bromo-2,3-dihydrobenzo[b][1,4]dioxine-6-carbaldehyde (F) (128 mg, 528 µmol). The reaction mixture was refluxed under inert atmosphere for 3 h. Following cooling to room temperature, sodium cyanoborohydride (90.0 mg, 1.36 mmol) was added in small portions and the resulting mixture allowed to stir at room temperature for 18 h. Solvent was removed under reduced pressure, and the residue taken up in ethyl acetate (10 mL) and washed with brine (3×10 mL). The organic layer was dried with anhydrous magnesium sulphate and solvent removed under reduced pressure. Purification by flash column chromatography on 4 g normal-phase silica using a 15% to 27% ethyl acetate-hexanes eluent system yielded MM627 (118 mg, 54%). MS-ESI: calculated: 420.0805; observed: 420.0798 m/z [M+H]$^+$. $^1$H NMR (400 MHz, CDCl$_3$) δ 7.02 (s, 1H), 6.83 (s, 1H), 6.77 (d, J=8.2 Hz, 1H), 6.67 (d, J=2.1 Hz, 1H), 6.63 (dd, J=8.2, 2.1 Hz, 1H), 4.23 (d, J=6.7 Hz, 8H), 3.77 (d, J=13.6 Hz, 1H), 3.67 (d, J=13.6 Hz, 1H), 2.90-2.79 (m, 1H), 2.67-2.51 (m, 2H), 1.76 (s, 1H), 1.10 (d, J=6.2 Hz, 3H). It is noted that compound MM627 corresponds with the compound having chemical formula A(XI):

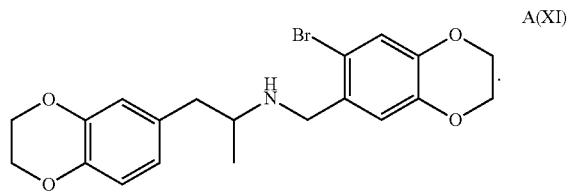 [SMILES: CC(Cc1ccc2c(c1)OCCO2)NCc1cc2c(cc1Br)OCCO2]

A(XI)

It is noted that compound E was synthesized as described in Example 9.

5-HT receptor radioligand competition assays. Activity at 5-HT$_{1A}$ and 5-HT$_{2A}$ receptors were assessed as described for Example 15, except the compound with formula A(XI) was evaluated in place of the compound with formula A(XIV). Table 1 shows radioligand competition assay results for positive controls, negative controls, and compound with formula A(XI), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XI) at the 5-HT$_{1A}$ receptor (0.507 µM, Table 1) indicates ligand-receptor binding. Similarly, the K$_i$ value obtained for the compound with formula A(XI) at the 5-HT$_{2A}$ receptor (7 µM, Table 1) indicates ligand-receptor binding.

5-HT transporter (SERT) radioligand competition assay. Activity at the serotonin transporter (SERT) was assessed as described for Example 2, except the compound with formula A(XI) was evaluated in place of the compound with formula A(VI). Table 3 shows radioligand competition assay results for positive controls, negative controls, and compound with formula A(XI), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XI) at SERT (0.191 µM, Table 3) indicates ligand binding to SERT.

In Vitro Survey of Pharmacological Interaction Profiles at Receptors and Transporters Linked to Targeted Health Conditions.

The compound with formula A(XI) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XI) was used in place of the compound with formula A(XIV). Overall assay conditions are summarized in Tables 4 and 5 for GPCR and transporters, respectively. Results for all calibrator compounds, control compounds, and test compounds including the compound with formula A(XI) are summarized in Table 6.

Example 12—Preparation and Pharmacological Analysis of a Twelfth Fused Heterocyclic Mescaline Derivative Referring to FIG. 14, to a solution of E (100 mg, 517 µmol) in Methanol (3.07 mL) under argon was added piperonal 4 (77.7 mg, 517 µmol). The reaction mixture was refluxed under inert atmosphere for 2.5 h. Following cooling to room temperature, sodium cyanoborohydride (71.9 mg, 1.09 mmol) was added in small portions and the resulting mixture allowed to stir at room temperature for 3 days. Solvent was removed under reduced pressure, and the residue taken up in ethyl acetate (10 mL) and washed with brine (3×10 mL). The organic layer was dried with anhydrous magnesium sulphate and solvent removed under reduced pressure. Purification by flash column chromatography on 4 g normal-phase silica using a 5% to 30% ethyl acetate-hexanes eluent system yielded MM628 as a colourless oil (67 mg, 40%). MS-ESI: calculated: 328.1543; observed: 328.1545 m/z [M+H]$^+$. $^1$H NMR (600 MHz, CDCl$_3$) δ 6.77 (d, J=8.2 Hz, 1H), 6.73-6.70 (m, 2H), 6.67 (dd, J=7.3, 1.7 Hz, 2H), 6.62 (dd, J=8.2, 2.1 Hz, 1H), 5.91 (s, 2H), 4.23 (s, 4H), 3.74 (d, J=13.1 Hz, 1H), 3.62 (d, J=13.1 Hz, 1H), 2.86 (h, J=6.4 Hz, 1H), 2.62 (dd, J=13.5, 7.1 Hz, 1H), 2.52 (dd, J=13.5, 6.4 Hz, 1H), 1.47 (s, 1H), 1.07 (d, J=6.3 Hz, 3H). It is noted that compound MM628 corresponds with the compound having chemical formula A(XII):

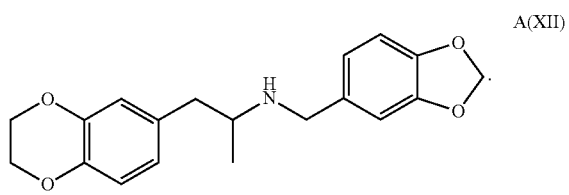 [SMILES: CC(Cc1ccc2c(c1)OCCO2)NCc1ccc2c(c1)OCO2]

A(XII)

It is noted that compound E was synthesized as described in Example 9.

5-HT receptor radioligand competition assays. Activity at 5-HT$_{1A}$ and 5-HT$_{2A}$ receptors were assessed as described for Example 15, except the compound with formula A(XII) was evaluated in place of the compound with formula A(XIV). Table 1 shows radioligand competition assay results for positive controls, negative controls, and compound with formula A(XII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XII) at the 5-HT$_{1A}$ receptor (1.2 µM, Table 1) indicates ligand-receptor binding. Similarly, the $K_i$ value obtained for the compound with formula A(XII) at the 5-HT$_{2A}$ receptor (26 µM, Table 1) indicates ligand-receptor binding.

5-HT transporter (SERT) radioligand competition assay. Activity at the serotonin transporter (SERT) was assessed as described for Example 2, except the compound with formula A(XII) was evaluated in place of the compound with formula A(VI). Table 3 shows radioligand competition assay results for positive controls, negative controls, and compound with formula A(XII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XII) at SERT (2.39 µM, Table 3) indicates ligand binding to SERT.

In Vitro Survey of Pharmacological Interaction Profiles at Receptors and Transporters Linked to Targeted Health Conditions.

The Compound with formula A(XII) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XII) was used in place of the compound with formula A(XIV). Overall assay conditions are summarized in Tables 4 and 5 for GPCR and transporters, respectively. Results for all calibrator compounds, control compounds, and test compounds including the compound with formula A(XII) are summarized in Table 6.

Example 13—Preparation and Pharmacological Analysis of a Thirteenth Fused Heterocyclic Mescaline Derivative Referring to FIG. 15, to a solution of E (100 mg, 517 µmol) in methanol (3.07 mL) under argon was added 1,4-Benzodioxan-6-carboxaldehyde 6 (86.6 mg, 528 µmol). The reaction mixture was refluxed under inert atmosphere for 3 h. Following cooling to room temperature, sodium cyanoborohydride (70.9 mg, 1.07 mmol) was added in small portions and the resulting mixture allowed to stir at room temperature for 3 days. Solvent was removed under reduced pressure, and the residue taken up in ethyl acetate (10 mL)

and washed with brine (3×10 mL). The organic layer was dried with anhydrous magnesium sulphate and solvent removed under reduced pressure. Purification by flash column chromatography on 4 g normal-phase silica using a 7% to 35% ethyl acetate-hexanes eluent system yielded MM629 as a colourless oil (92 mg, 52%). MS-ESI: calculated: 342.1700; observed: 342.1698 m/z [M+H]$^+$. $^1$H NMR (600 MHz, CDCl$_3$) δ 6.78-6.73 (m, 3H), 6.70-6.65 (m, 2H), 6.62 (dd, J=8.2, 2.1 Hz, 1H), 4.22 (d, J=2.8 Hz, 8H), 3.72 (d, J=13.1 Hz, 1H), 3.61 (d, J=13.1 Hz, 1H), 2.87 (h, J=6.4 Hz, 1H), 2.63 (dd, J=13.5, 7.0 Hz, 1H), 2.51 (dd, J=13.5, 6.4 Hz, 1H), 1.51 (s, 1H), 1.06 (d, J=6.3 Hz, 3H). It is noted that compound MM629 corresponds with the compound having chemical formula A(XIII):

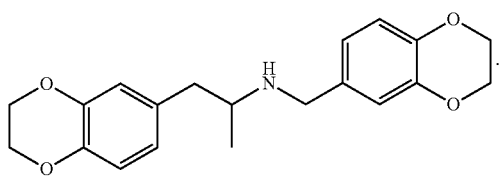

A(XIII)

It is noted that compound E was synthesized as described in Example 9.

5-HT receptor radioligand competition assays. Activity at 5-HT$_{1A}$ and 5-HT$_{2A}$ receptors were assessed as described for Example 15, except the compound with formula A(XIII) was evaluated in place of the compound with formula A(XIV). Table 1 shows radioligand competition assay results for positive controls, negative controls, and compound with formula A(XIII), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(XIII) at the 5-HT$_{1A}$ receptor (1.5 μM, Table 1) indicates ligand-receptor binding. Similarly, the K$_i$ value obtained for the compound with formula A(XIII) with formula at the 5-HT$_{2A}$ receptor (102 μM, Table 1) indicates ligand-receptor binding.

5-HT transporter (SERT) radioligand competition assay. Activity at the serotonin transporter (SERT) was assessed as described for Example 2, except the compound with formula A(XIII) was evaluated in place of the compound with formula A(VI). Table 3 shows radioligand competition assay results for positive controls, negative controls, and compound with formula A(XIII), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(XIII) at SERT (2.91 μM, Table 3) indicates ligand binding to SERT.

In Vitro Survey of Pharmacological Interaction Profiles at Receptors and Transporters Linked to Targeted Health Conditions.

The compound with formula A(XIII) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A (α$_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XIII) was used in place of the compound with formula A(XIV). Overall assay conditions are summarized in Tables 4 and 5 for GPCR and transporters, respectively. Results for all calibrator compounds, control compounds, and test compounds including the compound with formula A(XIII) are summarized in Table 6.

Example 14—Preparation and Pharmacological Analysis of a Fourteenth Fused Heterocyclic Mescaline Derivative Referring to FIG. 16A, to a solution of G (400 mg, 1.19 mmol) in DMF (4.58 mL) and H$_2$O (1.53 mL) was added pyrrolidine (504 μL, 6.01 mmol). Upon heating to 90° C. the solid completely dissolved and the mixture was left to react for 4 hours. At this point the starting material vicinal dibromide was no longer present in the reaction mixture (TLC, UV, 4:1 Hex:EtOAc) and the reaction was stopped. The mixture was poured into a separatory funnel containing 15 mL DCM and 15 mL 0.1 M HCl (aq). The aqueous phase was extracted with DCM (3×15 mL), all organic phases were combined, washed with 0.1 M HCl (aq), brine and dried over magnesium sulfate. The organic phase was concentrated to a yellow solid which was purified by chromatography on a Combi-Flash system (12 g, 100% DCM, 10% MeOH in DCM, 20% MeOH in DCM). The product was obtained as a brown solid MM631 (154 mg, 49%). MS-ESI: C$_{14}$H$_{18}$NO$_4$ ([M+H]$^+$); calculated: 264.1230, observed: 264.1229 $^1$H NMR (400 MHz, CDCl$_3$) δ 6.77 (s, 1H), 6.51 (s, 1H), 5.89 (s, 2H), 3.76 (s, 3H) 3.57 (s, 2H), 3.47 (br s, 4H), 1.89 (br s, 4H). It is noted that compound MM631 corresponds with the compound having chemical formula A(XXI):

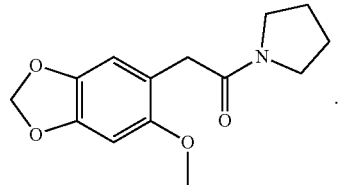

A(XXI)

Referring to FIG. 16B, it is noted that compound G was synthesized as follows. Carbon tetrabromide (2.85 g, 8.33 mmol) was dissolved in 15 mL of DCM and cooled to 0° C. Slowly added to this, in a drop-wise manner was Triphenylphosphine (4.41 g, 16.7 mmol) in 7 mL DCM. This mixture was left to stir for 20 minutes at 0° C. and then a solution of 6-Methoxy-1,3-benzodioxole-5-carbaldehyde (9) (750 mg, 4.16 mmol) in 8 mL of DCM was added in a drop-wise manner. The mixture was left at 0° C. for 4 hours. At this point no starting material was observed in the mixture (TLC-UV, 4:1 Hex:EtOAc) and the mixture was slowly added to 150 mL of diethyl ether under rapid stirring. The resulting white precipitate was filtered away and the filtrate was washed with water (2×50 mL), brine and dried with MgSO$_4$. The organic layer was concentrated to provide a white solid as a crude mixture. After purification (CombiFlash system, 24 g silica column, Hex:EtOAc 100:0 to 80:20) intermediate G (1.10 g, 78%) was isolated as a white solid. $^1$H NMR (400 MHz, CDCl$_3$) δ 7.54 (s, 1H), 7.31 (s, 1H), 6.50 (s, 1H), 5.95 (s, 2H), 3.78 (s, 3H).

5-HT receptor radioligand competition assays. Activity at 5-HT$_{1A}$ and 5-HT$_{2A}$ receptors were assessed as described for Example 15, except the compound with formula A(XXI) was evaluated in place of the compound with formula A(XIV). Table 1 shows radioligand competition assay results for positive controls, negative controls, and compound with formula A(XXI), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(XXI) at the 5-HT$_{1A}$ receptor (71.3 μM, Table 1) indicates ligand-receptor binding. Similarly, the K$_i$ value obtained for the compound with formula A(XXI) at the 5-HT$_{2A}$ receptor (338.1 μM, Table 1) indicates ligand-receptor binding.

5-HT transporter (SERT) radioligand competition assay. Activity at the serotonin transporter (SERT) was assessed as described for Example 2, except the compound with formula A(XXI) was evaluated in place of the compound with formula A(VI). Table 3 shows radioligand competition assay results for positive controls, negative controls, and compound with formula A(XXI), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(XXI) at SERT (846.7 μM, Table 3) suggests SERT binding at higher ligand concentrations.

In Vitro Survey of Pharmacological Interaction Profiles at Receptors and Transporters Linked to Targeted Health Conditions.

The compound with formula A(XXI) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($α_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XXI) was used in place of the compound with formula A(XIV). Overall assay conditions are summarized in Tables 4 and 5 for GPCR and transporters, respectively. Results for all calibrator compounds, control compounds, and test compounds including the compound with formula A(XXI) are summarized in Table 6.

Example 15—Preparation and Pharmacological Analysis of a Fifteenth Fused Heterocyclic Mescaline Derivative Referring to FIG. 17, under argon atmosphere was dissolved MM631 (100 mg, 380 μmol) in dry THF (3.44 mL) and cooled to 0° C. Once cool, lithium aluminum hydride in THF (2 M, 190 μL, 380 μmol) was carefully added. The mixture was warmed to room temperature and left to react overnight. Monitoring by TLC (UV, DCM:MeOH 9:1) showed that a reaction had occurred. The flask was cooled to 0° C. and any remaining LiAlH$_4$ was quenched with water. The resulting mixture was poured into a separatory funnel containing 15 mL of water and 15 mL of EtOAc. The aqueous layer was extracted with EtOAc (3×15 mL), all organic layers were combined, washed with brine, dried (MgSO$_4$) and concentrated under reduced pressure. Purification was carried out on a CombiFlash system (4 g silica, DCM:MeOH 100% DCM to 90:10) to yield MM632 (65.0 mg, 69%) as a light brown oil. MS-ESI: C$_{14}$H$_{20}$NO$_3$ [M+H]$^+$; calculated: 250.1438, observed: 250.1434 $^1$H NMR (400 MHz, CDCl$_3$) δ 6.67 (s, 1H), 6.50 (s, 1H), 5.88 (s, 2H), 3.75 (s, 3H), 2.80-2.76 (m, 2H), 2.65-2.61 (m, 6H), 1.86-1.79 (m, 4H). It is noted that compound MM632 corresponds with the compound having chemical formula A(XIV):

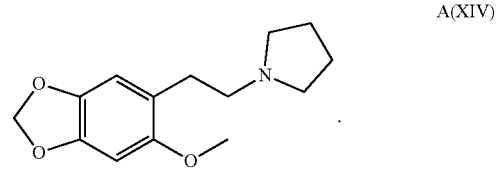 [SMILES: COc1cc2c(cc1CCN1CCCC1)OCO2]

A(XIV)

5-HT Receptor Radioligand Competition Assays

Figure 35A:
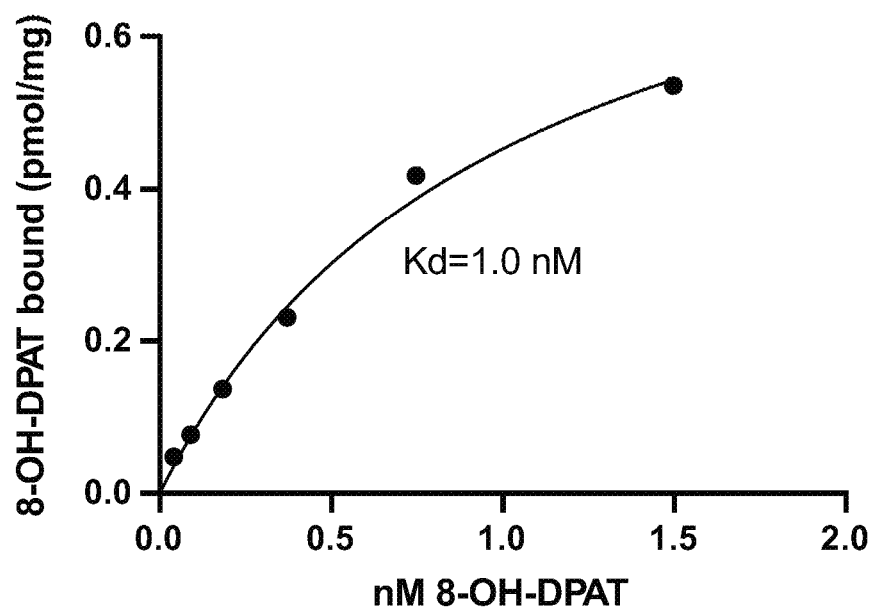
FIGS. 35A, 35B, 35C, 35D, 35E, 35F, 35G, 35H, 35I, 35J, 35K, and 35L depict various graphs representing certain experimental results, notably graphs obtained in the performance of experimental assays to evaluate the pharmaceutical efficacy of an example compound having chemical formula A(XIV), notably a radioligand $5\text{-HT}_{1A}$ receptor saturation binding assay using radiolabeled 8-hydroxy-DPAT [propyl-2,3-ring-1,2,3-$^3$H] (binding curve) (FIG. 35A); a $5\text{-HT}_{1A}$ receptor competition assay using DMSO (negative control) (FIG. 35B); a $5\text{-HT}_{1A}$ receptor competition assay using tryptophan (negative control) (FIG. 35C); a $5\text{-HT}_{1A}$ receptor competition assay using serotonin (positive control) (FIG. 35D); a $5\text{-HT}_{1A}$ receptor competition assay using mescaline (positive control) (FIG. 35E); a $5\text{-HT}_{1A}$ receptor competition assay using 2C-B (positive control) (FIG. 35F); a $5\text{-HT}_{1A}$ receptor competition assay using MDMA (positive control) (FIG. 35G); a $5\text{-HT}_{1A}$ receptor competition assay using escaline (FIG. 35H); a $5\text{-HT}_{1A}$ receptor competition assay using proscaline (FIG. 35I); a $5\text{-HT}_{1A}$ receptor competition assay using fluoxetine (positive control) (FIG. 35J); a 5-HT$_{1A}$ receptor competition assay using vortioxetine (positive control) (FIG. 35K); a 5-HT$_{1A}$ receptor competition assay using the compound with formula A(XIV) (FIG. 35L).
Figure 35B:
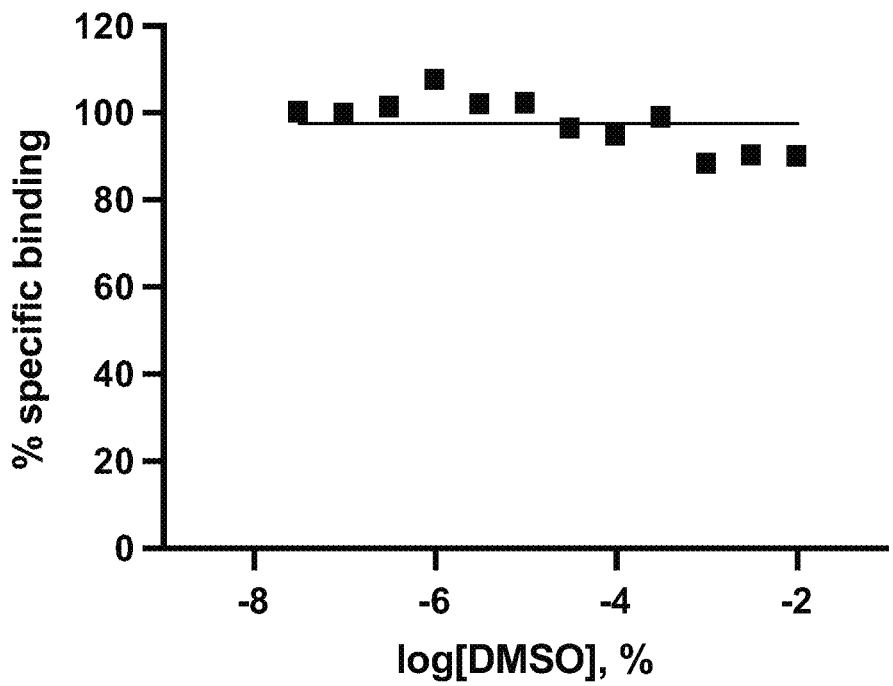
Figure 35C:
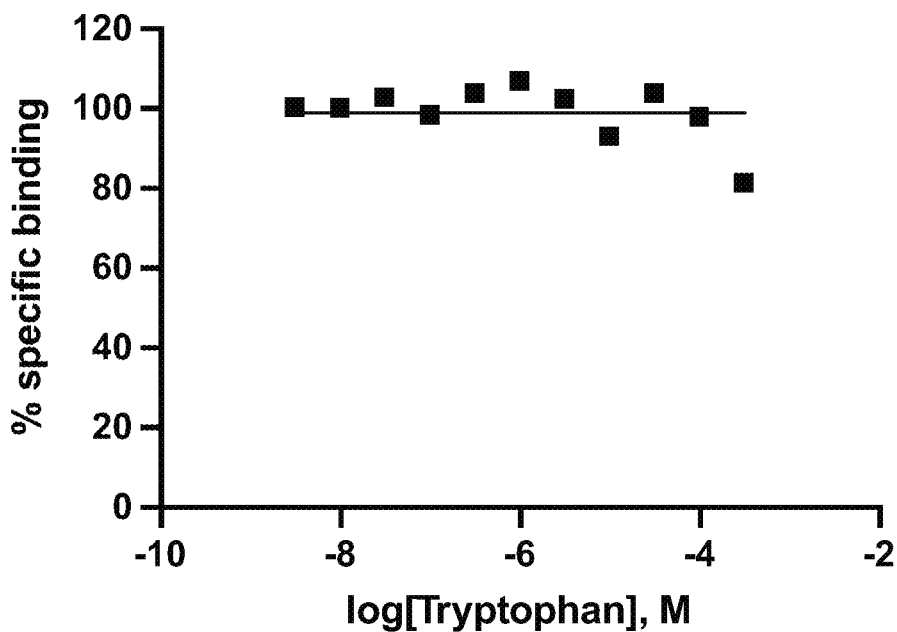
Figure 35D:
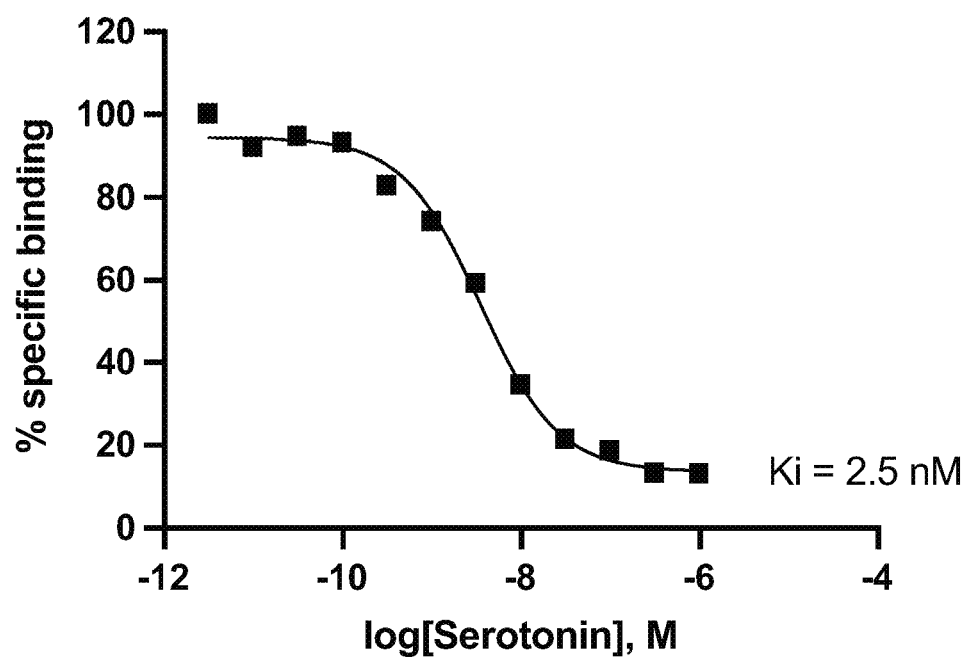
Figure 35E:
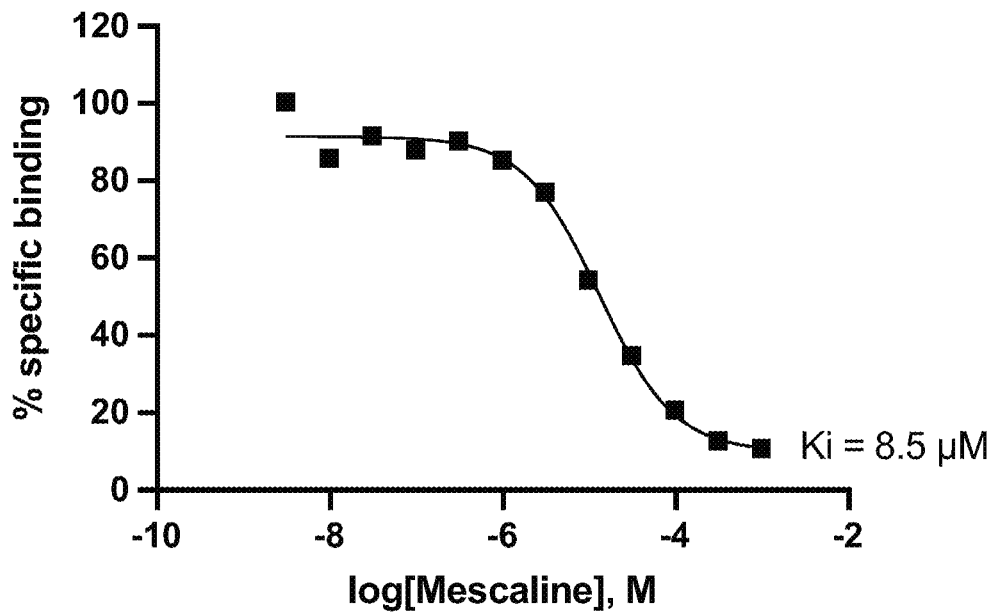
Figure 35F:
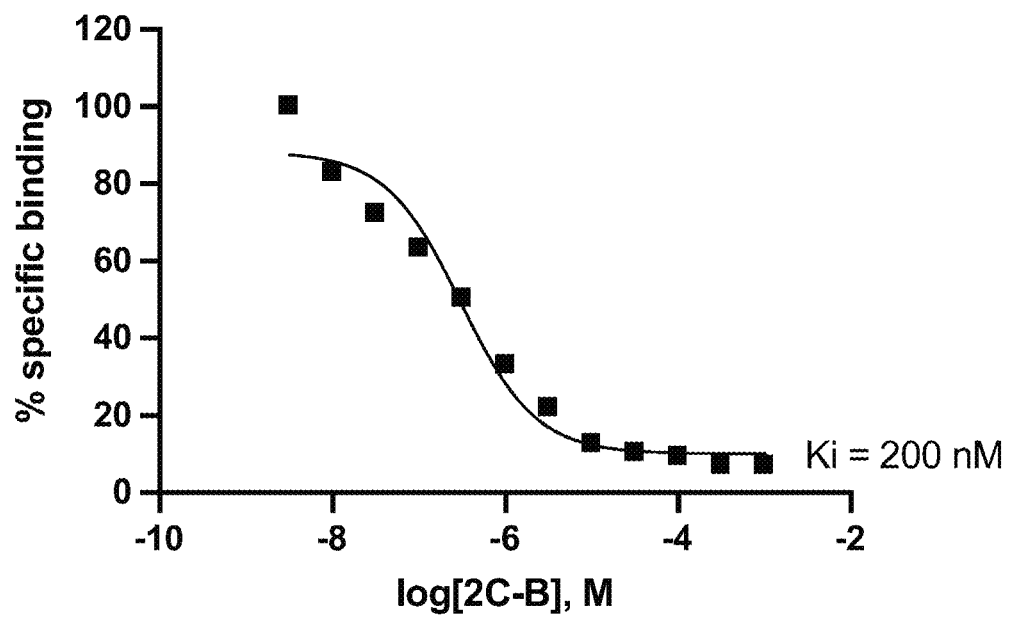
Figure 35G:
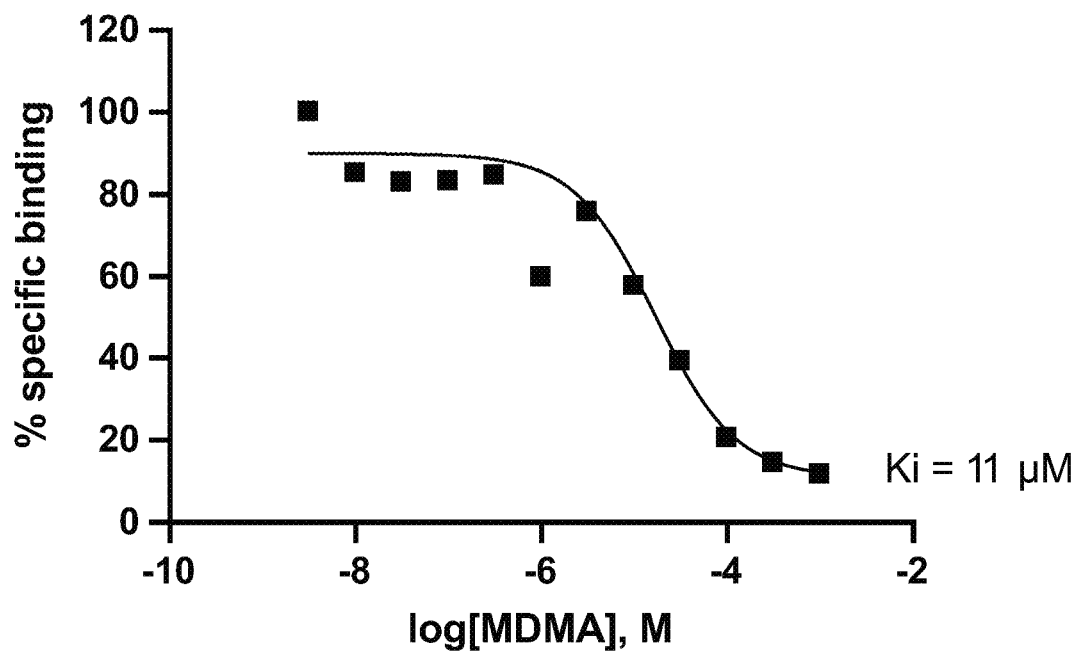
Figure 35H:
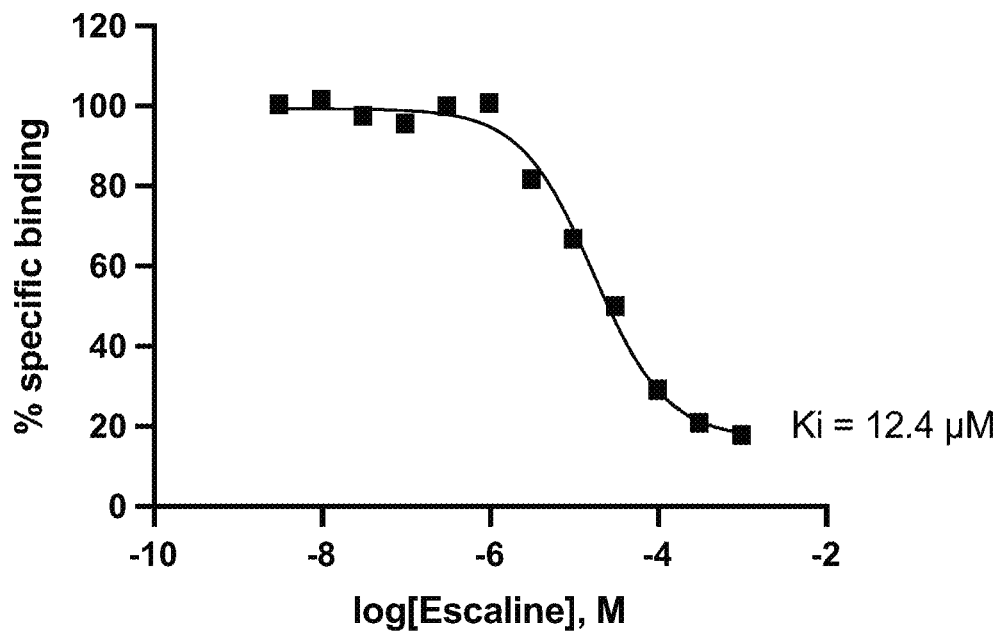
Figure 35I:
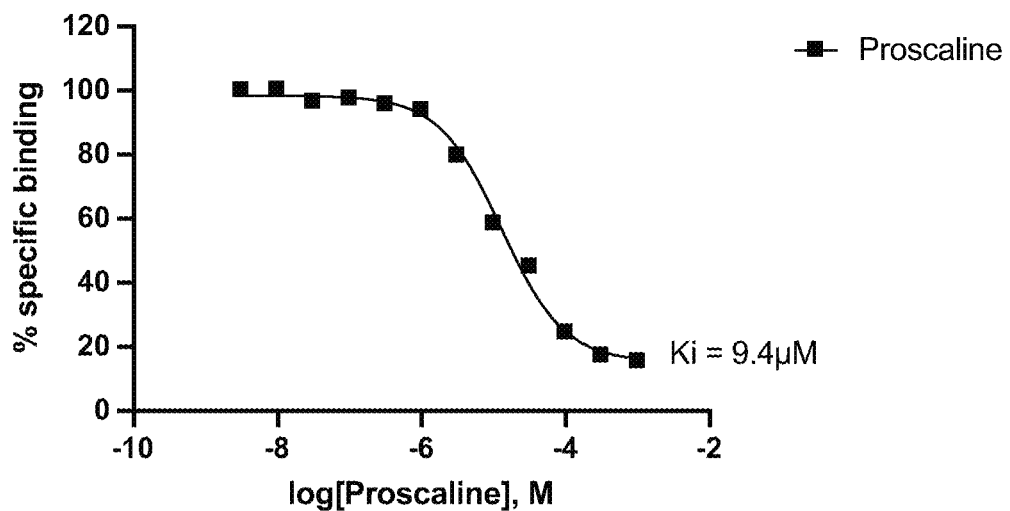
Figure 35J:
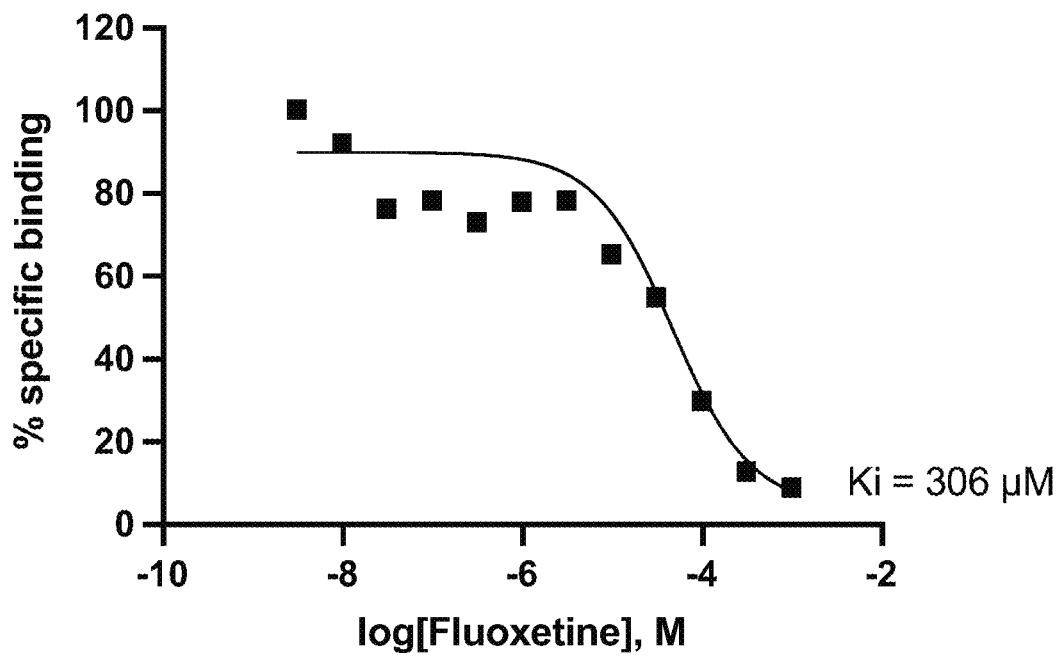
Figure 35K:
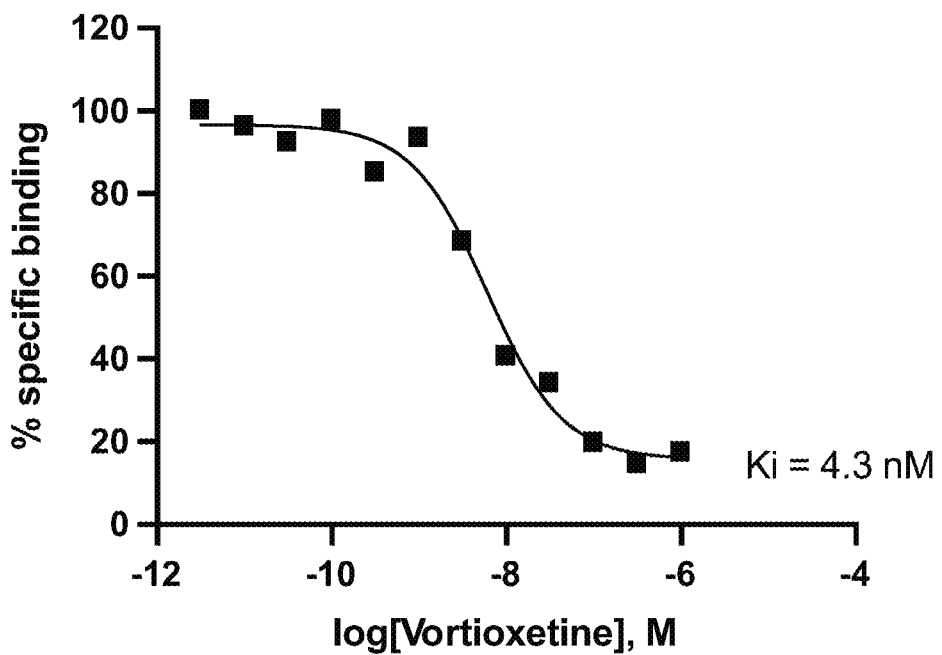
Figure 35L:
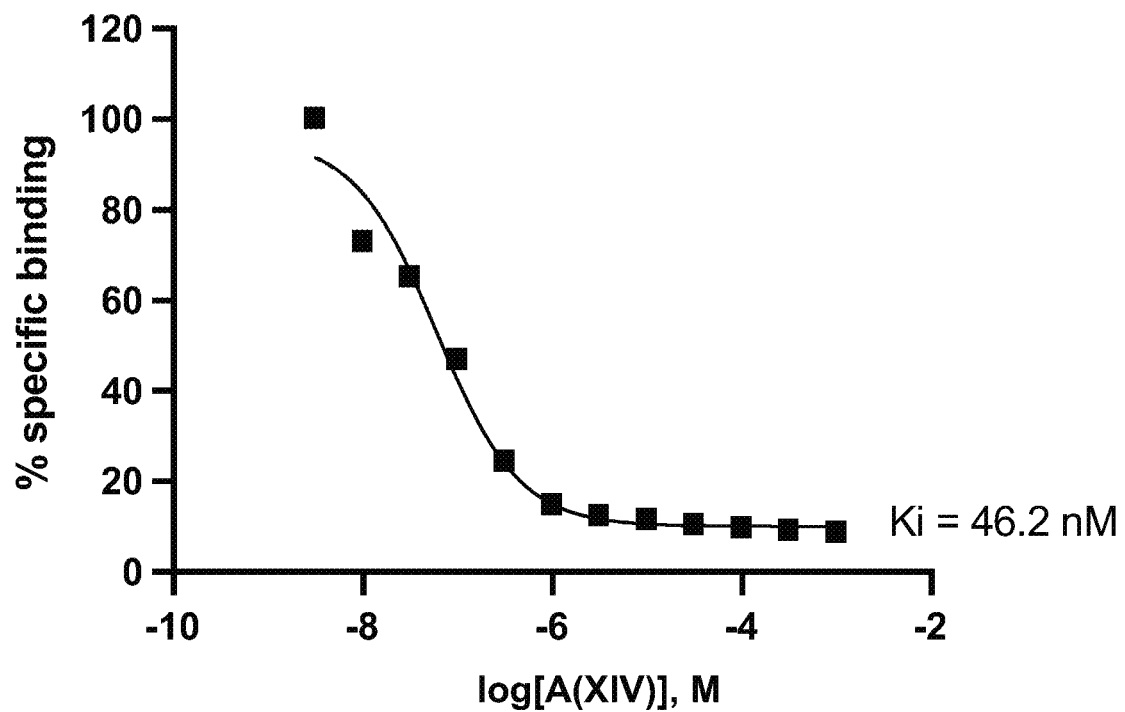

5-HT$_{1A}$ receptor. Competition assays were performed as follows: SPA beads (RPNQ0011), radiolabeled 8-hydroxy-DPAT [propyl-2,3-ring-1,2,3-$^3$H] (labelled 7-(dipropylamino)-5,6,7,8-tetrahydronaphthalen-1-ol; NET929250U0), membranes containing 5-HT$_{1A}$ (6110501400UA), and isoplate-96 microplate (6005040) were from Perkin Elmer (perkinelmer.com). Radioactive binding assays were carried out using a scintillation proximity assay (SPA; Maguire et al., 2012, Methods in Molecular Biology 897:31-77). For saturation binding assays, mixtures of 10 μg of membrane containing HT$_{1A}$ receptor was pre-coupled to 1 mg of SPA beads at room temperature in a tube rotator for 1 h in binding buffer [50 mM Tris-HCl pH 7.4, 10 mM magnesium sulfate, 0.5 mM EDTA, 3.7% (v/v) glycerol, 1 mM ascorbic acid, 10 μM pargyline HCl]. After pre-coupling, the beads and membrane were aliquoted in an isoplate-96 microplate with increasing amounts of 8-hydroxy-DPAT [propyl-2,3-ring-1,2,3-$^3$H] (0.1525 nM to 5 nM) and incubated for two hours at room temperature in the dark with shaking. After incubation, the samples were read on a MicroBeta 2 Microplate Counter (perkinelmer.com). Non-specific binding was carried out in the presence of 100 μM of metergoline (M3668-500MG, Sigma-Aldrich). Equilibrium binding constant for 8-hydroxy-DPAT (K$_D$) was determined from a saturation binding curve using one-site saturation binding analysis from GraphPad PRISM software (Version 9.2.0). Test compound was dissolved to 100 mM in dimethylsulfoxide (DMSO), and dilutions were carried out in assay buffer. Competition binding assays were performed using 0.5 nM hot 8-hydroxy-DPAT and different concentrations of DMSO (up to 1%), tryptophan (3 nM to 1 mM), or unlabelled test compounds (3 nM to 1 mM) similar to the saturation binding assay. K$_i$ values were calculated from the competition displacement data using the competitive binding analysis from GraphPad PRISM software. Serotonin was used as a positive control, as it is the natural, endogenous ligand for all serotonergic receptors. 2C-B, MDMA and mescaline were used as positive controls since they are phenylalkylamine-type molecules with relatively strong (2C-B; Rickli et al., 2015, Neuropharmacology 99: 546) or more moderate (MDMA, Simmler et al., 2013, British J. Pharmacol. 168: 458; mescaline, Rickli et al., 2016, Eur. Neuropharm. 26: 1327) 5-$HT_{1A}$ receptor binding activities, respectively. Escaline and proscaline were included in this study for comparative purposes, for although their 5-$HT_{1A}$ receptor binding mode(s) are understudied they are established mescaline-type hallucinogens with therapeutic potential (Shulgin and Shulgin, 1990. *PIHKAL: A Chemical Love Story*. 1$^{st}$ ed., Transform Press). Fluoxetine and vortioxetine were included as positive controls as they are widely prescribed pharmaceuticals with established binding to the 5-$HT_{1A}$ receptor (Owens et al., 1997, Journal of Pharmacology and Experimental Therapeutics 283:1305-1322; Celada et al., 2013, CNS Drugs 27:703-716). FIG. 35A illustrates the binding curve used to determine the $K_D$ of 8-hydroxy-DPAT. FIGS. 35B and 35C illustrate binding curves of negative controls DMSO and tryptophan. As seen in FIGS. 35B and 35C, data precluded $K_i$ determination (i.e., $K_i$>1000 μM) which indicated no binding for these negative controls. Binding curves illustrated in FIGS. 35D, 35E, 35F, and 35G reveal data permitting $K_i$ determinations for the positive controls: serotonin, mescaline, 2C-B, and MDMA respectively. The sigmoidal curves and $K_i$ values (i.e., $K_i$<1000 μM) in FIGS. 35D, 35E, 35F, and 35G reveal 5-$HT_{1A}$ receptor binding at indicated ligand concentrations. Data in FIGS. 35H and 35I suggest binding to 5-$HT_{1A}$ receptor of escaline and proscaline respectively, at the indicated concentrations. Data in FIGS. 35J and 35K indicate binding to the 5-$HT_{1A}$ receptor of fluoxetine and vortioxetine respectively. Data in FIG. 35L indicates strong binding to the 5-$HT_{1A}$ receptor of the compound with formula A(XIV). Resulting $K_i$ data for controls and test compounds in 5-$HT_{1A}$ receptor binding assays is summarized in Table 1.

Figure 36A:
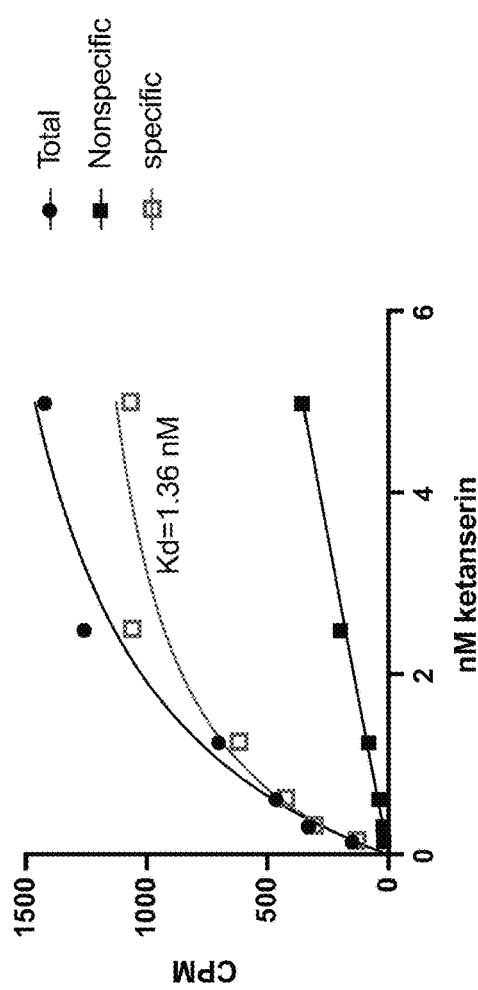
FIGS. 36A, 36B, 36C, 36D, 36E, 36F, 36G, and 36H depict various graphs representing certain experimental results, notably graphs obtained in the performance of experimental assays to evaluate the pharmaceutical efficacy of an example compound having chemical formula A(XIV), notably a radioligand 5-HT$_{2A}$ receptor saturated binding assay using radiolabeled [$^3$H-ketanserin] (binding curves) (FIG. 36A); a 5-HT$_{2A}$ receptor competition assay using psilocin (positive control) (FIG. 36B); a 5-HT$_{2A}$ receptor competition assay using tryptophan (negative control) (FIG. 36C); a 5-HT$_{2A}$ receptor competition assay using escaline (FIG. 36D); a 5-HT$_{2A}$ receptor competition assay using proscaline (FIG. 36E); a 5-HT$_{2A}$ receptor competition assay using 2C-B (positive control) (FIG. 36F); and a 5-HT$_{2A}$ receptor competition assay using MDMA (positive control) (FIG. 36G), and; a 5-HT$_{2A}$ receptor competition assay using the compound with formula A(XIV) (FIG. 36H).
Figure 36A:
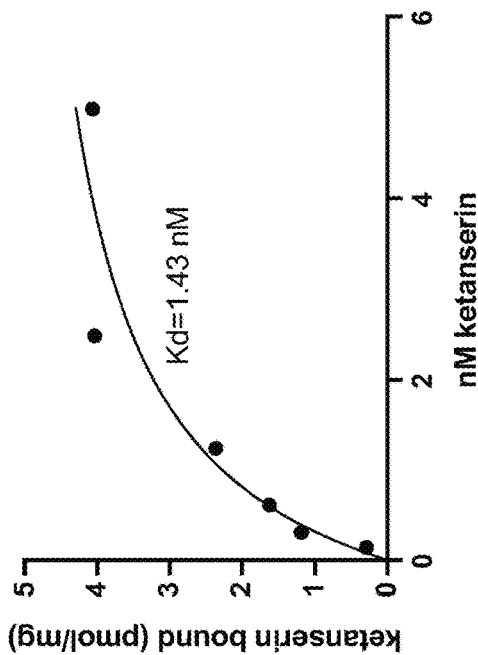
Figure 36B:
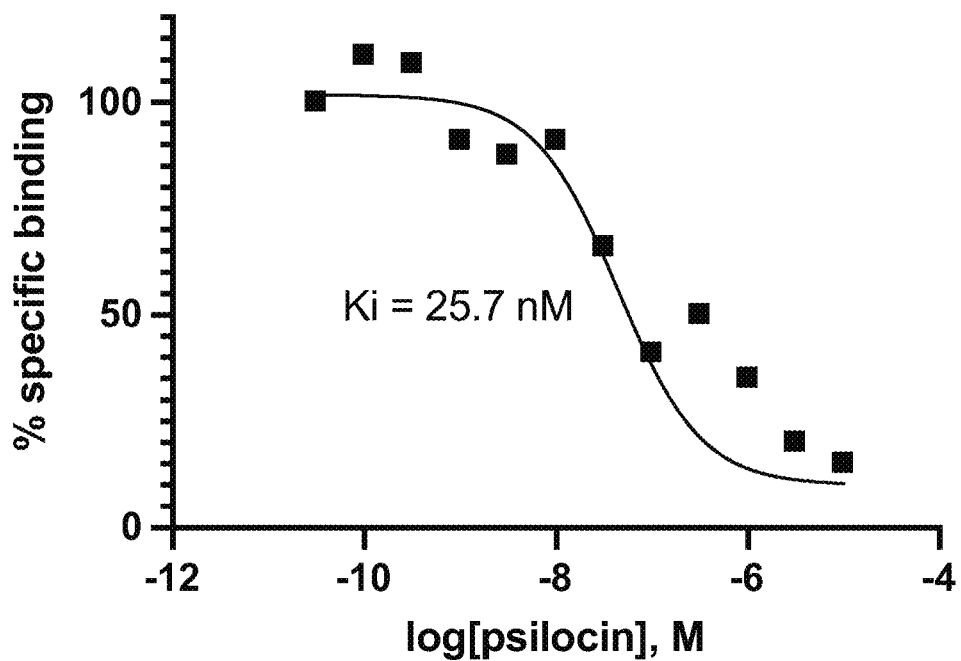
Figure 36C:
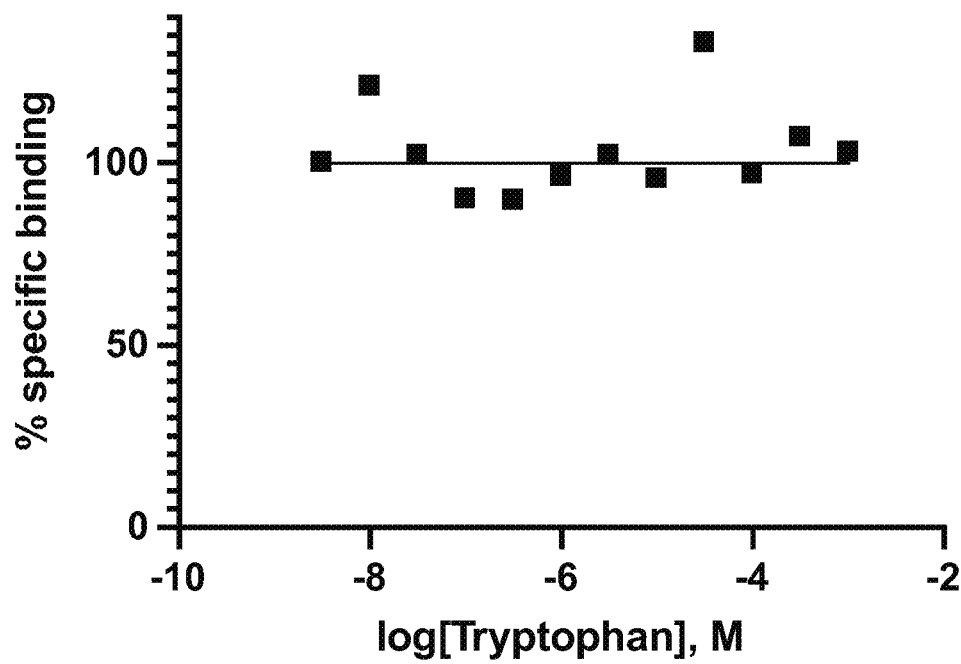
Figure 36D:
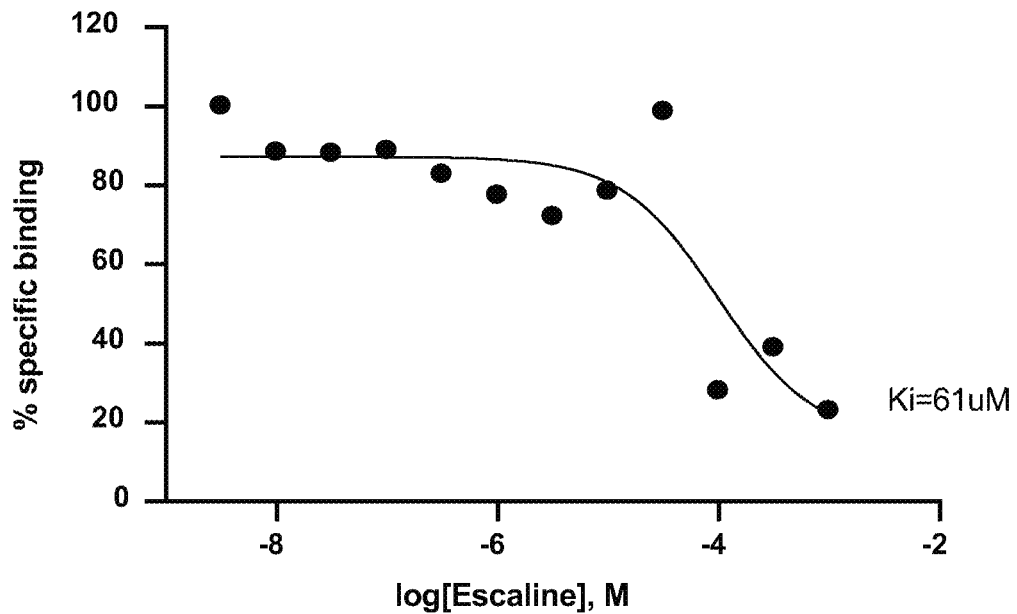
Figure 36E:
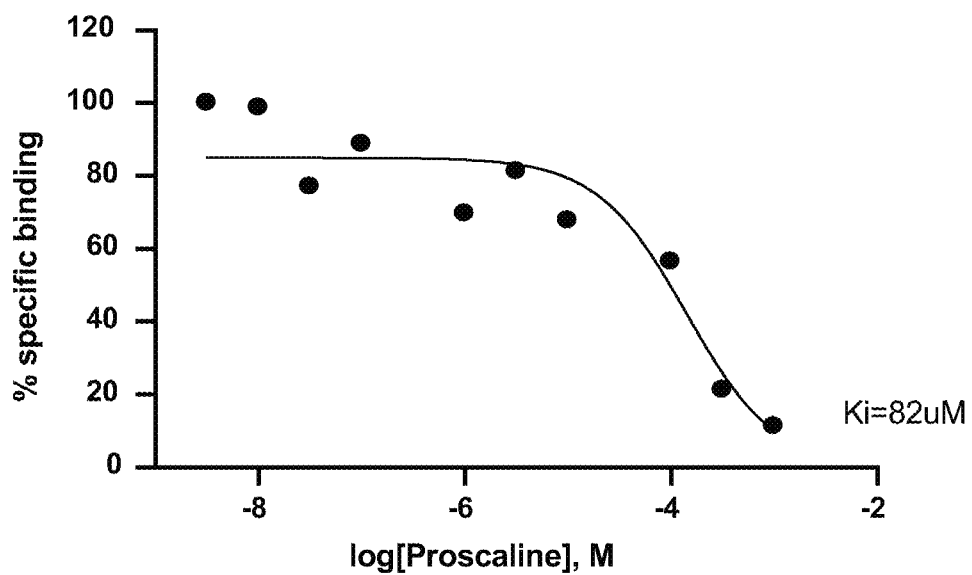
Figure 36F:
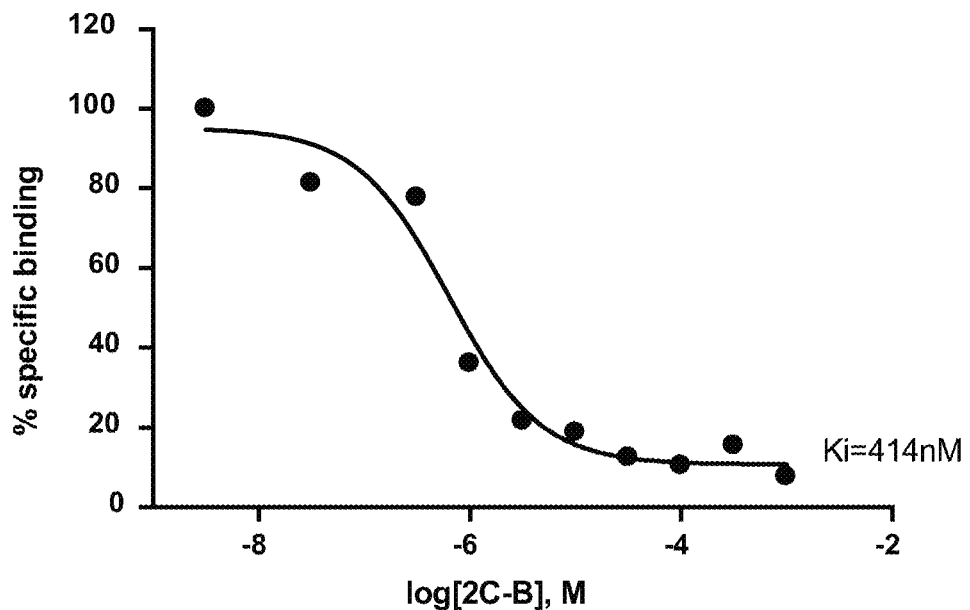
Figure 36G:
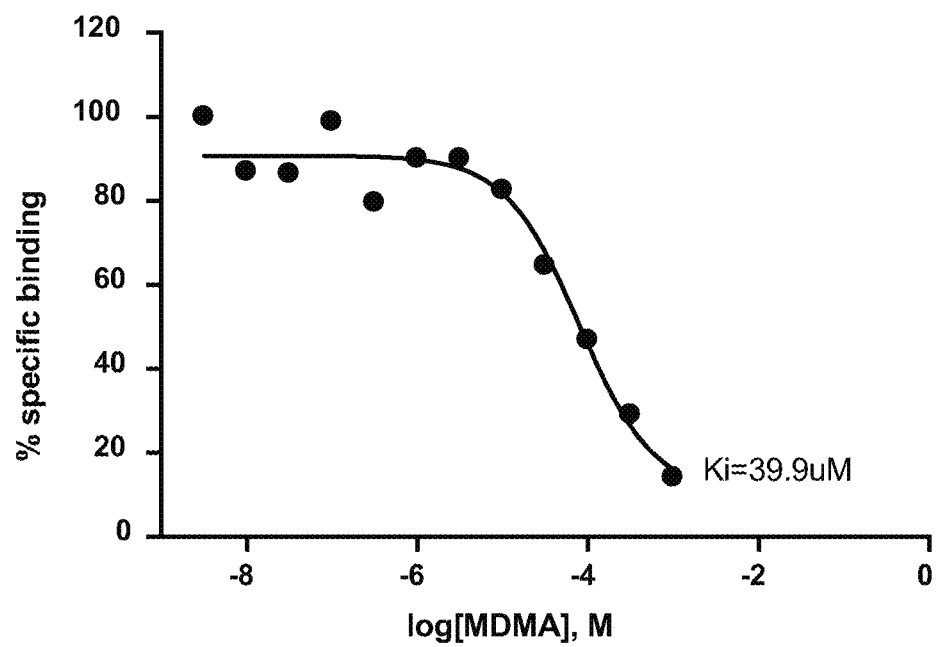
Figure 36H:
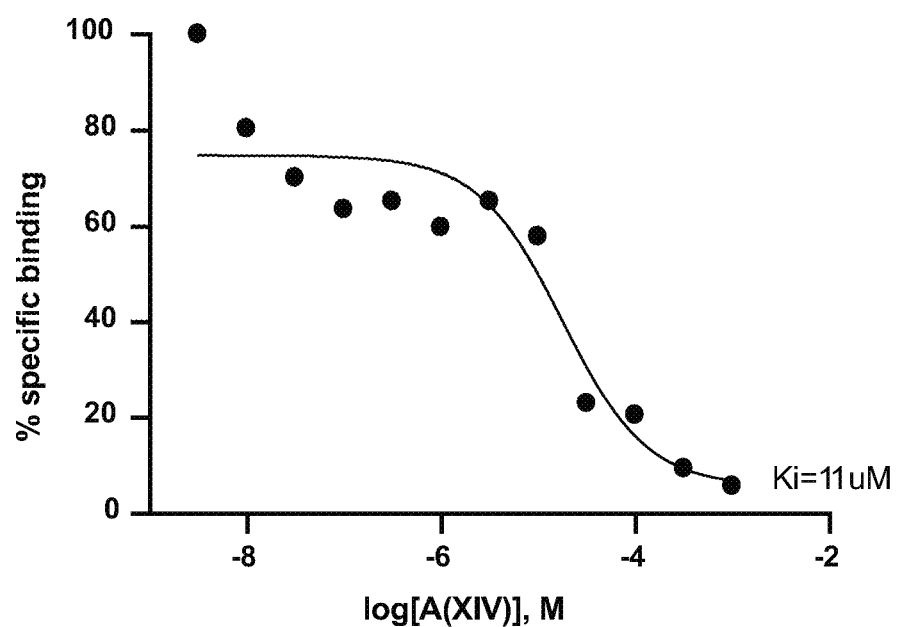

5-$HT_2A$ receptor. Competition assays were performed as for 5-$HT_{1A}$ assays with the following differences. SPA beads (RPNQ0010), [$^3$H]ketanserin (NET1233025UC), and membranes containing 5-$HT_{2A}$ (ES-313-M400UA) were from PerkinElmer. After pre-coupling, the beads and membrane were aliquoted in an isoplate-96 microplate with increasing amounts of [$^3$H]ketanserin (0.1525 nM to 5 nM). Determination of non-specific binding was carried out in the presence of 20 mM of spiperone (S7395-250MG, Sigma-Aldrich). Equilibrium binding constant for ketanserin ($K_d$) was determined from saturation binding curves using the 'one-site saturation binding analysis' method in GraphPad PRISM software (Version 9.2.0). Competition binding assays were performed using fixed (1 nM) [$^3$H]ketanserin and different concentrations of unlabeled test compounds (3 nM to 1 mM) similar to the saturation binding assay. Tryptophan was included as a negative control as it has no activity at the 5-$HT_{2A}$ receptor. In contrast, 2C-B and MDMA were used as positive controls since they are phenylalkylamine-type molecules with relatively strong (Marcher-Rørsted et al., 2020, ACS Chem. Neurosci. 11: 1238) or more moderate (Simmler et al., 2013, British J. Pharmacol. 168: 458) 5-$HT_{2A}$ receptor binding activities, respectively. Escaline and proscaline were included in this study for comparative purposes, for although their 5-$HT_{2A}$ receptor binding mode is understudied they are established mescaline-type hallucinogens known to induce head-twitch responses in mice (Halberstadt et al., 2019, J. Psychopharm. 33: 406-414). Mouse head-twitch response has been correlated with 5-$HT_{2A}$ receptor engagement (Halberstadt, 2015, Behav. Brain Res. 277: 99). Psilocin is included as an additional positive control as it exhibits well-established binding to 5-$HT_{2A}$ receptor as a partial agonist. FIG. 36A illustrates data in support of overall $K_D$ determination for ketanserin (Panel 1), in addition to the $K_D$ owed to specific binding (Panel 2). FIG. 36B illustrates data obtained for psilocin and supports binding at the 5-$HT_{2A}$ receptor for this positive control. FIG. 36C illustrates data obtained for tryptophan and supports a lack of binding at the 5-$HT_{2A}$ receptor for this negative control. FIGS. 36D and 36E reveal binding data for escaline and proscaline, respectively, and resulting $K_i$ values (i.e., <1000 μM) reveal binding at the 5-$HT_{2A}$ receptor at indicated concentrations. FIG. 36F reveals binding data for 2C-B and the resulting $K_i$ value (i.e., <1000 μM) reveals binding at the 5-$HT_{2A}$ receptor. FIG. 36G reveals binding data for MDMA and the resulting $K_i$ value (i.e., <1000 μM) reveals binding at the 5-$HT_{2A}$ receptor at the indicated concentrations. Data in FIG. 36H indicates binding to the 5-$HT_{2A}$ receptor of the compound with formula A(XIV). Resulting $K_i$ data for controls and test compounds in 5-$HT_{2A}$ receptor binding assays is summarized in Table 1.

TABLE 1

Data summary for 5-$HT_{1A}$ and 5-$HT_{2A}$ receptors radioligand competition assays.

| Molecule | 5-$HT_{1A}$, $K_i$ (μM) | 5-$HT_{2A}$, $K_i$ (μM) |
| --- | --- | --- |
| DMSO | >1000 | >1000 |
| tryptophan | >1000 | >1000 |
| serotonin | 0.0025 | N.D. |
| psilocin | N.D. | 0.0257 |
| mescaline | 8.5 | N.D. |
| 2C-B | 0.200 | 0.414 |
| MDMA | 11 | 39.9 |
| escaline | 12.4 | 61 |
| proscaline | 9.4 | 82 |
| fluoxetine | 0.306 | N.D. |
| vortioxetine | 0.0043 | N.D. |
| A(I) | 20.8 | 516.9 |
| A(II) | 0.926 | 13 |
| A(III) | 38.6 | 42 |
| A(IV) | 1.6 | 15 |
| A(V) | 1.88 | 19 |
| A(VI) | 1.52 | 5.3 |
| A(VII) | 24.1 | 6 |
| A(VIII) | 19.6 | 3.38 |
| A(IX) | 0.986 | 19 |
| A(X) | 1.1 | 12 |
| A(XI) | 0.507 | 7 |
| A(XII) | 1.2 | 26 |
| A(XIII) | 1.5 | 102 |
| A(XIV) | 0.0462 | 11 |
| A(XV) | 3.1 | 86 |
| A(XVI) | 1.4 | 39 |
| A(XVII) | 23.3 | 187.8 |
| A(XVIII) | >1000 | N.D. |
| A(XIX) | 586 | 18.76 |
| A(XX) | 123 | 42.08 |
| A(XXI) | 71.3 | 338.1 |
| A(XXII) | >1000 | N.D. |
| A(XXIII) | 5.58 | 70 |
| A(XXIV) | 0.993 | 26 |
| A(XXV) | 0.06348 | 7.65 |
| A(XXVI) | 44.44 | 31.03 |
| A(XXVII) | >1000 | N.D. |
| A(XXVIII) | 1.98 | 15.55 |
| A(XXIX) | 0.01323 | 8 |
| A(XXX) | 0.2953 | 11.7 |
| A(XXXII) | N.D. | 0.465 |

N.D. = not determined

Functional Receptor Potency Assays

Figure 37A:
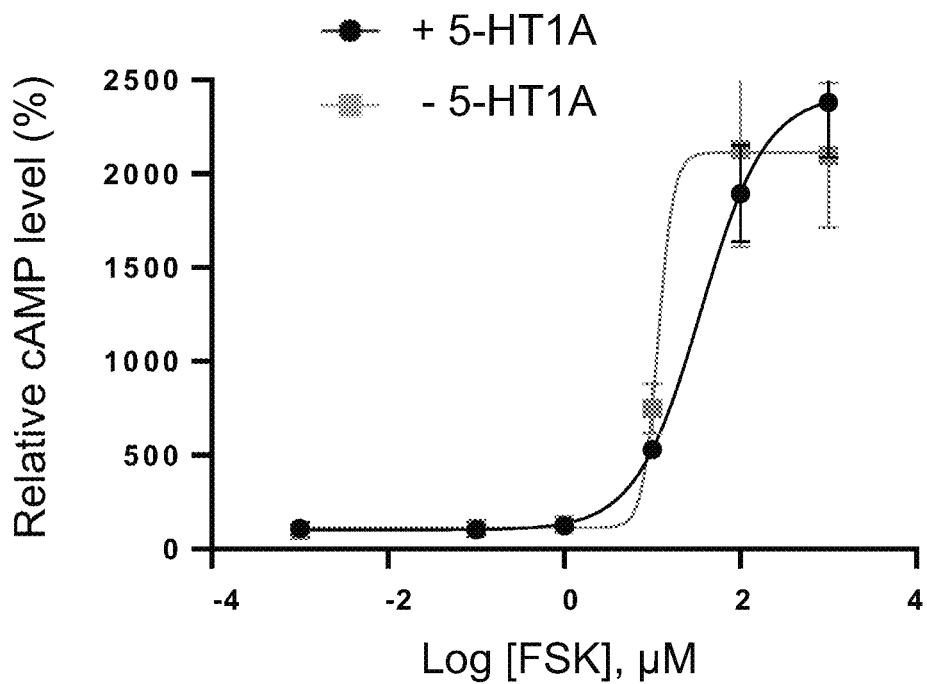
FIGS. 37A, 37B, 37C, 37D, 37E, 37F, 37G, and 37H depict various graphs representing certain experimental results, notably graphs obtained in the performance of experimental assays to evaluate the pharmaceutical efficacy of an example compound having chemical formula A(XIV), notably a 5-HT$_{1A}$ cAMP receptor assay to detect relative levels of cAMP in cells with (+5-HT$_{1A}$) and without (−5-HT$_{1A}$) 5-HT$_{1A}$ receptors stimulated with varying amounts of forskolin (FIG. 37A); a 5-HT$_{1A}$ cAMP receptor assay to detect relative levels of cAMP in cells with (+5-HT$_{1A}$) and without (−5-HT$_{1A}$) 5-HT$_{1A}$ receptors stimulated with 4 µM forskolin and varying amounts of 8-OH-DPAT (FIG. 37B); a 5-HT$_{1A}$ cAMP receptor assay to detect relative levels of cAMP in cells with (+5-HT$_{1A}$) and without (−5-HT$_{1A}$) 5-HT$_{1A}$ receptors stimulated with 4 µM forskolin and varying amounts of serotonin (FIG. 37C); a 5-HT$_{1A}$ cAMP receptor assay to detect relative levels of cAMP in cells with (+5-HT$_{1A}$) and without (−5-HT$_{1A}$) 5-HT$_{1A}$ receptors stimulated with 4 µM forskolin and varying amounts of psilocin (FIG. 37D); a 5-HT$_{1A}$ cAMP receptor assay to detect relative levels of cAMP in cells with (+5-HT$_{1A}$) and without (−5-HT$_{1A}$) 5-HT$_{1A}$ receptors stimulated with 4 µM forskolin and varying amounts of mescaline (FIG. 37E); a 5-HT$_{1A}$ cAMP receptor assay to detect relative levels of cAMP in cells with (+5-HT$_{1A}$) and without (−5-HT$_{1A}$) 5-HT$_{1A}$ receptors stimulated with 4 µM forskolin and varying amounts of MDMA (FIG. 37F); a 5-HT$_{1A}$ cAMP receptor assay to detect relative levels of cAMP in cells with (+5-HT$_{1A}$) and without (−5-HT$_{1A}$) 5-HT$_{1A}$ receptors stimulated with 4 µM forskolin and varying amounts of 2C-B (FIG. 37G); and a 5-HT$_{1A}$ cAMP receptor assay to detect relative levels of cAMP in cells with (+5-HT$_{1A}$) and without (−5-HT$_{1A}$) 5-HT$_{1A}$ receptors stimulated with 4 µM forskolin and varying amounts of compound A (XIV) (FIG. 37H).
Figure 37B:
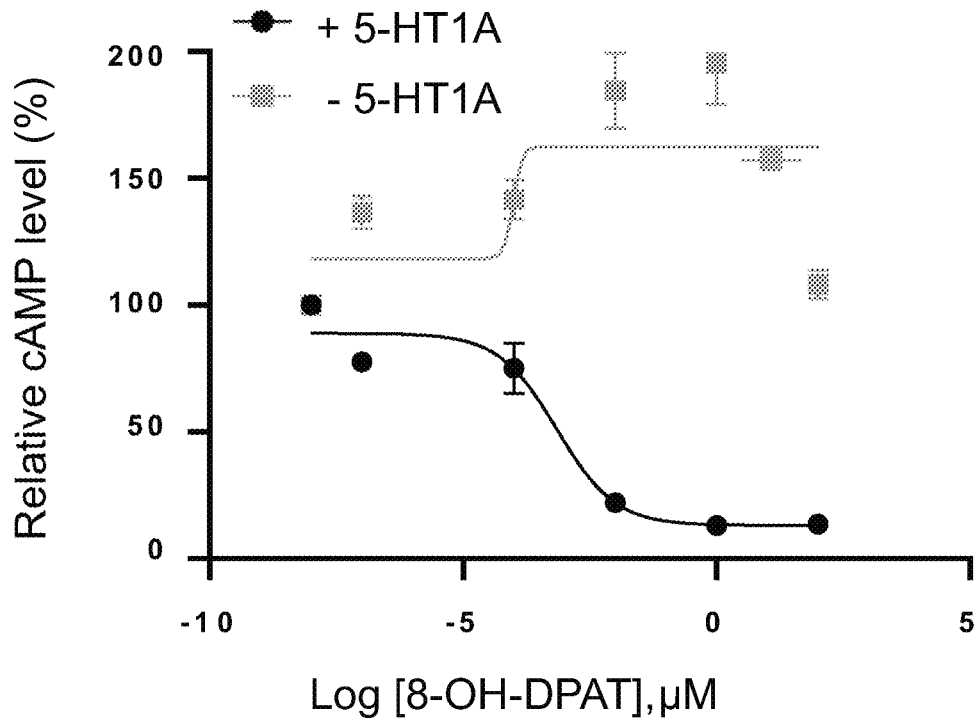
Figure 37C:
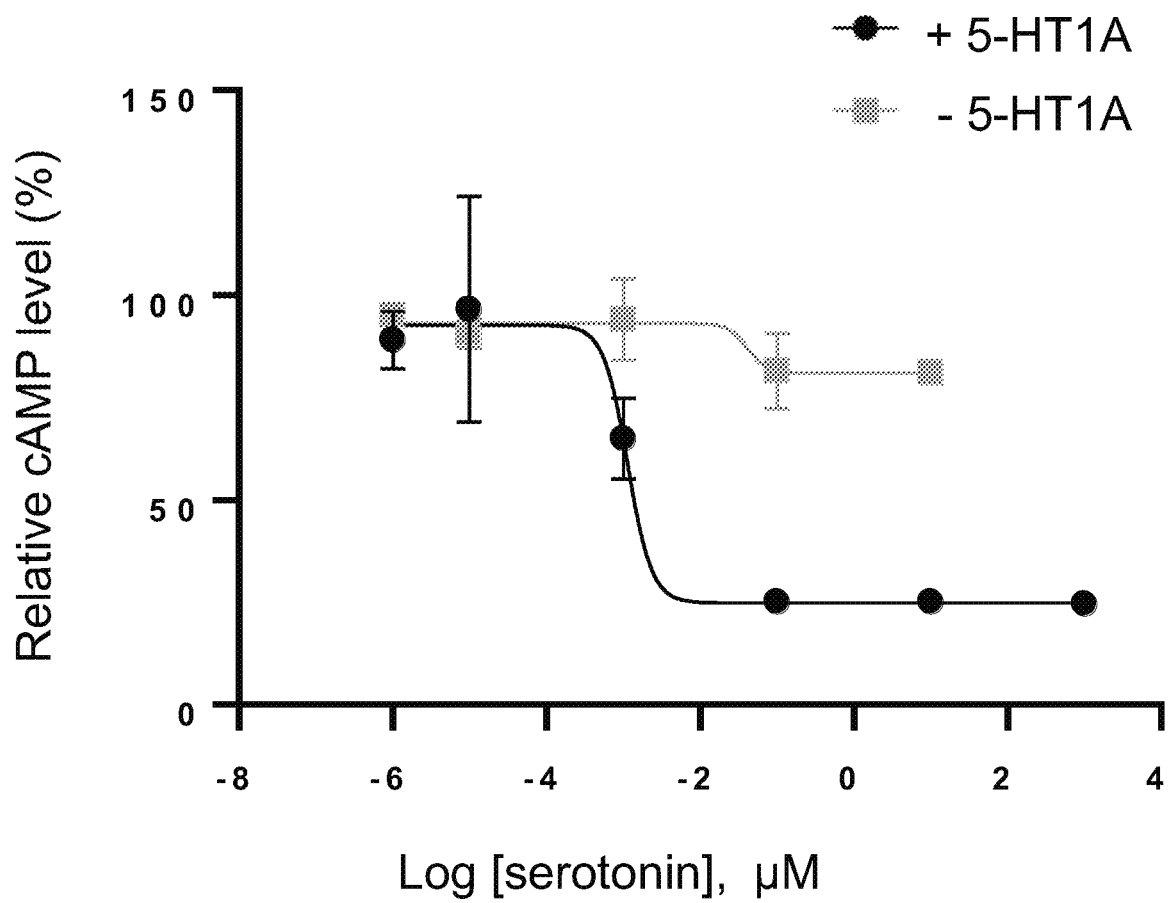
Figure 37D:
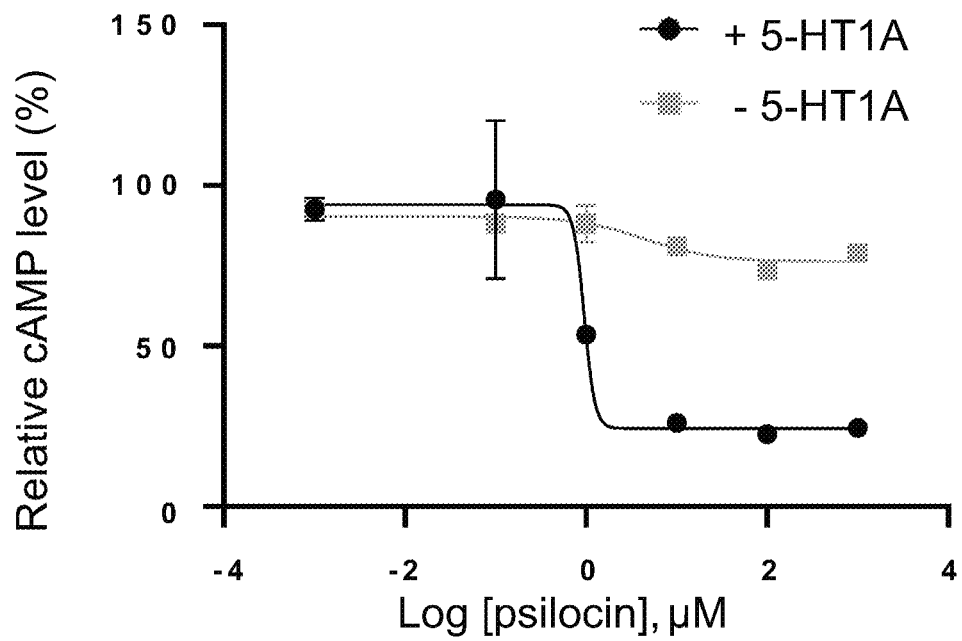

5-$HT_{1A}$ receptor. The Chinese hamster ovary (CHO)-derived cell line, CHO-K1/5-$HT_{1A}$/Gα15 (GenScript M00330), stably transformed to express 5-$HT_{1A}$ serotonin receptor, was used to evaluate specific agonist-mediated stimulation of 5-HT$_1$A signal transduction. In these non-neuronal cells, stimulation of 5-HT$_{1A}$ activates the G$\alpha_{i/o}$ protein leading to inhibition of adenylyl cyclase (AC) type I (Rojas and Felder, 2016, Frontiers in Cellular Neuroscience 10:272; Polter and Li, 2010, Cell Signalling 22:1406-1412). In cells stimulated with 4 µM forskolin, which directly stimulates AC to elevate intracellular cAMP levels, 5-HT$_{1A}$ activation was assessed quantitatively by measuring reduced intracellular cAMP levels. All cells were grown and maintained as a monolayer in Ham's F12 nutrient mix supplemented with 10% fetal bovine serum (FBS), 200 µg/mL zeocin or 100 µg/mL hygromycin, all obtained from ThermoFisher Scientific and used according to the manufacturer's instructions. Cells were cultured and incubated at 37° C. in a humidified oxygen atmosphere with 5% $CO_2$. To evaluate the activation of 5-HT$_{1A}$ signal transduction, cells were first seeded in tissue culture-treated, white-walled, clear-bottom 96-well plates (Corning, corning.com) at a density of 30,000 cells/well in 100 mL complete growth media. Cells were cultured for 24 h in a humidified incubator at 37° C. and 5% $CO_2$. Cells were then stimulated for 20 min with test compounds, prepared in titration beginning at 1 mM and dissolved in an induction medium (serum-free culture medium containing 4 µM forskolin (Sigma-Aldrich), 500 µM isobutyl-1-methylxanthine (IBMX, Sigma-Aldrich) and 100 µM RO 20-1724 (Sigma-Aldrich). Changes in intracellular cAMP levels were measured using the commercially available cAMP-Glo Assay Kit (Promega, promega.ca) following the manufacturers protocol. The level of luminescence derived from cells stimulated with induction medium alone was used to establish the max level of intracellular cAMP (100%) for each assay run. FIG. 37A shows increasing levels of cAMP in cultured cells incubated with increasing concentrations of forskolin independent of 5-HT$_{1A}$ expression. FIG. 37B illustrates reduction in cAMP levels in 5-HT$_{1A}$ receptor expressing cells (+5-HT$_{1A}$) stimulated with 4 µM forskolin as levels of 8-OH-DPAT increase, indicating 5-HT$_{1A}$ receptor binding by 8-OH-DPAT in these cells. Conversely, this trend of decreasing % cAMP levels with increasing 8-OH-DPAT is not observed in cells lacking expression of 5-HT$_{1A}$ receptor. 8-OH-DPAT (7-(dipropylamino)-5,6,7,8-tetrahydronaphthalen-1-ol) is a well-established full agonist of the 5-HT$_{1A}$ receptor (Larsson et al., 1990, Neuropharmacology 29:85-91), and was included as a positive control to ensure functionality of the cellular response system. FIG. 37C illustrates reduction in cAMP levels in 5-HT$_{1A}$ receptor expressing cells (+5-HT$_1$A) stimulated with 4 µM forskolin as levels of serotonin increase, indicating 5-HT$_1$A receptor binding by serotonin in these cells. Conversely, this trend of decreasing % cAMP levels with increasing serotonin is not observed in cells lacking expression of 5-HT$_{1A}$ receptor. Serotonin is the innate ligand of the 5-HT$_{1A}$ receptor and was thus included as a positive control. Psilocin, MDMA and 2C-B were included as calibrator compounds, since whereas these compounds are all known to bind 5-HT$_{1A}$ receptor to various degrees (Marcher-Rørsted et al., 2020, ACS Chem. Neurosci. 11: 1238, Simmler et al., 2013, British J. Pharmacol. 168: 458) their ability to elicit a cellular response in this particular functional assay is unknown. The binding mode of mescaline to the 5-HT$_{1A}$ receptor remains understudied but owing to the structural similarity of its phenylethylamine-type backbone to other derivatives within this application, it was included for comparative purposes. FIG. 37D illustrates reduction in cAMP levels in 5-HT$_{1A}$ receptor expressing cells (+5-HT$_{1A}$) stimulated with 4 mM forskolin as levels of psilocin increase, indicating 5-HT$_{1A}$ receptor binding by psilocin in these cells.

Figure 37E:
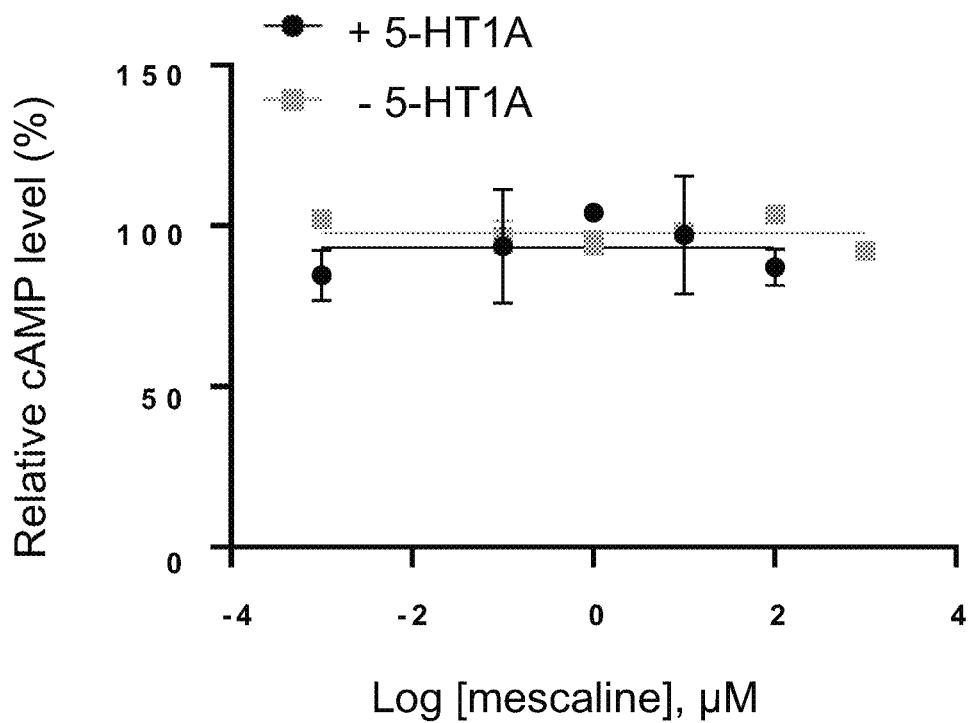
Figure 37F:
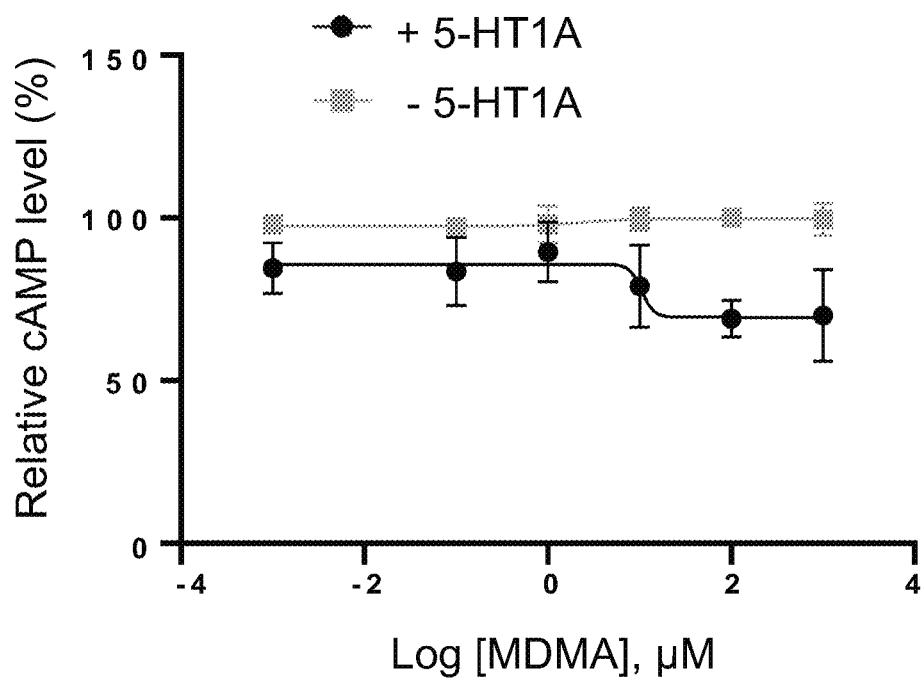
Figure 37G:
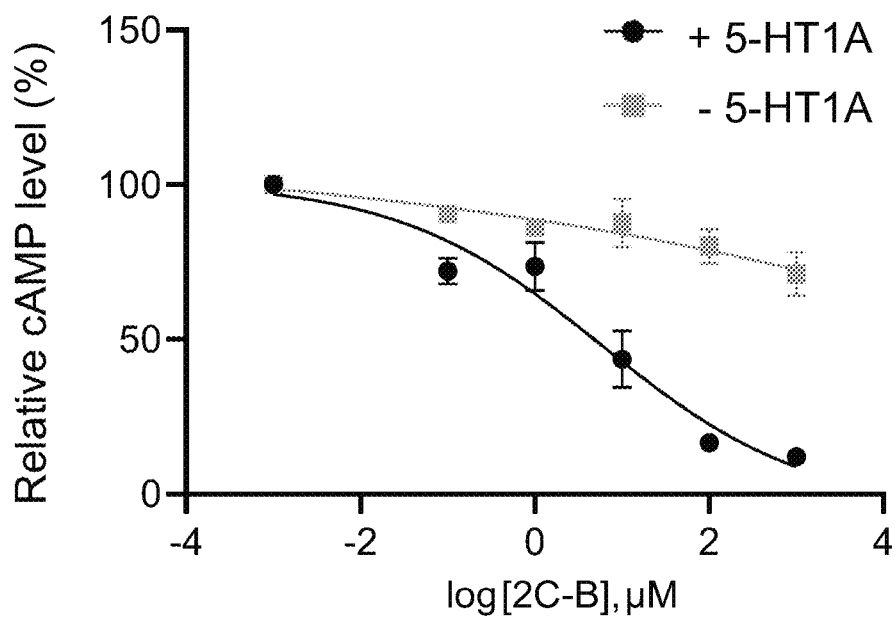
Figure 37H:
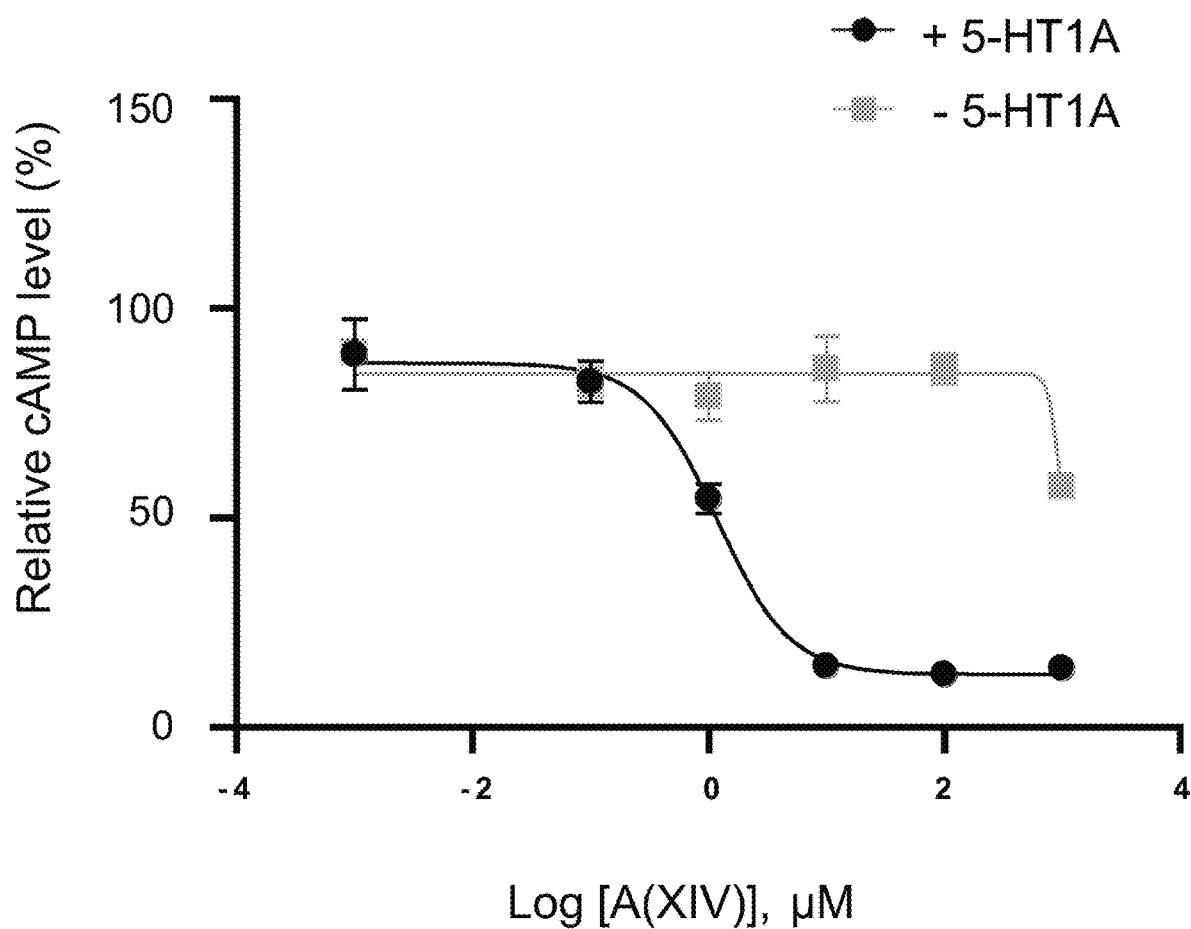

Conversely, this trend of decreasing % cAMP levels with increasing psilocin is not observed in cells lacking expression of 5-HT$_{1A}$ receptor. FIG. 37F and FIG. 37E illustrate mild or no change in cAMP levels in 5-HT$_{1A}$ receptor expressing cells (+5-HT$_{1A}$) stimulated with 4 µM forskolin as levels of MDMA and mescaline increase, respectively. These results indicate mild or no 5-HT$_{1A}$ receptor engagement by MDMA or mescaline in this cellular system, respectively. FIG. 37G illustrates reduction in cAMP levels in 5-HT$_{1A}$ receptor expressing cells (+5-HT$_{1A}$) stimulated with 4 mM forskolin as levels of 2C-B increase, indicating 5-HT$_{1A}$ receptor engagement by 2C-B in these cells. Conversely, this trend of decreasing % cAMP levels with increasing 2C-B is not observed in cells lacking expression of 5-HT$_{1A}$ receptor. 5-HT$_{1A}$ receptor engagement evaluation for the compound with formula A(XIV) (designated simply "A(XIV)" along the x-axis) is shown in FIG. 37H. Comparison of data acquired in +5-HT$_{1A}$ cultures with those acquired in −5-HT$_{1A}$ cultures indicates receptor modulation at evaluated ligand concentrations ($EC_{50}$=1.173 µM). Table 2 summarizes $EC_{50}$ data for all control, calibrator, and test compounds acquired using this functional 5-HT$_{1A}$ receptor assay.

TABLE 2

Data summary for functional 5-HT1A receptor assay.

| Molecule | 5-HT$_{1A}$, $EC_{50}$ (µM) |
|---|---|
| 5-OH-DPAT | 0.0007118 |
| serotonin | 0.001142 |
| psilocin | 0.9567 |
| mescaline | >1000 |
| 2C-B | 5.945 |
| MDMA | >1000 |
| A(XIV) | 1.173 |
| A(XXIV) | 32.28 |
| A(XXV) | 0.3424 |
| A(XXVIII) | 373.6 |
| A(XXIX) | 0.3519 |
| A(XXX) | 11.68 |

5-HT transporter (SERT) radioligand competition assay. Activity at the serotonin transporter (SERT) was assessed as described for Example 2, except the compound with formula A(XIV) was evaluated in place of the compound with formula A(VI). Table 3 shows radioligand competition assay results for positive controls, negative controls, and compound with formula A(XIV), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XIV) at SERT (23.2 µM, Table 3) indicates ligand binding to SERT.

In Vitro Survey of Pharmacological Interaction Profiles at Receptors and Transporters Linked to Targeted Health Conditions.

To expand pharmacological profiling to include a broader range of targets with known involvement in, or connection to, brain neurological disorders, the compound with formula A(XIV) was evaluated with respect to binding and/or interaction at 11 different receptors and transporters. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 G-protein coupled receptors (GPCR) receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT$_1$ (MT$_1$)) and 2 transporters (DAT, NET). Assay conditions are summarized in Tables 4 and 5 for GPCR and transporters, respectively. On-site positive controls are routinely applied as part of standard industry practice at Eurofins Cerep (https://www.eurofins.com/contact-us/worldwide-interactive-map/france/eurofins-cerep-france/) to ensure functionality of each assay. To further calibrate each assay specifically for compounds bearing the phenylalkylamine (PAA) structural scaffold, a suite of six, PAA-type calibrator compounds were additionally submitted for assays: MDMA, mescaline, 2C-B, escaline, proscaline, and DOB. Additional tryptamine-type calibrators employed in these assays included serotonin and melatonin. Tryptophan was submitted as a negative control for all assays, as tryptophan is not known to interact with any of the 11 target receptors or transporters. Seven widely marketed pharmaceuticals used in the treatment of mental health disorders with long-established pharmacological profiles were additionally submitted for assay calibration purposes: vortioxetine, trazodone, duloxetine, imipramine, agomelatine, bupropion, and vilazodone. Results for all calibrator compounds, control compounds, and test compounds including the compound with formula A(XIV) are summarized in Table 6.

ration was conducted at 4° C. Binding experiments were conducted using 100 µL membrane suspension incubated with radioligand, cold ligand to ensure specific binding by test ligand, and test molecule (10 µM) in 400 µL final volume of Tris-Mg$^{2+}$ buffer. Incubations were quenched with the addition of 4 mL ice cold washing buffer (10 mM Tris-HCl, 0.5 mM MgCl$_2$). Bound and free radioligand were separated by filtration through GF/C Whatman filters under vacuum. The filters were then washed and subjected to scintillation counting. Results were expressed as a percent of control-specific binding ([measured specific binding/control-specific binding]*100). Results for the compound with formula A(XIV) are shown in Table 6.

ii. Competition Assay to Measure Binding Affinity at D$_{2L}$ Receptor.

Assays were conducted according to methodology described by Hall and Strange [Brit. J. Pharmacol. 121:731-736, 1997] using conditions summarized in Table 4. As the purpose of this experiment was to gauge general binding potential of test ligand, rather than obtain detailed binding information yielding K$_i$ values, only a single concentration of test ligand was used (10 µM). Briefly, HEK-293 cells were used to express recombinant receptor, and membrane preparation was conducted at 4° C. Binding experiments were conducted using 100 µL membrane suspension (~25 µg

TABLE 4

Conditions summary for GPCR (receptor) binding assays.
Cold ligand is included in assays to ensure only specific binding is evaluated.
Abbreviations: h, human; r, rat.

| Receptor | Hot ligand Name | Hot ligand Type | Concentration nM | Kd nM | Cold ligand* Name | Cold ligand* µM | Incubation min/° C. |
|---|---|---|---|---|---|---|---|
| alpha2A (h) | [3H]RX 821002 | Antagonist | 1 | 0.8 | (-)epinephrine | 100 | 60/20 |
| D$_2$ (h) | [3H]methylspiperon | Antagonist | 0.3 | 0.1 | butaclamol | 10 | 60/20 |
| D$_3$ (h) | [3H]methylspiperone | Antagonist | 0.25 | 0.25 | (+)butaclamol | 10 | 60/20 |
| MT1 (ML1A) (h) | [125I]2-iodomelatonin | Agonist | 0.01 | 0.04 | melatonin | 1 | 240/20 |
| 5-HT$_{1B}$ (h) | [3H]GR125743 | Antagonist | 1 | 0.8 | serotonin | 30 | 60/37 |
| 5-HT$_{1D}$ (r) | [3H]serotonin | Agonist | 1 | 0.5 | serotonin | 10 | 60/20 |
| 5-HT$_{2B}$ (h) | [3H]mesulergine | Antagonist | 2 | 2.4 | SB206553 | 10 | 60/20 |
| 5-HT$_{2C}$ (h) | [125I](±)DOI | Agonist | 0.1 | 0.9 | (±)DOI | 10 | 60/37 |
| 5-HT$_7$ (h) | [3H]LSD | Agonist | 4 | 2.3 | serotonin | 10 | 120/20 | i. Competition Assay to Measure Binding Affinity at alpha2A Receptor.

TABLE 5

Conditions summary for transporter binding assays. Cold
ligand is included in assays to ensure only specific binding is evaluated.
Abbreviations: h, human; r, rat.

| Transporter | Hot ligand Name | Hot ligand Type | Concentration nM | Kd nM | Cold ligand* Name | Cold ligand* µM | Incubation min/° C. |
|---|---|---|---|---|---|---|---|
| NET (h) | [3H]nisoxetine | Antagonist | 1 | 2.9 | desipramine | 1 | 120/4 |
| DAT (h) | [3H]BTCP | Antagonist | 4 | 4.5 | BTCP | 10 | 120/4 |

Assays were conducted according to methodology described by Langin et al., [Eur. J. Pharmacol. 167:95-104, 1989] using conditions summarized in Table 4. As the purpose of this experiment was to gauge general binding potential of test ligand, rather than obtain detailed binding information yielding K$_i$ values, only a single concentration of test ligand was used (10 µM). Briefly, CHO cells were used to express recombinant receptor, and membrane prepamembrane protein) incubated with 100 mM NaCl, 100 µM GTP, radioligand, cold ligand to ensure specific binding by test ligand, and test molecule (10 µM) in a final volume of 250 µL. Bound and free radioligand were separated by filtration through GF/C Whatman filters under vacuum. The filters were then washed and subjected to scintillation counting. Results were expressed as a percent of control-specific binding ([measured specific binding/control-specific binding]*100). Results for the compound with formula A(XIV) are shown in Table 6.

iii. Competition Assay to Measure Binding Affinity at $D_3$ Receptor.

Assays were conducted according to methodology described by Mackenzie et al., [Eur. J. Pharmacol. 266:79-85, 1994] using conditions summarized in Table 4. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using 100 µL membrane suspension, radioligand, cold ligand to ensure specific binding by test ligand, and test molecule (10 µM) in a final volume of 400 µL. Bound and free radioligand were separated by filtration through GF/C Whatman filters under vacuum. The filters were then washed and subjected to scintillation counting. Results were expressed as a percent of control-specific binding ([measured specific binding/control-specific binding]*100). Results for the compound with formula A(XIV) are shown in Table 6.

iv. Competition Assay to Measure Binding Affinity at $MT_1$ Receptor.

Assays were conducted according to methodology described by Witt-Endersby and Dubocovich [Mol. Pharmacol. 50:166-174, 1996] using conditions summarized in Table 4. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using 100 µL membrane suspension, radioligand, cold ligand to ensure specific binding by test ligand, and test molecule (10 µM) in a final volume of 500 µL. Bound and free radioligand were separated by filtration through GF/C Whatman filters under vacuum. The filters were then washed and subjected to scintillation counting. Results were expressed as a percent of control-specific binding ([measured specific binding/control-specific binding]*100). Results for the compound with formula A(XIV) are shown in Table 6.

v. Competition Assay to Measure Binding Affinity at $5\text{-}HT_{1B}$ Receptor.

Assays were conducted according to methodology described by Maier et al., [J. Pharmacol. Exp. Therap. 330:342-351, 2009] using conditions summarized in Table 4. As the purpose of this experiment was to gauge general binding potential of test ligand, rather than obtain detailed binding information yielding $K_i$ values, only a single concentration of test ligand was used (10 µM). Briefly, Chem-1 (RBL) cells were used to express recombinant receptor, and membrane preparation was conducted at 4° C. On the day of the assay, frozen membrane preparation was diluted in assay buffer (50 mM Tris, 4 mM $MgCl_2$, 4 mM $CaCl_2$, 1 mM EDTA). Binding experiments were conducted using 80 µL membrane suspension, radioligand, cold ligand to ensure specific binding by test ligand, and test molecule (10 µM) in a final volume of 200 µL. Bound and free radioligand were separated by filtration through Beckman GF/B filters under vacuum. The filters were then washed and subjected to scintillation counting. Results were expressed as a percent of control-specific binding ([measured specific binding/control-specific binding]*100). Results for the compound with formula A(XIV) are shown in Table 6.

vi. Competition Assay to Measure Binding Affinity at $5\text{-}HT_{1D}$ Receptor.

Assays were conducted according to methodology described by Wurch et al., [J. Neurochem. 68: 410-418, 1997] using conditions summarized in Table 4. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using radioligand, 0.4 mL (~20 µg protein) membrane suspension, cold ligand to ensure specific binding by test ligand, and test molecule (10 µM). Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula A(XIV) are shown in Table 6.

vii. Competition Assay to Measure Binding Affinity at $5\text{-}HT_{2B}$ Receptor.

Assays were conducted according to methodology described by Kursar et al., [Mol. Pharmacol. 46: 227-234, 1994] using conditions summarized in Table 4. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using radioligand, 0.2 mL (~100 µg protein) membrane suspension, cold ligand to ensure specific binding by test ligand, and test molecule (10 µM) in 50 mM Tris pH 7.4. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula A(XIV) are shown in Table 6.

viii. Competition Assay to Measure Binding Affinity at $5\text{-}HT_{2C}$ Receptor.

Assays were conducted according to methodology described by Bryant et al., [Life Sci. 15: 1259-1268, 1996] using conditions summarized in Table 4. As the purpose of this experiment was to gauge general binding potential of test ligand, rather than obtain detailed binding information yielding $K_i$ values, only a single concentration of test ligand was used (10 µM). Briefly, HEK-293 cells were used to express recombinant receptor, and membrane preparation was conducted at 4° C. Binding experiments were conducted using radioligand, 0.2 mL (~100 µg protein) membrane suspension, cold ligand to ensure specific binding by test ligand, and test molecule (10 µM) to final volume of 800 µL with 3 mM $CaCl_2$), 0.1% sodium ascorbate, and 50 mM Tris pH 7.4. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula A(XIV) are shown in Table 6.

ix. Competition Assay to Measure Binding Affinity at $5\text{-}HT_7$ Receptor.

Assays were conducted according to methodology described by Shen et al., [J. Biol. Chem. 268: 18200-18204, 1993] using conditions summarized in Table 4. As the purpose of this experiment was to gauge general binding potential of test ligand, rather than obtain detailed binding information yielding $K_i$ values, only a single concentration of test ligand was used (10 µM). Briefly, HEK-293 cells were used to express recombinant receptor, and membrane preparation was conducted at 4° C. Binding experiments were conducted using radioligand, 30 µg protein (membrane suspension), cold ligand to ensure specific binding by test ligand, and test molecule (10 µM) to final volume of 200 µL. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula A(XIV) are shown in Table 6.

x. Competition Assay to Measure Binding Affinity at Norepinephrine Transporter (NET).

Assays were conducted according to methodology described by Pacholczyk et al., [Nature 350: 350-354, 1991] using conditions summarized in Table 5. As the purpose of this experiment was to gauge general binding potential of test ligand, rather than obtain detailed binding information yielding $K_i$ values, only a single concentration of test ligand was used (10 µM). Briefly, CHO cells were used to express recombinant transporter, and membrane preparation was conducted at 4° C. Binding experiments were conducted using radioligand, 30 µg protein (membrane suspension), cold ligand to ensure specific binding by test ligand, and test molecule (10 µM) to final volume of 200 µL. Bound and free radioligand were separated by filtration through Whatman glass fibre filters under vacuum. The filters were then washed and subjected to scintillation counting. Results were expressed as a percent of control-specific binding ([measured specific binding/control-specific binding]*100). Results for the compound with formula A(XIV) are shown in Table 6.

xi. Competition Assay to Measure Binding Affinity at Dopamine Transporter (DAT).

Assays were conducted according to methodology described by Pristupa et al., [Mol. Pharmacol. 45: 125-135, 1994] using conditions summarized in Table 5. As the purpose of this experiment was to gauge general binding potential of test ligand, rather than obtain detailed binding information yielding $K_i$ values, only a single concentration of test ligand was used (10 µM). Briefly, CHO cells were used to express recombinant transporter, and membrane preparation was conducted at 4° C. Binding experiments were conducted using radioligand, 50 µg protein (membrane suspension), cold ligand to ensure specific binding by test ligand, and test molecule (10 µM) to final volume of 200 µL. Bound and free radioligand were separated by filtration through Whatman glass filters under vacuum. The filters were then washed and subjected to scintillation counting. Results were expressed as a percent of control-specific binding ([measured specific binding/control-specific binding]*100). Results for the compound with formula A(XIV) are shown in Table 6.

TABLE 6

Results for GPCR and transporter competition-based binding assays. Data is shown as percent of control-specific binding.

| Compound | HT1B | HT1D | HT2B | HT2C | HT7 | α-2A | D2 | D3 | DAT | MT1 | NET |
|---|---|---|---|---|---|---|---|---|---|---|---|
| MDMA | −21 | 18 | 85 | 96 | 58 | 27 | −10 | 18 | 28 | 1 | 3 |
| Mescaline | 11 | 70 | 80 | 95 | 38 | 57 | 3 | −13 | −1 | 6 | −9 |
| 2C-B | 77 | 100 | 99 | 98 | 88 | 88 | 42 | 43 | 5 | 86 | 13 |
| Escaline | 0 | 42 | 81 | 95 | 16 | 45 | 5 | 0 | 0 | 0 | 6 |
| Proscaline | −13 | 25 | 85 | 97 | 5 | 40 | −11 | 4 | −2 | 3 | −9 |
| DOB | 20 | 84 | 97 | 98 | 65 | 66 | 9 | 25 | 3 | −3 | 6 |
| Serotonin | 97 | 101 | 96 | 102 | 100 | 18 | 15 | 73 | 8 | 7 | −3 |
| Melatonin | 0 | 13 | 52 | 19 | 8 | −7 | −20 | 2 | 4 | 98 | −2 |
| Tryptophan | −22 | 3 | 0 | 25 | 11 | −4 | −19 | −23 | 1 | −2 | 1 |
| Vortioxetine | 101 | 100 | 97 | 99 | 100 | 62 | 51 | 88 | 90 | 26 | 99 |
| Trazodone | 61 | 92 | 97 | 93 | 99 | 91 | 61 | 89 | 24 | 14 | −1 |
| Duloxetine | 52 | 63 | 95 | 92 | 94 | 54 | 24 | 66 | 94 | 23 | 99 |
| Imipramine | 36 | 39 | 94 | 98 | 93 | 57 | 82 | 92 | 23 | 29 | 99 |
| Agomelatine | −9 | 10 | 93 | 92 | 20 | 2 | −4 | 6 | 1 | 99 | 1 |
| Bupropion | 9 | −1 | −2 | 1 | 4 | 2 | −5 | 3 | 92 | 83 | 12 |
| Vilazodone | 67 | 97 | 96 | 92 | 83 | 65 | 97 | 99 | 98 | 84 | 99 |
| A(I) | 0 | 0 | 37 | 28 | 5 | 35 | 15 | 24 | 98 | 2 | 62 |
| A(II) | 17 | 43 | 84 | 94 | 59 | 60 | 13 | 56 | 86 | 3 | 77 |
| A(III) | 0 | 0 | 13 | 3 | 3 | 32 | 12 | 9 | 9 | 0 | 0 |
| A(IV) | 15 | 13 | 94 | 69 | 79 | 75 | 37 | 84 | 20 | 3 | 15 |
| A(V) | 0 | 0 | 92 | 90 | 68 | 74 | 19 | 23 | 84 | 23 | 83 |
| A(VI) | 0 | 47 | 99 | 97 | 67 | 74 | 39 | 42 | 79 | 20 | 55 |
| A(VII) | 0 | 0 | 12 | 4 | 14 | 5 | 3 | 4 | 18 | 0 | 0 |
| A(VIII) | 0 | 0 | 67 | 79 | 17 | 8 | 12 | 18 | 38 | 33 | 2 |
| A(IX) | 1 | 83 | 97 | 88 | 72 | 82 | 35 | 45 | 75 | 24 | 47 |
| A(X) | 0 | 10 | 89 | 63 | 59 | 81 | 13 | 25 | 84 | 15 | 49 |
| A(XI) | 7 | 31 | 94 | 63 | 62 | 92 | 40 | 36 | 47 | 15 | 64 |
| A(XII) | 0 | 24 | 86 | 31 | 51 | 66 | 26 | 58 | 92 | 6 | 69 |
| A(XIII) | 11 | 38 | 85 | 34 | 52 | 77 | 28 | 54 | 90 | 12 | 50 |
| A(XIV) | 7 | 28 | 63 | 90 | 75 | 54 | 12 | 46 | 0 | 7 | 0 |
| A(XV) | 1 | 29 | 58 | 36 | 58 | 6 | 0 | 53 | 39 | 0 | 11 |
| A(XVI) | 27 | 37 | 90 | 79 | 62 | 86 | 21 | 82 | 16 | 3 | 24 |
| A(XVII) | 0 | 0 | 47 | 20 | 24 | 64 | 2 | 19 | 84 | 1 | 18 |
| A(XVIII) | 6 | 0 | 9 | 3 | 6 | 0 | 0 | 5 | 5 | 6 | 1 |
| A(XIX) | 0 | 0 | 7 | 22 | 1 | 10 | 0 | 0 | 0 | 15 | 0 |
| A(XX) | 0 | 14 | 53 | 41 | 26 | 3 | 24 | 0 | 39 | 14 | 1 |
| A(XXI) | 0 | 14 | 33 | 32 | 20 | 0 | 0 | 7 | 29 | 7 | 0 |
| A(XXII) | 0 | 5 | 14 | 15 | 20 | 0 | 0 | 3 | 0 | 18 | 1 |

TABLE 6-continued

Results for GPCR and transporter competition-based binding assays. Data is shown as percent of control-specific binding.

| Compound | HT1B | HT1D | HT2B | HT2C | HT7 | α-2A | D2 | D3 | DAT | MT1 | NET |
|---|---|---|---|---|---|---|---|---|---|---|---|
| A(XXIII) | 0 | 29 | 66 | 42 | 34 | 60 | 9 | 38 | 91 | 3 | 88 |
| A(XXIV) | 0 | 29 | 43 | 76 | 35 | 11 | 7 | 13 | 5 | 0 | 0 |
| A(XXV) | 0 | 30 | 76 | 87 | 71 | 61 | 21 | 70 | 11 | 1 | 28 |
| A(XXVI) | 0 | 0 | 1 | 1 | 0 | 0 | 0 | 0 | 0 | 30 | 0 |
| A(XXVII) | 0 | 2 | 5 | 9 | 0 | 0 | 0 | 0 | 5 | 2 | 15 |
| A(XXVIII) | 0 | 1 | 15 | 53 | 15 | 26 | 6 | 16 | 0 | 0 | 0 |
| A(XXIX) | 3 | 44 | 48 | 87 | 48 | 57 | 0 | 22 | 49 | 1 | 2 |
| A(XXX) | 0 | 39 | 54 | 57 | 61 | 6 | 4 | 30 | 0 | 0 | 6 |

Example 16—Preparation and Pharmacological Analysis of a Sixteenth Fused Heterocyclic Mescaline Derivative Referring to FIG. 18, compound C (58.0 mg, 353 µmol) was dissolved in MeOH (3 mL) followed by the addition of Acetic acid (23.3 µL, 406 µmol), reaction mixture was stirred for a few minutes before the addition of t-Butyl azetidin-3-ylcarbamate (127 mg, 714 µmol), pH of reaction mixture was checked (around 6), reaction mixture was then stirred at room temperature for a few minutes, followed by the addition of Sodium cyanoborohydride (65.8 µL, 1.08 mmol). Mixture was stirred overnight at room temperature. Half sat. NaHCO$_3$ and EtOAc was added to the mixture, aqueous phase was extracted with EtOAc, combined organics was dried over Na$_2$SO$_4$, filtered, and concentrated in vacuo. crude material was purified twice on silica gel column (0 to 20% MeOH in DCM) to afford MM653 (28.00 mg, 25.0%) colourless oil. MS-ESI: calculated: 320.17361 observed: M+H=321.18079 m/z [M+H]$^+$ $^1$H NMR (400 MHz, CDCl$_3$) δ 6.72 (d, J=7.9 Hz, 1H), 6.67 (d, J=1.7 Hz, 1H), 6.62 (dd, J=7.9, 1.7 Hz, 1H), 5.92 (s, 2H), 5.04-4.84 (m, 1H), 4.38-4.21 (m, 1H), 3.73-3.64 (m, 2H), 2.97 (s, 2H), 2.75-2.66 (m, 2H), 2.58 (t, J=7.5 Hz, 2H), 1.43 (s, 9H). It is noted that compound MM653 corresponds with the compound having chemical formula A(XV):

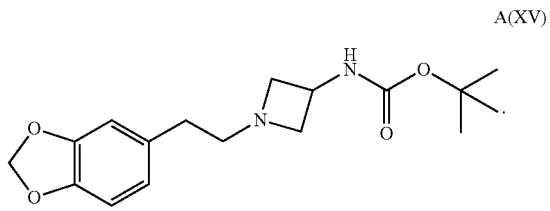 [SMILES: CC(C)(C)OC(=O)NC1CN(CCc2ccc3c(c2)OCO3)C1]

A(XV)

It is noted that compound C was synthesized as described in Example 6.

5-HT receptor radioligand competition assays. Activity at 5-HT$_{1A}$ and 5-HT$_{2A}$ receptors were assessed as described for Example 15, except the compound with formula A(XV) was evaluated in place of the compound with formula A(XIV). Table 1 shows radioligand competition assay results for positive controls, negative controls, and compound with formula A(XV), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XV) at the 5-HT$_{1A}$ receptor (3.1 µM, Table 1) indicates ligand-receptor binding. Similarly, the K$_i$ value obtained for the compound with formula A(XV) at the 5-HT$_{2A}$ receptor (86 µM, Table 1) indicates ligand-receptor binding.

5-HT transporter (SERT) radioligand competition assay. Activity at the serotonin transporter (SERT) was assessed as described for Example 2, except the compound with formula A(XV) was evaluated in place of the compound with formula A(VI). Table 3 shows radioligand competition assay results for positive controls, negative controls, and compound with formula A(XV), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XV) at SERT (64.3 µM, Table 3) indicates ligand binding to SERT.

In Vitro Survey of Pharmacological Interaction Profiles at Receptors and Transporters Linked to Targeted Health Conditions.

The compound with formula A(XV) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A (α$_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XV) was used in place of the compound with formula A(XIV). Overall assay conditions are summarized in Tables 4 and 5 for GPCR and transporters, respectively. Results for all calibrator compounds, control compounds, and test compounds including the compound with formula A(XV) are summarized in Table 6.

Example 17—Preparation and Pharmacological Analysis of a Seventeenth Fused Heterocyclic Mescaline Derivative Referring to FIG. 19, compound B (100 mg, 520 µmol) was dissolved in MeOH (4 mL) followed by the addition of Acetic acid (35.7 µL, 624 µmol). Reaction mixture was stirred for a few minutes before the addition of t-Butyl azetidin-3-ylcarbamate (187 mg, 1.05 mmol); pH was checked (around 8), reaction mixture was then heated at 65° C. and stirred for 2 hours. After 2 hours, Sodium cyanoborohydride (105 mg, 1.59 mmol) was added to the mixture and reaction was stirred overnight at room temperature. Half sat. NaHCO$_3$ and EtOAc was added to the mixture, aqueous phase was extracted with EtOAc, combined organics was dried over Na$_2$SO$_4$, filtered, and concentrated in vacuo. crude material was purified on silica gel column (0 to 20% MeOH in DCM), fractions contained product were pooled, dried in vacuo to afford MM654 (36.8 mg, 20%) as deep orange solid. MS-ESI: calculated: 348.20491 observed: M+H=349.21194 m/z [M+H]$^+$ $^1$H NMR (400 MHz, CDCl$_3$) δ 6.75 (d, J=8.1 Hz, 1H), 6.64 (d, J=2.1 Hz, 1H), 6.60 (dd, J=8.2, 2.1 Hz, 1H), 5.19-5.12 (m, 1H), 4.32-4.17 (m, 5H), 3.73 (q, J=6.8 Hz, 2H), 3.13 (s, 2H), 2.69 (dd, J=13.3, 4.6 Hz, 1H), 2.57 (s, 1H), 2.26 (dd, J=13.3, 8.7 Hz, 1H), 1.41 (s, 9H), 0.89 (d, J=6.2 Hz, 3H). It is noted that compound MM654 corresponds with the compound having chemical formula A(XVI):

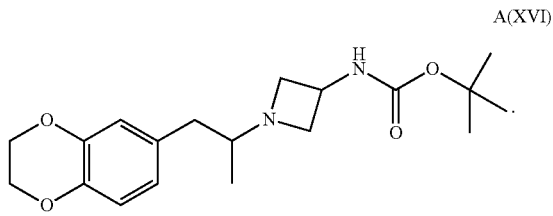 [SMILES: CC(Cc1ccc2c(c1)OCCO2)N1CC(NC(=O)OC(C)(C)C)C1]

A(XVI)

Referring to FIG. 19B, it is noted that compound B was synthesized as follows. 1,4-benzodioxane-6-acetic acid 2 (2.00 g, 10.3 mmol) was dissolved in acetic anhydride (4.97 mL, 51.5 mmol) at room temperature, and the solution was stirred and purged with nitrogen for several minutes. The reaction was initiated by the dropwise addition of 1-methylimidazole (415 µL, 5.15 mmol), and was continuously purged with a slow flow of nitrogen at room temperature until the starting material completely disappeared (TLC). After completion (16 h), water (5 mL) was added to the reaction flask. The reaction mixture was extracted with ethyl acetate (3×25 mL). The organic layers were combined and washed with saturated aq. NaHCO$_3$ (25 mL), followed by water, then dried over Na$_2$SO$_4$, filtered and concentrated. The crude product was purified using silica gel (25 g, EA/hex 0:100 to 70:30, 12 CV, products eluting at 30% EA) to afford the pure product (B) as a clear colorless oil (760 mg, 38%). $^1$H NMR (400 MHz, CDCl$_3$) δ 6.82 (d, J=8.1 Hz, 1H), 6.72 (d, J=2.1 Hz, 1H), 6.68-6.65 (m, 1H), 4.25 (s, 4H), 3.58 (s, 2H), 2.14 (s, 3H).

5-HT receptor radioligand competition assays. Activity at 5-HT$_{1A}$ and 5-HT$_{2A}$ receptors were assessed as described for Example 15, except the compound with formula A(XVI) was evaluated in place of the compound with formula A(XIV). Table 1 shows radioligand competition assay results for positive controls, negative controls, and compound with formula A(XVI), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XVI) at the 5-HT$_{1A}$ receptor (1.4 µM, Table 1) indicates ligand-receptor binding. Similarly, the K$_i$ value obtained for the compound with formula A(XVI) at the 5-HT$_{2A}$ receptor (39 µM, Table 1) indicates ligand-receptor binding.

5-HT transporter (SERT) radioligand competition assay. Activity at the serotonin transporter (SERT) was assessed as described for Example 2, except the compound with formula A(XVI) was evaluated in place of the compound with formula A(VI). Table 3 shows radioligand competition assay results for positive controls, negative controls, and compound with formula A(XVI), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XVI) at SERT (58.1 µM, Table 3) indicates ligand binding to SERT.

In Vitro Survey of Pharmacological Interaction Profiles at Receptors and Transporters Linked to Targeted Health Conditions.

The compound with formula A(XVI) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XVI) was used in place of the compound with formula A(XIV). Overall assay conditions are summarized in Tables 4 and 5 for GPCR and transporters, respectively. Results for all calibrator compounds, control compounds, and test compounds including the compound with formula A(XVI) are summarized in Table 6.

Example 18—Preparation and Pharmacological Analysis of an Eighteenth Fused Heterocyclic Mescaline Derivative Referring to FIG. 20, compound B (50.0 mg, 260 µmol) was dissolved in MeOH (3.00 mL) followed by the addition of Acetic acid (40.1 µL, 700 µmol). Reaction mixture was stirred for a few minutes before the addition of Cyclobutylamine (38.5 mg, 531 µmol). Reaction mixture was then heated up to 65° C. and stirred for 2 hours; pH of the reaction mixture was checked (around 6). After 2 hours, Sodium cyanoborohydride (51.6 mg, 780 µmol) was added to the mixture and reaction was stirred overnight at room temperature. Half sat. NaHCO$_3$ and EtOAc was added to the mixture, aqueous phase was extracted with EtOAc, combined organics was dried over Na$_2$SO$_4$, filtered, and concentrated in vacuo. crude material was purified on silica gel column (0 to 20% MeOH in DCM), fractions contained product were pooled, dried in vacuo to afford MM655 (9.0 mg, 14%) as colourless oil. MS-ESI: calculated: 247.15723 observed: M+H=248.16374 m/z [M+H]$^+$ $^1$H NMR (400 MHz, CDCl$_3$) δ 6.79 (d, J=8.1 Hz, 1H), 6.68 (d, J=2.1 Hz, 1H), 6.64 (dd, J=8.2, 2.1 Hz, 1H), 4.70 (s, 2H), 4.24 (s, 4H), 3.59 (p, J=8.1 Hz, 1H), 3.07 (dp, J=8.7, 6.3 Hz, 1H), 2.89 (dd, J=13.4, 5.5 Hz, 1H), 2.56 (dd, J=13.4, 8.7 Hz, 1H), 2.27 (dddt, J=18.2, 10.3, 7.4, 3.6 Hz, 2H), 2.13 (q, J=9.9 Hz, 1H), 2.02 (q, J=9.9 Hz, 1H), 1.84 (tdd, J=10.1, 6.4, 2.9 Hz, 1H), 1.73 (tdd, J=10.6, 8.1, 2.4 Hz, 1H), 1.14 (d, J=6.4 Hz, 3H). It is noted that compound MM655 corresponds with the compound having chemical formula A(XVII):

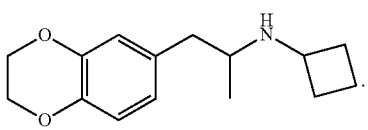

A(XVII)

It is noted that compound B was synthesized as described in Example 17.

5-HT receptor radioligand competition assays. Activity at 5-HT$_{1A}$ and 5-HT$_{2A}$ receptors were assessed as described for Example 15, except the compound with formula A(XVII) was evaluated in place of the compound with formula A(XIV). Table 1 shows radioligand competition assay results for positive controls, negative controls, and compound with formula A(XVII), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XVII) at the 5-HT$_{1A}$ receptor (23.3 µM, Table 1) indicates ligand-receptor binding. Similarly, the K$_i$ value obtained for the compound with formula A(XVII) at the 5-HT$_{2A}$ receptor (187.8 µM, Table 1) indicates ligand-receptor binding.

5-HT transporter (SERT) radioligand competition assay. Activity at the serotonin transporter (SERT) was assessed as described for Example 2, except the compound with formula A(XVII) was evaluated in place of the compound with formula A(VI). Table 3 shows radioligand competition assay results for positive controls, negative controls, and compound with formula A(XVII), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XVII) at SERT (1.71 µM, Table 3) indicates ligand binding to SERT.

In Vitro Survey of Pharmacological Interaction Profiles at Receptors and Transporters linked to targeted health conditions.

The compound with formula A(XVII) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XVII) was used in place of the compound with formula A(XIV). Overall assay conditions are summarized in Tables 4 and 5 for GPCR and transporters, respectively. Results for all calibrator compounds, control compounds, and test compounds including the compound with formula A(XVII) are summarized in Table 6.

Example 19—Preparation and Pharmacological Analysis of a Nineteenth Fused Heterocyclic Mescaline Derivative Referring to FIG. 21, compound A (100 mg, 561 µmol) was dissolved in MeOH (6 mL) followed by the addition of Acetic acid (38.6 µL, 673 µmol) and 1,1-dimethylhydroxime hydrochloride (109.6 mg, 1.17 mmol) and then Sodium cyanoborohydride (106 mg, 1.75 mmol). The mixture was then stirred at room temp for overnight and monitored by TLC (H:E 5:1), The reaction was quenched by sat. aq. NaHCO$_3$ and then extracted with DCM three times. The combined organic layers were dried over anhydrous Na$_2$SO$_4$ and concentrated under reduced pressure. The resulting residue was purified on a silica gel column (4 g) on CombiFlash system (5% EtOAc in hexane) to provide the desired compound MM683 as colorless oil (55.2 mg, 44%), MS-ESI: C$_{12}$H$_{18}$NO$_3$ [M+H]$^+$; calculated: 224.1287, observed: 224.1282 $^1$H NMR (400 MHz, CDCl$_3$) δ 6.84-6.56 (m, 3H), 5.94 (s, 2H), 3.56 (s, 3H), 3.09 (dd, J=13.2, 4.1 Hz, 1H), 2.94-275 (m, 1H), 2.63 (s, 3H), 2.38 (dd, J=13.2, 9.6 Hz, 1H), 0.97 (d, J=6.5 Hz, 3H). It is noted that compound MM683 corresponds with the compound having chemical formula A(XVIII):

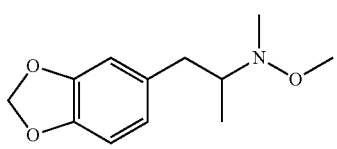

A(XVIII)

It is noted that compound A was synthesized as described in Example 3.

5-HT receptor radioligand competition assays. Activity at 5-HT$_{1A}$ receptor was assessed as described for Example 15, except the compound with formula A(XVIII) was evaluated in place of the compound with formula A(XIV). Table 1 shows radioligand competition assay results for positive controls, negative controls, and compound with formula A(XVIII), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XVIII) at the 5-HT$_{1A}$ receptor (>1000 µM, Table 1) indicates no ligand-receptor binding.

5-HT transporter (SERT) radioligand competition assay. Activity at the serotonin transporter (SERT) was assessed as described for Example 2, except the compound with formula A(XVIII) was evaluated in place of the compound with formula A(VI). Table 3 shows radioligand competition assay results for positive controls, negative controls, and compound with formula A(XVIII), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XVIII) at SERT (98 µM, Table 3) indicates binding to SERT at higher ligand concentrations.

In Vitro Survey of Pharmacological Interaction Profiles at Receptors and Transporters linked to targeted health conditions.

The compound with formula A(XVIII) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XVIII) was used in place of the compound with formula A(XIV). Overall assay conditions are summarized in Tables 4 and 5 for GPCR and transporters, respectively. Results for all calibrator compounds, control compounds, and test compounds including the compound with formula A(XVIII) are summarized in Table 6.

Example 20—Preparation and Pharmacological Analysis of a Twentieth Fused Heterocyclic Mescaline Derivative Referring to FIG. 22, to a solution of H (100 mg, 260 µmol) in DMF (1 mL) and H$_2$O (333 µL) was added ethanolamine (80 µL, 1.31 mmol). Upon heating to 90° C., the solid completely dissolved and the mixture was left to react at this temperature for 4 hours. At this point the starting material H was no longer present in the reaction mixture (TLC, UV, 4:1 Hex:EtOAc) and the stirring was stopped. The mixture was poured into a separatory funnel containing 10 mL DCM and 10 mL 0.1 M HCl (aq.). The aqueous phase was extracted with DCM (3×10 mL) all organic phases were combined, washed with 0.1 M HCl (aq), brine and dried over magnesium sulfate. The organic phase was concentrated to a yellow solid which was purified by chromatography on a Combi-Flash system (4 g, 100% DCM, 10% MeOH in DCM, 20% MeOH in DCM). The desired product MM611 (42.0 mg, 54%) was recovered as a white solid. MS-ESI: C$_{11}$H$_{13}$BrNO$_4$ [M+H]$^+$; calculated: 302.0022; observed: 302.0022 m/z. $^1$H NMR (400 MHz, CDCl$_3$) δ 7.04 (s, 1H), 6.83 (s, 1H), 6.00 (s, 2H), 5.89 (s, 1H), 3.73-3.68 (m, 2H), 3.63 (s, 2H), 3.43-3.38 (m, 2H). It is noted that compound MM611 corresponds with the compound having chemical formula A(XIX):

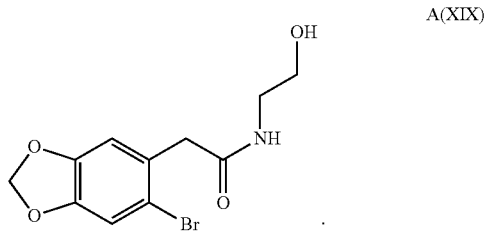 [SMILES: O=C(Cc1cc2c(cc1Br)OCO2)NCCO]

A(XIX)

5-HT receptor radioligand competition assays. Activity at 5-HT$_{1A}$ and 5-HT$_{2A}$ receptors were assessed as described for Example 15, except the compound with formula A(XIX) was evaluated in place of the compound with formula A(XIV). Table 1 shows radioligand competition assay results for positive controls, negative controls, and compound with formula A(XIX), in the form of K$_i$ values. In view of results for both positive and negative controls, wherein negative controls yield data insufficient for reliable K$_i$ calculations (i.e., K$_i$>1000 M) the K$_i$ value obtained for the compound with formula A(XIX) at the 5-HT$_{1A}$ receptor (586 µM, Table 1) indicates ligand-receptor binding. Similarly, the K$_i$ value obtained for the compound with formula A(XIX) at the 5-HT$_{2A}$ receptor (18.76 µM, Table 1) indicates ligand-receptor binding.

5-HT transporter (SERT) radioligand competition assay. Activity at the serotonin transporter (SERT) was assessed as described for Example 2, except the compound with formula A(XIX) was evaluated in place of the compound with formula A(VI). Table 3 shows radioligand competition assay results for positive controls, negative controls, and compound with formula A(XIX), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XIX) at SERT (>1000 µM, Table 3) indicates no ligand binding to this transporter.

In Vitro Survey of Pharmacological Interaction Profiles at Receptors and Transporters Linked to Targeted Health Conditions.

The compound with formula A(XIX) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XIX) was used in place of the compound with formula A(XIV). Overall assay conditions are summarized in Tables 4 and 5 for GPCR and transporters, respectively. Results for all calibrator compounds, control compounds, and test compounds including the compound with formula A(XIX) are summarized in Table 6.

Example 21—Preparation and Pharmacological Analysis of a Twenty-First Fused Heterocyclic Mescaline Derivative Referring to FIG. 23, Compound C (50.0 mg, 305 µmol) was dissolved in MeOH (2.00 mL) followed by the addition of cyclobutylamine (45.1 mg, 634 µmol). The reaction mixture was stirred for 10 minutes before the addition of potassium cyanide (78.1 mg, 1.15 mmol), reaction mixture was then stirred at room temperature for 2 hours. Half-saturated NaHCO$_3$ (aq.) and EtOAc were added to the mixture, aqueous phase was extracted with EtOAc, combined organic layers were dried over Na$_2$SO$_4$, filtered, and concentrated in vacuo. Crude material was purified on a silica gel column (0 to 40% EtOAc in Hexanes), fractions containing the desired product were pooled, concentrated, and dried in vacuo to afford MM618 (43.2 mg, 58%) as a colourless oil. MS-ESI: calculated: 244.2940 observed: M+H=245.1282 m/z [M+H]$^+$ $^1$H NMR (400 MHz, CDCl$_3$) δ 6.80-6.76 (m, 2H), 6.73 (dd, J=7.9, 1.6 Hz, 1H), 5.95 (s, 2H), 3.63 (dd, J=7.4, 5.6 Hz, 1H), 3.51-3.40 (m, 1H), 3.01-2.85 (m, 2H), 2.30 (dtdt, J=10.4, 7.0, 5.0, 2.1 Hz, 1H), 2.24-2.15 (m, 1H), 1.87-1.75 (m, 1H), 1.75-1.60 (m, 3H), 1.40 (br, s, 1H). It is noted that compound MM618 corresponds with the compound having chemical formula A(XX):

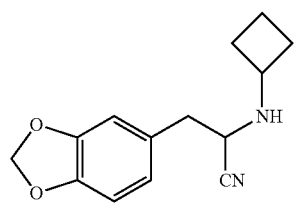

A(XX)

It is noted that compound C was synthesized as described in Example 6.

5-HT receptor radioligand competition assays. Activity at 5-$HT_{1A}$ and 5-$HT_{2A}$ receptors were assessed as described for Example 15, except the compound with formula A(XX) was evaluated in place of the compound with formula A(XIV). Table 1 shows radioligand competition assay results for positive controls, negative controls, and compound with formula A(XX), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XX) at the 5-$HT_{1A}$ receptor (123 µM, Table 1) indicates ligand-receptor binding. Similarly, the $K_i$ value obtained for the compound with formula A(XX) at the 5-$HT_{2A}$ receptor (42.08 µM, Table 1) indicates ligand-receptor binding.

5-HT transporter (SERT) radioligand competition assay. Activity at the serotonin transporter (SERT) was assessed as described for Example 2, except the compound with formula A(XX) was evaluated in place of the compound with formula A(VI). Table 3 shows radioligand competition assay results for positive controls, negative controls, and compound with formula A(XX), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XX) at SERT (286 µM, Table 3) indicates ligand binding to SERT at higher concentrations.

In Vitro Survey of Pharmacological Interaction Profiles at Receptors and Transporters Linked to Targeted Health Conditions.

The compound with formula A(XX) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-$HTR_{1B}$), HTR1D (5-$HT_{1D}$), HTR2B (5-$HT_{2B}$), HTR2C (5-$HT_{2C}$), HTR7 (5-$HT_7$), alpha2A ($\alpha_{2A}$), D2 ($D_2$), D3 ($D_3$), MT1 ($MT_1$)) and 2 transporters (DAT, NET). Assays were conducted using the same materials and procedures outlined in Example 15, except the compound with formula A(XX) was used in place of the compound with formula A(XIV). Overall assay conditions are summarized in Tables 4 and 5 for GPCR and transporters, respectively. Results for all calibrator compounds, control compounds, and test compounds including the compound with formula A(XX) are summarized in Table 6.

Example 22—Preparation and Pharmacological Analysis of a Twenty-Second Fused Heterocyclic Mescaline Derivative Referring to FIG. 24, to a solution of G (100 mg, 298 µmol) in DMF (1.14 mL) and $H_2O$ (382 µL) was added ethanolamine (272 µL, 4.46 mmol). Upon heating to 90° C., the solids completely dissolved, and the mixture was left to react for 4 hours. At this point a product spot was identified in the mixture as a major component (TLC, UV, 9:1 DCM: MeOH) and the reaction was stopped. The mixture was poured into a separatory funnel containing 10 mL DCM and 10 mL 0.1 M HCl(aq). The aqueous phase was extracted with DCM (3×10 mL) all organic phases were combined, washed with 0.1 M HCl(aq), brine and dried over magnesium sulfate. The organic phase was concentrated to a yellow solid which was purified by chromatography on a Combi-Flash system (4 g, 100% DCM, 10% MeOH in DCM, 20% MeOH in DCM). The desired product MM678 (16.0 mg, 21%) was recovered as a white solid. MS-ESI: $C_{12}H_{16}NO_5$ ([M+H]+); calculated: 254.1023, observed: 254.1021 $^1$H NMR (400 MHz, $CDCl_3$) δ 6.73 (s, 1H), 6.56 (s, 1H), 6.14 (s, 1H), 5.93 (s, 2H), 3.80 (s, 3H), 3.68-3.66 (m, 2H), 3.49 (s, 2H), 3.38-3.34 (m, 2H). It is noted that compound MM678 corresponds with the compound having chemical formula A(XXII):

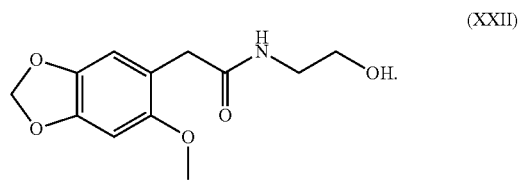 [SMILES: COc1cc2c(cc1CC(=O)NCCO)OCO2]

(XXII)

It is noted that compound G was synthesized as described in Example 14.

5-HT receptor radioligand competition assays. Activity at 5-$HT_{1A}$ receptor was assessed as described for Example 15, except the compound with formula A(XXII) was evaluated in place of the compound with formula A(XIV). Table 1 shows radioligand competition assay results for positive controls, negative controls, and compound with formula A(XXII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XXII) at the 5-$HT_{1A}$ receptor (>1000 µM, Table 1) indicates no ligand-receptor binding.

5-HT transporter (SERT) radioligand competition assay. Activity at the serotonin transporter (SERT) was assessed as described for Example 2, except the compound with formula A(XXII) was evaluated in place of the compound with formula A(VI). Table 3 shows radioligand competition assay results for positive controls, negative controls, and compound with formula A(XXII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XXII) at SERT (52.3 µM, Table 3) indicates ligand binding to SERT.

In Vitro Survey of Pharmacological Interaction Profiles at Receptors and Transporters Linked to Targeted Health Conditions.

The compound with formula A(XXII) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XXII) was used in place of the compound with formula A(XIV). Overall assay conditions are summarized in Tables 4 and 5 for GPCR and transporters, respectively. Results for all calibrator compounds, control compounds, and test compounds including the compound with formula A(XXII) are summarized in Table 6.

Example 23—Preparation and Pharmacological Analysis of a Twenty-Third Fused Heterocyclic Mescaline Derivative Referring to FIG. 25, to a solution of E (100 mg, 517 μmol) in methanol (3.07 mL) under argon was added benzaldehyde (53.1 μL, 517 μmol). The reaction mixture was refluxed under inert atmosphere for 3 h. Following cooling to room temperature, sodium cyanoborohydride (90.0 mg, 1.36 mmol) was added in small portions and the resulting mixture allowed to stir at room temperature for 18 h. Solvent was removed under reduced pressure, and the residue taken up in ethyl acetate (10 mL) and washed with brine (3×10 mL). The organic layer was dried with anhydrous magnesium sulphate and solvent removed under reduced pressure. Purification by flash column chromatography on 4 g normal-phase silica using a 10% to 25% ethyl acetate-hexanes eluent system yielded MM695 as a colourless oil (70 mg, 48%).

MS-ESI: C$_{18}$H$_{21}$NO$_2$ ([M+H]+); calculated: 284.1645, observed: 284.1643 $^1$H NMR (400 MHz, CDCl$_3$) δ 7.36-7.30 (m, 2H), 7.29-7.21 (m, 3H), 6.81 (d, J=8.2 Hz, 1H), 6.71 (d, J=2.0 Hz, 1H), 6.66 (dd, J=8.2, 2.1 Hz, 1H), 4.26 (s, 4H), 3.88 (d, J=13.3 Hz, 1H), 3.76 (d, J=13.3 Hz, 1H), 2.92 (h, J=6.4 Hz, 1H), 2.69 (dd, J=13.5, 7.1 Hz, 1H), 2.57 (dd, J=13.5, 6.4 Hz, 1H), 1.83 (s, 1H), 1.12 (d, J=6.2 Hz, 3H). It is noted that compound MM695 corresponds with the compound having chemical formula A(XXIII):

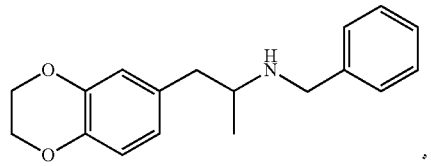

A(XXIII)

It is noted that compound E was synthesized as described in Example 1.

5-HT receptor radioligand competition assays. Activity at 5-HT$_{1A}$ and 5-HT$_{2A}$ receptors were assessed as described for Example 15, except the compound with formula A(XXIII) was evaluated in place of the compound with formula A(XIV). Table 1 shows radioligand competition assay results for positive controls, negative controls, and compound with formula A(XXIII), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(XXIII) at the 5-HT$_{1A}$ receptor (5.58 μM, Table 1) indicates ligand-receptor binding. Similarly, the K$_i$ value obtained for the compound with formula A(XXIII) at the 5-HT$_{2A}$ receptor (70 μM, Table 1) indicates ligand-receptor binding.

5-HT transporter (SERT) radioligand competition assay. Activity at the serotonin transporter (SERT) was assessed as described for Example 2, except the compound with formula A(XXIII) was evaluated in place of the compound with formula A(VI). Table 3 shows radioligand competition assay results for positive controls, negative controls, and compound with formula A(XXIII), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(XXIII) at SERT (2.75 μM, Table 3) indicates ligand binding to SERT.

In Vitro Survey of Pharmacological Interaction Profiles at Receptors and Transporters Linked to Targeted Health Conditions.

The compound with formula A(XXIII) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XXIII) was used in place of the compound with formula A(XIV). Overall assay conditions are summarized in Tables 4 and 5 for GPCR and transporters, respectively. Results for all calibrator compounds, control compounds, and test compounds including the compound with formula A(XXIII) are summarized in Table 6.

Example 24—Preparation and Pharmacological Analysis of a Twenty-Fourth Fused Heterocyclic Mescaline Derivative Referring to FIG. 26, into a round bottomed flask was added MM678 (synthesized as described in Example 22) (76.0 mg, 300 μmol) this was dissolved in dry THF (2.73 mL) and cooled to 0° C. Once cool, lithium aluminum hydride (225 μL, 450 μmol) was carefully added and the mixture was warmed to room temperature and left to react overnight. Monitoring by TLC (UV, DCM:MeOH 9:1) showed that a reaction had occurred but was not complete. An additional portion of lithium aluminum hydride (225 μL, 450 μmol) was added and the reaction was again left overnight. The flask was cooled to 0° C. and any remaining LiAlH$_4$ was quenched with water. The resulting mixture was poured into a separatory funnel containing 15 mL of water and 15 mL of EtOAc. The aqueous layer was extracted with EtOAc (3×15 mL), all organic layers were combined, washed with brine, dried (MgSO$_4$) and concentrated under reduced pressure. After purification on a CombiFlash system (4 g silica, DCM to 9:1 DCM:MeOH), the product, MM685 (28.1 mg, 39%), was obtained as a light brown oil.

MS-ESI: C$_{12}$H$_{18}$NO$_4$ ([M+H]$^+$); calculated: 240.1230, observed: 240.1228. $^1$H NMR (400 MHz, CDCl$_3$) δ 6.65 (s, 1H), 6.51 (s, 1H), 5.89 (s, 2H), 3.66-3.63 (m, 2H), 2.96-2.83 (m, 2H), 2.83-2.80 (m, 4H), 2.75-2.72 (m, 2H).

It is noted that compound MM685 corresponds with the compound having chemical formula A(XXIV):

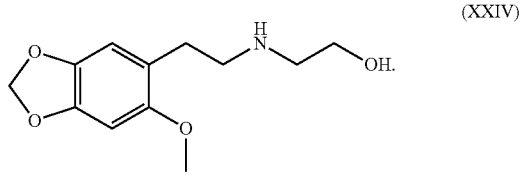 [SMILES: COc1cc2c(cc1CCNCCO)OCO2]

(XXIV)

5-HT receptor radioligand competition assays. Activity at 5-HT$_{1A}$ and 5-HT$_{2A}$ receptors were assessed as described for Example 15, except the compound with formula A(XXIV) was evaluated in place of the compound with formula A(XIV). Table 1 shows radioligand competition assay results for positive controls, negative controls, and compound with formula A(XXIV), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(XXIV) at the 5-HT$_{1A}$ receptor (0.993 μM, Table 1) indicates ligand-receptor binding. Similarly, the K$_i$ value obtained for the compound with formula A(XXIV) at the 5-HT$_{2A}$ receptor (26 μM, Table 1) indicates ligand-receptor binding.

5-HT$_{1A}$ receptor functional cellular response assay. Functional engagement of the 5-HT$_{1A}$ receptor within an engineered cell system was assessed as described for Example 15, except the compound with formula A(XXIV) was evaluated in place of the compound with formula A(XIV). Table 2 shows functional assay results for positive controls, calibrators, and compound with formula A(XXIV), in the form of EC$_{50}$ values. In view of results for controls and calibrator compounds, wherein a negative cellular response corresponded to an EC$_{50}$ value>1000 μM, the EC$_{50}$ value for the compound with formula A(XXIV) in this assay (32.28 μM, Table 1) suggested ligand-receptor engagement.

5-HT transporter (SERT) radioligand competition assay. Activity at the serotonin transporter (SERT) was assessed as described for Example 2, except the compound with formula A(XXIV) was evaluated in place of the compound with formula A(VI). Table 3 shows radioligand competition assay results for positive controls, negative controls, and compound with formula A(XXIV), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(XXIV) at SERT (52.18 μM, Table 3) indicates ligand binding to SERT.

In Vitro Survey of Pharmacological Interaction Profiles at Receptors and Transporters Linked to Targeted Health Conditions.

The compound with formula A(XXIV) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HT$_{1B}$), HTR1D (5-HT$_{1D}$), HTR2B (5-HT$_{2B}$), HTR2C (5-HT$_{2C}$), HTR7 (5-HT$_7$), alpha2A (α$_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XXIV) was used in place of the compound with formula A(XIV). Overall assay conditions are summarized in Tables 4 and 5 for GPCR and transporters, respectively. Results for all calibrator compounds, control compounds, and test compounds including the compound with formula A(XXIV) are summarized in Table 6.

Example 25—Preparation and Pharmacological Analysis of a Twenty-Fifth Fused Heterocyclic Mescaline Derivative Referring to FIGS. 27A-27C, Compound 1 (500 mg, 2.78 mmol) was dissolved in DCM (10.0 mL) added to this was 1-(3-Dimethylaminopropyl)-3-ethylcarbodiimide hydrochloride, EDC (616 mg, 3.05 mmol), and triethylamine (778 μL, 5.55 mmol). The mixture was left to stir for 20 minutes and then pyrrolidine (256 μL, 3.05 mmol) was added. After stirring overnight a new spot was observed by TLC (UV, DCM:MeOH 9:1) and the reaction mixture was poured into a separatory funnel containing 25 mL water and 25 mL EtOAc. The aqueous phase was extracted with EtOAc (3×25 mL), all organic layers were combined, washed with saturated sodium bicarbonate solution (2×50 mL), brine, dried over magnesium sulfate and concentrated under vacuum. The resulting crude material was purified on a CombiFlash system (12 g silica, DCM to DCM:MeOH 9:1) to provide MM680 (301 mg, 46%) as a white solid (see: FIG. 27A).

MS-ESI: C$_{13}$H$_{16}$NO$_3$ ([M+H]$^+$); calculated: 234.1125, observed: 234.1121. $^1$H NMR (400 MHz, CDCl$_3$) δ 6.81 (d, J=1.9 Hz, 1H), 6.74 (d, J=7.9 Hz, 1H), 6.70 (dd, J=7.9 Hz, 1.8 Hz, 1H), 5.93 (s, 2H), 3.56 (s, 2H), 3.48-3.43 (m, 4H), 1.92-1.84 (m, 4H).

Into a round bottomed flask was added MM680 (285 mg, 1.22 mmol) this was dissolved in dry THF (11.1 mL) and cooled to 0° C. Once cool, lithium aluminum hydride (2.0 M in THF, 916 μL, 1.83 mmol) was carefully added and the mixture was warmed to room temperature and left to react overnight. In the morning the starting material had disappeared (TLC, UV, 9:1 DCM:MeOH). The mixture was cooled to 0° C. and the excess LiAlH$_4$ quenched with cold water. The resulting solution was poured into a separatory funnel containing 30 mL of water and the aqueous phase was extracted with EtOAc (4×30 mL). All organic layers were combined, washed with brine, dried (MgSO$_4$), filtered and concentrated to leave a colourless oil. After chromatographic purification on a CombiFlash system (12 g silica, DCM to 9:1 DCM:MeOH) the product MM681 (215 mg, 80%) was obtained as a colourless solid (see: FIG. 27B).

MS-ESI: C$_{13}$H$_{18}$NO$_2$ ([M+H]$^+$); calculated: 220.1332, observed: 220.1334. $^1$H NMR (400 MHz, CDCl$_3$) δ 6.73 (d, J=7.9 Hz, 1H), 6.71 (d, J=1.6 Hz, 1H), 6.66 (dd, J=7.9, 1.7 Hz, 1H), 5.92 (s, 2H), 2.81-2.66 (m, 8H), 1.85 (s, 4H).

The aryl pyrrolidine compound MM681 (187 mg, 853 µmol) was dissolved in AcOH (4.50 mL). Added to this was a solution of bromine (48 µL, 935 µmol) in AcOH (0.480 mL). This was left to react at room temperature for 3 hours, at which point the starting material was no longer present (TLC-UV, DCM:MeOH 9:1). The mixture was poured into a separatory funnel containing 30 mL of water. The pH of this solution was adjusted to ~10 with 1 M NaOH and the aqueous layer was extracted with EtOAc (4×20 mL). All organic layers were combined, washed with brine, dried (MgSO$_4$), filtered and concentrated. The resulting light brown solid was purified on a CombiFlash system (12 g silica, DCM:MeOH, 100:0 to 90:10) to provide MM686 (149 mg, 59%) as a colourless solid (see: FIG. 27C).

MS-ESI: $C_{13}H_{17}BrNO_2$ ([M+H]$^+$); calculated: 298.0437, observed: 298.0437. $^1$H NMR (400 MHz, CDCl$_3$) δ 6.96 (s, 1H), 6.87 (s, 1H), 5.95 (s, 2H), 3.25-3.09 (m, 8H), 2.13-2.09 (m, 4H).

It is noted that compound MM686 corresponds with the compound having chemical formula A(XXV):

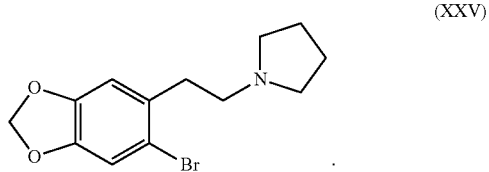 [SMILES: Brc1cc2c(cc1CCN1CCCC1)OCO2]

(XXV)

5-HT receptor radioligand competition assays. Activity at 5-HT$_{1A}$ and 5-HT$_{2A}$ receptors were assessed as described for Example 15, except the compound with formula A(XXV) was evaluated in place of the compound with formula A(XIV). Table 1 shows radioligand competition assay results for positive controls, negative controls, and compound with formula A(XXV), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XXV) at the 5-HT$_{1A}$ receptor (0.06348 µM, Table 2) indicates ligand-receptor binding. Similarly, the K$_i$ value obtained for the compound with formula A(XXV) at the 5-HT$_{2A}$ receptor (7.65 µM, Table 1) indicates ligand-receptor binding.

5-HT$_{1A}$ receptor functional cellular response assay. Functional engagement of the 5-HT$_{1A}$ receptor within an engineered cell system was assessed as described for Example 15, except the compound with formula A(XXV) was evaluated in place of the compound with formula A(XIV). Table 2 shows functional assay results for positive controls, calibrators, and compound with formula A(XXV), in the form of EC$_{50}$ values. In view of results for controls and calibrator compounds, wherein a negative cellular response corresponded to an EC$_{50}$ value>1000 µM, the EC$_{50}$ value for the compound with formula A(XXV) in this assay (0.3424 µM, Table 1) suggested ligand-receptor engagement.

5-HT transporter (SERT) radioligand competition assay. Activity at the serotonin transporter (SERT) was assessed as described for Example 2, except the compound with formula A(XXV) was evaluated in place of the compound with formula A(VI). Table 3 shows radioligand competition assay results for positive controls, negative controls, and compound with formula A(XXV), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XXV) at SERT (10.89 µM, Table 3) indicates ligand binding to SERT.

In Vitro Survey of Pharmacological Interaction Profiles at Receptors and Transporters Linked to Targeted Health Conditions.

The compound with formula A(XXV) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A (α$_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XXV) was used in place of the compound with formula A(XIV). Overall assay conditions are summarized in Tables 4 and 5 for GPCR and transporters, respectively. Results for all calibrator compounds, control compounds, and test compounds including the compound with formula A(XXV) are summarized in Table 6.

Example 26—Preparation and Pharmacological Analysis of a Twenty-Sixth Fused Heterocyclic Mescaline Derivative Referring to FIGS. 28A and 28B, carbon tetrabromide (2.84 g, 8.32 mmol) was dissolved in 7 mL of DCM and cooled to 0° C. Added to this in a drop-wise manner was triphenylphosphine (4.41 g, 16.6 mmol) in 15 mL DCM. This mixture was left to stir for 20 minutes at 0° C. and then a solution of compound 1, 5-bromo-1,3-benzodioxole-4-carboxaldehyde, (982 mg, 4.16 mmol) in 8 mL of DCM was added in a drop-wise manner. The mixture was left at 0° C. for 4 hours. At this point no starting material was observed (TLC-UV, 4:1 Hex:EtOAc) and the mixture was slowly added to 150 mL of diethyl ether under rapid stirring. The resulting white precipitate was filtered away and the filtrate was washed with water (2×50 mL), brine and dried with MgSO$_4$. The organic layer was concentrated to provide a white solid as a crude mixture. After purification (Combi-Flash system, 24 g silica column, Hex:EtOAc 100:0 to 80:20) L was isolated as a colourless oil (500 mg, 31%) (see: FIG. 28A).

$^1$H NMR (400 MHz, CDCl$_3$) δ 7.27 (d, J=0.6 Hz, 1H), 7.05 (d, J=8.3 Hz, 1H), 6.70 (dd, J=8.3 Hz, 0.6 Hz, 1H), 6.04 (s, 2H).

To a solution of L (300 mg, 780 µmol) in DMF (3.00 mL) and H$_2$O (1.0 mL) was added pyrrolidine (330 µL, 3.94 mmol). The vicinal dibromide was initially not soluble in this solvent mixture. Upon heating to 90° C. the mixture completely dissolved and was left to react for 4 hours. At this point the starting material vicinal dibromide was no longer present in the reaction mixture (TLC, UV, 4:1 Hex:EtOAc) and the reaction was stopped. The mixture was poured into a separatory funnel containing 10 mL DCM and 10 mL 0.1 M HCl(aq). The aqueous phase was extracted with DCM (3×10 mL) all organic phases were combined, washed with 0.1 M HCl(aq), water, brine and dried over magnesium sulfate. The organic phase was concentrated to a brown solid which was purified by chromatography on a Combi-Flash system (12 g, 100% DCM to 10% MeOH in DCM). MM737 was obtained as a light yellow solid (193 mg, 79%) (see: FIG. 28B).

LRMS-HESI: 312.05 m/z [M+H]$^+$ $^1$H NMR (400 MHz, CDCl$_3$) δ 7.03 (d, J=8.3 Hz, 1H), 6.61 (d, J=8.3 Hz, 1H), 5.98 (s, 2H), 3.71 (s, 2H), 3.60-3.47 (m, 4H), 2.00-1.91 (m, 4H).

It is noted that compound MM737 corresponds with the compound having chemical formula A(XXVI):

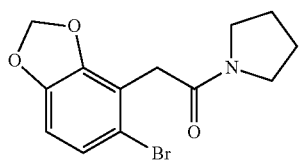

A(XXVI)

5-HT receptor radioligand competition assays. Activity at 5-HT$_{1A}$ and 5-HT$_{2A}$ receptors were assessed as described for Example 15, except the compound with formula A(XXVI) was evaluated in place of the compound with formula A(XIV). Table 1 shows radioligand competition assay results for positive controls, negative controls, and compound with formula A(XXVI), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XXVI) at the 5-HT$_{1A}$ receptor (44.44 µM, Table 1) indicates ligand-receptor binding. Similarly, the K$_i$ value obtained for the compound with formula A(XXVI) at the 5-HT$_{2A}$ receptor (31.03 µM, Table 1) indicates ligand-receptor binding.

In Vitro Survey of Pharmacological Interaction Profiles at Receptors and Transporters Linked to Targeted Health Conditions.

The compound with formula A(XXVI) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($α_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XXVI) was used in place of the compound with formula A(XIV). Overall assay conditions are summarized in Tables 4 and 5 for GPCR and transporters, respectively. Results for all calibrator compounds, control compounds, and test compounds including the compound with formula A(XXVI) are summarized in Table 6.

Example 27—Preparation and Pharmacological Analysis of a Twenty-Seventh Fused Heterocyclic Mescaline Derivative Referring to FIGS. 29A and 29B, carbon tetrabromide (2.85 g, 8.33 mmol) was dissolved in 7 mL of DCM and cooled to 0° C. Added to this in a drop-wise manner was triphenylphosphine (4.41 g, 16.7 mmol) dissolved in 15 mL DCM. This mixture was left to stir for 20 minutes at 0° C. and then a solution of compound 1, 2,2-difluoro-5-formyl-benzodioxole, (800 mg, 4.16 mmol) dissolved in 8 mL of DCM was added in a drop-wise manner. The mixture was left at 0° C. for 4 hours. At this point no starting material was observed (TLC-UV, 4:1 Hex:EtOAc) and the mixture was slowly added to 150 mL of diethyl ether under rapid stirring. The resulting white precipitate was filtered away and the filtrate was washed with water (2×50 mL), brine and dried with MgSO4. The organic layer was concentrated to provide a white solid as a crude mixture. After purification (CombiFlash system, 24 g silica column, Hex:EtOAc 100:0 to 80:20) M was isolated as a colourless oil (910 mg, 64%) (see: FIG. 29A).

$^1$H NMR (400 MHz, CDCl$_3$) δ 7.43 (s, 1H), 7.40 (d, J=1.8 Hz, 1H), 7.16 (ddd, J=8.3 Hz, 1.7 Hz, 0.8 Hz, 1H), 7.05 (d, J=8.3 Hz, 1H).

To a solution of M (267 mg, 780 µmol) in DMF (3.00 mL) and H$_2$O (1.0 mL) was added pyrrolidine (330 µL, 3.94 mmol). The vicinal dibromide was initially not soluble in this solvent mixture. Upon heating to 90° C. the material completely dissolved, and the mixture was left to react for 4 hours. At this point the starting material vicinal dibromide was no longer present in the reaction mixture (TLC, UV, 4:1 Hex:EtOAc) and the reaction was stopped. The mixture was poured into a separatory funnel containing 10 mL DCM and 10 mL 0.1 M HCl(aq). The aqueous phase was extracted with DCM (3×10 mL) all organic phases were combined, washed with 0.1 M HCl(aq), water, brine and dried over magnesium sulfate. The organic phase was concentrated to a waxy colourless solid which was purified by chromatography on a Combi-Flash system (12 g, 100% DCM to 10% MeOH in DCM). MM738 was obtained as a colourless solid (185 mg, 88%) (see: FIG. 29B). LRMS-HESI: 270.12 m/z [M+H]$^+$. $^1$H NMR (400 MHz, CDCl$_3$) δ 7.05 (s, 1H), 6.99-6.94 (m, 2H), 3.62 (s, 2H), 3.50-3.43 (m, 4H), 1.98-1.86 (m, 4H).

It is noted that compound MM738 corresponds with the compound having chemical formula A(XXVII):

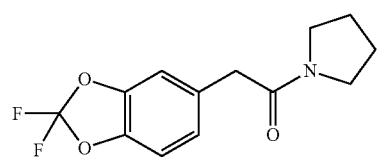

A(XXVII)

5-HT receptor radioligand competition assays. Activity at 5-HT$_{1A}$ receptor was assessed as described for Example 15, except the compound with formula A(XXVII) was evaluated in place of the compound with formula A(XIV). Table 1 shows radioligand competition assay results for positive controls, negative controls, and compound with formula A(XXVII), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XXVII) at the 5-HT$_{1A}$ receptor (>1000 µM, Table 1) indicates no ligand-receptor binding.

5-HT transporter (SERT) radioligand competition assay. Activity at the serotonin transporter (SERT) was assessed as described for Example 2, except the compound with formula A(XXVII) was evaluated in place of the compound with formula A(VI). Table 3 shows radioligand competition assay results for positive controls, negative controls, and compound with formula A(XXVII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XXVII) at SERT (633.9 µM, Table 3) indicates binding to SERT at higher ligand concentrations.

In Vitro Survey of Pharmacological Interaction Profiles at Receptors and Transporters Linked to Targeted Health Conditions.

The compound with formula A(XXVII) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XXVII) was used in place of the compound with formula A(XIV). Overall assay conditions are summarized in Tables 4 and 5 for GPCR and transporters, respectively. Results for all calibrator compounds, control compounds, and test compounds including the compound with formula A(XXVII) are summarized in Table 6.

Example 28—Preparation and Pharmacological Analysis of a Twenty-Eighth Fused Heterocyclic Mescaline Derivative Referring to FIG. 30, into a round bottomed flask was added MM738 (97.9 mg, 364 µmol) (see: Example 27) this was dissolved in dry THF (3.30 mL) and cooled to 0° C. Once cool, lithium aluminum hydride, 2.0 M in THF (545 µL, 1.09 mmol) was carefully added and the mixture was warmed to room temperature and left to react overnight. In the morning the starting material had disappeared (TLC, UV, 9:1 DCM:MeOH). The mixture was cooled to 0° C., diluted with diethyl ether and the reaction was quenched using the Fieser work-up conditions for lithium aluminum hydride reactions (x=g of LiAlH$_4$; add x mL water, x mL 15% NaOH, 3x mL water, dry with MgSO$_4$). The resulting mixture was filtered and concentrated to leave a colourless oil. This was subjected to purification on a CombiFlash system (4 g silica, DCM:MeOH 100:0 to 90:10) to provide the pure desired product, MM739 (50.0 mg, 54%), as a colourless waxy oil.

LRMS-HESI: 256.14 m/z [M+H]$^+$. $^1$H NMR (400 MHz, CDCl$_3$) δ 6.96-6.93 (m, 2H), 6.90 (dd, J=8.0 Hz, 1.7 Hz, 1H), 2.84-2.80 (m, 2H), 2.69-2.65 (m, 2H), 2.58-2.55 (m, 4H), 1.82-1.80 (m, 4H).

It is noted that compound MM739 corresponds with the compound having chemical formula A(XXVIII):

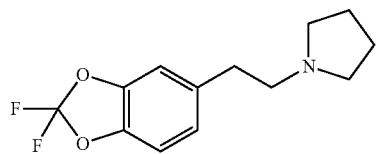

(XXVIII)

5-HT receptor radioligand competition assays. Activity at 5-HT$_{1A}$ and 5-HT$_{2A}$ receptors were assessed as described for Example 15, except the compound with formula A(XXVIII) was evaluated in place of the compound with formula A(XIV). Table 1 shows radioligand competition assay results for positive controls, negative controls, and compound with formula A(XXVIII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XXVIII) at the 5-HT$_{1A}$ receptor (1.98 µM, Table 1) indicates ligand-receptor binding. Similarly, the $K_i$ value obtained for the compound with formula A(XXVIII) at the 5-HT$_{2A}$ receptor (15.55 µM, Table 1) indicates ligand-receptor binding.

5-HT$_{1A}$ receptor functional cellular response assay. Functional engagement of the 5-HT$_{1A}$ receptor within an engineered cell system was assessed as described for Example 15, except the compound with formula A(XXVIII) was evaluated in place of the compound with formula A(XIV). Table 2 shows functional assay results for positive controls, calibrators, and compound with formula A(XXVIII), in the form of EC$_{50}$ values. In view of results for controls and calibrator compounds, wherein a negative cellular response corresponded to an EC$_{50}$ value>1000 µM, the EC$_{50}$ value for the compound with formula A(XXVIII) in this assay (373.6 µM, Table 2) suggested ligand-receptor engagement.

5-HT transporter (SERT) radioligand competition assay. Activity at the serotonin transporter (SERT) was assessed as described for Example 2, except the compound with formula A(XXVIII) was evaluated in place of the compound with formula A(VI). Table 3 shows radioligand competition assay results for positive controls, negative controls, and compound with formula A(XXVIII), in the form of $K_i$ values. In view of results for both positive and negative controls, wherein negative controls yield data insufficient for reliable $K_i$ calculations (i.e., $K_i$>1000 µM) the $K_i$ value obtained for the compound with formula A(XXVIII) at SERT (23.72 µM, Table 3) indicates ligand binding to SERT.

In Vitro Survey of Pharmacological Interaction Profiles at Receptors and Transporters Linked to Targeted Health Conditions.

The compound with formula A(XXVIII) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XXVIII) was used in place of the compound with formula A(XIV). Overall assay conditions are summarized in Tables 4 and 5 for GPCR and transporters, respectively. Results for all calibrator compounds, control compounds, and test compounds including the compound with formula A(XXVIII) are summarized in Table 6.

Example 29—Preparation and Pharmacological Analysis of a Twenty-Ninth Fused Heterocyclic Mescaline Derivative Referring to FIG. 31, into a round bottomed flask was added MM737 (114 mg, 364 µmol) (see: Example 26) this was dissolved in dry THF (3.30 mL) and cooled to 0° C. Once cool, lithium aluminum hydride, 2.0 M in THF (546 µL, 1.09 mmol) was carefully added and the mixture was warmed to room temperature and left to react overnight. In the morning the starting material had disappeared (TLC, UV, 9:1 DCM:MeOH). The mixture was cooled to 0° C., diluted with diethyl ether and the reaction was quenched using the Fieser work-up conditions for lithium aluminum hydride reactions (x=g of LiAlH$_4$ add x mL water, x mL 15% NaOH, 3x mL water, dry with MgSO$_4$). LCMS analysis of the crude mixture revealed that the majority of the product was the debrominated compound MM741. The resulting mixture was filtered and concentrated to leave a colourless oil. This was subjected to purification on a CombiFlash system (4 g silica, DCM:MeOH 100:0 to 90:10) to provide MM741 (16.0 mg, 20%) as a colourless oil.

LRMS-HESI: 220.17 m/z [M+H]$^+$. $^1$H NMR (400 MHz, CDCl$_3$) δ 6.77-6.75 (m, 1H), 6.73-6.68 (m, 2H), 5.93 (s, 2H), 2.84-2.80 (m, 2H), 2.73-2.69 (m, 2H), 2.60-2.57 (m, 4H), 1.82-1.79 (m, 4H).

It is noted that compound MM741 corresponds with the compound having chemical formula A(XXIX):

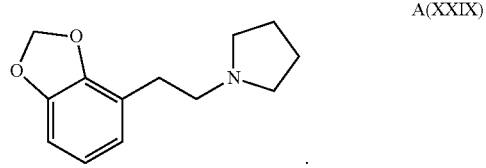 [SMILES: c1cc(CCN2CCCC2)c2c(c1)OCO2]

A(XXIX)

5-HT receptor radioligand competition assays. Activity at 5-HT$_{1A}$ and 5-HT$_{2A}$ receptors were assessed as described for Example 15, except the compound with formula A(XXIX) was evaluated in place of the compound with formula A(XIV). Table 1 shows radioligand competition assay results for positive controls, negative controls, and compound with formula A(XXIX), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XXIX) at the 5-HT$_{1A}$ receptor (0.01323 µM, Table 1) indicates ligand-receptor binding. Similarly, the K$_i$ value obtained for the compound with formula A(XXIX) at the 5-HT$_{2A}$ receptor (8 µM, Table 1) indicates ligand-receptor binding.

5-HT$_{1A}$ receptor functional cellular response assay. Functional engagement of the 5-HT$_{1A}$ receptor within an engineered cell system was assessed as described for Example 15, except the compound with formula A(XXIX) was evaluated in place of the compound with formula A(XIV). Table 2 shows functional assay results for positive controls, calibrators, and compound with formula A(XXIX), in the form of EC$_{50}$ values. In view of results for controls and calibrator compounds, wherein a negative cellular response corresponded to an EC$_{50}$ value>1000 µM, the EC$_{50}$ value for the compound with formula A(XXIX) in this assay (0.3519 µM, Table 2) suggested ligand-receptor engagement.

5-HT transporter (SERT) radioligand competition assay. Activity at the serotonin transporter (SERT) was assessed as described for Example 2, except the compound with formula A(XXIX) was evaluated in place of the compound with formula A(VI). Table 3 shows radioligand competition assay results for positive controls, negative controls, and compound with formula A(XXIX), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XXIX) at SERT (10.08 µM, Table 3) indicates ligand binding to SERT.

In Vitro Survey of Pharmacological Interaction Profiles at Receptors and Transporters Linked to Targeted Health Conditions.

The compound with formula A(XXIX) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HT$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XXIX) was used in place of the compound with formula A(XIV). Overall assay conditions are summarized in Tables 4 and 5 for GPCR and transporters, respectively. Results for all calibrator compounds, control compounds, and test compounds including the compound with formula A(XXIX) are summarized in Table 6.

Example 30—Preparation and Pharmacological Analysis of a Thirtieth Fused Heterocyclic Mescaline Derivative Referring to FIGS. 32A-32C, compound 1 (500 mg, 2.78 mmol) was dissolved in DCM (10.0 mL) added to this was 1-(3-Dimethylaminopropyl)-3-ethylcarbodiimide hydrochloride (616 mg, 3.05 mmol), triethylamine (778 µL, 5.55 mmol) and 4-dimethylaminopyridine (34 mg, 278 µmol). The mixture was left to stir for 20 minutes and then compound 2 (186 µL, 3.05 mmol) was added. After stirring overnight a new spot was observed by TLC (UV, DCM: MeOH 9:1) and the reaction mixture was poured into a separatory funnel containing 25 mL water and 25 mL EtOAc. The aqueous phase was extracted with EtOAc (3×25 mL), all organic layers were combined, washed with saturated sodium bicarbonate solution (2×50 mL), brine, dried over magnesium sulfate and concentrated under vacuum. The resulting crude material was purified on a CombiFlash system (12 g silica, DCM to DCM:MeOH 9:1) to provide MM679 (140 mg, 23%) as a white solid (See: FIG. 32A).

MS-ESI: C$_{11}$H$_{14}$NO$_4$ ([M+H]$^+$); calculated: 224.0917, observed: 224.0919. $^1$H NMR (400 MHz, CDCl$_3$) δ 6.79 (d, J=7.8 Hz, 1H), 6.75 (d, J=1.8 Hz, 1H), 6.70 (dd, J=7.8 Hz, 1.8 Hz, 1H), 5.96 (s, 2H), 5.92 (br s, 1H), 3.70-3.67 (m, 2H), 3.51 (s, 2H), 3.40-3.37 (m, 2H).

Into a round bottomed flask was added MM679 (200 mg, 896 μmol) this was dissolved in dry THF (8.15 mL) and cooled to 0° C. Once cool, lithium aluminum hydride (2.0 M, 672 μL, 1.34 mmol) was carefully added and the mixture was warmed to room temperature and left to react overnight. Monitoring by TLC (UV, DCM:MeOH 9:1) showed that a reaction had occurred but had not gone to completion. Additional Lithium aluminum hydride (2.0 M, 672 μL, 1.34 mmol) was added and the reaction was again left overnight. The flask was cooled to 0° C. and any remaining LiAlH$_4$ was quenched with water. The resulting mixture was poured into a separatory funnel containing 15 mL of water and 15 mL of EtOAc. The aqueous layer was extracted with EtOAc (3×15 mL), all organic layers were combined, washed with brine, dried (MgSO$_4$) and concentrated under reduced pressure. After purification on a CombiFlash system (4 g silica, DCM to 9:1 DCM:MeOH), MM684 was obtained as a colourless oil (69.0 mg, 37%) (See: FIG. 32B).

MS-ESI: $C_{11}H_{16}NO_3$ ([M+H]$^+$); calculated: 210.1125, observed: 210.1124. $^1$H NMR (400 MHz, CDCl$_3$) δ 6.73 (d, J=7.9 Hz, 1H), 6.69 (d, J=1.7 Hz, 1H), 6.64 (dd, J=7.8, 1.7 Hz, 1H), 5.92 (s, 2H), 3.68-3.61 (m, 2H), 2.96-2.83 (m, 2H), 2.83-2.77 (m, 2H), 2.77-2.70 (m, 2H).

MM684 (60.0 mg, 287 μmol) was dissolved in AcOH (1.51 mL). Added to this was a solution of bromine (16.2 μL, 315 μmol) in AcOH (163 μL). This was left to react at room temperature for 3 hours, at which point the starting material was no longer present (TLC-UV, DCM:MeOH 9:1). At this point, the mixture was poured into water (15 mL) and the pH was increased to ~10 with 1 M NaOH. The aqueous layer was extracted with DCM (3×25 mL). All organic layers were combined, washed with brine, dried (MgSO$_4$). Once concentrated the product, MM697 (25.0 mg, 30%), was obtained as a white solid which needed no further purification (See: FIG. 32C).

MS-ESI: $C_{11}H_{15}BrNO_3$ ([M+H]$^+$); calculated: 288.0230, observed: 288.0229. $^1$H NMR (400 MHz, DMSO) δ 7.14 (s, 1H), 6.95 (s, 1H), 6.02 (s, 2H), 4.48 (s, 1H), 3.43 (t, J=5.6 Hz, 2H), 2.77-2.65 (m, 4H), 2.60 (t, J=5.7 Hz, 2H).

It is noted that compound MM697 corresponds with the compound having chemical formula A(XXX):

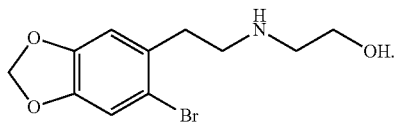

A(XXX)

5-HT receptor radioligand competition assays. Activity at 5-HT$_{1A}$ and 5-HT$_{2A}$ receptors were assessed as described for Example 15, except the compound with formula A(XXX) was evaluated in place of the compound with formula A(XIV). Table 1 shows radioligand competition assay results for positive controls, negative controls, and compound with formula A(XXX), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(XXX) at the 5-HT$_{1A}$ receptor (0.2953 μM, Table 1) indicates ligand-receptor binding. Similarly, the K$_i$ value obtained for the compound with formula A(XXX) at the 5-HT$_{2A}$ receptor (11.7 μM, Table 1) indicates ligand-receptor binding.

5-HT$_{1A}$ receptor functional cellular response assay. Functional engagement of the 5-HT$_{1A}$ receptor within an engineered cell system was assessed as described for Example 15, except the compound with formula A(XXX) was evaluated in place of the compound with formula A(XIV). Table 2 shows functional assay results for positive controls, calibrators, and compound with formula A(XXX), in the form of EC$_{50}$ values. In view of results for controls and calibrator compounds, wherein a negative cellular response corresponded to an EC$_{50}$ value>1000 μM, the EC$_{50}$ value for the compound with formula A(XXX) in this assay (11.68 μM, Table 2) suggested ligand-receptor engagement.

5-HT transporter (SERT) radioligand competition assay. Activity at the serotonin transporter (SERT) was assessed as described for Example 2, except the compound with formula A(XXX) was evaluated in place of the compound with formula A(VI). Table 3 shows radioligand competition assay results for positive controls, negative controls, and compound with formula A(XXX), in the form of K$_i$ values. In view of results for both positive and negative controls, wherein negative controls yield data insufficient for reliable K$_i$ calculations (i.e., K$_i$>1000 μM) the K$_i$ value obtained for the compound with formula A(XXX) at SERT (84.26 μM, Table 3) indicates binding to SERT at higher ligand concentrations.

In Vitro Survey of Pharmacological Interaction Profiles at Receptors and Transporters Linked to Targeted Health Conditions.

The compound with formula A(XXX) was evaluated with respect to binding and/or interaction at 11 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 9 GPCR receptors: HTR1B (5-HTR$_{1B}$), HTR1D (5-HT$_{1D}$), HTR2B (5-HT$_{2B}$), HTR2C (5-HT$_{2C}$), HTR7 (5-HT$_7$), alpha2A ($\alpha_{2A}$), D2 (D$_2$), D3 (D$_3$), MT1 (MT$_1$)) and 2 transporters (DAT, NET). Assays were conducted using the same materials and procedures outlined in Example 15, except the compound with formula A(XXX) was used in place of the compound with formula A(XIV). Overall assay conditions are summarized in Tables 4 and 5 for GPCR and transporters, respectively. Results for all calibrator compounds, control compounds, and test compounds including the compound with formula A(XXX) are summarized in Table 6.

Example 31—Preparation and Pharmacological Analysis of a Thirty-First Fused Heterocyclic Mescaline Derivative Under nitrogen atmosphere, A (190 mg, 1.07 mmol) was dissolved in methanol (7.11 mL) followed by the addition of acetic acid (58.0 μL, 1.01 mmol) and the reaction mixture was stirred for 5 minutes before the addition of tryptamine (278 mg, 1.68 mmol). The reaction mixture was then heated to 60° C. and stirred for 4 h. The reaction was cooled to room temperature and sodium cyanoborohydride (212 mg, 3.20 mmol) was added to the mixture and stirring was continued at room temperature for 18 h. At this point the mixture was added to a separatory funnel containing 50 mL DCM and 50 mL water. Saturated sodium bicarbonate was added to the mixture to adjust the aqueous pH to ~9 (pH paper). The aqueous layer was extracted with DCM (3×50 mL). The combined organic extracts were washed with water (30 mL), brine (30 mL), and dried over anhydrous magnesium sulphate. After concentration a yellow-green oil was isolated as the crude material. Purification by column chromatography on 12 g normal-phase silica using a 0-10% methanol-dichloromethane eluent gradient yielded MM801 as a light yellow oil (268 mg, 78%).

MS-HESI: 323.24 m/z [M+H]$^+$. $^1$H NMR (400 MHz, CDCl$_3$) δ 8.18 (s, 1H), 7.58 (d, J=7.8 Hz, 1H), 7.36 (dt, J=8.1, 0.9 Hz, 1H), 7.20 (ddd, J=8.2, 7.0, 1.2 Hz, 1H), 7.11 (ddd, J=8.0, 7.0, 1.1 Hz, 1H), 6.95 (d, J=2.2 Hz, 1H), 6.61 (d, J=7.9 Hz, 1H), 6.56 (d, J=1.7 Hz, 1H), 6.48 (dd, J=7.9, 1.7 Hz, 1H), 5.92 (dd, J=2.5, 1.5 Hz, 2H), 3.03-2.83 (m, 4H), 2.68-2.51 (m, 4H), 1.11 (d, J=6.3 Hz, 3H).

It is noted that compound MM801 corresponds with the compound having chemical formula A(XXXI):

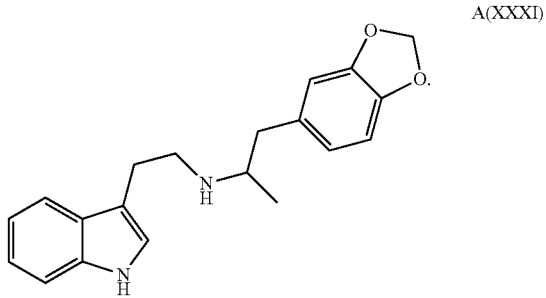 [SMILES: CC(Cc1ccc2c(c1)OCO2)NCCc1c[nH]c2ccccc12]

A(XXXI)

It is noted that compound A was synthesized as described in Example 5.

Neuroplastogenicity Assay Using Human Model (NT2) Neurons.

Figure 41A:
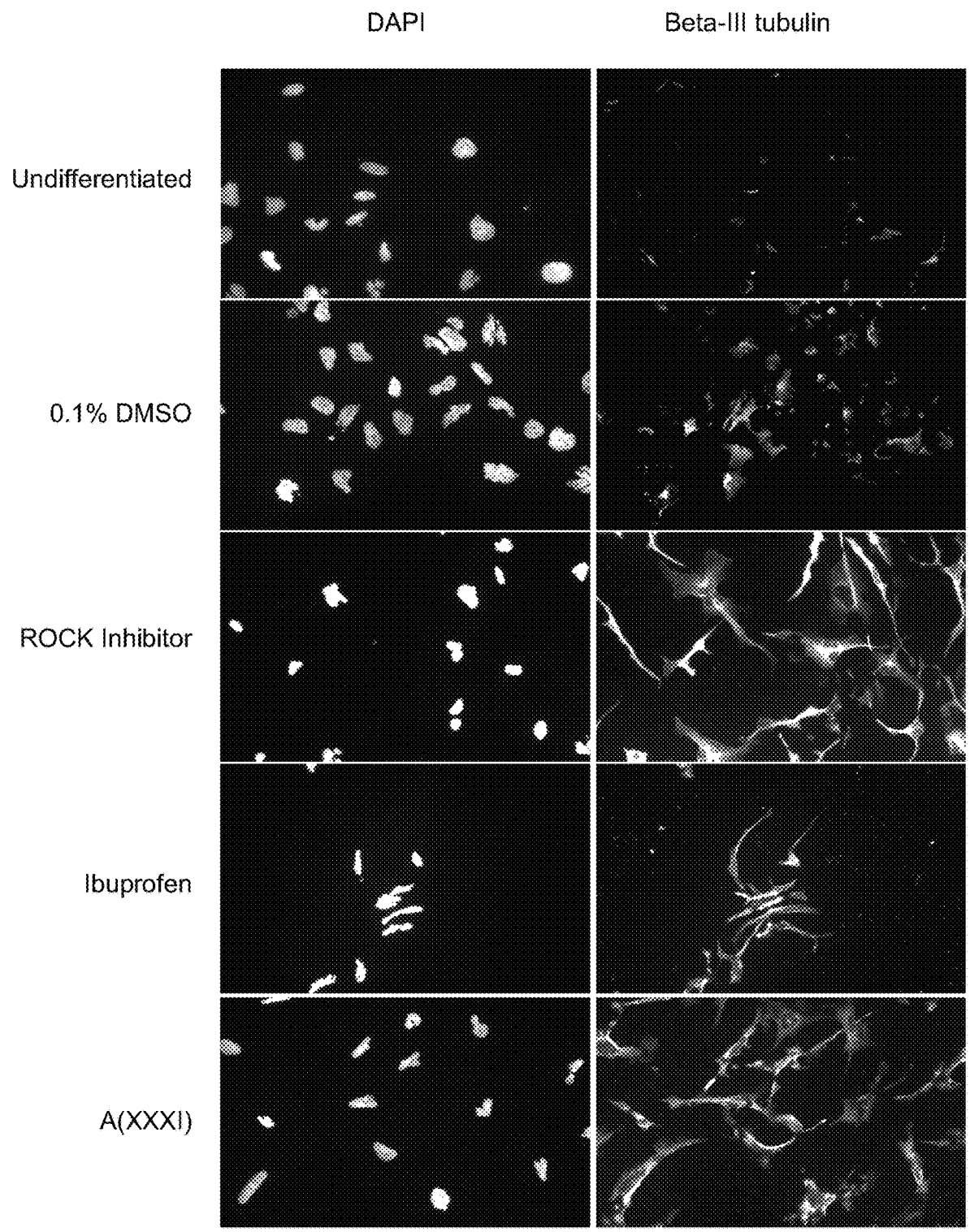
FIGS. 41A and 41B depict microscopic images representing certain experimental results, notably results obtained in the performance of immunofluorescence assays using human neuronal NT2 cells (human NT2/D1 precursor cells (NT2/D1)) to evaluate cellular differentiation, notably neuroplasticity, in response to contacting of the NT2 cells with example compounds A(XXXI) and A(XXXII). Images were obtained following various treatments of NT2 cells, notably: no treatment with retinoic acid (RA) ("undifferentiated"), or treatment with RA, followed by treatment with: 0.1% DMSO (negative control) ("0.1% DMSO"); ROCK inhibitor Y-27632, (Dihydrochloride, Sigma-Aldrich) (positive control) ("ROCK Inhibitor"); Ibuprofen (positive control) ("Ibuprofen"); and compound A(XXXI) ("A(XXXI)") (FIG. 41A) or compound A(XXXII) ("A(XXXII)") (FIG. 41B). Cells were examined for the presence of cell nuclei using 4'6-diamidino-2-phenylindole dihydrochloride stain ("DAPI") and β-III-tubulin ("Beta-Ill-tubulin").

Neuroplastogenicity assays were conducted using the same methods, materials and control compounds as outlined for Example 32, except that the compound with formula A(XXXI) was used in place of the compound with formula A(XXXII). Results are shown in FIG. 41A. Undifferentiated cells lacking RA treatment (marked as "Undifferentiated" in FIG. 41A) displayed no signs of neurite outgrowth. This conclusion is based on the following observations and analysis flow: (1) DAPI-stained nuclei identified the location and number of cells present (left panel); (2) when these same DAPI-identified cells were examined for β-III-tubulin-based immunofluorescence (marked "beta-III tubulin", right panel), no immunofluorescence was observed above background levels normally associated with glass microscope slides, indicating no neurite outgrowth. Differentiating, RA-treated cells additionally exposed to drug-free 'vehicle' (marked as "0.1% DMSO" in FIG. 41A) displayed no substantive signs of neurite outgrowth (or alternatively defined as 'slow' outgrowth) during the test period. This 'vehicle' (0.1% DMSO) treatment was used as a negative control for the overall experiment. This conclusion is based on the following observations and analysis flow: (1) DAPI-stained nuclei identified the location and number of cells present (left panel); (2) when these same DAPI-identified cells were examined for β-III-tubulin-based immunofluorescence (marked "beta-III tubulin", right panel), no substantive immunofluorescence was observed, indicating no neurite outgrowth. Differentiating, RA-treated cells additionally exposed to 1 µM Rho kinase inhibitor Y-27632 (marked as "ROCK Inhibitor" in FIG. 41A) as a positive control displayed strong signs of neurite outgrowth (or alternatively defined as 'enhanced' outgrowth) compared to negative control treatment. This conclusion is based on the following observations and analysis flow: (1) DAPI-stained nuclei identified the location and number of cells present (left panel); (2) when these same DAPI-identified cells were examined for β-III-tubulin-based immunofluorescence (marked "beta-III tubulin", right panel), enhanced immunofluorescence was observed compared to 'vehicle' (0.1% DMSO) treatment, indicating strong (or enhanced) neurite outgrowth. Differentiating, RA-treated cells additionally exposed to 1 µM ibuprofen (marked as "Ibuprofen" in FIG. 41A) as a positive control displayed strong signs of neurite outgrowth (or alternatively defined as 'enhanced' outgrowth) compared to negative control treatment. This conclusion is based on the following observations and analysis flow: (1) DAPI-stained nuclei identified the location and number of cells present (left panel); (2) when these same DAPI-identified cells were examined for β-III-tubulin-based immunofluorescence (marked "beta-III tubulin", right panel), enhanced immunofluorescence was observed compared to 'vehicle' (0.1% DMSO) treatment, indicating strong (or enhanced) neurite outgrowth. Differentiating, RA-treated cells additionally exposed to 1 µM of compound with formula A(XXXI) (marked as "A(XXXI)" in FIG. 41A) as a potential neuroplastogen displayed strong signs of neurite outgrowth (or alternatively defined as 'enhanced' outgrowth) compared to negative control treatment. This conclusion is based on the following observations and analysis flow: (1) DAPI-stained nuclei identified the location and number of cells present (left panel); (2) when these same DAPI-identified cells were examined for β-III-tubulin-based immunofluorescence (marked "beta-III tubulin", right panel), enhanced immunofluorescence was observed compared to 'vehicle' (DMSO) treatment, indicating strong (or enhanced) neurite outgrowth; (3) results were comparable to those obtained for the positive control treatments (ROCK Inhibitor and Ibuprofen data, respectively).

Example 32—Preparation and Pharmacological Analysis of a Thirty-Second Fused Heterocyclic Mescaline Derivative To a stirring solution of MM801 (30.0 mg, 93.1 µmol) (see: Example 31) in methanol (0.500 mL) under nitrogen atmosphere at 0° C. was added acetic acid (26.6 µL, 465 µmol), followed by sodium cyanoborohydride (12.3 mg, 186 µmol). An aqueous solution of 37% formaldehyde (20.8 µL, 279 µmol) in methanol (100 µL) was added dropwise over 10 minutes. The resulting solution was allowed to warm to room temperature and stirred for 18 h. At this point the mixture was added to a separatory funnel containing 50 mL DCM and 50 mL water. Saturated sodium bicarbonate was added to the mixture to adjust the aqueous pH to ~9 (pH paper). The aqueous layer was extracted with 3×30 mL DCM. All organic layers were combined, washed with water (20 mL), brine (20 mL), dried over anhydrous magnesium sulphate and concentrated under reduced pressure. Purification by column chromatography on 4 g normal-phase silica using a 0-10% methanol-dichloromethane yielded MM809 as a translucent, colourless solid (12.2 mg, 39%).

MS-HESI: 337.26 m/z [M+H]$^+$. $^1$H NMR (400 MHz, CDCl$_3$) δ 8.07 (s, 1H), 7.63 (dt, J=7.8, 0.9 Hz, 1H), 7.38 (dt, J=8.1, 1.0 Hz, 1H), 7.21 (ddd, J=8.2, 7.0, 1.3 Hz, 1H), 7.14 (ddd, J=8.0, 7.0, 1.1 Hz, 1H), 7.06 (d, J=2.2 Hz, 1H), 6.73 (d, J=7.8 Hz, 1H), 6.68 (d, J=1.7 Hz, 1H), 6.62 (dd, J=8.0, 1.7 Hz, 1H), 5.93 (s, 2H), 3.13-2.97 (m, 4H), 2.90 (d, J=9.0 Hz, 2H), 2.50 (s, 3H), 2.39 (dd, J=12.8, 9.5 Hz, 1H), 1.02 (d, J=6.4 Hz, 3H).

It is noted that compound MM809 corresponds with the compound having chemical formula A(XXXII):

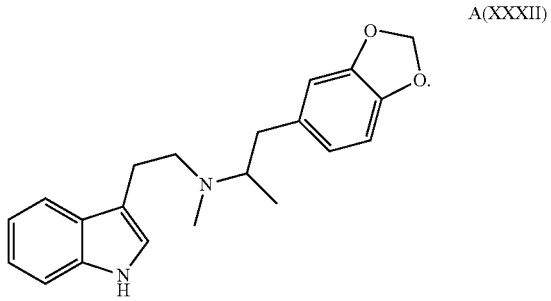 [SMILES: CC(Cc1ccc2c(c1)OCO2)N(C)CCc1c[nH]c2ccccc12]

A(XXXII)

5-HT receptor radioligand competition assays. Activity at 5-HT$_{2A}$ receptor was assessed as described for Example 15, except the compound with formula A(XXXII) was evaluated in place of the compound with formula A(XIV). Table 1 shows radioligand competition assay results for positive controls, negative controls, and compound with formula A(XXXII), in the form of K$_i$ values. In view of results for both positive and negative controls, wherein negative controls yield data insufficient for reliable K$_i$ calculations (i.e., K$_i$>1000 µM) the K$_i$ value obtained for the compound with formula A(XXXII) at the 5-HT$_{1A}$ receptor (0.465 µM, Table 1) indicates ligand-receptor binding.

Neuroplastogenicity Assay Using Human Model (NT2) Neurons.

Neuroplasticity refers to the nervous system's ability to reorganize its structure and function and adapt to its dynamic environment. Evidence has long demonstrated that neuroplasticity is disrupted in mood disorders and in animal models of stress (Pittenger and Duman, 2008, Neuropsychopharmacology 33:88-109). It has also been shown that antidepressant treatment produces opposing effects and can enhance neuroplasticity. The broad therapeutic potential of psychedelic-type drugs is suggested to rest on an ability to rescue cortical atrophy common to many neuropsychiatric and neurodegenerative diseases (Saeger and Olson, 2022, Journal of Neurochemistry 162:109-127). Psychedelics appear to be particularly effective catalysts for the growth of prefrontal cortical neurons, ultimately leading to restoration of synaptic activity in this critical brain region (Olson, 2022, Biochemistry 61:127-136). Neuroplasticity is manifested at multiple levels, including structural which can entail morphological changes in spine and dendrite anatomy. Commonly applied measures of neuroplasticity are neuronal or dendrite or outgrowth assays, wherein potential neuroplastogens are applied to natural or induced neuronal cells followed by qualitative or quantitative assessment of enhanced morphologies. For example, enhanced neurite outgrowth of human model (NT2) neurons can be achieved through application of Rho/ROCK signalling inhibitors and small molecules with neuroplastogenic potential including psychedelics. Commonly used positive controls known to induce neuroplasticity are the Rho/ROCK inhibitor Y-27632, the anti-inflammatory ibuprofen (Roloff et al., 2015, PLOS ONE e0118536:1-14) and the psychedelics DMT, MDMA, and LSD (Ly et al., 2018, Cell Reports 23:3170-3182). Negative controls generally consist of 'vehicle' applications, wherein solution without drug is applied to neurons.

The compound with formula A(XXXII) was assayed for neuroplastogenic potential using the following procedure. Human NT2/D$_1$ precursor cells (NT2/D$_1$) were purchased from the American Type Culture Collection (ATCC, Manassas, VA, USA). The neuronal differentiation was carried out as previously described (Roloff et al., 2015, PLOS ONE e0118536:1-14; Roloff et al., 2013, BMC Neuroscience 14:141-155) with minor modifications. First, NT2/D$_1$ cells were seeded in T-25 suspension culture flasks (REF #690190, Greiner bio-one, Germany). Each flask contained a minimum of 5×10$^6$ cells in 10 ml of DMEM/F12 supplemented with 10% fetal bovine serum (FBS), 1% penicillin and streptomycin and 10 µM retinoic acid (RA medium) to start neuronal differentiation. The cells were cultured for 3 days in free floating medium. At the end of the incubation, cells were trypsinized and collected by centrifugation, mechanically dispersed, and counted. Counted cells were seeded on Poly D-Lysine (PDL) coated cover slips (12 mm; diameter round, Fisher Scientific; GG-12-PDL) containing minimum of 0.1×10$^5$ cells in culture medium without RA. The next day, culture medium was replaced with RA medium containing 2% of FBS. These cells were cultured for 5 days, with a change of RA medium two days later. For the neuronal outgrowth assay, after cells had successfully attached and established under coverslips, the RA medium was replaced with one of the following: (1) test molecules at one of two different concentrations (10 µm or 1 µm); (2) positive control ROCK inhibitor Y-27632, (Dihydrochloride, Sigma-Aldrich); (2) positive control ibuprofen (14883-1G; Sigma-Aldrich), or (4) negative control culture medium containing 2% of FBS. Cells under these conditions were incubated for 48 hours under standard conditions (37° C., 5% CO$_2$) in an incubator prior to the immunofluorescent assay.

Figure 41B:
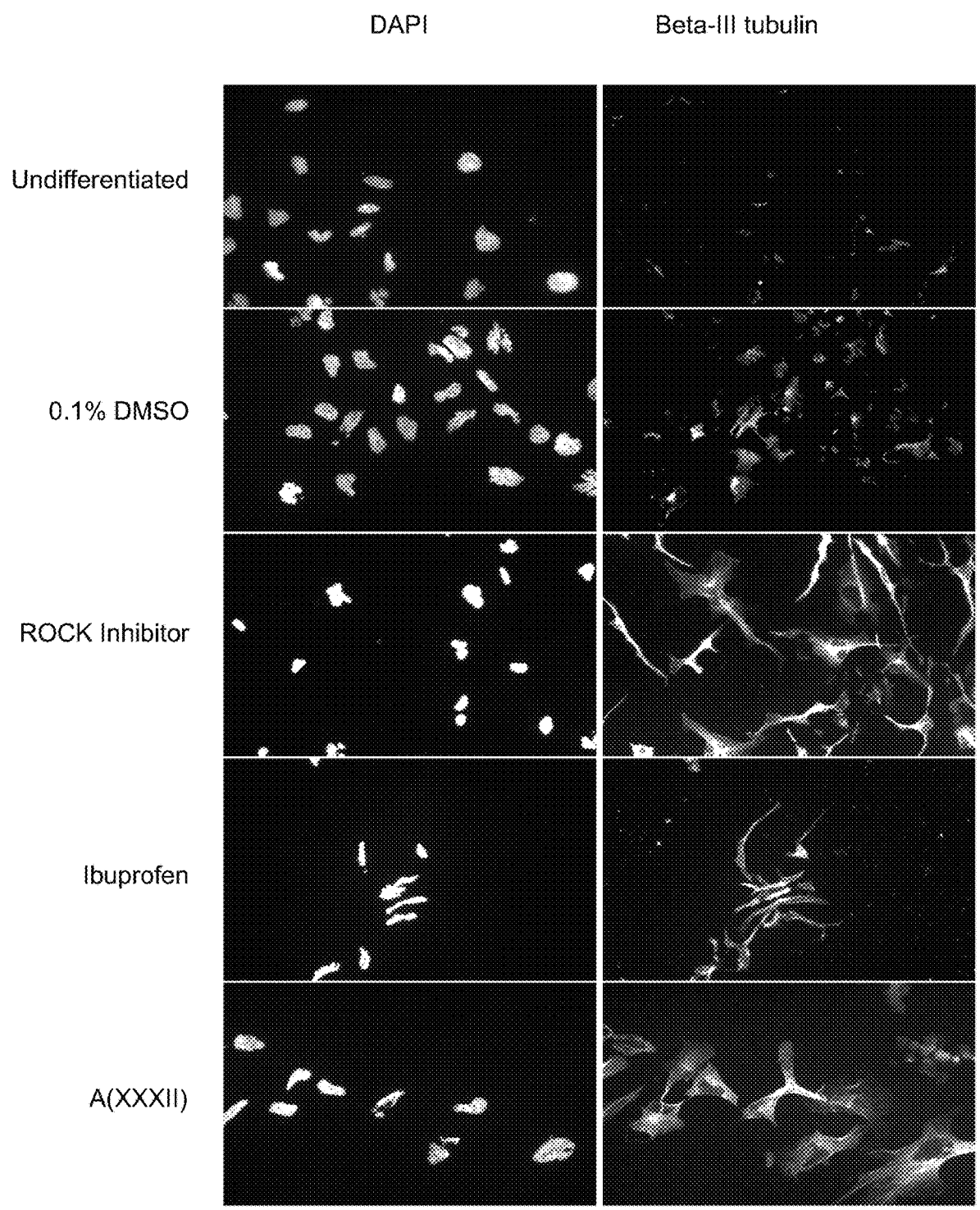

For the immunofluorescent assay, the treated cells housed under coverslips were collected after 48 hours of drug treatments. These coverslips washed with calcium chloride-free and magnesium chloride-free phosphate buffered saline (PBS) pH 7.4 (Gibco, #70011-044) and fixed using paraformaldehyde (PFA) 4% in PBS (#J61899, thermoscientific) for 15 min at room temperature (RT) and washed three times with 0.01% of Triton-X$_{100}$ in PBS (PBST) to remove remaining PFA and to permeabilize the cells. Unspecific binding sites were blocked with 5% Bovine Serum Albumin (BSA) solution (#9048-46-8, Millipore) in PBST for 60 minutes at RT. Rabbit monoclonal antibody β-III-Tubulin (1:5,000, ab52623, Abcam) was applied overnight (O/N) at 4° C. The next day, cells are washed three times in PBST, and neurons were incubated with secondary antibody donkey anti-rabbit IgG(H+L) Alexa Fluor™ Plus488 (1:5000 #A32790, Invitrogen) for 1 hours at RT. The slides were treated with Gluoromount-G™, using 4'6-diamidino-2-phenylindole dihydrochloride (DAPI) (#E141818, Invitrogen). Finally, the immunofluorescence images were detected by using Olympus VS110 slide scanner microscope. Results are shown in FIG. 41B. Undifferentiated cells lacking RA treatment (marked as "Undifferentiated" in FIG. 41B) displayed no signs of neurite outgrowth. This conclusion is based on the following observations and analysis flow: (1) DAPI-stained nuclei identified the location and number of cells present (left panel); (2) when these same DAPI-identified cells were examined for β-III-tubulin-based immunofluorescence (marked "beta-III tubulin", right panel), no immunofluorescence was observed above background levels normally associated with glass microscope slides, indicating no neurite outgrowth. Differentiating, RA-treated cells additionally exposed to drug-free 'vehicle' (marked as "0.1% DMSO" in FIG. 41B) displayed no substantive signs of neurite outgrowth (or alternatively defined as 'slow' outgrowth) during the test period. This 'vehicle' (0.1% DMSO) treatment was used as a negative control for the overall experiment. This conclusion is based on the following observations and analysis flow: (1) DAPI-stained nuclei identified the location and number of cells present (left panel); (2) when these same DAPI-identified cells were examined for β-III-tubulin-based immunofluorescence (marked "beta-III tubulin", right panel), minimal immunofluorescence was observed, indicating no substantive neurite outgrowth. Differentiating, RA-treated cells additionally exposed to 1 µM Rho kinase inhibitor Y-27632 (marked as "ROCK Inhibitor" in FIG. 41B) as a positive control displayed strong signs of neurite outgrowth (or alternatively defined as 'enhanced' outgrowth) compared to negative control treatment. This conclusion is based on the following observations and analysis flow: (1) DAPI-stained nuclei identified the location and number of cells present (left panel); (2) when these same DAPI-identified cells were examined for β-III-tubulin-based immunofluorescence (marked "beta-III tubulin", right panel), enhanced immunofluorescence was observed compared to 'vehicle' (0.1% DMSO) treatment, indicating strong (or enhanced) neurite outgrowth. Differentiating, RA-treated cells additionally exposed to 1 µM ibuprofen (marked as "Ibuprofen" in FIG. 41B) as a positive control displayed strong signs of neurite outgrowth (or alternatively defined as 'enhanced' outgrowth) compared to negative control treatment. This conclusion is based on the following observations and analysis flow: (1) DAPI-stained nuclei identified the location and number of cells present (left panel); (2) when these same DAPI-identified cells were examined for β-III-tubulin-based immunofluorescence (marked "beta-III tubulin", right panel), enhanced immunofluorescence was observed compared to 'vehicle' (0.1% DMSO) treatment, indicating strong (or enhanced) neurite outgrowth. Differentiating, RA-treated cells additionally exposed to 1 µM of compound with formula A(XXXII) (marked as "A(XXXII)" in FIG. 41B) as a potential neuroplastogen displayed strong signs of neurite outgrowth (or alternatively defined as 'enhanced' outgrowth) compared to negative control treatment. This conclusion is based on the following observations and analysis flow: (1) DAPI-stained nuclei identified the location and number of cells present (left panel); (2) when these same DAPI-identified cells were examined for β-III-tubulin-based immunofluorescence (marked "beta-III tubulin", right panel), enhanced immunofluorescence was observed compared to 'vehicle' (DMSO) treatment, indicating strong (or enhanced) neurite outgrowth; (3) results were comparable to those obtained for the positive control treatments (ROCK Inhibitor and Ibuprofen data, respectively).

The invention claimed is:

1. A chemical compound selected from a first chemical compound having chemical formula (I), and a second chemical compound having chemical formula (II):

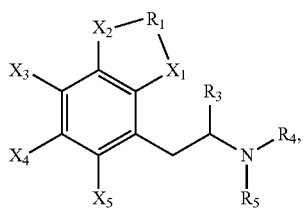

(I)

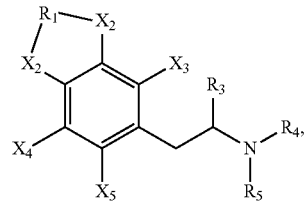

(II)

wherein, in each chemical formula (I) and (II)
$R_1$ is an optionally substituted alkylene group having 1-3 carbon atoms or a carbonyl group (—C(=O));
$X_1$ and $X_2$ are independently selected from an oxygen atom, a sulfur atom, —NH, or an N-alkyl group, and $X_3$, $X_4$, or $X_5$ are independently a hydrogen atom, a halogen atom, an alkyl group, an alkoxy group, an acyl group, an amino group, an N-substituted amino group, an amide group, a substituted amide group, a substituted amido group, a hydroxy group, a cyano group, a carboxy group, a thiol group, or a thioether group, and wherein two or three of $X_3$, $X_4$, or $X_5$ are a hydrogen atom;
$R_3$ is a methyl group, a cyano group, or a hydrogen atom; and
$R_4$ and $R_5$ are independently selected from an alkyl group, an alkoxy group, a hydroxyalkyl group, an N-substituted amino group, an alkyl-heteroaryl group wherein the heteroaryl is optionally substituted, or a hydrogen atom, and wherein at least one of $R_4$ and $R_5$ is an alkyl-aryl group, wherein the aryl group is substituted by being fused to a 5 or 6 membered heterocyclic ring containing two oxygen atoms, and wherein the aryl group is additionally substituted with a halogen atom, wherein further the amino group (—$NR_4R_5$) in each of compounds of formula (I) and (II) is optionally protonated to form (—$N^+HR_4R_5$), and chemical formula (I) or (II) further includes a negatively charged anion balancing the positively charged nitrogen atom.

2. A chemical compound according to claim 1, wherein the amino group (—$NR_4R_5$) in the compounds of formula (I) and (II) are protonated to form (—$N^+HR_4R_5$), and chemical formula (I) or (II) further includes a negatively charged anion balancing the positively charged nitrogen atom.

3. A chemical compound according to claim 1, wherein $R_1$ is an alkylene group having one carbon atom and $X_1$ and $X_2$ each are an oxygen atom.

4. A chemical compound according to claim 1, wherein $R_1$ is a substituted alkylene group having one carbon atom, wherein the carbon atom is substituted with one or two halogen atoms, optionally fluorine atoms, and $X_1$ and $X_2$ each are an oxygen atom.

5. A chemical compound according to claim 1, wherein $R_1$ is an alkylene group having two carbons atom and $X_1$ and $X_2$ each are an oxygen atom.

6. A chemical compound according to claim 1, wherein $X_3$, $X_4$, and $X_5$ each are a hydrogen atom.

7. A chemical compound according to claim 1, wherein one of $X_3$, $X_4$, and $X_5$ is a halogen or an alkoxy group.

8. A chemical compound according to claim 1, wherein $X_5$ is a halogen, optionally a bromine, or an alkoxy group, optionally an ($C_1$-$C_{10}$)-alkoxy group, or optionally an ($C_1$-$C_3$)-alkoxy group, optionally a methoxy group.

9. A chemical compound according to claim 1, wherein the alkyl group in the alkyl-aryl group is a ($C_1$-$C_{10}$) alkylene group.

10. A chemical compound according to claim 1, wherein one of the $R_4$ and $R_5$ groups is an ($C_1$-$C_{10}$)-alkyl group or a ($C_1$-$C_3$)-alkyl group.

11. A chemical compound according to claim 1, wherein one of the $R_4$ and $R_5$ groups is a $(C_3-C_{10})$-cyclo-alkyl group, a $(C_3-C_6)$-cyclo-alkyl group, or a $C_4$-cyclo-alkyl group.

12. A chemical compound according to claim 1, wherein one of the $R_4$ and $R_5$ groups is a $(C_1-C_{10})$-alkoxy group or a $(C_1-C_3)$-alkoxy group.

13. A chemical compound according to claim 1, wherein one of the $R_4$ and $R_5$ groups is a $(C_1-C_{10})$-hydroxyalkyl group or a $(C_1-C_3)$-hydroxyalkyl group.

14. A chemical compound according to claim 1, wherein one of the $R_4$ and $R_5$ groups is a substituted amino group, optionally a $(C_1-C_{10})$-alkyl substituted amino group, or optionally a $(C_1-C_3)$-alkyl substituted amino group.

15. A chemical compound according to claim 1, wherein the chemical compound having formula (I) or formula (II) is selected from the group of compounds selected from: A(VI); A(IX); and A(XI):

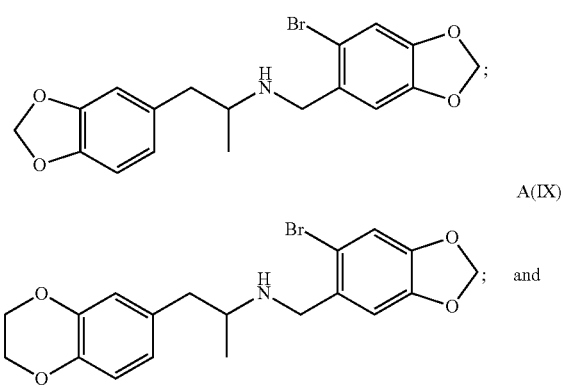

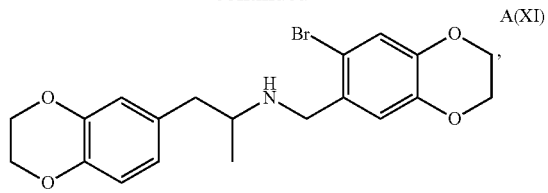

wherein in each of compound A(VI), A(IX), and A(XI), optionally, the nitrogen atom of the ethyl amine chain may be protonated and includes a negatively charged anion balancing the positively charged nitrogen atom.

16. A chemical compound according to claim 1, wherein the compound is at least about 95% (w/w) pure.

17. A pharmaceutical drug formulation comprising an effective amount of the chemical compound of claim 1 together with a pharmaceutically acceptable excipient, diluent, or carrier.

18. A chemical compound according to claim 15, wherein the compound is at least about 95% (w/w) pure.

19. A pharmaceutical drug formulation comprising an effective amount of the chemical compound of claim 15 together with a pharmaceutically acceptable excipient, diluent, or carrier.

* * * * *